(12) United States Patent
Woods et al.

(10) Patent No.: US 11,602,348 B2
(45) Date of Patent: Mar. 14, 2023

(54) BRIDGING PERIPHERAL NERVE GAPS WITH CONDUITS FOR ENHANCED NERVE REGENERATION

(71) Applicant: Newrotex Limited, Oxford (GB)

(72) Inventors: Alexander Woods, Oxford (GB); Robyn Plowright, Bicester (GB); Friedrich Vollrath, Oxford (GB)

(73) Assignee: NEWROTEX LIMITED, Oxford (GB)

( * ) Notice: Subject to any disclaimer, the term of this patent is extended or adjusted under 35 U.S.C. 154(b) by 0 days.

(21) Appl. No.: 17/481,592

(22) Filed: Sep. 22, 2021

(65) Prior Publication Data

US 2022/0031328 A1 Feb. 3, 2022

Related U.S. Application Data

(63) Continuation of application No. PCT/GB2021/051746, filed on Jul. 8, 2021.

(60) Provisional application No. 63/093,866, filed on Oct. 20, 2020, provisional application No. 63/049,289, filed on Jul. 8, 2020.

(51) Int. Cl.
*A61B 17/11* (2006.01)
*A61L 31/04* (2006.01)
*A61L 31/16* (2006.01)

(52) U.S. Cl.
CPC ........ *A61B 17/1128* (2013.01); *A61L 31/044* (2013.01); *A61L 31/16* (2013.01); *A61L 2430/32* (2013.01)

(58) Field of Classification Search
CPC .... A61B 17/1128; A61L 31/044; A61L 31/16; A61L 2430/32
See application file for complete search history.

(56) References Cited

U.S. PATENT DOCUMENTS

| 4,963,146 | A  | * | 10/1990 | Li ......................... A61L 31/146 606/152 |
| 6,589,257 | B1 | * | 7/2003  | Shimizu .................. A61L 31/06 606/152 |
| 6,716,225 | B2 | * | 4/2004  | Li ....................... A61B 17/1128 600/36 |
| 8,106,014 | B2 |   | 1/2012  | Priestley et al. |
| 2003/0028204 | A1 | * | 2/2003 | Li ......................... A61L 31/044 606/152 |
| 2013/0345729 | A1 | * | 12/2013 | Li ...................... A61L 27/3878 156/80 |
| 2016/0074042 | A1 |   | 3/2016  | Vogt et al. |
| 2018/0280567 | A1 | * | 10/2018 | Kohn ..................... C08G 69/40 |

OTHER PUBLICATIONS

"Alessandrino, et al., "SilkBridge™: a novel biomimetic and biocompatible silk-based nerve conduit" Biomater Sci. Oct. 1, 2019;7(10):4112-4130. doi: 10.1039/c9bm00783k.".

(Continued)

*Primary Examiner* — Katherine M Shi
*Assistant Examiner* — Mohammed S Adam
(74) *Attorney, Agent, or Firm* — Wilson Sonsini Goodrich & Rosati

(57) ABSTRACT

Disclosed herein are compositions comprising containers and silk elements. Disclosed herein are methods of regenerating an at least partially severed nerve cell. Disclosed herein are compositions for regenerating an at least partially severed nerve cell.

24 Claims, 63 Drawing Sheets

(56) References Cited

OTHER PUBLICATIONS

"Allmeling C, Jokuszies A, Reimers K, Kall S, Vogt PM. Use of spider silk fibres as an innovative material in a biocompatible artificial nerve conduit. J Cell Mol Med. Jul.-Sep. 2006;10(3):770-7. doi: 10.1111/j.1582-4934.2006.tb00436.x. PMID: 16989736; PMCID: PMC3933158. https://pubmed.ncbi.nlm.nih.gov/16989736/".
"Arslantunali, et al., "Peripheral nerve conduits: techology update" (2014)Medical Devices: Ev idence and Research 201 4:7 405-424".
"Bassilios Habre S, Bond G, Jing XL, Kostopoulos E, Wallace RD, Konofaos P. The Surgical Management of Nerve Gaps: Present and Future. Ann Plast Surg. Mar. 2018;80(3):252-261. doi: 10.1097/SAP.0000000000001252. PMID: 29166306.https://pubmed.ncbi.nlm.nih.gov/29166306/".
"Battiston B, Geuna S, Ferrero M, Tos P. Nerve repair by means of tubulization: literature review and personal clinical experience comparing biological and synthetic conduits for sensory nerve repair. Microsurgery 2005;25:258-67. https://pubmed.ncbi.nlm.nih.gov/15934044/".
"Bekler HI, Rosenwasser MP, Akilina Y, Bulut G. The use of an absorbable collagen cover (NeuraWrap) improves patency of interpositional vein grafts. Acta Orthop Traumatol Turc. 2010;44(2):157-61. doi: 10.3944/AOTT.2010.2298. PMID: 20676019. https://pubmed.ncbi.nlm.nih.gov/20676019/".
"Bhardwaj, et al., "Freeze-gelled silk fibroin protein scaffolds for potential applications in soft tissue engineering" (2011) Int J Biol Macromol 49(3):260-7".
"Bibbo C, Rodrigues-Colazzo E, Finzen AG. Superficial Peroneal Nerve to Deep Peroneal Nerve Transfer With Allograft Conduit for Neuroma in Continuity. J Foot Ankle Surg. May-Jun. 2018;57(3):514-517. doi: 10.1053/j.jfas.2017.11.022. PMID: 29685562. https://pubmed.ncbi.nlm.nih.gov/29685562/".
"Bin Liu, Wang Xin, Jian-Rong Tan, Rui-Ping Zhu, Ting Li, Dan Wang, Sha-Sha Kan, Ding-Kui Xiong, Huan-Huan Li, Meng-Meng Zhang, Huan-Huan Sun, William Wagstaff, Chan Zhou, Zhi-Jian Wang, Yao-Guang Zhang, and Tong-Chuan He (2019) Myelin sheath structure and regeneration in peripheral nerve injury repair PNAS 116 (44) 22347-22352; doi.org/10.1073/pnas.1910292116https://pubmed.ncbi.nlm.nih.gov/31611410/".
"Brenner MJ, Tung TH, Jensen JN, Mackinnon SE. The spectrum of complications of immunosuppression: is the time right for hand transplantation? J Bone Joint Surg Am. Oct. 2002;84(10):1861-70. PMID: 12377920.https://pubmed.ncbi.nlm.nih.gov/12377920/".
"Casañas J, de la Torre J, Soler F, Garcia F, Rodellar C, Pumarola M, Climent J, Soler R, Orozco L. Peripheral nerve regeneration after experimental section in ovine radial and tibial nerves using synthetic nerve grafts, including expanded bone marrow mesenchymal cells: morphological and neurophysiological results. Injury. Oct. 2014;45 Suppl 4:S2-6. doi: 10.1016/S0020-1383(14)70003-8. PMID: 25384470.https://pubmed.ncbi.nlm.nih.gov/25384470/".
"Deal, et al., "Nerve Conduits for Nerve Repair or Reconstruction" (2012) Journal of the American Academy of Orthopaedic Surgeons, vol. 20, Issue 2 pp. 63-68".
"Deumens R, Bozkurt A, Meek MF, Marcus MA, Joosten EA, Weis J, Brook GA. Repairing injured peripheral nerves: Bridging the gap. Prog Neurobiol. Nov. 2010;92(3):245-76. doi: 10.1016/j.pneurobio.2010.10.002. Epub Oct. 13, 2010. PMID: 20950667. https://pubmed.ncbi.nlm.nih.gov/20950667/".
"Di Summa PG, Kingham PJ, Campisi CC, Raffoul W, Kalbermatten DF. Collagen (NeuraGen®) nerve conduits and stem cells for peripheral nerve gap repair. Neurosci Lett. Jun. 20, 2014;572:26-31. doi: 10.1016/j.neulet.2014.04.029. Epub May 2, 2014. PMID: 24792394. https://pubmed.ncbi.nlm.nih.gov/24792394/".
"Diogo CC, Camassa JA, Pereira JE, Costa LMD, Filipe V, Couto PA, Geuna S, Mauricio AC, Varejão AS. The use of sheep as a model for studying peripheral nerve regeneration following nerve injury: review of the literature. Neurol Res. Oct. 2017;39(10):926-939. doi: 10.1080/01616412.2017.1331873. Epub Jun. 11, 2017. PMID: 28604272.https://pubmed.ncbi.nlm.nih.gov/28604272/".

"Ducic I, Safa B, DeVinney E. Refinements of nerve repair with connector-assisted coaptation. Microsurgery. Mar. 2017;37(3):256-263. doi: 10.1002/micr.30151. Epub Dec. 30, 2016. PMID: 28035702. https://pubmed.ncbi.nlm.nih.gov/28035702/".
"Serban, et al., "Silk Fibroin an polyethylene glycol-based biocompatible tissues adhesives" (2011) J Biomed Mater Res A 98(4) p. 567-575".
"Fan, et al., "Macroporous Hydrogel Scaffolds for Three-Dimensional Cell Culture and Tissue Engineering"".
"Farole A, Jamal BT. A bioabsorbable collagen nerve cuff (NeuraGen) for repair of lingual and inferior alveolar nerve injuries: a case series. J Oral Maxillofac Surg. Oct. 2008;66(10):2058-62. doi: 10.1016/j.joms.2008.06.017. PMID: 18848102. https://pubmed.ncbi.nlm.nih.gov/18848102/".
"Frey M, Gruber H, Happak W, Girsch W, Gruber I, Koller R. Ipsilateral and cross-over elongation of the motor nerve by nerve grafting: an experimental study in sheep. Plast Reconstr Surg. Jan. 1990;85(1):77-89; discussion 90-1. doi: 10.1097/00006534-199001000-00014. PMID: 2293740.".
"Ghoreishian M, Rezaei M, Beni BH, Javanmard SH, Attar BM, Zalzali H. Facial nerve repair with Gore-Tex tube and adipose-derived stem cells: an animal study in dogs. J Oral Maxillofac Surg. Mar. 2013;71(3):577-87. doi: 10.1016/j.joms.2012.05.025. Epub Aug. 4, 2012. PMID: 22868036.https://pubmed.ncbi.nlm.nih.gov/22868036/".
"Grinsell D, Keating CP. Peripheral nerve reconstruction after injury: a review of clinical and experimental therapies. Biomed Res Int. 2014;2014:698256. doi: 10.1155/2014/698256. Epub Sep. 3, 2014. PMID: 25276813; PMCID: PMC4167952.".
"Haastert-Talini K, Geuna S, Dahlin LB, Meyer C, Stenberg L, Freier T, Heimann C, Barwig C, Pinto LF, Raimondo S, Gambarotta G, Samy SR, Sousa N, Salgado AJ, Ratzka A, Wrobel S, Grothe C. Chitosan tubes of varying degrees of acetylation for bridging peripheral nerve defects. Biomaterials. Dec. 2013;34(38):9886-904. doi: 10.1016/j.biomaterials.2013.08.074. Epub Sep. 17, 2013. PMID: 24050875.https://pubmed.ncbi.nlm.nih.gov/24050875/".
"Heidemann SR, Lamoureux P, Buxbaum RE. On the cytomechanics and fluid dynamics of growth cone motility. J Cell Sci Suppl. 1991;15:35-44. doi: 10.1242/jcs.1991.supplement_15.6. PMID: 1824105.".
"Hibner M, Castellanos ME, Drachman D, Balducci J. Repeat operation for treatment of persistent pudendal nerve entrapment after pudendal neurolysis. J Minim Invasive Gynecol. May-Jun. 2012;19(3):325-30. doi: 10.1016/j.jmig.2011.12.022. Epub Feb. 4, 2012. PMID: 22305742.".
"Holland C, Numata K, Rnjak-Kovacina J, Seib FP. The Biomedical Use of Silk: Past, Present, Future. Adv Healthc Mater. Jan. 2019;8(1):e1800465. doi: 10.1002/adhm.201800465. Epub Sep. 20, 2018. PMID: 30238637.".
"Huang, et al., "Regenerative potential of silk conduits in repair of peripheral nerve injury in adult rats" (2012) Biomaterials".
"Hudson TW, Liu SY, Schmidt CE. Engineering an improved acellular nerve graft via optimized chemical processing. Tissue Eng. Sep.-Oct. 2004;10(9-10):1346-58. doi: 10.1089/ten.2004.10.1641. PMID: 15588395".
"Ikeda, et al., "Hyaluronic acid prevents peripheral nerve adhesion" (2003) The British Association of Plastic Surgeons, 56, 342-347".
"Isaacs J, Safa B, Evans PJ, Greenberg J. Technical Assessment of Connector-Assisted Nerve Repair. J Hand Surg Am. Jul. 2016;41(7):760-6. doi: 10.1016/j.jhsa.2016.04.015. Epub May 14, 2016. PMID: 27189149.".
"Jastrzebska, et al., "Silk as an innovative biomaterial for cancer therapy" Reports of Practical Oncology and Radiotherapy 20 (2015) 87-98".
"Jiang H, Qian Y, Fan C, Ouyang Y. Polymeric Guide Conduits for Peripheral Nerve Tissue Engineering. Front Bioeng Biotechnol. Sep. 25, 2020;8:582646. doi: 10.3389/fbioe.2020.582646. PMID: 33102465; PMCID: PMC7546820.".
"Kehoe, et al., "FDA approved guidance conduits and wraps for peripheral nerve injury: a review of materials and efficacy"".
"Kim PD, Hayes A, Amin F, Akelina Y, Hays AP, Rosenwasser MP. Collagen nerve protector in rat sciatic nerve repair: A morphometric

(56) References Cited

OTHER PUBLICATIONS and histological analysis. Microsurgery. Jul. 2010;30(5):392-6. doi: 10.1002/micr.20760. PMID: 20146385.".
"Kitahara AK, Suzuki Y, Qi P, Nishimura Y, Suzuki K, Kiyotani T, Takimoto Y, Nakamura T, Shimizu Y, Endo K. Facial nerve repair using a collagen conduit in cats. Scand J Plast Reconstr Surg Hand Surg. Jun. 1999;33(2):187-93. doi: 10.1080/02844319950159442. PMID: 10450576.".
"Kokkalis ST, Mavrogenis AF, Vottis C, Papatheodorou L, Papagelopoulos PJ, Soucacos PN, Sotereanos DG. Median nerve biodegradable wrapping : Clinical outcome of 10 patients. Acta Orthop Belg. Aug. 2016;82(2):351-357. PMID: 27682299.".
"Kopp, et al., "Production and Characterization of Porous FibroinScaffolds for Regenerative Medical Application" (2019) in vivo 33: 757-762".
"Leckenby JI, Furrer C, Haug L, Juon Personeni B, Vögelin E. A Retrospective Case Series Reporting the Outcomes of Avance Nerve Allografts in the Treatment of Peripheral Nerve Injuries. Plast Reconstr Surg. Feb. 2020;145(2):368e-381e. doi:10.1097/PRS. 0000000000006485.".
"Li, et al., "Regenerative potential of silk conduits in repair of peripheral nerve injury in adult rats" (2002) Int J Biol Macromol 30(2):89-94".
"Lu, et al,. "Silk/agarose scaffolds with tunable properties via SDS assisted rapid gelation" (2017) RSC Adv, 7 p. 1-9".
"Lundborg G, Rosén B, Dahlin L, Holmberg J, Rosén I. Tubular repair of the median or ulnar nerve in the human forearm: a 5-year follow-up. J Hand Surg Br. Apr. 2004;29(2):100-7. doi: 10.1016/j.jhsb.2003.09.018. PMID: 15010152.".
"Mackinnon SE, Dellon AL. Clinical nerve reconstruction with a bioabsorbable polyglycolic acid tube. Plast Reconstr Surg. Mar. 1990;85(3):419-24. doi: 10.1097/00006534-199003000-00015. PMID: 2154831".
"Madduri S, Feldman K, Tervoort T, Papaloïzos M, Gander B. Collagen nerve conduits releasing the neurotrophic factors GDNF and NGF. J Control Release. Apr. 19, 2010;143(2):168-74.".
"Magaz A, Faroni A, Gough JE, Reid AJ, Li X, Blaker JJ. Bioactive Silk-Based Nerve Guidance Conduits for Augmenting Peripheral Nerve Repair. Adv Healthc Mater. Dec. 2018;7(23):e1800308. doi: 10.1002/adhm.201800308. Epub Sep. 10, 2018. PMID: 30260575".
"Mahar M, Cavalli V. Intrinsic mechanisms of neuronal axon regeneration. Nat Rev Neurosci. Jun. 2018;19(6):323-337. doi: 10.1038/s41583-018-0001-8. PMID: 29666508; PMCID: PMC5987780.".
"Matsumoto, et al., "Peripheral nerve regeneration across an 80-mm gap bridged by a polyglycolic acid (PGA)-collagen tube filled with laminin-coated collagen fibers: a histological and electrophysiological evaluation of regenerated nerves" (2000) Brain Research, vol. 868, Issue 2, pp. 315-328".
"Matsuyama T, Midha R, Mackinnon SE, Munro CA, Wong PY, Ang LC. Long nerve allografts in sheep with Cyclosporin A immunosuppression. J Reconstr Microsurg. Apr. 2000;16(3):219-25. doi: 10.1055/s-2000-7556. PMID: 10803627.".
"No Author, "Nerve guidance conduit" https://en.wikipedia.org/wiki/Nerve_guidance_conduit Retrieved online Sep. 23, 2021".
"Song S, Wang X, Wang T, Yu Q, Hou Z, Zhu Z, Li R. Additive Manufacturing of Nerve Guidance Conduits for Regeneration of Injured Peripheral Nerves. Front Bioeng Biotechnol. Sep. 25, 2020;8:590596".

"Panzer KV, Burrell JC, Helm KVT, Purvis EM, Zhang Q, Le AD, O'Donnell JC, Cullen DK. Tissue Engineered Bands of Büngner for Accelerated Motor and Sensory Axonal Outgrowth. Front Bioeng Biotechnol. Nov. 20, 2020;8:580654. doi: 10.3389/fbioe.2020. 580654. PMID: 33330416; PMCID: PMC7714719.".
"Papatheodorou LK, Williams BG, Sotereanos DG. Preliminary results of recurrent cubital tunnel syndrome treated with neurolysis and porcine extracellular matrix nerve wrap. J Hand Surg Am. May 2015;40(5):987-92. doi: 10.1016/j.jhsa.2015.02.031. PMID: 25911210".
"Radtke C, Allmeling C, Waldmann KH, Reimers K, Thies K, Schenk HC, Hillmer A, Guggenheim M, Brandes G, Vogt PM. Spider silk constructs enhance axonal regeneration and remyelination in long nerve defects in sheep. PLoS One. Feb. 25, 2011;6(2):e16990. doi: 10.1371/journal.pone.0016990.".
"Rbia N, Shin AY. The Role of Nerve Graft Substitutes in Motor and Mixed Motor/Sensory Peripheral Nerve Injuries. J Hand Surg Am. May 2017;42(5):367-377. doi: 10.1016/j.jhsa.2017.02.017. PMID: 28473159.".
"Ribeiro, et al., "The role of dialysis and freezing on structural conformation, thermal properties and morphology of silk fibroin hydrogels" (2014) Biomatter, 4, pp. 1-4".
"Rinker B, Vyas KS. Clinical applications of autografts, conduits, and allografts in repair of nerve defects in the hand: current guidelines. Clin Plast Surg. Jul. 2014;41(3):533-50".
"Starritt NE, Kettle SA, Glasby MA. Sutureless repair of the facial nerve using biodegradable glass fabric. Laryngoscope. Aug. 2011;121(8):1614-9.".
"Tyner TR, Parks N, Faria S, Simons M, Stapp B, Curtis B, Sian K, Yamaguchi KT. Effects of collagen nerve guide on neuroma formation and neuropathic pain in a rat model. Am J Surg. Jan. 2007;193(1):".
"Weber RA, Breidenbach WC, Brown RE, Jabaley ME, Mass DP. A randomized prospective study of polyglycolic acid conduits for digital nerve reconstruction in humans. Plast Reconstr Surg. Oct. 2000;106(5):1036-45; discussion 1046-8".
"Xuan, et al., "Freestamdomg Hyaluronic Acid/Silk-based Self-healing Coating towards Tissue Repair with Antibacterial Surface" ACS Publications. Journal contribution. https://doi.org/10.1021/acsabm.9b01196.s001".
"Yi S, Xu L, Gu X. Scaffolds for peripheral nerve repair and reconstruction. Exp Neurol. Sep. 2019;319:112761. doi: 10.1016/j.expneurol.2018.05.016. Epub Jun. 2, 2018.".
"Zhang M, Li C, Zhou LP, Pi W, Zhang PX. Polymer Scaffolds for Biomedical Applications in Peripheral Nerve Reconstruction. Molecules. May 5, 2021;26(9):2712. doi: 10.3390/molecules26092712. PMID: 34063072; PMCID: PMC8124340.".
"Zuniga JR. Sensory outcomes after reconstruction of lingual and inferior alveolar nerve discontinuities using processed nerve allograft—a case series. J Oral Maxillofac Surg. Apr. 2015;73(4):734-44.".
"Allmeling, et al., "Use of spider silk fibres as an innovative material in a biocompatible artificial nerve conduit" Journal of Cellular and Molecular Medicine, University Press Carol Davila, Bucharest, RO, (2006), vol. 10, No. 3, pp. 770-777".
"International Search Report and Written Opinion in PCT/GB2021/051746 dated Dec. 13, 2021".
"Matsumoto, et al., "peripheral nerve regeneration across an 80-mm gap bridged by a polyglycolic acid (PGA)-collagen tube filled with laminin-coated collagen fibers: a histological and electrophysiological evaluation of regenerated nerves", Brain Research, Elsevier (2000) vol. 868, No. 2, pp. 315-328".

\* cited by examiner

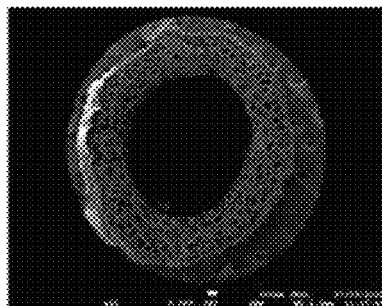 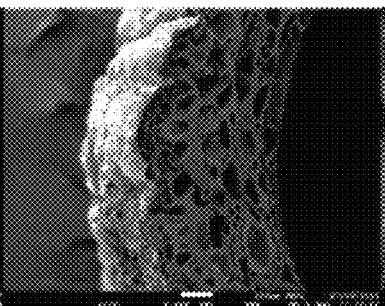 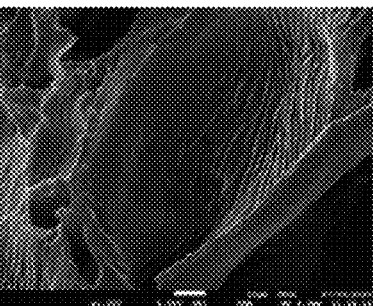
FIG. 6A          FIG. 6B          FIG. 6C
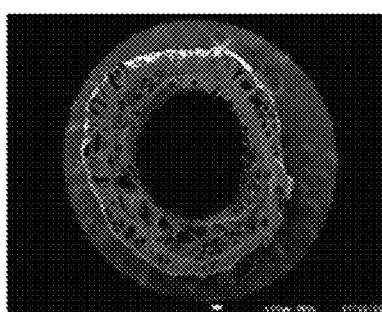 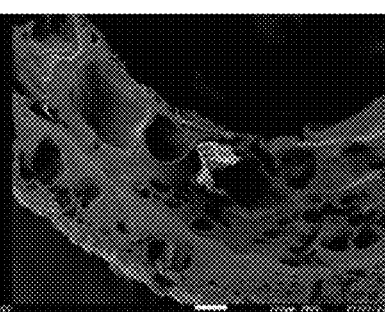 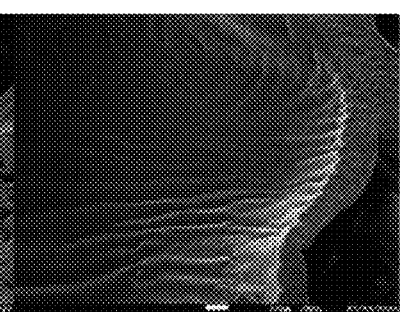
FIG. 6D          FIG. 6E          FIG. 6F
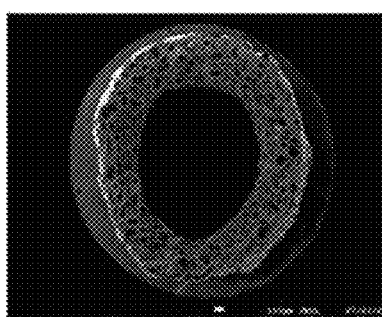 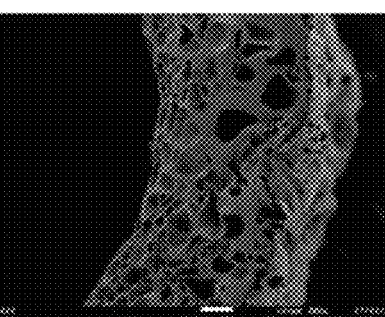 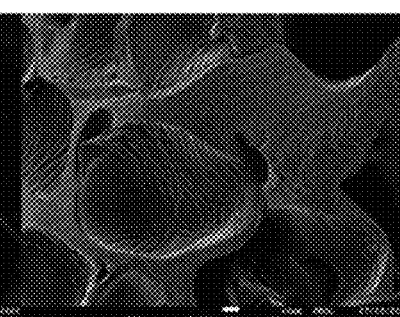
FIG. 6G          FIG. 6H          FIG. 6I

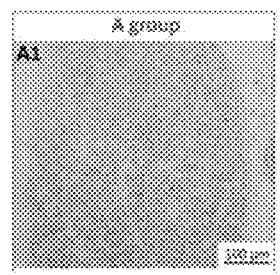
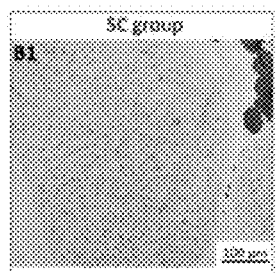
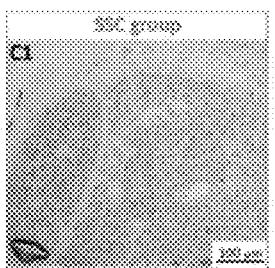
FIG. 26A  FIG. 26D  FIG. 26G
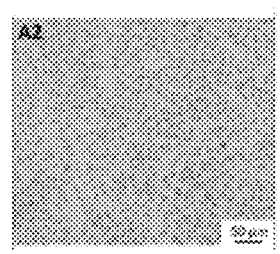
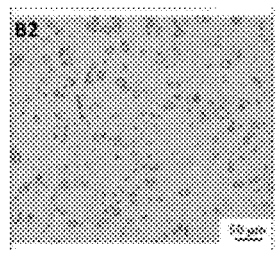
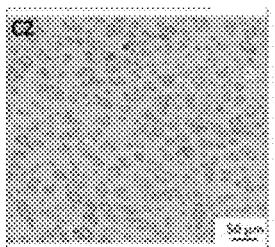
FIG. 26B  FIG. 26E  FIG. 26H
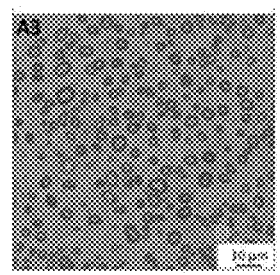
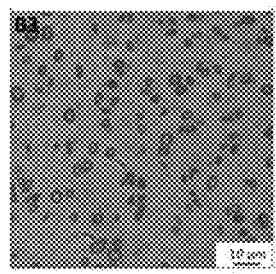
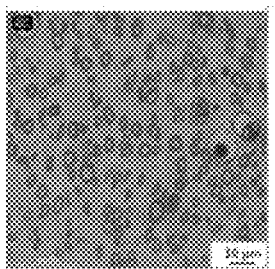
FIG. 26C  FIG. 26F  FIG. 26I

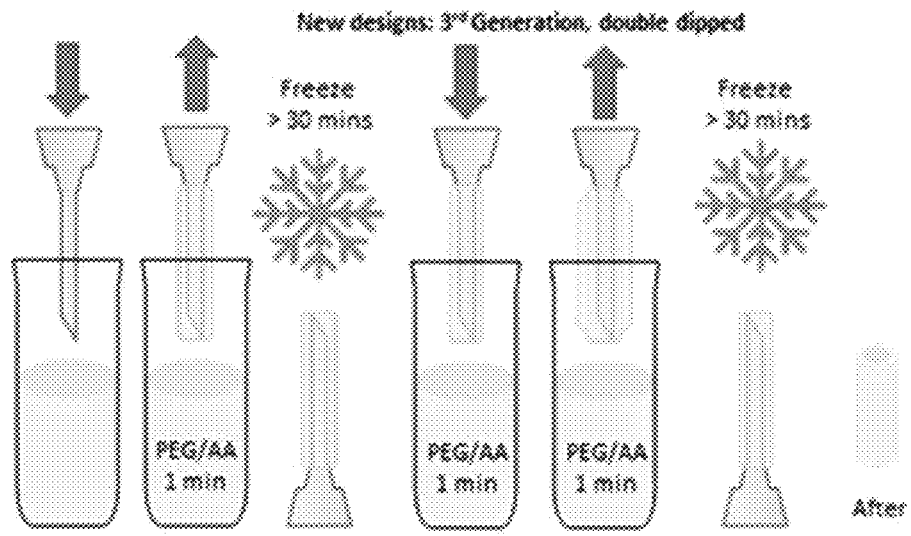

FIG. 53

| Generation | Method | | | | | | |
|---|---|---|---|---|---|---|---|
| 1st | Painted silk, air drying | ☒ | ☒ | ☒ | ☒ | ☒ | Too stiff and brittle |
| 2nd | Single dipped | ☒ | ☒ | ☒ | ☒ | Mostly, larger batches have to be made and the optimal sheaths selected | Similar to previous trials. Floppy making them harder to use |
| | Freeze-gel-freeze | ☒ | ☒ | ☒ | ☒ Reasonable flexibility | Well defined shapes and pores | Good handling |
| | Freeze-gel-freeze dry-gel | ☒ | ☒ | ☒ | ☒ | Well defined shapes and pores | Excellent handling |
| 3rd | Double dipped | ☒ | ☒ | ☒ | ☒ | Mostly | Better than single dip, floppier than gelling methods |

FIG. 54

| Trial | Method | Handling | Comments |
|---|---|---|---|
| 2nd | Single dipped | Similar to previous trials. Floppy making them harder to use | |
| | Freeze-gel-freeze | Good handling | Despite being less easy to use, the double dipped method stents are thin and resemble a refined version of the original sheaths used in previous animal trials |
| | Freeze-gel-freeze dry-gel | Excellent handling | |
| 3rd | Double dipped | Better than single dip, floppier than gelling methods | |

FIG. 55

BRIDGING PERIPHERAL NERVE GAPS WITH CONDUITS FOR ENHANCED NERVE REGENERATION

CROSS-REFERENCE

This application claims priority to PCT application No. PCT/GB2021/051746, filed Jul. 8, 2021, which claims priority to U.S. Provisional Application No. 63/049,289, filed Jul. 8, 2020, and U.S. Provisional Application No. 63/093,866, filed Oct. 20, 2020, which applications are incorporated herein by reference.

SUMMARY OF THE INVENTION

Disclosed herein in some embodiments is a medical device. In some embodiments, a medical device can comprise a container configured to encourage a regrowth of at least a portion of a nerve cell in vivo within a container, wherein a container: (a) can be at least in part flexible, (b) can be configured to at least partially allow an influx of nutrients, an outflow of waste, or both, through openings in a container, (c) can comprise an entrance and an exit, wherein a container can be configured to allow at least a portion of a nerve cell to enter and exit a container through an entrance and an exit, (d) can comprise an interior and an exterior, and (e) can comprise at least partially in an interior an element, wherein an element can comprise a fiber, filament, or combination thereof, spanning at least a portion of a length of a container. In some embodiments, an element can span a majority of a length of a container. In some embodiments, an element can be treated so that it is hydrophilic. In some embodiments, a container can be configured to encourage, guide, orientate, support, or any combination thereof, an in vivo regrowth of an at least a portion of a nerve cell. In some embodiments, at least in part flexible can comprise an ability to bend a container into less than about a 90° angle between a proximal end and a distal end of a container. In some embodiments, at least in part flexible can comprise an ability to bend a container into less than about a 50° angle between a proximal end and a distal end of a container. In some embodiments, after a force that bends a container ceases to be applied, a container can return at least in part to a pre-bend shape. In some embodiments, bending a container can comprise bending without breaking a container, without kinking a container, while maintaining a patency of a container, while maintaining a patency of a lumen of a container, or any combination thereof. In some embodiments, a container can comprise a smooth structure, a pitted structure, a grooved structure, a ridged structure, a channel, or any combination thereof. In some embodiments, a channel can comprise a sloped channel. In some embodiments, an angle of a sloped channel can at least partially guide a nerve cell arrangement, orientate a nerve cell, or any combination thereof. In some embodiments, a container can comprise a protein, a collagen, a gelatin, a silicone, a polymer, a polyester, a hydrophilic material, a polyol, a hybrid composition, an isolated tissue, an isolated tissue product, a decellularized nerve conduit, a carbohydrate, a biomimetic material, a silk, a silk composite, or any combination thereof. In some embodiments, a collagen can comprise a type I collagen, a type II collagen, a type III collagen, a type V collagen, a type X collagen, a salt of any of these, or any combination thereof. In some embodiments, a polyester can comprise a polyglycolide. In some embodiments, a polymer can comprise polyurethane. In some embodiments, a biomimetic material can comprise a laminin. In some embodiments, an isolated tissue, isolated tissue product, or combination thereof can comprise an isolated at least partially decellularized tissue, an isolated at least partially decellularized tissue product, or any combination thereof. In some embodiments, an isolated at least partially decellularized tissue can comprise an isolated at least partially decellularized vasculature. In some embodiments, an isolated at least partially decellularized vasculature can comprise an isolated at least partially decellularized vein. In some embodiments, a silk can comprise a silk protein, a silk fiber, a silk filament, a silk nano-filament, or any combination thereof. In some embodiments, a silk can comprise a silk solid, a silk liquid, or any combination thereof. In some embodiments, a container can comprise a first plurality of silk proteins. In some embodiments, at least one protein in a first plurality of silk proteins can comprise a fibroin, a spidroin, a recombinant silk protein, an analog of any of these, or any combination thereof. In some embodiments, a fibroin can comprise regenerated fibroin. In some embodiments, a spidroin can comprise regenerated spidroin. In some embodiments, a container does not comprise a protein, a collagen, a gelatin, a silicone, a polyester, a polyurethane, a hydrophilic material, a polyol, a hybrid composition, an isolated tissue, an isolated tissue product, a decellularized nerve conduit, a carbohydrate, a biomimetic material, a silk, a silk composite, or any combination thereof. In some embodiments, a container does not comprise a polyester, wherein a polyester can comprise a polyglycolide. In some embodiments, a container does not comprise a polyurethane. In some embodiments, a container does not comprise a biomimetic material, wherein a biomimetic material can comprise a laminin. In some embodiments, a container does not comprise an isolated tissue, isolated tissue product, or combination thereof. In some embodiments, a container does not comprise an isolated tissue, isolated tissue product, or combination thereof, wherein an isolated tissue, isolated tissue product, or any combination thereof can comprise an isolated at least partially decellularized tissue, an isolated at least partially decellularized tissue product, or any combination thereof. In some embodiments, an isolated at least partially decellularized tissue can comprise an isolated at least partially decellularized vasculature. In some embodiments, an isolated at least partially decellularized vasculature can comprise an isolated at least partially decellularized vein. In some embodiments, a container does not comprise a silk, wherein a silk can comprise a silk protein, a silk fiber, a silk filament, a silk nano-filament, or any combination thereof. In some embodiments, a container does not comprise a polyglycolide. In some embodiments, a container does not comprise a collagen. In some embodiments, an element can comprise a second plurality of silk elements. In some embodiments, an element can comprise a protein, a collagen, a gelatin, a silicone, a polyester, a polyurethane, a hydrophilic material, a polyol, a hybrid composition, an isolated tissue, an isolated tissue product, a decellularized nerve conduit, a carbohydrate, a biomimetic material, a silk, a silk composite, or any combination thereof. In some embodiments, a collagen can comprise a type I collagen, a type II collagen, a type III collagen, a type V collagen, a type X collagen, a salt of any of these, or any combination thereof. In some embodiments, a conduit can comprise a conduit for nerve regrowth. In some embodiments, a conduit can comprise a scaffold for nerve regrowth. In some embodiments, a silk element can comprise a fibroin, a spidroin, a recombinant silk protein, an analog of any of these, or any combination thereof. In some embodiments, a fibroin can comprise a regenerated fibroin. In some embodiments, a spidroin can comprise a regenerated spidroin. In some embodiments, a fibroin can comprise *Bombyx mori, Hyalophora cecropia, Gonometra* spp, *Antheraea* spp., or *Samia cynthia* silkworm silk fibroin. In some embodiments, a spidroin can comprise a spider silk spidroin. In some embodiments, a spider silk spidroin can comprise a spider dragline silk, a Major Ampullate silk, a major spider silk, a Minor Ampullate silk, a Cylindriform silk, a pyriform silk, or any combination thereof. In some embodiments, a spider silk spidroin can comprise a spider silk derived from a polypeptide construct. In some embodiments, at least some silk elements in a plurality can be at least partially covered in a hydrophilic substance. In some embodiments, at least some silk elements in a plurality can be treated to make at least some silk elements at least partially hydrophilic. In some embodiments, a hydrophilic substance can comprise a substance which when contacted with water at least partially forms a gel. In some embodiments, a gel can comprise a hydrogel. In some embodiments, a hydrophilic substance can comprise a polysaccharide, a glycosaminoglycan, an alginate, a casein, a protein, a salt of any of these, or any combination thereof. In some embodiments, a polysaccharide or a salt thereof can comprise a carboxylic acid moiety or a salt thereof. In some embodiments, a polysaccharide or a salt thereof can comprise a hydroxyl group. In some embodiments, a polysaccharide or a salt thereof can comprise an amide or a salt thereof. In some embodiments, a polysaccharide or a salt thereof can comprise a hyaluronan (hyaluronic acid) or a salt thereof. In some embodiments, a glycosaminoglycan or a salt thereof can be combined with a laminin mimetic peptide or a salt thereof. In some embodiments, a matrix can comprise a hydrophilic substance in a matrix. In some embodiments, an element can be at least partially held within a matrix. In some embodiments, a matrix can be at least in part pH controlled, crosslinked, or any combination thereof. In some embodiments, a medical device can comprise genipin. In some embodiments, a second plurality of silk elements can comprise from about 1 to about 100,000 silk elements. In some embodiments, a second plurality of silk proteins can comprise about 13,000 silk proteins. In some embodiments, at least one fiber of a plurality of fibers can be at least partially biodegradable. In some embodiments, an element does not comprise a protein, a collagen, a gelatin, a silicone, a polyester, a polyurethane, a hydrophilic material, a polyol, a hybrid composition, an isolated tissue, an isolated tissue product, a decellularized nerve conduit, a carbohydrate, a biomimetic material, a silk, a silk composite, or any combination thereof. In some embodiments, an element does not comprise a polyester, wherein a polyester can comprise a polyglycolide. In some embodiments, an element does not comprise a polyurethane. In some embodiments, an element does not comprise a biomimetic material, wherein a biomimetic material can comprise a laminin. In some embodiments, an element does not comprise an isolated tissue, isolated tissue product, or combination thereof. In some embodiments, an element does not comprise an isolated tissue, isolated tissue product, or combination thereof, wherein an isolated tissue, isolated tissue product, or any combination thereof can comprise an isolated at least partially decellularized tissue, an isolated at least partially decellularized tissue product, or any combination thereof. In some embodiments, an isolated at least partially decellularized tissue can comprise an isolated at least partially decellularized vasculature. In some embodiments, an isolated at least partially decellularized vasculature can comprise an isolated at least partially decellularized vein. In some embodiments, an element does not comprise a silk, wherein a silk can comprise a silk protein, a silk fiber, a silk filament, a silk nano-filament, or any combination thereof. In some embodiments, an element does not comprise a collagen. In some embodiments, an element does not comprise a laminin. In some embodiments, openings comprise a plurality of pores. In some embodiments, at least one pore of a plurality of pores traverses an interior of a container through to an exterior of a container. In some embodiments, at least one of a plurality of pores has a maximum diameter of about 200 μm. In some embodiments, at least one of a plurality of pores has a maximum size that can be small enough to prevent a cell from entering. In some embodiments, pores can be distributed substantially throughout a length of a container. In some embodiments, pores can be substantially uniformly distributed throughout a length of a container. In some embodiments, pores can be substantially non-uniformly distributed throughout a length of a container. In some embodiments, a device can at least partially prevent scar tissue infiltration into an interior of a container. In some embodiments, a container can comprise a proximal end and a distal end. In some embodiments, at least part of a container can comprise an additional constituent. In some embodiments, an additional constituent can be distributed in a gradient from a proximal end to a distal end, and wherein an additional constituent at least partially encourages a growth of an axon. In some embodiments, at least a portion of an additional constituent increases in concentration from a proximal end of a container to a distal end of a container. In some embodiments, at least a portion of an additional constituent decreases in concentration from a proximal end to a distal end. In some embodiments, an additional constituent can comprise a microtubule, an actin filament, a neurofilament, a nestin, or any combination thereof. In some embodiments, a container can comprise a greater concentration of microtubules and actin filaments at a proximal end, and a greater concentration of neurofilaments at a distal end. In some embodiments, an additional constituent can comprise a growth factor, an elastomer, a peptide, a cytokine blocker, a free-radical binder, an anti-inflammatory, a membrane stabilizer, a corticosteroid; a salt of any of these; an isolated cell; or any combination thereof. In some embodiments, a growth factor or a salt thereof can comprise a brain-derived neurotrophic factor, a nerve growth factor, a neurotrophin-3, a neurotrophin-4, a ciliary neurotrophic factor, a glial cell line-derived neurotrophic factor, an artemin, a neurturin, a salt of any of these, or any combination thereof. In some embodiments, an elastomer can comprise a synthetic elastomer, a biological elastomer, or any combination thereof. In some embodiments, an elastomer can be functionalized to control physical properties or biological binding. In some embodiments, a peptide or a salt thereof, wherein a peptide or a salt thereof binds to a growth factor. In some embodiments, a peptide or a salt thereof that binds to a growth factor can comprise a laminin. In some embodiments, a peptide or a salt thereof that binds to a growth factor or a salt thereof can be known to bind to nerve regenerating growth factors. In some embodiments, a peptide that binds to a growth factor, increases a concentration of a growth factor at an injury site. In some embodiments, a cytokine inhibitor can comprise a chemokine inhibitor, a compound that targets a cholinergic anti-inflammatory pathway, a platelet activating factor (PAF) inhibitor, an HMGB1 antibody, a resolvin, a lipoxin, a protectin, a COX-2 inhibitor, a compound targeting a chemokine, a compound targeting a T-reg cell, a prostaglandin, a prostaglandin E2 cyclooxygenase inhibitor, a salt of any of these, or any combination thereof. In some embodiments, a free-radical binder can comprise an enzyme, an antioxidant, a salt of any of these, or any combination thereof. In some embodiments, an anti-inflammatory can comprise an aspirin, an ibuprofen, a naproxen, a celecoxib, a diclofenac, a diflunisal etodolac, a famotidine/ibuprofen, a flurbiprofen, an indomethacin, a ketoprofen, a mefenamic acid, a meloxicam, a nabumetone, an oxaprozin, a piroxicam, a sulindac, a celecoxib, a salt of any of these, or any combination thereof. In some embodiments, a membrane stabilizer can comprise a phosphatidylcholine membrane stabilizer. In some embodiments, a corticosteroid can comprise a glucocorticoid or a mineralocorticoid. In some embodiments, a corticosteroid can comprise a prednisone, a prednisolone, a triamcinolone, an aristospan intralesional, a methylprednisolone, a dexamethasone, a cortisol (hydrocortisone), a cortisone, a dexamethasone, a betamethasone, a triamcinolone, a fludrocortisone acetate, a deoxycorticosterone acetate, a corticosterone, an aldosterone, a deoxycorticosterone, or any combination thereof. In some embodiments, a cell can comprise a Schwann cell, an at least partially multipotent cell, an at least partially pluripotent cell, a cell derived from an at least partially multipotent cell, a cell derived from an at least partially pluripotent cell, or any combination thereof. In some embodiments, an additional constituent can comprise ions. In some embodiments, a container can be in a form of a tube. In some embodiments, a tube can comprise one or more branches. In some embodiments, a container can be in a form of a sheath. In some embodiments, a medical device further can comprise an opening to allow for an at least partial entry of a stem cell, a Schwann cell, an endothelial cell, or any combination thereof. In some embodiments, a container can have a fascicular structure comprising a plurality of hydraulic compartments within an interior. In some embodiments, a plurality of hydraulic compartments within an interior can be configured to at least partially protect a regenerating nerve within a compartment from mechanical injury. In some embodiments, an element can comprise a perineurium layer, an epineurium layer, an endoneurium layer, or any combination thereof. In some embodiments, a container can comprise a glycosaminoglycan-rich gel. In some embodiments, a container can comprise an outer surface that at least partially prevents a container adhering to a subject into which a container can be implanted. In some embodiments, an outer surface at least partially prevents fibrillation of a tissue in contact with a container, integration of a container to a subject, or any combination thereof. Disclosed herein in some embodiments, is a kit comprising a medical device, and a packaging. In some embodiments, a packaging can be sterile. In some embodiments, a kit can comprise instructions. Disclosed herein in some embodiments, is a method comprising implanting a device into a subject, in a space previously at least partially occupied by at least a portion of a nerve cell. In some embodiments, a nerve cell has been severed. In some embodiments, a device can be implanted in proximity to an at least partially severed nerve cell. In some embodiments, a method can comprise a method of at least partially reconnecting a severed nerve cell. In some embodiments, a gap over which a severed nerve cell can be reconnected can be greater than about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, or about 20 cm. In some embodiments, a gap over which a severed nerve cell can be reconnected can be from about 6 cm to about 20 cm. In some embodiments, a medical device can be at least partially placed in an electromagnetic field after an implanting in a subject. In some embodiments, a method can at least partially restore a function of a limb of a subject. In some embodiments, at least partial restoration of function of a limb can comprise an at least partially improved ability to extend a limb, an at least partially improved control of a limb, an at least partial increase in sensation in a limb, or any combination thereof. In some embodiments, a medical device can comprise an isolated at least partially decellularized vein that can be xenogeneic to a subject. In some embodiments, a medical device can comprise an isolated at least partially decellularized vein that can be autologous to a subject. In some embodiments, a nerve cell body that can be targeted for at least partial in vivo axonal regrowth, can be positioned closest to a proximal end of a container.

Disclosed herein in some embodiments is a method comprising contacting an at least partially frozen solution comprising silk with a porogen. In some embodiments, a porogen can comprise a polyether, an acid, a salt, a natural polymer, a synthetic polymer, any salt thereof, or any combination thereof. In some embodiments, an acid can comprise an acetic acid. In some embodiments, a polyether can comprise a polyethyleneglycol (PEG) or a salt thereof. In some embodiments, a polyethyleneglycol can comprise a polyethyleneglycol cisphenol A epichlorohydrin copolymer or a salt thereof. In some embodiments, a salt can comprise sodium chloride, sodium bicarbonate, potassium dichromate, calcium chloride, sodium bisulfate, copper sulfate, or any combination thereof. In some embodiments, a natural polymer can comprise a saccharide, a polysaccharide, any salt thereof, or any combination thereof. In some embodiments, a synthetic polymer can comprise a polypropylene or a salt thereof. In some embodiments, a method can further comprise freeze drying an at least partially frozen solution. In some embodiments, a method can further comprise crystallizing an at least partially frozen solution. In some embodiments, a freezing can occur during a semi-continuous flow manufacturing process. In some embodiments, a semi-continuous flow manufacturing process can comprise an extrusion process. In some embodiments, a freezing can occur at least partially in an extrusion die. In some embodiments, a method further can comprise drawing a silk through a second extrusion die. In some embodiments, drawing a silk through a second extrusion die can at least partially remove excess hydrogel. In some embodiments, a silk can be at least partially air-dried. In some embodiments, a method can further comprise drawing a silk through a third extrusion die. In some embodiments, drawing a silk through a third extrusion die at least partially adds a coating of concentrated viscous collagen or concentrated regenerated silk protein or any combination thereof. In some embodiments, a method can further comprise contacting a silk with an acid. In some embodiments, a contacting can at least partially gel a fibroin, a collagen, or any combination thereof. In some embodiments, an extrusion die can comprise an annular extrusion die. Disclosed herein in some embodiments is a composition produced by a method as disclosed herein. Disclosed herein is a method comprising implanting a composition as disclosed herein into a subject. In some embodiments, a composition can be implanted in a space previously at least partially occupied by a nerve cell. In some embodiments, a nerve cell has been severed. In some embodiments, a device can be implanted in proximity to an at least partially severed nerve cell. In some embodiments, a method can comprise a method of at least partially reconnecting a severed nerve cell. In some embodiments, a severed nerve cell at least partially regenerates while at least partially in contact with a composition. In some embodiments, a silk element can be at least partially degraded by a nerve cell. In some embodiments, a gap over which a severed nerve cell can be reconnected can be greater than about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, or about 20 cm. In some embodiments, a gap over which a severed nerve cell can be reconnected can be from about 6 cm to about 20 cm. In some embodiments, a composition can be at least partially placed in an electromagnetic field after an implanting in a subject. In some embodiments, a method at least partially restores a function of a limb of a subject. In some embodiments, at least partial restoration of function of a limb can comprise an at least partially improved ability to extend a limb, an at least partially improved control of a limb, an at least partial increase in sensation in a limb, or any combination thereof. In some embodiments, a composition further can comprise an isolated at least partially decellularized vein that can be xenogeneic to a subject. In some embodiments, a composition further can comprise an isolated at least partially decellularized vein that can be autologous to a subject. In some embodiments, a nerve cell body that can be targeted for at least partial in vivo axonal regrowth, can be positioned closest to a proximal end of a container.

Disclosed herein in some embodiments, is a composition comprising (a) an at least partially frozen solution comprising a silk protein, and (b) a polyether, a carboxylic acid, a salt of any of these, or any combination thereof. In some embodiments, a polyether can comprise a polyethyleneglycol (PEG), or a salt thereof. In some embodiments, a polyethyleneglycol can comprise a polyethyleneglycol cisphenol A epichlorohydrin copolymer, or a salt thereof. In some embodiments, a carboxylic acid or a salt thereof can comprise an acetic acid or a salt thereof. Disclosed herein in some embodiments is a composition produced by a method as disclosed herein. Disclosed herein is a method comprising implanting a composition as disclosed herein into a subject. In some embodiments, a composition can be implanted in a space previously at least partially occupied by a nerve cell. In some embodiments, a nerve cell has been severed. In some embodiments, a device can be implanted in proximity to an at least partially severed nerve cell. In some embodiments, a method can comprise a method of at least partially reconnecting a severed nerve cell. In some embodiments, a severed nerve cell at least partially regenerates while at least partially in contact with a composition. In some embodiments, a silk element can be at least partially degraded by a nerve cell. In some embodiments, a gap over which a severed nerve cell can be reconnected can be greater than about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, or about 20 cm. In some embodiments, a gap over which a severed nerve cell can be reconnected can be from about 6 cm to about 20 cm. In some embodiments, a composition can be at least partially placed in an electromagnetic field after an implanting in a subject. In some embodiments, a method at least partially restores a function of a limb of a subject. In some embodiments, at least partial restoration of function of a limb can comprise an at least partially improved ability to extend a limb, an at least partially improved control of a limb, an at least partial increase in sensation in a limb, or any combination thereof. In some embodiments, a composition further can comprise an isolated at least partially decellularized vein that can be xenogeneic to a subject. In some embodiments, a composition further can comprise an isolated at least partially decellularized vein that can be autologous to a subject. In some embodiments, a nerve cell body that can be targeted for at least partial in vivo axonal regrowth, can be positioned closest to a proximal end of a container.

Disclosed herein in some embodiments, is a method comprising at least partially freezing a solution comprising a silk protein in a tubular shape using a mold: a method comprising: (a) at least partially freezing a solution one or more times to form an at least partially frozen solution, and (b) contacting an at least partially frozen solution with a gelling agent, wherein at least one of (a) or (b) occurs at least partially in a mold, wherein a mold can comprise a solid inner component, a solid outer component, and a space in between a solid inner component and a solid outer component. In some embodiments, a solid inner component can comprise a substantially cylindrical or helical shape. In some embodiments, a solid outer component can comprise a substantially cylindrical shape. In some embodiments, a mold further can comprise an extrusion die mold, an extruder, a screw, a heater, a freezer, a die, an orifice, or any combination thereof. In some embodiments, a solution can comprise fibroin, spidroin, or any combination thereof. In some embodiments, a tubular body can comprise a cross-sectional diameter of about 0.1 mm to about 20 mm. In some embodiments, a tubular shape can comprise an external cross-sectional diameter of about 1 mm to about 25 mm. In some embodiments, a tubular shape can comprise an external cross-sectional diameter of about 25 mm to about 50 mm. In some embodiments, a tubular shape can comprise an external cross-sectional diameter of about 50 mm to about 100 mm. In some embodiments, a tubular shape can comprise a length of from about 0.1 cm to about 1 cm. In some embodiments, a tubular shape can comprise a length of from about 0.5 cm to about 10 cm. In some embodiments, a tubular shape can comprise a length of from about 5 cm to about 50 cm. In some embodiments, a tubular shape can comprise a length of from about 10 cm to about 120 cm. Disclosed herein in some embodiments is a composition produced by a method as disclosed herein. Disclosed herein is a method comprising implanting a composition as disclosed herein into a subject. In some embodiments, a composition can be implanted in a space previously at least partially occupied by a nerve cell. In some embodiments, a nerve cell has been severed. In some embodiments, a device can be implanted in proximity to an at least partially severed nerve cell. In some embodiments, a method can comprise a method of at least partially reconnecting a severed nerve cell. In some embodiments, a severed nerve cell at least partially regenerates while at least partially in contact with a composition. In some embodiments, a silk element can be at least partially degraded by a nerve cell. In some embodiments, a gap over which a severed nerve cell can be reconnected can be greater than about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, or about 20 cm. In some embodiments, a gap over which a severed nerve cell can be reconnected can be from about 6 cm to about 20 cm. In some embodiments, a composition can be at least partially placed in an electromagnetic field after an implanting in a subject. In some embodiments, a method at least partially restores a function of a limb of a subject. In some embodiments, at least partial restoration of function of a limb can comprise an at least partially improved ability to extend a limb, an at least partially improved control of a limb, an at least partial increase in sensation in a limb, or any combination thereof. In some embodiments, a composition further can comprise an isolated at least partially decellularized vein that can be xenogeneic to a subject. In some embodiments, a composition further can comprise an isolated at least partially decellularized vein that can be autologous to a subject. In some embodiments, a nerve cell body that can be targeted for at least partial in vivo axonal regrowth, can be positioned closest to a proximal end of a container.

Disclosed herein in some embodiments, is a composition comprising a tubular body and a plurality of silk proteins within a tubular body, wherein: (a) at least one individual silk protein can be at least partially coated with a first hydrophilic coating, and (b) wherein a plurality can be at least partially coated with a second hydrophilic coating. In some embodiments, a tubular body can comprise a cross-sectional diameter of about 0.1 mm to about 20 mm. In some embodiments, a tubular shape can comprise an external cross-sectional diameter of about 1 mm to about 25 mm. In some embodiments, a tubular shape can comprise an external cross-sectional diameter of about 25 mm to about 50 mm. In some embodiments, a tubular shape can comprise an external cross-sectional diameter of about 50 mm to about 100 mm. In some embodiments, a tubular shape can comprise a length of from about 0.1 cm to about 1 cm. In some embodiments, a tubular shape can comprise a length of from about 0.5 cm to about 10 cm. In some embodiments, a tubular shape can comprise a length of from about 5 cm to about 50 cm. In some embodiments, a tubular shape can comprise a length of from about 10 cm to about 120 cm. Disclosed herein in some embodiments is a composition produced by a method as disclosed herein. Disclosed herein is a method comprising implanting a composition as disclosed herein into a subject. In some embodiments, a composition can be implanted in a space previously at least partially occupied by a nerve cell. In some embodiments, a nerve cell has been severed. In some embodiments, a device can be implanted in proximity to an at least partially severed nerve cell. In some embodiments, a method can comprise a method of at least partially reconnecting a severed nerve cell. In some embodiments, a severed nerve cell at least partially regenerates while at least partially in contact with a composition. In some embodiments, a silk element can be at least partially degraded by a nerve cell. In some embodiments, a gap over which a severed nerve cell can be reconnected can be greater than about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, or about 20 cm. In some embodiments, a gap over which a severed nerve cell can be reconnected can be from about 6 cm to about 20 cm. In some embodiments, a composition can be at least partially placed in an electromagnetic field after an implanting in a subject. In some embodiments, a method at least partially restores a function of a limb of a subject. In some embodiments, at least partial restoration of function of a limb can comprise an at least partially improved ability to extend a limb, an at least partially improved control of a limb, an at least partial increase in sensation in a limb, or any combination thereof. In some embodiments, a composition further can comprise an isolated at least partially decellularized vein that can be xenogeneic to a subject. In some embodiments, a composition further can comprise an isolated at least partially decellularized vein that can be autologous to a subject. In some embodiments, a nerve cell body that can be targeted for at least partial in vivo axonal regrowth, can be positioned closest to a proximal end of a container.

Disclosed herein in some embodiments, is a composition comprising a plurality of silk elements running substantially parallel to each other, wherein a plurality of silk elements can be at least partially continually spaced from one another along their length, wherein a plurality of silk elements can be coated substantially along a length of an element with a hydrophilic substance that at least partly maintains continual spacing of a plurality of elements. In some embodiments, an element can comprise a fiber, a filament, a nano-filament, or any combination thereof. Disclosed herein in some embodiments is a composition produced by a method as disclosed herein. Disclosed herein is a method comprising implanting a composition as disclosed herein into a subject. In some embodiments, a composition can be implanted in a space previously at least partially occupied by a nerve cell. In some embodiments, a nerve cell has been severed. In some embodiments, a device can be implanted in proximity to an at least partially severed nerve cell. In some embodiments, a method can comprise a method of at least partially reconnecting a severed nerve cell. In some embodiments, a severed nerve cell at least partially regenerates while at least partially in contact with a composition. In some embodiments, a silk element can be at least partially degraded by a nerve cell. In some embodiments, a gap over which a severed nerve cell can be reconnected can be greater than about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, or about 20 cm. In some embodiments, a gap over which a severed nerve cell can be reconnected can be from about 6 cm to about 20 cm. In some embodiments, a composition can be at least partially placed in an electromagnetic field after an implanting in a subject. In some embodiments, a method at least partially restores a function of a limb of a subject. In some embodiments, at least partial restoration of function of a limb can comprise an at least partially improved ability to extend a limb, an at least partially improved control of a limb, an at least partial increase in sensation in a limb, or any combination thereof. In some embodiments, a composition further can comprise an isolated at least partially decellularized vein that can be xenogeneic to a subject. In some embodiments, a composition further can comprise an isolated at least partially decellularized vein that can be autologous to a subject. In some embodiments, a nerve cell body that can be targeted for at least partial in vivo axonal regrowth, can be positioned closest to a proximal end of a container.

Disclosed herein in some embodiments, is a composition comprising a group of silk proteins running substantially parallel to one another, wherein a group can comprise at least two subgroups of silk proteins, wherein a group can comprise a hydrophilic coating around at least part of a group, and at least one subgroup can comprise a hydrophilic coating around at least part of a subgroup. In some embodiments, a subgroup can comprise a further secondary subgroup, wherein a secondary subgroup can comprise a hydrophilic coating around at least part of a secondary subgroup. In some embodiments, a secondary subgroup can comprise a further tertiary subgroup, wherein a tertiary subgroup can comprise a hydrophilic coating around at least part of a tertiary subgroup. Disclosed herein in some embodiments is a composition produced by a method as disclosed herein. Disclosed herein is a method comprising implanting a composition as disclosed herein into a subject. In some embodiments, a composition can be implanted in a space previously at least partially occupied by a nerve cell. In some embodiments, a nerve cell has been severed. In some embodiments, a device can be implanted in proximity to an at least partially severed nerve cell. In some embodiments, a method can comprise a method of at least partially reconnecting a severed nerve cell. In some embodiments, a severed nerve cell at least partially regenerates while at least partially in contact with a composition. In some embodiments, a silk element can be at least partially degraded by a nerve cell. In some embodiments, a gap over which a severed nerve cell can be reconnected can be greater than about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, or about 20 cm. In some embodiments, a gap over which a severed nerve cell can be reconnected can be from about 6 cm to about 20 cm. In some embodiments, a composition can be at least partially placed in an electromagnetic field after an implanting in a subject. In some embodiments, a method at least partially restores a function of a limb of a subject. In some embodiments, at least partial restoration of function of a limb can comprise an at least partially improved ability to extend a limb, an at least partially improved control of a limb, an at least partial increase in sensation in a limb, or any combination thereof. In some embodiments, a composition further can comprise an isolated at least partially decellularized vein that can be xenogeneic to a subject. In some embodiments, a composition further can comprise an isolated at least partially decellularized vein that can be autologous to a subject. In some embodiments, a nerve cell body that can be targeted for at least partial in vivo axonal regrowth, can be positioned closest to a proximal end of a container.

Disclosed herein in some embodiments, is a method comprising: (a) submerging each of a plurality of silk proteins in a hydrophilic substance individually, and (b) submerging a plurality of silk proteins in a hydrophilic substance while one or more fibers are substantially in contact with each other. In some embodiments, a hydrophilic substance can be dried on an individual fiber prior to submerging a plurality of silk proteins in a hydrophilic substance while one or more fibers are substantially in contact with each other. Disclosed herein in some embodiments is a composition produced by a method as disclosed herein. Disclosed herein is a method comprising implanting a composition as disclosed herein into a subject. In some embodiments, a composition can be implanted in a space previously at least partially occupied by a nerve cell. In some embodiments, a nerve cell has been severed. In some embodiments, a device can be implanted in proximity to an at least partially severed nerve cell. In some embodiments, a method can comprise a method of at least partially reconnecting a severed nerve cell. In some embodiments, a severed nerve cell at least partially regenerates while at least partially in contact with a composition. In some embodiments, a silk element can be at least partially degraded by a nerve cell. In some embodiments, a gap over which a severed nerve cell can be reconnected can be greater than about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, or about 20 cm. In some embodiments, a gap over which a severed nerve cell can be reconnected can be from about 6 cm to about 20 cm. In some embodiments, a composition can be at least partially placed in an electromagnetic field after an implanting in a subject. In some embodiments, a method at least partially restores a function of a limb of a subject. In some embodiments, at least partial restoration of function of a limb can comprise an at least partially improved ability to extend a limb, an at least partially improved control of a limb, an at least partial increase in sensation in a limb, or any combination thereof. In some embodiments, a composition further can comprise an isolated at least partially decellularized vein that can be xenogeneic to a subject. In some embodiments, a composition further can comprise an isolated at least partially decellularized vein that can be autologous to a subject. In some embodiments, a nerve cell body that can be targeted for at least partial in vivo axonal regrowth, can be positioned closest to a proximal end of a container.

Disclosed herein in some embodiments, is a method comprising at least partially coating a bundle comprising a plurality of silk proteins with a hydrophilic coating, wherein each individual silk protein in a bundle can comprise a hydrophilic coating at least partially around an individual silk protein. Disclosed herein in some embodiments is a composition produced by a method as disclosed herein. Disclosed herein is a method comprising implanting a composition as disclosed herein into a subject. In some embodiments, a composition can be implanted in a space previously at least partially occupied by a nerve cell. In some embodiments, a nerve cell has been severed. In some embodiments, a device can be implanted in proximity to an at least partially severed nerve cell. In some embodiments, a method can comprise a method of at least partially reconnecting a severed nerve cell. In some embodiments, a severed nerve cell at least partially regenerates while at least partially in contact with a composition. In some embodiments, a silk element can be at least partially degraded by a nerve cell. In some embodiments, a gap over which a severed nerve cell can be reconnected can be greater than about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, or about 20 cm. In some embodiments, a gap over which a severed nerve cell can be reconnected can be from about 6 cm to about 20 cm. In some embodiments, a composition can be at least partially placed in an electromagnetic field after an implanting in a subject. In some embodiments, a method at least partially restores a function of a limb of a subject. In some embodiments, at least partial restoration of function of a limb can comprise an at least partially improved ability to extend a limb, an at least partially improved control of a limb, an at least partial increase in sensation in a limb, or any combination thereof. In some embodiments, a composition further can comprise an isolated at least partially decellularized vein that can be xenogeneic to a subject. In some embodiments, a composition further can comprise an isolated at least partially decellularized vein that can be autologous to a subject. In some embodiments, a nerve cell body that can be targeted for at least partial in vivo axonal regrowth, can be positioned closest to a proximal end of a container.

Disclosed herein in some embodiments, is a composition comprising a tube comprising silk proteins with a proximal end and a distal end, wherein at least part of a tube can comprise an additional constituent, wherein an additional constituent can be distributed in a gradient from a proximal end to a distal end, and wherein an additional constituent encourages a growth of an axon. In some embodiments, a gradient can comprise a chemotactic gradient, a diffusible gradient, an adherent gradient, or any combination thereof. In some embodiments, an additional constituent can increase in concentration from a proximal end to a distal end. In some embodiments, an additional constituent decreases in concentration from a proximal end to a distal end. In some embodiments, an additional constituent can comprise microtubules, actin filaments, neurofilaments, nestin, or any combination thereof. In some embodiments, a tube can comprise a greater concentration of microtubules and actin filaments at a proximal end, and a greater concentration of neurofilaments at a distal end. In some embodiments, an additional constituent can comprise a growth factor, a hormone, a peptide, a small molecule, a drug, a genetic vector, or any combination thereof. Disclosed herein is a method comprising implanting a composition as disclosed herein into a subject. In some embodiments, a composition can be implanted in a space previously at least partially occupied by a nerve cell. In some embodiments, a nerve cell has been severed. In some embodiments, a device can be implanted in proximity to an at least partially severed nerve cell. In some embodiments, a method can comprise a method of at least partially reconnecting a severed nerve cell. In some embodiments, a severed nerve cell at least partially regenerates while at least partially in contact with a composition. In some embodiments, a silk element can be at least partially degraded by a nerve cell. In some embodiments, a gap over which a severed nerve cell can be reconnected can be greater than about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, or about 20 cm. In some embodiments, a gap over which a severed nerve cell can be reconnected can be from about 6 cm to about 20 cm. In some embodiments, a composition can be at least partially placed in an electromagnetic field after an implanting in a subject. In some embodiments, a method at least partially restores a function of a limb of a subject. In some embodiments, at least partial restoration of function of a limb can comprise an at least partially improved ability to extend a limb, an at least partially improved control of a limb, an at least partial increase in sensation in a limb, or any combination thereof. In some embodiments, a composition further can comprise an isolated at least partially decellularized vein that can be xenogeneic to a subject. In some embodiments, a composition further can comprise an isolated at least partially decellularized vein that can be autologous to a subject. In some embodiments, a nerve cell body that can be targeted for at least partial in vivo axonal regrowth, can be positioned closest to a proximal end of a container.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A, FIG. 1B, and FIG. 1C show a single coated fiber. FIG. 1D, FIG. 1E, and FIG. 1F show primer bundles of three. FIG. 1G, FIG. 1H, and FIG. 1I show dimer bundles of nine (three bundles of three silk elements). FIG. 1J, FIG. 1K, and FIG. 1L show trimer bundles of 48, (3 bundles of 4 bundles of 4 silk elements).

FIG. 2 shows bundles of silk elements created through HA coatings, each individually coated before being bundled together and held in place with new coatings.

FIG. 6 shows SEM imaging of sheaths produced with both gelling and pore defining agents, producing pores tubes, with excess time in gelling solution resulting in less defined sheath production. Sheath gelling was performed using 2.25% PEG and 2.5% acetic acid for 15 minutes (FIG. 6A, FIG. 6B, and FIG. 6C), 30 minutes (FIG. 6D, FIG. 6E, and FIG. 6F), and 60 minutes (FIG. 6G, FIG. 6H, and FIG. 6I).

FIG. 8 shows a flexible nerve conduit produced using a new gelling method, employing a gelling solution containing both a gelling and pore defining agent, to a molded frozen silk solution before crystallizing using aqueous ethanol.

FIG. 13 shows immunofluorescent imaging of a nerve regenerating into an outer wall of a conduit (mid-conduit).

FIG. 17A shows Hematoxylin and Eosin staining (HE staining). FIG. 17B shows Masson Goldner Trichrome staining.

FIG. 21 shows scanning electron microscopy analysis of a silk-in-silk conduit.

FIG. 22 shows a comparison of SFI values between all groups until week 14 post-surgery.

FIG. 23 shows immunostainings of longitudinal sections of the central part, of all groups after 14 weeks of regeneration. FIG. 23 depicts representative immunofluorescence images of the central part of the A group (FIG. 23A, FIG. 23B, FIG. 23C, and FIG. 23D), SC group (FIG. 23E, FIG. 23F, FIG. 23G, and FIG. 23H), and SSC group (FIG. 23I, FIG. 23J, FIG. 23K, and FIG. 23L).

FIG. 24 B, FIG. 24 F, and FIG. 24 J show staining for S100 positive Schwann cells. FIG. 24 C, FIG. 24 G, and FIG. 24 K show staining for neurofilament 200 (NF200) positive axons. FIG. 24 D, FIG. 24 H, and FIG. 24 L show staining for DAPI. FIG. 24 A, FIG. 24 E, and FIG. 24 I show merged images. The white dotted line indicates the silk conduit.

FIG. 25 depicts representative immunofluorescence images of the distal part of the A group (FIG. 25A, FIG. 25B, FIG. 25C, and FIG. 25D), SC group (FIG. 25E, FIG. 25F, FIG. 25G, and FIG. 25H), and SSC group (FIG. 25I, FIG. 25J, FIG. 25K, and FIG. 25L).

FIG. 26 depicts histomorphometric evaluation of distal nerve segments after 14 weeks of regeneration. Representative images and magnifications of osmium tetroxide stained myelin sheets on distal nerve cross sections of the A group (FIG. 26A, FIG. 26B, and FIG. 26C, n=5), SC group (FIG. 26D, FIG. 26E, and FIG. 26F, n=3), and SSC group (FIG. 26G, FIG. 26H, and FIG. 26I, n=5) used for semi-automated image analysis.

FIG. 27 depicts bar diagrams of the results of the semi-automated image analysis of FIG. 26 for the A group in grey, the SC group in blue, and the SSC group in orange.

FIG. 53 depicts the methods by which sheaths were produced by double dipping. Sheaths were dipped in silk fibroin solution, dipped in PEG/AA for 1 minute, frozen for more than 30 minutes, dipped in PEG/AA for 1 minute, dipped in PEG/AA for 1 minute, and frozen again for more than 30 minutes.

FIG. 54 depicts a comparison of the different methods disclosed herein and the resulting determination of porosity, toughness, strength, flexibility, uniformness, and surgeon handling for the sheaths produced.

FIG. 55 depicts a comparison of the different methods produced. The single dipped sheaths were floppy, making them harder to use. The freeze-gel-freeze produced sheaths had good handling. The freeze-gel-freeze-dry-gel produced sheaths had excellent handling. The double dipped sheaths were better than the single dipped sheaths, and were floppier than the gelling methods.

DETAILED DESCRIPTION OF THE INVENTION

Figure 1A:
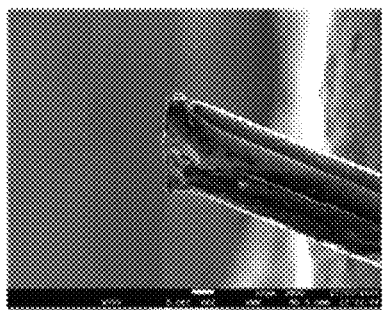
FIGS. 1A-L show bundles of silk elements created on a large scale to compare mechanical properties with respect to bundle diameter and number of silk elements in each bundle.

In some embodiments, disclosed herein are compositions comprising a device. In some embodiments, a device can comprise a silk element, a lumen, a matrix, a hydrophilic coating, an opening for a nerve, or any combination thereof. In some embodiments, a device can enhance a healing of peripheral nerves, central nervous tissue, or any combination thereof. In some embodiments, disclosed herein are methods for manufacturing a device, construction of a device, use of a device, or any combination thereof.

Definitions

Unless defined otherwise, all technical and scientific terms used herein have the same meaning as is commonly understood by one of ordinary skill in the art.

The terminology used herein is for the purpose of describing particular embodiments only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof as used herein mean "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, or within 2-fold, of a value. Where particular values are described in the application and claims, unless otherwise stated, the term "about" meaning within an acceptable error range for the particular value should be assumed.

As used herein, a "cell" can generally refer to a biological cell. A cell can be the basic structural, functional and/or biological unit of a living organism. A cell can originate from any organism having one or more cells. Some non-limiting examples include: a prokaryotic cell, eukaryotic cell, a bacterial cell, an archaeal cell, a cell of a single-cell eukaryotic organism, a protozoa cell, a cell from a plant, an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), and etcetera. Sometimes a cell may not originate from a natural organism (e.g. a cell can be synthetically made, sometimes termed an artificial cell). Of particular interest are mammalian cells, from e.g., mammals including test animals and humans.

The term "nerve" or "nerve cell" as used herein can refer to a nerve cell, a nerve cluster, a nerve cord, a neuron, an axon, a portion of any of these, a plurality of any of these, or any combination thereof.

The term "substantially" as used herein may refer to a value approaching 100% of a given value. In some embodiments, the term may refer to an amount that may be at least about 90%, 91%, 92%, 93%, 94%, 95%, 96%, 97%, 98%, 99%, 99.9%, or 99.99% of a total amount. In some embodiments, the term may refer to an amount that may be about 100% of a total amount.

The term "decellularized" or "decellularization" as used herein may refer to a biostructure (e.g., an isolated tissue, isolated tissue product, or combination thereof), from which a cellular and tissue content has been removed leaving behind an intact or substantially intact acellular infra-structure. Organs such as veins and vasculature can be composed of various specialized tissues. Specialized tissue structures of an organ, or parenchyma, can provide specific function associated with an organ. Supporting a fibrous network of an isolated organ can be a stroma. Most organs have a stromal framework composed of unspecialized connecting tissue which supports the specialized tissue. The process of decellularization may at least partially remove a cellular portion of a tissue, leaving behind a complex three-dimensional network of extracellular matrix (ECM). An ECM infrastructure can primarily be composed of collagen but can include cytokines, proteoglycans, laminin, fibrillin, endosomes, extracellular bound vesicles, and other proteins secreted by cells. Decellularized biostructures may be rigid, semi-rigid, or flexible, having an ability to alter their shapes.

The term "effective amount" or "therapeutically effective amount" can refer to a quantity of a composition, for example a composition comprising isolated cells such as Schwann cells, that can be sufficient to result in a desired activity upon introduction into subject disclosed herein.

The term "function" and its grammatical equivalents as used herein may refer to a capability of operating, having, or serving an intended purpose. Functional may comprise any percent from baseline to 100% of an intended purpose. For example, functional may comprise or comprise about 5%, 10%, 15%, 20%, 25%, 30%, 35%, 40%, 45%, 50%, 55%, 60%, 65%, 70%, 75%, 80%, 85%, 90%, 95%, or up to about 100% of an intended purpose. In some embodiments, the term functional may mean over or over about 100% of normal function, for example, 125%, 150%, 175%, 200%, 250%, 300%, 400%, 500%, 600%, 700% or up to about 1000% of an intended purpose.

The term "subject" and its grammatical equivalents as used herein may refer to a human or non-human animal. A subject may be a mammal. A subject may be a human mammal of a male or female biological gender. A subject may be of any age. A subject may be an embryo. A subject may be a newborn or up to about 100 years of age. A subject may be in need thereof. A subject may have a disease such as cancer. A subject may be premenopausal, menopausal, or have induced menopause. A subject can also be in need thereof, such as needing treatment for a disease such as a nerve injury. In some embodiments, a subject can be in need thereof of a preventative therapy. A subject may not be in need thereof in other cases.

The terms "treatment" or "treating" and their grammatical equivalents may refer to the medical management of a subject with an intent to cure, ameliorate, stabilize, or prevent a disease, condition, or disorder. Treatment may include active treatment, that is, treatment directed specifically toward the improvement of a disease, condition, or disorder. Treatment may include causal treatment, that is, treatment directed toward removal of the cause of the associated disease, condition, or disorder. In addition, this treatment may include palliative treatment, that is, treatment designed for the relief of symptoms rather than the curing of the disease, condition, or disorder. Treatment may include preventative treatment, that is, treatment directed to minimizing or partially or completely inhibiting the development of a disease, condition, or disorder. Treatment may include supportive treatment, that is, treatment employed to supplement another specific therapy directed toward the improvement of the disease, condition, or disorder. In some embodiments, a condition may be pathological. In some embodiments, a treatment may not completely cure, ameliorate, stabilize or prevent a disease, condition, or disorder.

Disclosed herein in some embodiments, are compositions comprising a medical device. In some embodiments, a medical device can comprise a container. Disclosed herein in some embodiments, are compositions comprising a container. In some embodiments, a container can be configured to allow at least a portion of a nerve cell to enter and exit a container. In some embodiments, a container can be configured to encourage regrowth of at least a portion of a nerve cell in vivo within a container. In some embodiments, a container can comprise a form of a tube. In some embodiments, a tube can comprise one or more branches. In some embodiments, a container can comprise a form of a sheath. In some embodiments, a sheath can comprise a form of a tube, a spiral, or a combination thereof. In some embodiments, a tube can comprise a folded ribbon. In some embodiments, a folded ribbon can be folded at an edge. In some embodiments, folding at an edge can comprise pulling, rolling, or any combination thereof. In some embodiments, a container can comprise a rolled sheet of silk. In some embodiments, a tube can be formed by extrusion. In some embodiments, extrusion can generate an extrudate. In some embodiments, an extrudate can be cut to an appropriate size.

In some embodiments, a container can comprise one or more openings. In some embodiments, one or more openings can allow for an at least partial entry of a stem cell, a Schwann cell, an endothelial cell, or any combination thereof. In some embodiments, a container can comprise a fascicular structure comprising a plurality of hydraulic compartments within an interior. In some embodiments, a plurality of hydraulic compartments within an interior can be configured to at least partially protect a regenerating nerve within a compartment from mechanical injury.

In some embodiments, one or more openings can comprise a plurality of pores. In some embodiments, at least one pore of a plurality of pores can traverse an interior of a container through to an exterior of a container. In some embodiments, at least one pore can have a maximum diameter of about 200 μm. In some embodiments, at least one pore can have a maximum size that can be small enough to prevent a cell from entering. In some embodiments, pores can be distributed substantially throughout a length of a container. In some embodiments, a pore can be substantially uniformly distributed throughout a length of a container. In some embodiments, a pore can be substantially non-uniformly distributed throughout a length of a container. In some embodiments, a device can at least partially prevent scar tissue infiltration into an interior of a container. In some embodiments, a container can comprise an interior and an exterior. In some embodiments, a container can comprise a lumen. In some embodiments, a container can comprise a proximal end and a distal end. In some embodiments, at least part of a container can comprise an additional constituent. In some embodiments, an additional constituent can be distributed in a gradient from a proximal end to a distal end, and wherein an additional constituent at least partially encourages a growth of an axon. In some embodiments, at least a portion of an additional constituent increases in concentration from a proximal end of a container to a distal end of a container. In some embodiments, at least a portion of an additional constituent decreases in concentration from a proximal end to a distal end.

Disclosed herein in some embodiments, is a medical device. In some embodiments, a medical device can comprise a tubular body having a lumen and a long axis. In some embodiments, a medical device can comprise a plurality of silk elements laid substantially parallel along a long axis of a lumen of a tubular body. In some embodiments, a medical device can comprise a container. In some embodiments, a container can comprise a lumen. In some embodiments, a container can comprise an element within a lumen. In some embodiments, an element can be intra-luminal. In some embodiments, an element can comprise a silk. In some embodiments, an element can comprise a luminal silk. In some embodiments, a container can comprise a material as described herein.

In some embodiments, a tubular body can comprise a resorbable material. In some embodiments, a resorbable material can comprise a protein or protein-based material, which may be natural or synthetic. In some embodiments, a synthetic material can include material synthesized by chemical processes, by recombinant DNA technology processes, or by any combination thereof. In some embodiments, a medical device can comprise a composite construction. In some embodiments, a composite construction can comprise fibers set in a matrix. In some embodiments, tubular walls of a device can be composed of silk fibers and a protein material. In some embodiments, a medical device can comprise *Antherea pernyii* silk with a matrix of regenerated *Bombyx mori* protein.

In some embodiments, a matrix can be formed from silk protein. In some embodiments, silk protein can comprise redissolved silk protein obtained from mulberry or non-mulberry silk worms, natural silk fibroin obtained from mulberry or non-mulberry silk worms, or any combination thereof. In some embodiments, silk can comprise *Antherea pernyii* silk. In some embodiments, a matrix can be stabilized by a cross-linking agent. In some embodiments, a cross-linking agent can comprise formaldehyde gas, glutaraldehyde, citrate ions, ribose, glyoxal, genipin, or any combination thereof.

Disclosed herein in some embodiments, are medical device comprising an element at least partially within a container. In some embodiments, an element can span a length of a container. In some embodiments, an element can comprise a material as disclosed herein. In some embodiments, an element can be set in a matrix. In some embodiments, an element can be at least partially held in place by a matrix. In some embodiments, an element can comprise a nerve conduit. In some embodiments, an element can at least in part encourage, guide, or encourage and guide an in vivo regrowth of at least a portion of a nerve cell.

In some embodiments, a container can comprise a silk fiber. In some embodiments, a silk fiber can comprise a plurality of silk fibers that are helically laid or braided. In some embodiments, silk elements in a lumen can be separated from each other at a distance between about 1 μm and about 100 μm. In some embodiments, a medical device can comprise a packing density of silk elements. In some embodiments, a packing density of silk elements can comprise a range of from about 1 to about 30 per 10,000 $\mu m^2$, about 1 to about 10 per 10,000 $\mu m^2$, or about 5 to about 10 per 10,000 $\mu m^2$.

In some embodiments, a container can comprise a tubular body with an external diameter of from about 0.1 mm to about 1.0 mm, from about 1.0 mm to about 2.5 mm, from about 1.5 mm to about 2.0 mm, from about 1.0 mm to about 1.5 mm, from about 1.4 mm to about 1.5 mm, from about 1.0 mm to about 20 mm, from about 10 mm to about 20 mm, from about 1.0 mm to about 25 mm, from about 15 mm to about 25 mm, or from about 15 mm to about 25 mm.

In some embodiments, a container can comprise a tubular body with an external diameter of about 0.1 mm, about 0.5 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, or about 30 mm.

In some embodiments, a container can comprise a tubular body with an internal diameter of from about 0.1 mm to about 1.0 mm, from about 1.0 mm to about 2.5 mm, from about 1.5 mm to about 2.0 mm, from about 1.0 mm to about 1.5 mm, from about 1.4 mm to about 1.5 mm, from about 1.0 mm to about 20 mm, from about 10 mm to about 20 mm, from about 1.0 mm to about 25 mm, from about 15 mm to about 25 mm, or from about 15 mm to about 25 mm.

In some embodiments, a container can comprise a tubular body with an internal diameter of about 0.1 mm, about 0.5 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, or about 30 mm.

In some embodiments, a surface of a container can have a thickness of from about 250 µm to about 750 µm, from about 300 µm to about 600 µm, from about 500 µm to about 700 µm, from about 700 µm to about 1000 µm, from about 1 mm to about 5 mm, from about 5 mm to about 10 mm, or from about 10 mm to about 20 mm. In some embodiments, a surface of a container can comprise a wall, a partition, or any combination thereof.

In some embodiments, a length of a container can be from about 0.5 mm to about 150 mm. In some embodiments, a length of a container can be chosen for suitability with a nerve to be repaired using a device. In some embodiments, a medical device can be for a repair of smaller nerves. In some embodiments, a medical device can be used for a repair of larger size nerves. In some embodiments, a length of a container can be from about 1 mm to about 5 mm, about 1.5 mm to about 2.5 mm, about 1 mm to about 2 mm, about 1 mm to about 5 mm. In some embodiments, a container can have a length of from about 10 mm to about 20 mm, from about, 20 mm to about 100 mm, from about 100 mm to about 1000 mm, from about 5 mm to about 10 mm, from about 10 mm to about 25 mm, from about 20 mm to about 50 mm, from about 10 mm to about 60 mm, from about 25 mm to about 75 mm, from about 75 mm to about 100 mm, from about 100 mm to about 200 mm, from about 200 mm to about 300 mm, or from about 300 mm to about 2500 mm.

In some embodiments, a length of a container can be about 0.1 mm, about 0.5 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, about 50 mm, about 60 mm, about 70 mm, about 80 mm, about 90 mm, about 100 mm, about 200 mm, about 300 mm, about 400 mm, about 500 mm, about 600 mm, about 700 mm, about 800 mm, about 900 mm, about 1000 mm, about 1100 mm, about 1200 mm, about 1300 mm, about 1400 mm, about 1500 mm, about 1600 mm, about 1700 mm, about 1800 mm, about 1900 mm, about 2000 mm, about 2100 mm, about 2200 mm, about 2300 mm, about 2400 mm, or about 2500 mm.

In some embodiments, an element or a plurality of elements can have a diameter of from about 0.1 mm to about 1.0 mm, from about 1.0 mm to about 2.5 mm, from about 1.5 mm to about 2.0 mm, from about 1.0 mm to about 1.5 mm, from about 1.4 mm to about 1.5 mm, from about 1.0 mm to about 20 mm, from about 10 mm to about 20 mm, from about 1.0 mm to about 25 mm, from about 15 mm to about 25 mm, or from about 15 mm to about 25 mm.

In some embodiments, an element or a plurality of elements can have a diameter of about 0.1 mm, about 0.5 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, or about 30 mm.

In some embodiments, a medical device can have a similar size to a size of a container.

In some embodiments, a medical device can have a diameter of from about 0.1 mm to about 1.0 mm, from about 1.0 mm to about 2.5 mm, from about 1.5 mm to about 2.0 mm, from about 1.0 mm to about 1.5 mm, from about 1.4 mm to about 1.5 mm, from about 1.0 mm to about 20 mm, from about 10 mm to about 20 mm, from about 1.0 mm to about 25 mm, from about 15 mm to about 25 mm, or from about 15 mm to about 25 mm.

In some embodiments, a medical device can have a diameter of about 0.1 mm, about 0.5 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, or about 30 mm.

In some embodiments, a length of a medical device can be from about 0.5 mm to about 150 mm. In some embodiments, a length of a container can be chosen for suitability with a nerve to be repaired using a device. In some embodiments, a medical device can be for a repair of smaller nerves. In some embodiments, a medical device can be used for a repair of larger size nerves. In some embodiments, a length of a container can be from about 1 mm to about 5 mm, about 1.5 mm to about 2.5 mm, about 1 mm to about 2 mm, about 1 mm to about 5 mm. In some embodiments, a container can have a length of from about 10 mm to about 20 mm, from about, 20 mm to about 100 mm, from about 100 mm to about 1000 mm, from about 5 mm to about 10 mm, from about 10 mm to about 25 mm, from about 20 mm to about 50 mm, from about 10 mm to about 60 mm, from about 25 mm to about 75 mm, from about 75 mm to about 100 mm, from about 100 mm to about 200 mm, from about 200 mm to about 300 mm, or from about 300 mm to about 2500 mm.

In some embodiments, a length of a medical device can be about 0.1 mm, about 0.5 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, about 50 mm, about 60 mm, about 70 mm, about 80 mm, about 90 mm, about 100 mm, about 200 mm, about 300 mm, about 400 mm, about 500 mm, about 600 mm, about 700 mm, about 800 mm, about 900 mm, about 1000 mm, about 1100 mm, about 1200 mm, about 1300 mm, about 1400 mm, about 1500 mm, about 1600 mm, about 1700 mm, about 1800 mm, about 1900 mm, about 2000 mm, about 2100 mm, about 2200 mm, about 2300 mm, about 2400 mm, or about 2500 mm.

In some embodiments, a medical device can be resorbable, flexible, non-friable, permeable, semipermeable, absorbable, porous, or any combination thereof. In some embodiments, a flexible medical device can at least partially avoid compression neuropathy. In some embodiments, a medical device can be substantially resorbed in vivo within 4-18 months. In some embodiments, a container can be kink-resistant. In some embodiments, a medical device can prevent neuromas during regeneration of a nerve cell. In some embodiments, a container can be positioned around at least part of an injured nerve cell. In some embodiments, a container can wrap around at least part of a regenerating nerve cell. In some embodiments, a container can at least partially protect a regenerating nerve cell. In some embodiments, a wall structure of a device can comprise a longitudinal slit. In some embodiments, use of a device can reduce scar formation. In some embodiments, a porous outer membrane can mechanically resist compression by surrounding tissues. In some embodiments, a medical device can be configured to minimize encapsulation and nerve entrapment. In some embodiments, a medical device can comprise an ability to create an environment suitable for regeneration. In some embodiment, a container can comprise a semipermeable inner membrane to allow nutrient transport.

In some embodiments, a container can comprise a smooth structure, a pitted structure, a grooved structure, a ridged structure, or any combination thereof. In some embodiments, a structure can comprise a sloped channel. In some embodiments, an angle of a channel can guide nerve cell arrangement. In some embodiments, a grooved structure can reduce a mechanical strength of a container. In some embodiments, an exterior of a container can comprise an outer surface. In some embodiments, an outer surface of a container can be slippery when implanted into a subject. In some embodiments, a container can comprise an outer surface that at least partially prevents a container adhering to a subject into which a container can be implanted. In some embodiments, an outer surface can at least partially prevent fibrillation of a tissue in contact with a container, integration of a container to a subject, or any combination thereof.

In some embodiments, an at least partially dry container can comprise a Young's modulus of less than about 100, about 90, about 80, about 70, about 60, about 50, about 40, about 30, about 20, about 10, or about 5 MPa. In some embodiments, an at least partially dry container can comprise a Young's modulus of more than about 100, about 90, about 80, about 70, about 60, about 50, about 40, about 30, about 20, about 10, or about 5 MPa.

In some embodiments, an at least partially wet container can comprise a Young's modulus of less than about 10, about 9, about 8, about 7, about 6, about 5, about 4, about 3, about 2, about 1, or about 0.5 MPa.

In some embodiments, an at least partially wet container can comprise a Young's modulus of more than about 10, about 9, about 8, about 7, about 6, about 5, about 4, about 3, about 2, about 1, or about 0.5 MPa.

In some embodiments, an at least partially wet container can comprise a tensile strength of more than about 10, about 9, about 8, about 7, about 6, about 5, about 4, about 3, about 2, about 1, or about 0.5 MPa.

In some embodiments, an at least partially wet container can comprise a tensile strength of about 10, about 9, about 8, about 7, about 6, about 5, about 4, about 3, about 2, about 1, or about 0.5 MPa.

In some embodiments, an at least partially dry container can comprise a tensile strength of more than about 10, about 9, about 8, about 7, about 6, about 5, about 4, about 3, about 2, about 1, or about 0.5 MPa.

In some embodiments, an at least partially dry container can comprise a tensile strength of about 10, about 9, about 8, about 7, about 6, about 5, about 4, about 3, about 2, about 1, or about 0.5 MPa.

In some embodiments, an at least partially wet container can comprise a maximum strength of more than about 10, about 9, about 8, about 7, about 6, about 5, about 4, about 3, about 2, about 1, or about 0.5 N/mm$^2$.

In some embodiments, an at least partially wet container can comprise a maximum strength of about 10, about 9, about 8, about 7, about 6, about 5, about 4, about 3, about 2, about 1, or about 0.5 N/mm$^2$.

In some embodiments, an at least partially dry container can comprise a maximum strength of more than about 10, about 9, about 8, about 7, about 6, about 5, about 4, about 3, about 2, about 1, or about 0.5 N/mm$^2$.

In some embodiments, an at least partially dry container can comprise a maximum strength of about 10, about 9, about 8, about 7, about 6, about 5, about 4, about 3, about 2, about 1, or about 0.5 N/mm$^2$.

In some embodiments, a container can comprise an element at least partially within an interior of a container. In some embodiments, an element can comprise a conduit. In some embodiments, a container can comprise at least partially in an interior, an element which at least in part encourages, guides, or encourages and guides a in vivo regrowth of at least a portion of a nerve cell. In some embodiments, an element can comprise a perineurium layer, an epineurium layer, an endoneurium layer, or any combination thereof.

In some embodiments, a container can be configured to at least partially allow an influx of nutrients, an outflow of waste, or both, through openings in a container.

In some embodiments, a medical device can be at least in part flexible. In some embodiments, a container, an element, or any combination thereof, can be at least in part flexible. In some embodiments, at least in part flexible can comprise an ability to bend a container. In some embodiments, a medical device can be designed to be flexible, to be bendable, to substantially retain a shape into which it is bent, or any combination thereof. In some embodiments, a container, an element, or any combination thereof can be designed to be flexible, to be bendable, to substantially retain a shape into which it is bent, or any combination thereof. In some embodiments, bending a container can comprise bending a container into less than about a 180° angle, about a 170° angle, about a 160° angle, about a 150° angle, about a 140° angle, about a 130° angle, about a 120° angle, about a 110° angle, about a 100° angle, about a 90° angle, about a 80° angle, about a 70° angle, about a 60° angle, about a 50° angle, about a 40° angle, about a 30° angle, about a 20° angle, about a 10° angle, or about a 0° angle between a proximal and a distal end of a container. In some embodiments, bending a container can comprise bending a container into more than about a 180° angle, about a 170° angle, about a 160° angle, about a 150° angle, about a 140° angle, about a 130° angle, about a 120° angle, about a 110° angle, about a 100° angle, about a 90° angle, about a 80° angle, about a 70° angle, about a 60° angle, about a 50° angle, about a 40° angle, about a 30° angle, about a 20° angle, about a 10° angle, or about a 0° angle between a proximal and a distal end of a container. In some embodiments, an angle can comprise a positive angle. In some embodiments, an angle can comprise a negative angle. In some embodiments, a positive angle can be measured on a top surface of a container. In some embodiments, a negative angle can be measured on a bottom surface of a container. In some embodiments, a container can comprise a tubular shape. In some embodiments, an angle can be measured by holding a tubular shaped container at each end and moving opposing end towards one another to create a bend in a container. In some embodiments, an angle can be measured in a bend in a container. In some embodiments, determining flexibility can comprise measuring an angle of a bend in a container. In some embodiments, determining flexibility can comprise measuring a maximum or minimum angle of a bend in a container without a container breaking, fracturing, losing patency, kinking, or any combination thereof. In some embodiments, bending a container can comprise bending without breaking a container, without kinking a container, while maintaining a patency of a container, while maintaining a patency of a lumen of a container, or any combination thereof. In some embodiments, a container can return at least in part to its pre-bend shape, after a force that bends a container ceases to be applied.

In some embodiments, a container can comprise a natural polymer, a synthetic polymer, a hybrid composition, or any combination thereof. In some embodiments, a natural polymer can comprise a protein, a polysaccharide, a silicone, a polyester, a biomimetic material, an isolated tissue, an isolated tissue product, or any combination thereof. In some embodiments, a protein can comprise a collagen, a silk, a silk composite, a gelatin, fibrinogen, elastin, keratin, or any combination thereof. In some embodiments, a polysaccharide can comprise a hyaluronic acid, a chitin an alginate, or any combination thereof. In some embodiments, a container can comprise a glycosaminoglycan-rich gel.

In some embodiments, an element can comprise a natural polymer, a synthetic polymer, a hybrid composition, or any combination thereof. In some embodiments, a natural polymer can comprise a protein, a polysaccharide, a silicone, a polyester, a biomimetic material, an isolated tissue, an isolated tissue product, or any combination thereof. In some embodiments, a protein can comprise a collagen, a silk, a silk composite, a gelatin, fibrinogen, elastin, keratin, or any combination thereof. In some embodiments, a polysaccharide can comprise a hyaluronic acid, a chitin an alginate, or any combination thereof. In some embodiments, a container can comprise a glycosaminoglycan-rich gel.

In some embodiments, a container, an element, or any combination thereof can comprise a collagen. In some embodiments, a collagen can comprise a triple helical structure. In some embodiments, a triple helical structure can form an extended rod. In some embodiments, a container, an element, or any combination thereof can comprise an extracellular matrix (ECM). In some embodiments, an extracellular matrix (ECM) can comprise collagen. In some embodiments, a collagen can comprise proline, hydroxyproline, glycine, or any combination thereof. In some embodiments, a collagen can comprise a glycine at every third position. In some embodiments, a collagen can comprise an Arginylglycylaspartic acid (RGD) peptide motif. In some embodiments, collagen can exist as fibrils in an endoneurium or as a non-fibrillar component of a basal lamina. In some embodiments, a nerve conduit can comprise collagen. In some embodiments, a collagen can be in the form of a hydrogel, particle, or foams. In some embodiments, a hydrogel scaffold can comprise a collagen. In some embodiments, a collagen can comprise a soluble collagen. In some embodiments, a hydrogel scaffold can comprise a lattice of nanofibrils. In some embodiments, a lattice of nanofibrils can be produced by a combination of compression and blotting using layers of mesh and paper sheets. In some embodiments, fibrils can be produced by unconfined plastic compression of hyperhydrated collagen gels. In some embodiments, scaffolds can be composed of aligned nanofibrils. In some embodiments, a sheet can be formed into a three-dimensional structure. In some embodiments, a three-dimensional structure can comprise a roll, a tube, or any combination thereof.

In some embodiments, manufacturing can include preservation of a natural fibrillar structure of a collagen and construction of a tubular matrix from fibrillar sheets.

In some embodiments, a tubular matrix can comprise a pore size in the range of 0.1-0.5 μm to allow for nutrient transfer.

In some embodiments, a container can comprise a semipermeable, collagen-based wrap. In some embodiments, a container can be unrolled and self-curled to at least partially match dimensions of an injured nerve cell. In some embodiments, a semipermeable membrane can allow diffusion of nutrients while at least partially preventing a migration of fibroblasts or at least partially preventing inflammation.

In some embodiments, collagen can be prepared by electrospinning. In some embodiments, electrospinning can comprise use of a spinning mandrel. In some embodiments, a collagen can comprise pure collagen or blended collagen.

In some embodiments, delivery of synergistically acting GDNF and NGF from a container, an element, or any combination thereof can assist successful repair of peripheral nerve defects. In some embodiments, a container, an element, or any combination thereof can comprise a composite scaffold. In some embodiments, a composite scaffold can be prepared by blending and crosslinking chitosan with collagen and icariin. In some embodiments, a micropatterned tubular collagen matrix can be produced by spin casting.

In some embodiments, a collagen can comprise a denatured collagen. In some embodiments, a denatured collagen can comprise gelatin. In some embodiments, a crosslinking agent can comprise genipin. In some embodiments, a collagen can be photofabricated. In some embodiments, gelatin can be cross-linked with genipin. In some embodiments, a container, an element, or any combination thereof can comprise a fabricated proanthocyanidin crosslinked gelatin material with a rough outer surface.

In some embodiments, a collagen can comprise a type I collagen, a type II collagen, a type III collagen, a type V collagen, a type X collagen, a salt of any of these, or any combination thereof. In some embodiments, a collagen can be semi-permeable.

In some embodiments, a container, an element, or any combination thereof can comprise a polyester. In some embodiments, a polyester can comprise a polyglycolide. In some embodiments, a polyglycolide can comprise a polyglycolic acid (PGA), a (poly(lactic-co-glycolic acid) with lactic acid, a poly(glycolide-co-caprolactone) with ε-caprolactone, a poly (glycolide-co-trimethylene carbonate) with trimethylene carbonate), or any combination thereof. In some embodiments, a container can comprise a woven polyglycolic acid mesh tube. In some embodiments, a polyester can comprise a biological polyester. In some embodiments, a biological polyester can be obtained at least in part from a microorganism. In some embodiments a biological polyester can comprise a polyhydroxyalkonats (PHAs). In some embodiments, a PHA can be biodegradable biocompatible, synthetic, thermoplastic, or any combination thereof. In some embodiments, a PHA can serve as an intracellular energy and carbon storage product. In some embodiments, a PHA can comprise poly(4-hydroxy-butyrate), polyhydroxyvalerate, polyhydroxyhexanoate, polyhydroxyoctanoate, polyhydroxybutyrate (PHB), poly(3-hydroxybutyrate) (P3HB), poly (3-hydroxybutyricacid-co-3-hydroxyvaleric acid), poly(3-hydroxybutyrate-co-3-hydroxyvalerate) (PHBV), an analog of any of these, a salt of any of these, or any combination thereof. In some embodiments, a polyester can comprise a resorbable sheet, particle or film. In some embodiments, copolymers of 3-hydroxybutyrate and 3-hydroxyvalerate can have an ability to tailor their physical characteristics according to a need. In some embodiments, 3-hydroxyvalerate can be incorporated into a polymer chain to increase chain flexibility, to decrease a glass transition temperature, to decrease a glass melting temperature, or any combination thereof.

In some embodiments, a polyester can comprise an ester functional group in their main backbone. In some embodiments, a polyester can comprise a polylactic acid (PLA), a poly(L-lactic acid) (PLLA), a polyglycolide (PGA), a poly-lactic-co-glycolic acid (PLGA), a polycaprolactone (PCL), a poly(D,L-lactide-co-ε-caprolactone)(PLC), or any combination thereof.

In some embodiments, PLA can be made from lactic acid. In some embodiments, lactic acid can be obtained from corn, sugar beet, wheat, or any combination thereof. In some embodiments, a polyester can be biocompatible. In some embodiments, a multilayer PLA can be manufactured by microbraiding to obtain adequate mechanical strength at an injury site. In some embodiments, a polyester can be manufactured by immersion precipitation.

In some embodiments, a container can comprise macropores on an exterior surface. In some embodiments macropores can be interconnected to an inner layer to provide a higher outflow rate than inflow rate.

In some embodiments, a polyester can be made by a melt-blow process. In some embodiments, a melt-blow process can comprise wrapping a polyester around a stainless steel core bar and heating. In some embodiments, a container, an element, or any combination thereof can comprise a PLA non-woven fabric, a silicone tube, a collagen gel, an isolated autologous nerve, or any combination thereof. In some embodiments, a container, an element, or any combination thereof can further comprise chitosan-nano Au, a fibroblast growth factor 1 (FGF1), NSCs, or any combination thereof.

In some embodiments, a PLLA can comprise a stereoregular and highly crystalline form of a PLA. In some embodiments, a polymer can be manufactured by extrusion. In some embodiments, a polyester can be highly porous with an interconnected pore structure. In some embodiments, a container can comprise a porous, micropatterned poly(D,L-lactic acid) (PDLLA) conduit. In some embodiments, a container can be seeded with Schwann cells. In some embodiments, Schwann cells can provide additional trophic, physical, chemical, and biological support. In some embodiments, a container can comprise a multi-walled PLLA. In some embodiments, a container can be prepared using solvent casting, physical imprinting, rolling-fusing, or any combination of these methods. In some embodiments, a container can comprise multiple intraluminal walls and precise topography along a longitudinal axis to provide an alignment along a conduit. In some embodiments, a regrowing neurite can align predominantly in a direction of an element.

In some embodiments, PLLA can be combined with polycaprolactone and NGF to promote neurite outgrowth using core-shell structured biodegradable nanofibers fabricated by coaxial electrospinning. In some embodiments, a container can comprise poly(L-lactide-co-ε-caprolactone) (P(LLA-CL)), bovine serum albumin (BSA), BSA/NGF, or any combination thereof.

In some embodiments, a polyester can comprise PGA. In some embodiments, PGA can be at least partially biodegradable, rigid, thermoplastic, crystalline, or any combination thereof. In some embodiments, PGA can exhibit a high tensile modulus with low solubility in organic solvents. In some embodiments, PGA can be combined with a natural polymer as disclosed herein.

In some embodiments, a polyester can comprise a copolyester. In some embodiments, a copolyester can comprise PLGA. In some embodiments, use of a PLGA can provide a low inflammatory response. In some embodiments, a container can comprise longitudinally aligned channels. In some embodiments, a container can be produced using a combined injection molding and thermally induced phase transition technique. In some embodiments, PLGA can be dissolved in acetic acid, injected into a cold mold, or any combination thereof. In some embodiments, a cold mold can induce solidification of a polymer solution and led to solid-liquid phase separation. In some embodiments a PLGA can comprise a foam. In some embodiments, a foam can comprise a macrostructure with high anisotropy due to a removal of acetic acid by sublimation. In some embodiments, macropores can be organized into bundles of channels up to 20 μm wide in a PLGA matrix. In some embodiments, NGF can be incorporated into a PLGA container or element. In some embodiments, a container can be fabricated from a mixture of PLGA microspheres and a porogen. In some embodiments, a PLGA microsphere and a porogen can be loaded into a mold and processed by gas foaming. In some embodiments, porosity can create open channels to allow tissue ingrowth. In some embodiments, PLGA hollow fiber membranes (HFMs) can be manufactured using a wet phase inversion technique to create nerve tract guidance channels. In some embodiments, HFMs with different size, inner and outer surface morphologies, porosity, and permeability can be produce. In some embodiments, PLGA can be combined with pluronic F127. In some embodiments, pluronic F127 can comprise a nonionic, surfactant polyol. In some embodiments, a polyester can be produced through a modified immersion-precipitation method. In some embodiments, an interior surface of a container can comprise nanosized pores (~50 nm). In some embodiments, nanosized pores can at least partially prevent fibrous tissue infiltration but allow permeation of nutrients and retain neurotrophic factors. In some embodiments, an exterior surface can comprise microsized pores (~50 μm). In some embodiments, microsized pores can allow vascular ingrowth to supply nutrients inside a tube. In some embodiments, a container, an element, or any combination thereof can comprise a PPy-coated, electrically conductive, electrospun PLGA nanofiber.

In some embodiments, a container, an element, or any combination thereof can comprise PLGA, poly(caprolactone-fumarate) (PCLF), a neutral oligo[(polyethylene glycol) fumarate] hydrogel a positively charged oligo[(polyethylene glycol)fumarate] hydrogel, a PCLF sleeve, or any combination thereof.

In some embodiments, a polyester can comprise polycaprolactone (PCL). In some embodiments PCL can comprise PCL-PLA. In some embodiments, a PCL can have high solubility in organic solvents, low melting temperature (55° C.-60° C.), low glass transition temperatures (−60° C.), or any combination thereof.

In some embodiments, a container, an element, or any combination thereof can comprise a Poly(D,L-lactide-co-ε-caprolactone)(PLC). In some embodiments, a container, an element, or any combination thereof can comprise a PLC. In some embodiments, poly(D,L-lactide-co-ε-caprolactone) can comprise a copolymer of lactic acid and caprolactone monomers. In some embodiments, a poly(D,L-lactide-co-ε-caprolactone) copolymer can be fabricated using an ink-jet system.

In some embodiments, a polyester can comprise a polyglycolide. In some embodiments, a polyglycolide can comprise a polyurethane (PU). In some embodiments, a PU can comprise a polymer with a backbone containing urethane linkages. In some embodiments, PU can be prepared by uniform coating on a rotating mandrel, by particle leaching method, or any combination thereof.

In some embodiments, a container, an element, or any combination thereof can comprise a polyol. In some embodiments, a polyol can comprise a polyvinyl alcohol (PVA). In some embodiments, PVA can be water soluble, nondegradable, synthetic or any combination thereof. In some embodiments, PVA can comprise a non-resorbable PVA hydrogel. In some embodiments, a container can be manufactured using a single screw extruder. In some embodiments, a container can be pre-seeded with Schwann cells. In some embodiments a porosity, a wall thickness, or a Schwann cell seeding density of a container can be varied. In some embodiments, PVA can be combined with chitosan.

In some embodiments, a container, an element, or any combination thereof can comprise a hybrid composition that can comprise multiple materials or constituents disclosed herein. In some embodiments, a hydrophobic material can be coated with a hydrophilic material. In some embodiments, a hydrophilic material can comprise a hyaluronic acid, an ECM protein, or any combination thereof. In some embodiments, a hybrid composition can comprise a natural polymer and a synthetic polymer.

In some embodiments, a PHBV can be combined with a synthetic polymer. In some embodiments, a porous micropatterned film (PHBV-P(L-D,L)LA-PLGA) can be wrapped around aligned electrospun fibers (PHBV-PLGA). In some embodiments, a hybrid composition can comprise a desired porosity or mechanical properties. In some embodiments, a polymer blends can be chosen so that a protective tube cover, or film part, can erode slower than a fibrous mat to achieve complete healing before a tube erodes. In some embodiments, fibers can be aligned parallel to a groove axis of a micropatterned film. In some embodiments, a container, an element, or any combination thereof can comprise an oriented architecture. In some embodiments, a container can comprise aligned, electrospun fibers (PHBV-PLGA) seeded with NSCs wrapped in a porous, micropatterned film (PHBV-P(L-D,L)LA-PLGA) with supportive cells. In some embodiments, supportive cells can be aligned along a microgroove to support an NSC. In some embodiments, cells, undifferentiated NSCs, and supportive cells can be oriented along a guiding and support element, a microgroove, or an aligned fiber. In some embodiments, cells can survive and maintain an alignment in vivo in a container.

In some embodiments, a polysaccharide can be combined with a synthetic polymer to prepare a container, an element, or any combination thereof.

In some embodiments, a parallel bundle of fibers or filaments can cause cells to exhibit a bipolar morphology that aligns with a fiber or filament direction. In some embodiments, parallel fibers can regulate a growth of a nerve cell along a fiber orientation.

In some embodiments, a chitosan-PVA nanofiber can be combined with a single-walled carbon nanotube (SWCNT). In some embodiments, SWCNTs can augment a morphology, porosity, a proliferation rate, or a structural property of a chitosan-PVA nanofiber composite. In some embodiments, a container can comprise electrospun PVA-chitosan nanofibrous scaffolds with large pore sizes for nervous tissue repair. In some embodiments, a chitosan-containing scaffold can be used for in vitro cell culture in contact with a nerve cell. In some embodiments, an addition of chitosan to a PVA scaffold can enhance a viability and proliferation of a nerve cell.

In some embodiments, a container, an element, or any combination thereof can comprise a natural polymer. In some embodiments, a natural polymer can comprise a protein, a polysaccharide, or any combination thereof. In some embodiments, a protein can comprise a collagen, a silk, a gelatin, a fibrinogen, an elastin, a keratin, or any combination thereof. In some embodiments, a polysaccharide can comprise a hyaluronic acid, a chitin an alginate, or any combination thereof. In some embodiments, a container can comprise a PGA fibrous mesh coated with collagen. In some embodiments, a hybrid composition can comprise a protein with a synthetic polymer.

In some embodiments, a container can comprise a PGA-collagen tube filled with laminin-coated collagen fibers. In some embodiments, a container can comprise a cylindrically woven PGA mesh. In some embodiments, an exterior, interior, or combination thereof can be coated with amorphous collagen coated with laminin. In some embodiments, PGA-collagen tubes can be filled with laminin-soaked collagen sponges. In some embodiments, a PGA tube can be prepared with a tubular braiding machine. In some embodiments, a container can be coated with collagen layers.

In some embodiments, a container, an element, or any combination thereof can comprise a biomimetic material. In some embodiments, a biomimetic material can comprise an ECM protein. In some embodiments, an ECM protein can comprise a glycoprotein. In some embodiments, an ECM protein can comprise a laminin, a fibronectin, a vitronectin, or any combination thereof. In some embodiments, a biomimetic material can comprise the tri-amino acid sequence of arginine-glycine-aspartate (RGD).

In some embodiments, a fibronectin can comprise a disulfide-linked glycoprotein. In some embodiments, fibronectin can assist cell adhesion, morphology, migration, differentiation, or any combination thereof. In some embodiments, a fibronectin can interact with collagen, heparin, fibrin, and cell surface receptors. In some embodiments, fibronectin can assist orientation of cells along a fibronectin pattern. In some embodiments, fibronectin can be used as a source for a release of supportive materials in nerve guidance conduits. In some embodiments, strands of a cell adhesive fibronectin can be used to bridge a nerve gap. In some embodiments, fibronectin can be added to a matrix as described herein. In some embodiments, a matrix can comprise an alginate matrix. In some embodiments, fibronectin can support Schwann cell viability. In some embodiments, fibronectin can augment axonal growth. In some embodiments, an ECM protein can be used to at least partially coat another composition as described herein. In some embodiments, a collagen scaffold can be at least partially coated with laminin and fibronectin.

In some embodiments, a container, an element, or any combination thereof can comprise a synthetic material. In some embodiments, a synthetic material can comprise a synthetic polymer. In some embodiments, a synthetic polymer can be biodegradable. In some embodiments, a synthetic material can be biocompatible, can at least partially avoid initiating an immunological response, can have mechanical properties and degradation rates that can be controlled by changing a process condition or component without changing a bulk features of a polymer, can be processed in various forms to enhance tissue ingrowth, or any combination thereof. In some embodiments, a biodegradable polyester can comprise poly(lactic acid) (PLA), poly(glycolic acid) (PGA), poly(lactic acid-co-glycolic acid) (PLGA), poly(ε-caprolactone) (PCL), polyurethanes (PUs), tri-methylene carbonate-co-ε-caprolactone, poly(D,L-lactide-co-ε-caprolactone), or any combination thereof. In some embodiments, a nonbiodegradable polymer can comprise a methacrylate-based hydrogel, a polystyrene, a silicone, a poly(tetrafluoroethylene), or any combination thereof. In some embodiments, a polymer can be manufactured by electrospinning, injection molding, photolithography, extrusion, or any combination thereof.

In some embodiments, a container, an element, or any combination thereof can comprise an isolated tissue, isolated tissue product, or any combination thereof. In some embodiments, an isolated tissue or isolated tissue product can comprise an isolated decellularized tissue. In some embodiments, an isolated decellularized tissue can comprise an isolated at least partially decellularized tissue, an isolated at least partially decellularized tissue product, or any combination thereof. In some embodiments, an isolated at least partially decellularized tissue can comprise an isolated at least partially decellularized vasculature. In some embodiments, an isolated at least partially decellularized vasculature can comprise an isolated at least partially decellularized vein.

In some embodiments, an isolated tissue, isolated tissue product or combination thereof can comprise an autograft. In some embodiments, an autograft can be harvested from a patient's own body. In some embodiments, an autograft can be harvested from another location to an injury site. In some embodiments, a nerve autograft can provide a structural guidance of a natural material for axonal progression from a proximal to a distal nerve stump. In some embodiments, a sural nerve, a superficial cutaneous nerve, or lateral and medial antebrachii cutaneous nerves can be donor sites for autograft nerve tissue.

In some cases, a nerve autograft can cause a second surgery site to harvest tissue from a donor site, which can be associated with donor site morbidity and loss of function. In some cases, an availability and a length of nerve that can be harvested can be limited. In some cases, use of autografts can be restricted to critical nerve gaps of about 5 cm length. In some cases, a device as described herein can facilitate regeneration of a nerve gap of greater than about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, or about 20 cm. In some embodiments, a gap over which a severed nerve cell can be reconnected can be from about 6 cm to about 20 cm. In some cases, a mismatch of donor nerve size and fascicular inconsistency between an autograft and a proximal and a distal stump of a recipient site can be a main limitation in a use of nerve autografts. In some cases, a type of nerve autograft can affect outcome. In some cases, a type of nerve chosen can comprise a sensory nerve, a motor nerve, or a mixed nerve. In some cases, a successful outcome, can require a match in axonal size, distribution, and alignment. In some cases, a match in axonal size can limit a regeneration capacity of an autograft. In some cases, a motor or mixed-nerve autograft can provide superior axon regeneration compared to a sensory nerve autograft. In some cases, a nerve autograft can have a potential risk of infection and formation of a painful neuroma. In some cases, a recovery time for a patient can be prolonged, owing to a need for a second surgery.

In some embodiments, an isolated tissue, isolated tissue product or combination thereof can comprise an allograft. In some embodiments, a nerve allograft can comprise a technique used to bridge a peripheral nerve lesion with tissues derived from a different individual of a same species. In some embodiments, an allograft nerve tissue can function as a support for guidance. In some embodiments, an allograft nerve tissue can be a source for viable donor-derived Schwann cells. In some embodiments, a Schwann cell can facilitate a connection of axons at a proximal end, a distal end, or any combination thereof, to achieve reinnervation of a target tissue or organ.

In some cases, use of an allograft can be limited by a risk of immune rejection, a risk of cross contamination, a risk of secondary infection, a limited supply, or any combination thereof. In some cases, an allograft can require a systemic immunosuppressive therapy. In some cases, a long-term immune suppression may not be desirable due to an increased risk of infection, a decrease of healing rate, a risk of tumor formation and other systemic effects, or any combination thereof. In some cases, a limitation as described herein can be overcome by processing nerve allografts with repeated freeze-thaw cycles, irradiation, and decellularization with detergents.

In some embodiments, an isolated tissue, isolated tissue product, or combination thereof can comprise a xenograft. In some embodiments, a xenograft can be obtained from a member of a species other than that of a recipient.

In some cases, a xenograft can require immunosuppression. In some cases, administering a xenograft to a subject can require immunosuppression of a subject. In some cases, a subject can require long-term immunosuppression. In some cases, immunosuppression can comprise RS-61443, FK-506, or any combination thereof. In some embodiments, a xenograft can provide less functional recovery than an isograft, or a composition as described herein. In some embodiments, a xenograft can comprise an acellular nerve xenograft. In some embodiments, a xenograft can be seeded with bone marrow stromal cells (BMSCs). In some embodiments, a xenograft can be as effective as an allograft in regenerating a neuron. In some cases, use of a xenograft can present a risk of cross-species disease transmission.

In some embodiments, an allograft or a xenograft can induce an immunogenic reaction in a host tissue. In some embodiments, an immunogenic reaction an immunogenic reaction can be suppressed with immunosuppressive drugs. In some embodiments, use of an immunosuppressive drug can cause more susceptibility to infections and tumor formation. In some embodiments, a cellular constituent that can cause an immunogenic reaction can be removed. In some embodiments a native extracellular matrix (ECM) can be preserved. In some embodiments, an ECM can enhance a regenerative capacity. In some embodiments, a "decellularization method" can be used. In some embodiments, an ECM of allografts or xenografts, a basal lamina of allografts or xenografts, or any combination thereof, can be conserved among various species. In some embodiments, an ECM of allografts or xenografts, a basal lamina of allografts or xenografts, or any combination thereof can create a means for mechanical guidance for regenerating axons. In some embodiments, a decellularization process can physical methods, chemical methods, enzymatic methods, or any combination thereof. In some embodiments, physical methods can comprise lyophilization, direct pressure, sonication, agitation, or any combination thereof. In some embodiments, freezing nerve tissue can cause disruption of a cell membrane and can result in cell lysis. In some embodiments, a freezing step causing disruption of an ECM by rapid freezing that produces ice crystals can be avoided. In some embodiments, decellularization can comprise application of direct pressure. In some embodiments, decellularization can comprise mechanical agitation, sonication, chemical treatment, or any combination thereof to disrupt cell membranes. In some embodiments, chemical methods can include use of alkaline and acid solutions; non-ionic, ionic, and zwitterionic detergents; hypotonic or hypertonic solutions; or any combination thereof. In some embodiments, treatment with acidic or alkaline solutions can solubilize cell components and disrupt nucleic acids. In some embodiments, ionic detergents can comprise sodium dodecyl sulfate and Triton X-200. In some embodiments, ionic detergents can solubilize cellular components and denature proteins. In some embodiments, nonionic detergents can leave protein-protein interactions intact. In some embodiments, nonionic detergents can comprise Triton X-100. In some embodiments, hypotonic and hypertonic solutions can comprise ethylenediamine tetraacetic acid (EDTA). In some embodiments, hypotonic and hypertonic solutions can result in osmotic shock and lead to cell lysis. In some embodiments, EDTA can be used in conjunction with treatments involving enzymes. In some embodiments, enzymes can comprise exonucleases, endonucleases, trypsin, or any combination thereof. In some embodiments, a decellularized tissue, isolated tissue product, or combination thereof can be washed. In some embodiments, a wash can at least partially remove any remaining chemicals, which may cause cell damage in the host tissue after implantation. In some cases, remaining chemicals, which may cause cell damage in the host tissue after implantation can be considered a disadvantage of decellularized graft materials. In some embodiments, compositions disclosed herein can avoid disadvantageous properties of xenografts. In some embodiments, trypsin proteolysis can be used for enzymatic degradation to decellularize dermis or heart valves. In some embodiments, a stability of an ECM can be limited by an alteration of collagen content after trypsin treatment.

In some embodiments, a container, an element, or any combination thereof can comprise a carbohydrate. In some embodiments, a carbohydrate can be used as a cross-linking agent. In some embodiments, a carbohydrate can comprise a monosaccharide, a disaccharide, a polysaccharide, or any combination thereof. In some embodiments, a polysaccharide can comprise chitin, chitosan, or any combination thereof.

In some embodiments, chitosan can comprise a linear polysaccharide composed of glucosamine and N-acetyl glucosamine units linked by β(1-4) glycosidic bonds. In some embodiments, chitosan can comprise a deacetylated form of chitin. In some embodiments, chitosan can be soluble in slightly acidic medium. In some embodiments, chitosan-based scaffolds can form interconnected porous structures. In some embodiments, an interconnected porous structure can comprise a sponge. In some embodiments, a cationic nature, and reasonable level of mechanical properties. In some embodiments, chitosan conduits can be combined with bone marrow MSCs to promote peripheral nerve regeneration. In some embodiments, BMSCs can differentiate into neural stem cells (NSCs) in vivo. In some embodiments, neural stem cells can bridge a gap between two portions of a severed nerve upon differentiation. In some embodiments, chitosan can be made with low, medium, or high degrees of deacetylation. In some embodiments, different levels of deacetylation can cause different levels and rates of degradation and different microenvironments for a regenerating nerve tissue. In some cases, a chitosan tubes, can show a high rate of degradation and low mechanical stability. In some embodiments, chitosan can be non-toxic. In some embodiments, chitosan can be laminin-coated.

In some embodiments, a polysaccharide can comprise a hyaluronan. In some embodiments, a polysaccharide can comprise hyaluronic acid. In some embodiments, a hyaluronic acid can be at least partially immunoneutral. In some embodiments, hyaluronic acid can be processed into many physical forms. In some embodiments, a physical form can comprise a viscoelastic solution, a hydrogel, an electrospun fiber, a non-woven mesh, a macroporous and fibrillar sponge, a flexible sheet, a nanoparticulate, or any combination thereof. In some embodiments, a hydrogel can comprise a construct of hyaluronic acid, collagen, laminin, or any combination thereof. In some embodiments, a Schwann cell can be encapsulated in a hydrogel. In some embodiments, encapsulation does not affect cell viability. In some embodiments, cells can remain viable for 2 weeks in a hydrogel. In some embodiments, in a co-culture of dissociated neurons with Schwann cells, neurons can extend neurites. In some embodiments, neurites can follow Schwann cells. In some embodiments, an element, a container, or any combination thereof can comprise a chitosan-gelatin porous scaffold. In some embodiments, a scaffold can comprise hyaluronic acid, heparan sulfate, or any combination thereof. In some embodiments, a scaffold can be fabricated using lyophilization. In some embodiments, a scaffold can promote adhesion of NSCs and progenitor cells and support growth in a 3D environment for a long duration.

Disclosed herein in some embodiments, are compositions comprising a silk. In some embodiments, an element, a container, or any combination thereof can comprise a silk. In some embodiments, a silk can comprise a silk fiber, a silk protein, or any combination thereof. In some embodiments, a silk can comprise fibroin, spidroin, spider dragline silk, a Major Ampullate silk, a major spider silk, a Minor Ampullate silk, a Cylindriform silk, a pyriform silk, or any combination thereof sericin, or any combination thereof. In some embodiments, a silk can be obtained from *Bombyx morii*. In some embodiments, a silk can be purified using a reagent comprising $CaCl_2$), ethanol, $Na_2CO_3$, $CaCl_2$-EtOH—$H_2O$ (Ajisawa's reagent), lithium bromide, or any combination thereof. In some embodiments, a silk can comprise a silk protein, a silk fiber, a silk filament, a silk nano-filament, or any combination thereof. In some embodiments, a silk can comprise a silk solid, a silk liquid, or any combination thereof.

In some embodiments, a silk can comprise a fibrous protein synthesized by a member of the class Arachnida or in the specialized epithelial cells that line the glands in worms of mites, butterflies, and moths. In some embodiments, silk can comprise repetitive protein sequences. In some embodiments, a silk can comprise hydrophobic domains of short side chain amino acids. In some embodiments, a general structure of silk fibroin can take a form of a β-sheet.

In some embodiments, an assembly of silk and its strength can originate from a hydrophobic region interspaced with small hydrophilic segments. In some embodiments, when compared with other protein-based biomaterials, there are many advantages of using silk such as a risk of infection and possibility of rejection of the other materials. In some embodiments, silk can comprise advantageous mechanical properties such as modulus, breaking strength, and elongation. In some embodiments an advantage of silk can comprise biocompatibility, water-based processing, biodegradability, or any combination thereof.

In some embodiments, an element can comprise chitosan, silk fibroin fibers, and seeded with Schwann cells for ECM deposition. In some embodiments, spider silk can at least partially support cell proliferation and regeneration.

In some embodiments, a container, an element, or any combination thereof can comprise a keratin. In some embodiments, a keratin can comprise spider silk. In some embodiments, a keratin can be produced by a keratinocyte. In some embodiments, keratin can comprise cysteine. In some embodiments, cysteine can comprise sulfur. In some embodiments, keratin can be obtained from hair. In some embodiments, oxidized keratin can be crosslinked to form a hydrogel. In some embodiments, a hydrogel can have a neuroinductive capacity. In some embodiments, a keratin hydrogel can be used as a nerve conduit luminal filler.

In some embodiments, a container can comprise a first plurality of silk proteins. In some embodiments, at least one protein in a first plurality of silk proteins can comprise a fibroin, a spidroin, a recombinant silk protein, an analog of any of these, or any combination thereof. In some embodiments, a fibroin can comprise regenerated fibroin. In some embodiments, a spidroin can comprise regenerated spidroin. In some embodiments, an element can comprise a second plurality of silk elements. In some embodiments, a conduit can comprise a conduit for nerve regrowth. In some embodiments, a conduit can comprise a scaffold for nerve regrowth. In some embodiments, a silk can comprise a fibroin, a spidroin, a recombinant silk protein, an analog of any of these, or any combination thereof. In some embodiments, a silk can comprise *Bombyx mori, Hyalophora cecropia, Gonometra* spp, *Antheraea* spp, or *Sarnia cynthia* silkworm silk fibroin. In some embodiments, a spidroin can comprise a spider silk spidroin. In some embodiments, a spider silk spidroin can comprise a spider dragline silk. In some embodiments, a second plurality of silk elements can comprise from about 1 to about 100,000 silk elements. In some embodiments, a second plurality of silk proteins can comprise about 13,000 silk proteins. In some embodiments, at least one fiber of a plurality of fibers can be at least partially biodegradable. In some embodiments, at least some of a silk elements in a plurality can be at least partially covered in a hydrophilic substance. In some embodiments, a hydrophilic substance can comprise a substance which when contacted with water at least partially forms a gel. In some embodiments, a gel can comprise a hydrogel.

In some embodiments, silk elements or fibers used in a medical device can comprise mulberry silkworm silk, non-mulberry silkworm silk, spider dragline silk, filaments spun from recombinant silk protein, an analog of any of these, a salt of any of these, or any combination thereof. In some embodiments, a silk can be derived from a non-mulberry silkworm. In some embodiments, a non-mulberry silkworm can be an *Antherea* species. In some embodiments, an *Antherea* species can be *Antherea pernyii*.

In some embodiments, a silk element can be in a form of sliver silk, reeled silk, or twisted silk. In some embodiments, a plurality of silk elements can be conveniently arranged in a substantially longitudinal orientation with respect to a wall of a device.

In some embodiments, to encourage cell migration, a silk element can have a principal silk protein containing at least eight repeats of a triplet RGD. In some embodiments, at least some triplets can be located immediately adjacent to turns or predicted turns of a structure of a principal silk protein. In some embodiments, principal silk protein can have sites from which one or more arginine groups of a principal protein can be blocked to tune cell adhesiveness. In some embodiments, a blocking can be achieved by one or more of deamination, sulfation, amide formation and blocking with cyclohexanedione.

In some embodiments, a blocking agent can produce a gradient in a density of free arginine groups from a distal to a proximal end of a device. In some embodiments, a gradient can be achieved by slowly and progressively lowering a proximal end of a device first into a solution of a blocking agent. Alternatively, a gradient of free arginine groups can be introduced into a silk element before it is introduced into a lumen of a tubular body. In some embodiments, a gradient can be linear or non-linear. In some embodiments, a gradient can encourage nerve cell processes to detach from a silk fiber at a proximal end of a device.

In some embodiments, to encourage nerve cell processes to enter and leave a device it may be preferable to arrange a substantially longitudinally oriented plurality of silk elements so that they protrude 0.1 to 10 mm beyond one or both ends of a tubular body of a device lumen.

In some embodiments, a silk fiber can comprise a hydrophilic coating as disclosed herein. In some embodiments, a silk fiber can comprise part of a bundle as disclosed herein.

Disclosed herein in some embodiments, are compositions comprising a bundle. In some embodiments, a bundle can comprise a plurality of silk elements.

In some embodiments, a container, an element, or any combination thereof can comprise a hydrophilic substance. In some embodiments, an element can be at least partially coated in a hydrophilic substance. In some embodiments, an element can be at least partially held in place by a matrix. In some embodiments, a matrix can comprise a hydrophilic substance. In some embodiments, a silk element can be set in a lumen matrix. In some embodiments, a lumen matrix can comprise a resorbable biocompatible polymer. In some embodiments, a resorbable biocompatible polymer can comprise a hydrogel. In some embodiments, a hydrogel can comprise alginate, hyaluronic acid with or without polylysine, casein, or any combination thereof. In some embodiments, a lumen matrix can comprise an extracellular matrix (ECM). In some embodiments, an ECM can comprise a fibronectin, a laminin, or any combination thereof. In some embodiments, a material can be added to a lumen matrix in a conduit or coated onto a silk filament in a lumen matrix.

In some embodiments, a hydrophilic substance can comprise a polysaccharide, a glycosaminoglycan, an alginate, a casein, a protein, an ECM protein, an ECM protein product, a salt of any of these, or any combination thereof. In some embodiments, a polysaccharide or a salt thereof can comprise a carboxylic acid moiety or a salt thereof. In some embodiments, a polysaccharide or a salt thereof, wherein a polysaccharide or a salt thereof can comprise a hydroxyl group. In some embodiments, a polysaccharide or a salt thereof, wherein a polysaccharide or a salt thereof can comprise an amide or a salt thereof. In some embodiments, a polysaccharide or a salt thereof can comprise a hyaluronan or a salt thereof. In some embodiments, a hyaluronan can comprise a hyaluronic acid. In some embodiments, a glycosaminoglycan or a salt thereof can be combined with a laminin mimetic peptide or a salt thereof. In some embodiments, a matrix can comprise a hydrophilic substance in a matrix. In some embodiments, an element can be at least partially held within a matrix. In some embodiments, a matrix can be at least in part pH controlled, crosslinked, or any combination thereof. In some embodiments, a cross-linking agent can comprise genipin.

Disclosed herein in some embodiments, is a composition comprising a tubular body. In some embodiments, a composition can further comprise a plurality of silk proteins within a tubular body. In some embodiments, at least one individual silk protein can be at least partially coated with a first hydrophilic coating. In some embodiments, a plurality can be at least partially coated with a second hydrophilic coating. In some embodiments, a tubular body can comprise a cross-sectional diameter of about 0.1 mm to about 20 mm. In some embodiments, a tubular shape can comprise an external cross-sectional diameter of about 1 mm to about 25 mm. In some embodiments, a tubular shape can comprise an external cross-sectional diameter of about 25 mm to about 50 mm. In some embodiments, a tubular shape can comprise an external cross-sectional diameter of about 50 mm to about 100 mm. In some embodiments, a tubular shape can comprise a length of from about 0.1 cm to about 1 cm. In some embodiments, a tubular shape can comprise a length of from about 0.5 cm to about 10 cm. In some embodiments, a tubular shape can comprise a length of from about 5 cm to about 50 cm. In some embodiments, a tubular shape can comprise a length of from about 10 cm to about 120 cm. In some embodiments, a plurality of silk elements running substantially parallel to each other, wherein a plurality of silk elements can be at least partially continually spaced from one another along their length, wherein a plurality of silk elements can be coated substantially along a length of a elements with a hydrophilic substance that at least partly maintains continual spacing of a plurality of elements. In some embodiments, an element can comprise a fiber, a filament, a nano-filament, or any combination thereof. In some embodiments, an element can be treated so that it is hydrophilic.

Disclosed herein in some embodiments, is a group of silk proteins running substantially parallel to one another, wherein a group can comprise at least two subgroups of silk proteins, wherein a group can comprise a hydrophilic coating around at least part of a group, and at least one of a subgroups can comprise a hydrophilic coating around at least part of a subgroup. In some embodiments, a subgroup can comprise a further secondary subgroup, and wherein a secondary subgroup can comprise a hydrophilic coating around at least part of a secondary subgroup. In some embodiments, a secondary subgroup can comprise a further tertiary subgroup, and wherein a tertiary subgroup comprise a hydrophilic coating around at least part of a tertiary subgroup.

Disclosed herein in some embodiments, is a method comprising submerging each of a plurality of silk proteins in a hydrophilic substance individually, and submerging a plurality of silk proteins in a hydrophilic substance while one or more fibers can be substantially in contact with each other. In some embodiments, a hydrophilic substance can be dried on an individual fibers prior to submerging a plurality of silk proteins in a hydrophilic substance while a fibers can be substantially in contact with each other.

Disclosed herein in some embodiments, is a method comprising at least partially coating a bundle comprising a plurality of silk proteins with a hydrophilic coating, wherein each individual silk protein in a bundle can comprise a hydrophilic coating at least partially around an individual silk protein.

Disclosed herein in some embodiments, are constituents. In some embodiments, a composition as disclosed herein can comprise an additional constituent. In some embodiments, a container, an element, or any combination thereof can comprise an additional constituent.

In some embodiments, an additional constituent can comprise a microtubule, an actin filament, a neurofilament, a nestin, or any combination thereof. In some embodiments, a container can comprise a greater concentration of microtubules and actin filaments at a proximal end, and a greater concentration of neurofilaments at a distal end.

In some embodiments, an additional constituent can comprise a growth factor, an elastomer, a peptide, a cytokine blocker, a free-radical binder, an anti-inflammatory, a membrane stabilizer, a corticosteroid; a salt of any of these; an isolated cell; or any combination thereof.

In some embodiments, a growth factor or a salt thereof can comprise a brain-derived neurotrophic factor, a nerve growth factor, a neurotrophin-3, a neurotrophin-4, a ciliary neurotrophic factor, a glial cell line-derived neurotrophic factor, an artemin, a neurturin, a salt of any of these, or any combination thereof. In some embodiments, an additional constituent can comprise a neurotrophic factor. In some embodiments, a neurotrophic factor can comprise a glial cell-derived neurotrophic factor (GDNF), a nerve growth factor (NGF), a salt of any of these, or any combination thereof.

In some embodiments, an elastomer can comprise a synthetic elastomer, a biological elastomer, or any combination thereof. In some embodiments, an elastomer can be functionalized to control physical properties or biological binding.

In some embodiments, a peptide or a salt thereof binds to a growth factor. In some embodiments, a peptide or a salt thereof that binds to a growth factor can comprise a laminin. In some embodiments, a peptide or a salt thereof that binds to a growth factor or a salt thereof can be known to bind to nerve regenerating growth factors. In some embodiments, a peptide that binds to a growth factor, increases a concentration of a growth factor at an injury site.

In some embodiments, a cytokine inhibitor can comprise a chemokine inhibitor, a compound that targets a cholinergic anti-inflammatory pathway, a platelet activating factor (PAF) inhibitor, an HMGB1 antibody, a resolvin, a lipoxin, a protectin, a COX-2 inhibitor, a compound targeting a chemokine, a compound targeting a T-reg cell, a prostaglandin, a prostaglandin E2 cyclooxygenase inhibitor, a salt of any of these, or any combination thereof.

In some embodiments, a free-radical binder can comprise an enzyme, an antioxidant, a salt of any of these, or any combination thereof.

In some embodiments, an anti-inflammatory can comprise an aspirin, an ibuprofen, a naproxen, a celecoxib, a diclofenac, a diflunisal etodolac, a famotidine/ibuprofen, a flurbiprofen, a indomethacin, a ketoprofen, a mefenamic acid, a meloxicam, a nabumetone, an oxaprozin, a piroxicam, a sulindac, a celecoxib, a salt of any of these, or any combination thereof.

In some embodiments, a membrane stabilizer can comprise a phosphatidylcholine membrane stabilizer.

In some embodiments, a corticosteroid can comprise a glucocorticoid or a mineralocorticoid.

In some embodiments, a corticosteroid can comprise a prednisone, a prednisolone, a triamcinolone, an aristospan intralesional, a methylprednisolone, a dexamethasone, a cortisol (hydrocortisone), a cortisone, a dexamethasone, a betamethasone, a triamcinolone, a fludrocortisone acetate, a deoxycorticosterone acetate, a corticosterone, an aldosterone, a deoxycorticosterone, or any combination thereof.

In some embodiments, an additional constituent can comprise an isolated cell. In some embodiments, an isolated cell, can comprise a Schwann cell, an at least partially multipotent cell, an at least partially pluripotent cell, a cell derived from an at least partially multipotent cell, a cell derived from an at least partially pluripotent cell, an hNGF-EcR-293 cell, a bone marrow stem cell (BMSC), or any combination thereof. In some embodiments, bone marrow stem cell can differentiate into a Schwann cell. In some embodiments, an isolated cell can comprise an hNGF-EcR-293 cell. In some embodiments an isolated cell can be genetically modified to deliver a growth factor in vitro or in vivo. In some embodiments, a container, an element, or any combination thereof can be seeded with an isolated cell.

In some embodiments, an additional constituent can comprise ions.

Disclosed herein in some embodiments, is a composition comprising a tube comprising silk proteins with a proximal end and a distal end, wherein at least part of a tube can comprise an additional constituent, wherein an additional constituent can be distributed in a gradient from a proximal end to a distal end, and wherein an additional constituent encourages a growth of an axon. In some embodiments, a gradient can comprise a chemotactic gradient, a diffusible gradient, an adherent gradient, or any combination thereof. In some embodiments, an additional constituent increases in concentration from a proximal end to a distal end. In some embodiments, an additional constituent decreases in concentration from a proximal end to a distal end. In some embodiments, an additional constituent can comprise microtubules, actin filaments, neurofilaments, nestin, or any combination thereof. In some embodiments, a tube can comprise a greater concentration of microtubules and actin filaments at a proximal end, and a greater concentration of neurofilaments at a distal end. In some embodiments, an additional constituent can comprise a growth factor, a hormone, a peptide, a small molecule, a drug, a genetic vector, or any combination thereof. In some embodiments, a growth factors, cytokine inhibitors, or any combination thereof.

In some embodiments, constituents can be growth factors, cytokines, antibiotics, immunosuppressants, steroids, non-steroidal anti-inflammatory drugs (NSAIDs), or any combination thereof.

In some embodiments, growth factors can comprise nerve growth factors. For example, nerve growth factors may be added to a lumen matrix surrounding a filament. In some embodiments, where a device is to be used to enhance a recovery of peripheral nerves, a nerve growth factor or a salt thereof can comprise peripheral nerve NGF. In some embodiments, where a device is to be used in a brain or spinal cord, a nerve growth factor or a salt thereof can comprise central nerve neurotrophin-3 (NT3), brain derived neurotrophic factor (BDNF), a salt of either of these, or any combination thereof. In some embodiments, other drugs or factors to promote nerve regeneration or to suppress a formation of glioma or fibrosis can be added to a lumen matrix surrounding a plurality of filaments. In some embodiments, drugs and other factors to enhance a function of a device can also be added to a matrix of a silk composite tube.

In some embodiments, an additional constituent can comprise an antibiotic, an immunosuppressant, a steroid or non-steroid anti-inflammatory drugs (NSAIDs), a biologically active substance, or any combination thereof. In some embodiments, a biologically active substance can include, a cAMP enhancer (such as rolipram or db-cAMP) to promote regeneration, a molecule that reduces scar formation such as TFGβ antisera and/or chondroitinase, or molecules that reduce myelin inhibition, e.g. anti-Nogo treatments.

In some embodiments, cells may be added to a device, such as Schwann cells or olfactory ensheathing cells (OECs) to assist in myelination of nerve re-growth and/or neural stem cells. In some embodiments, other cell types could also be added as required. In some embodiments, a cell can be endogenous cells from a patient into whom a device is to be implanted, or the cells can be exogenous cells from an external source, e.g. cells grown in culture. In some embodiments, cells may be autologous or non-autologous with respect to an immune system of patient.

Disclosed herein in some embodiments, is a method comprising contacting an at least partially frozen solution comprising silk with a porogen. In some embodiments, a porogen can comprise a polyether, an acid, a salt, a natural polymer, a synthetic polymer, any salt thereof, or any combination thereof.

In some embodiments, an acid can comprise an acetic acid.

In some embodiments, a polyether can comprise a polyethyleneglycol (PEG) or a salt thereof. In some embodiments, a polyethyleneglycol cisphenol A epichlorohydrin copolymer or a salt thereof.

In some embodiments, a salt can comprise sodium chloride, sodium bicarbonate, potassium dichromate, calcium chloride, sodium bisulfate, copper sulfate, or any combination thereof.

In some embodiments, a natural polymer, wherein a natural polymer can comprise a saccharide, a polysaccharide, any salt thereof, or any combination thereof.

In some embodiments, a synthetic polymer, wherein a synthetic polymer can comprise a polypropylene or a salt thereof.

In some embodiments, a method can further comprise freeze drying an at least partially frozen solution. In some embodiments, a method can further comprise crystallizing an at least partially frozen solution. In some embodiments, freezing can occur during a semi-continuous flow manufacturing process. In some embodiments, a semi-continuous flow manufacturing process can comprise an extrusion process. In some embodiments, a freezing occurs at least partially in an extrusion die. In some embodiments, a method can comprise drawing a silk elements through a second extrusion die. In some embodiments, drawing a silk element through a second extrusion die can at least partially remove excess hydrogel. In some embodiments, a silk element can be at least partially air-dried. In some embodiments, a method can further comprise drawing a silk elements through a third extrusion die. In some embodiments, drawing a silk element through a third extrusion die at least partially adds a coating of concentrated viscous collagen or concentrated regenerated silk protein or any combination thereof. In some embodiments, a method can further comprise contacting a silk elements with an acid. In some embodiments, a contacting at least partially gels a fibroin, a collagen, or any combination thereof. In some embodiments, an extrusion die can comprise an annular extrusion die.

Disclosed herein, in some embodiments, is a composition comprising an at least partially frozen solution comprising a silk protein, and a polyether, a carboxylic acid, a salt of any of these, or any combination thereof.

In some embodiments, a polyether can comprise a polyethyleneglycol (PEG), or a salt thereof. In some embodiments, a polyethyleneglycol can comprise polyethyleneglycol cisphenol A epichlorohydrin copolymer, or a salt thereof.

In some embodiments, a carboxylic acid or a salt thereof can comprise acetic acid or a salt thereof.

Disclosed herein in some embodiments, is a method comprising at least partially freezing a solution comprising a silk protein in a tubular shape using a mold. In some embodiments, a method can comprise at least partially freezing a solution one or more times to form an at least partially frozen solution. In some embodiments, a method can further comprise contacting an at least partially frozen solution with a gelling agent. In some embodiments, a freezing or a contacting can occur at least partially in a mold. In some embodiments, a mold can comprise a solid inner component, a solid outer component, and a space in between a solid inner component and a solid outer component. In some embodiments, a solid inner component can comprise a substantially cylindrical or helical shape. In some embodiments, a solid outer component can comprise a substantially cylindrical shape. In some embodiments, a mold further can comprise an extrusion die mold, an extruder, a screw, a heater, a freezer, a die, an orifice, or any combination thereof. In some embodiments, a solution can comprise fibroin, spidroin, or any combination thereof. In some embodiments, a tubular body can comprise a cross-sectional diameter of about 0.1 mm to about 20 mm. In some embodiments, a tubular shape can comprise an external cross-sectional diameter of about 1 mm to about 25 mm. In some embodiments, a tubular shape can comprise an external cross-sectional diameter of about 25 mm to about 50 mm. In some embodiments, a tubular shape can comprise an external cross-sectional diameter of about 50 mm to about 100 mm. In some embodiments, a tubular shape can comprise a length of from about 0.1 cm to about 1 cm. In some embodiments, a tubular shape can comprise a length of from about 0.5 cm to about 10 cm. In some embodiments, a tubular shape can comprise a length of from about 5 cm to about 50 cm. In some embodiments, a tubular shape can comprise a length of from about 10 cm to about 120 cm.

Disclosed herein in some embodiments, are methods of manufacturing a medical device comprising forming a tubular body and introducing a plurality of silk elements into a lumen of a tubular body. In some embodiments, a plurality of silk elements can be introduced so as to lie substantially parallel along a long axis of a lumen of a tubular body.

In some embodiments, formation of a tubular body can further comprise preparing a former on which a tubular body can be formed; laying down fibers on a former; applying a matrix to a plurality of silk fibers to form a composite body; and removing a former.

In some embodiments, formation of a tubular body can also comprise cross-linking a matrix. In some embodiments, a lumen matrix component can be introduced between a plurality of silk elements within a lumen of a tube.

In some embodiments, silk elements may be washed with a solution of a chelating agent. In some embodiments, a solution of chelating agent can comprise ethylene diamine tetra-acetic acid (EDTA) sodium salt to remove possible contaminants, such as transition metal ions which may be toxic.

In some embodiments, a silk can be degummed. In some embodiments, degumming can comprise treatment of a silk using a protease. In some embodiments, a protease can comprise a mild proteolytic enzyme. In some embodiments, a mild proteolytic enzyme can comprise subtilisin. In some embodiments, an enzyme can be washed out after treatment.

In some embodiments, a medical device can be constructed from biocompatible, resorbable material whose ability to provide binding sites for growing nerve axons, Schwann cells and glial cells can be tuned.

In some embodiments, a medical device can comprise a silk composite tube open at both ends and containing orientated silk filaments within its lumen. In some embodiments, a wall of a composite tube can comprise a substantially uniform thickness. In some embodiments a diameter can range in size depending on a location into which a device is to be implanted.

In some embodiments, a silk composite tube can comprise fine non-mulberry silk silver filaments laid in a helical pattern. In some embodiments, a helical pattern can comprise a crossing angle of approximately 55°. In some embodiments, silk filaments can be set in a matrix of regenerated silk fibroin. In some embodiments, regenerated silk fibroin can comprise redissolved silk fibroin. In some embodiments, regenerated silk fibroin can be obtained from mulberry or non-mulberry silk worms. In some embodiments, other resorbable biocompatible filaments, resorbable biocompatible matrices, or any combination thereof can be used. In some embodiments, a matrix can be substantially composed of native silk fibroin extracted from a silk gland of mulberry or non-mulberry silkworms. In some embodiments, a matrix is stabilized by covalent cross-links. In one embodiment this is achieved by treating with formaldehyde gas, but other cross-linking agents could be used. In a further embodiment a silk composite tube can be prepared from a braided silk tube prepared directly from 1 or 7-13 bave degummed non-mulberry silk using a braiding machine. In some embodiments, a silk can comprise a density of about 1 bave, about 2 bave, about 3 bave, about 4 bave, about 5 bave, about 6 bave, about 7 bave, about 8 bave, about 9 bave, about 10 bave, about 11 bave, about 12 bave, about 13 bave, about 14 bave, about 15 bave, about 16 bave, about 17 bave, about 18 bave, about 19 bave, about 20 bave, about 21 bave, about 22 bave, about 23 bave, about 24 bave, about 25 bave, about 30 bave, about 40 bave, about 50 bave, about 60 bave, about 70 bave, about 80 bave, about 90 bave, about 100 bave, or any combination thereof. In some embodiments, a silk can comprise a density of about 1 denier, about 2 denier, about 3 denier, about 4 denier, about 5 denier, about 6 denier, about 7 denier, about 8 denier, about 9 denier, about 10 denier, about 11 denier, about 12 denier, about 13 denier, about 14 denier, about 15 denier, about 16 denier, about 17 denier, about 18 denier, about 19 denier, about 20 denier, about 21 denier, about 22 denier, about 23 denier, about 24 denier, about 25 denier, about 30 denier, about 40 denier, about 50 denier, about 60 denier, about 70 denier, about 80 denier, about 90 denier, about 100 denier, or any combination thereof. In some embodiments, a braided silk tube can be treated with a solution of one or more resorbable biocompatible polymers such as regenerated mulberry or non-mulberry silk to form a matrix between a plurality of silk threads of a braided silk tube.

In some embodiments, a silk composite tube contains non-mulberry silk filaments set in a lumen matrix containing hyaluronic acid (other lumen matrix materials include hydrogels such as hyaluronic acid with polylysine, alginate with or without polylysine and casein). In some embodiments, filaments can be orientated substantially longitudinally with respect to a long axis of a silk composite tube and can be cut off flush with the ends of a tube. In further embodiments a plurality of silk filaments and lumen matrix either extend a short distance beyond an end of a tube or end a short distance short of an end of a tube. In some embodiments, filaments can be packed together in a lumen of a tube with a density of 1 to 10 filaments per 10,000 $\mu m^2$ giving an average spacing of approximately 30 to 100 μm between a filament, but lower density packings can be used.

In some embodiments, a length of a medical device can be prepared to be inserted into a brain or spinal cord with an aim of encouraging a repair of injured or degenerated white matter. In some embodiments, a medical device can be used in conjunction with cell seeding techniques with an aim of directing and encouraging implanted neurons, formed from implanted neuroblast stem cells, to connect to appropriate parts of a central nervous system.

In some embodiments, biologically active substances or cells can be added to a container. In some embodiments, a concentration gradient (linear or non-linear) may be established with a higher concentration of substance or cells at one end (e.g. a proximal end) as opposed to another end (e.g. a distal end) of a container. In some embodiments, a depot of substances or cells can be added to only one end of a device.

In some embodiments, a medical device can comprise orientated silk filaments. In some embodiments, a medical device can comprise orientated silk filaments with no container. In some embodiments, orientated silk filaments can be set in a resorbable matrix. In some embodiments, orientated silk filaments can be implanted into a subject. In some embodiments, a silk composite tube can be omitted and orientated silk filaments set in a resorbable matrix can be implanted directly.

In some embodiments, appropriate diameter device for implantation can be selected according to a diameter of a nerve or white matter tract to be repaired. In some embodiments, an appropriate length of a device can be cut off with a sharp blade or other instrument. In some embodiments, a device can be at least partially held in place by one or more sutures. In another embodiment a device can be at least partially held in place with fibrin glue. In some embodiments, device can be implanted dry or can be soaked for five minutes to five hours in an appropriate physiological saline solution before use.

In some embodiments, a composition disclosed herein can be part of a kit. In some embodiments, a kit can comprise a packaging, instructions, or any combination thereof. In some embodiments, a packaging can be at least partially sterile. In some embodiments, instructions can comprise instructions for storage, implantation into a subject, or any combination thereof.

In some embodiments, disclosed herein a device can be used to treat an injury. In some embodiments, an injury can comprise a nerve injury. In some embodiments, a nerve lesion or injury can be in a body part. In some embodiments, a body part can comprise an arm, elbow, forearm, wrist, palm, finger, thumb, leg, foot, toe, spine, or any combination thereof. In some embodiments, a nerve can comprise a nerve cell, an axon, a peripheral nerve, or any combination thereof. In some embodiments, an injury can be caused by trauma or surgery. In some embodiments, an injury can lead to a loss of sensation, movement, or any combination thereof. In some embodiments, a loss of sensation, movement, or any combination thereof can be dependent on a site of injury. In some embodiments, a rate and extent of recovery can be slow, incomplete, variable, or any combination thereof. In some embodiments, a loss of function can cause distress to a subject. In some embodiments, an injury to a cavernosal nerve can cause male impotence. In some embodiments, a spinal transection across a spinal cord can cause paralysis, wasting of voluntary muscles, complete sensory loss in dermatomes supplied caudad to a transection, or any combination thereof. In some embodiments, loss of control of urinary and rectal sphincters can result in double incontinence. In some embodiments, transections within an upper neck vertebrae can lead to paralysis of a diaphragm as it is innervated from phrenic nerve emerging from a third to fifth neck vertebrae. In some embodiments, an injury paralysis of intercostal muscles (innervated by thoracic nerves) can stop breathing movements. In some embodiments, an injury can cause potentially fatal consequences. In some embodiments, it can be necessary to ventilate a subject with an injury for the rest of a subject's life. In some embodiments, degenerative diseases can cause degeneration of nerve tracks in a central nervous system. In some embodiments, degeneration of nerve tracks can comprise Parkinson's disease or multiple sclerosis. In some embodiments, degeneration of nerve tracks can lead to debilitating and highly distressing conditions such as motor impairment, sensory loss and reduction in arousal.

In some embodiments, a peripheral injury comprise transection of a nerve. In some embodiments, an injury can be described as neurotmesis. In some embodiments, a clinical definition of an injury can be referred to under the "Sunderland System" as either fourth-degree or fifth-degree neurotmesis. In some embodiments, fourth-degree neurotmesis can comprise an interruption of all neural and supporting elements. In some embodiments, an epineurium can be intact. In some embodiments, a nerve can be enlarged. In some embodiments, fifth-degree neurotmesis can comprise complete transection with a loss of continuity of a nerve.

In some embodiments, some degree of recovery after peripheral nerve injury can occur. In some embodiments, a recovery can result from regrowth of axons, reconnection of axons, or any combination thereof.

Disclosed herein in some embodiments, are methods of treating a subject. In some embodiments, a method can comprise implanting a composition or medical device as disclosed herein into a subject. In some embodiments, implanting into a subject can comprise implanting in a space previously at least partially occupied by at least a portion of a nerve cell. In some embodiments, a nerve cell can be severed. In some embodiments, a device can be implanted in proximity to an at least partially severed nerve cell. In some embodiments, a method can comprise a method of at least partially reconnecting a severed nerve cell. In some embodiments, a gap over which a severed nerve cell can be reconnected can be greater than about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, or about 20 cm. In some embodiments, a gap over which a severed nerve cell can be reconnected can be from about 6 cm to about 20 cm. In some embodiments, a device can at least partially be placed in an electromagnetic field after implanting in a subject. In some embodiments, a medical device can be stimulated by an electrical current, an electromagnetic field, an ultrasound, or any combination thereof. In some embodiments, an ultrasound can comprise a low intensity pulse ultrasound (US).

In some embodiments, a method can at least partially restore a function of a limb of a subject. In some embodiments, at least partial restoration of function of a limb can comprise an at least partially improved ability to extend a limb, an at least partially improved control of a limb, an at least partial increase in sensation in a limb, or any combination thereof.

In some embodiments, a regeneration of a nerve can be assessed. In some embodiments, an assessment can comprise a functional evaluation of vibrissae movements and electrophysiological assessment, retrograde labeling of facial motor neurons, morphological analysis, or any combination thereof. In some embodiments, a degree of nerve regeneration, functional recovery of peripheral nerve lesions, or any combination thereof can be determined by functional analysis, histology, microscopy, a level of a functional recovery of a body part of a subject, or any combination thereof. In some embodiments, a functional recovery of a body part of a subject can be determined by electrophysiological examination, sciatic nerve functional index evaluation, morphological analysis, a measurement, or any combination thereof.

In some embodiments, a measurement can comprise measuring a density of Schwann cells, a density of axons, an extent of nerve regrowth, a muscle mass, tract tracing, a percentage of neurite bearing cells, a median neurite length, a degree of conductivity of a nerve, an axonal density, an axonal diameter in distal segments, a neurite length, a neurite formation, a number of neurite-bearing cells, a number of myelinated nerve fibers, a number of unmyelinated nerve fibers, a creatine phosphokinase level, an indicator of tissue activity in muscle, a trophic factor expression, an increase in a weight of a muscle, a concentration of creatine phosphokinase enzyme, a subject's grip strength, microscopy of a tissue, a regeneration of both myelinated and unmyelinated axons, an amount of vascularized nerve tissue, compound muscle action potentials, motor-evoked potentials, somatosensory-evoked potentials, or any combination thereof.

In some embodiments, electrophysiological examinations can measure restoration of evoked electromyograms, sensory-evoked potentials, or any combination thereof. In some embodiments, electrophysiological examinations can be recorded from a cerebral cortex, a spinal cord, a peripheral nerve, or any combination thereof.

In some embodiments, a compound muscle action potential, a motor-evoked potential, a somatosensory-evoked potential, a latency, or any combination thereof can indicate a functional establishment of a nerve connection with a target organ.

In some embodiments, a medical device as described herein can guide or assist orientation of nerve fibers. In some embodiments, a regeneration can be assisted by a release of a growth factor and/or by the activity of an endogenous Schwann cell. In some embodiments, regeneration can comprise regeneration of a myelinic membrane. In some embodiments, a sciatic nerve trunk can be reconstructed with restoration of nerve continuity and formatted nerve fibers with myelination. In some embodiments, a repair of peripheral nerves can occur over a time period. In some embodiments, a time period can comprise about 1 week, about 2 weeks, about 3 weeks, about 4 weeks, about 2 months, about 3 months, about 4 months, about 5 months, about 6 months, about 7 months, about 8 months, about 9 months, about 10 months, about 11 months, about 1 year, about 2 years, about 3 years, about 4 years, or about 5 years.

In some embodiments, after an implantation, an inner surface of a container can remain intact during a regeneration time. In some embodiments, an inner surface remaining intact can prevent an ingrowth of connective tissues. In some embodiments, functional recovery, electrophysiological testing, retrograde labeling, immunohistochemistry analysis, or any combination thereof can be used to determine a nerve conduction velocity, a regenerated myelin area, a myelinated axon count or any combination thereof.

In some embodiments, a medical device can comprise an isolated at least partially decellularized vein that can be xenogeneic to a subject. In some embodiments, a medical device can comprise an isolated at least partially decellularized vein that can be autologous to a subject into which a medical device is implanted. In some embodiments, a nerve cell body that can be targeted for at least partial in vivo axonal regrowth, can be positioned closest to a proximal end of a container. In some embodiments, a container can comprise an outer surface that at least partially prevents a container adhering to a subject into which a container can be implanted. In some embodiments, an outer surface can at least partially prevent fibrillation of a tissue in contact with a container, integration of a container to a subject, or any combination thereof.

In some embodiments, a composition can be implanted in a space previously at least partially occupied by a nerve cell. In some embodiments, a nerve cell can be severed. In some embodiments, a device can be implanted in proximity to an at least partially severed nerve cell. In some embodiments, a method can comprise a method of at least partially reconnecting a severed nerve cell. In some embodiments, a severed nerve cell at least partially regenerates while at least partially in contact with a composition. In some embodiments, a silk element can be at least partially degraded by a nerve cell. In some embodiments, a gap over which a severed nerve cell can be reconnected can be greater than about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, or about 20 cm. In some embodiments, a gap over which a severed nerve cell can be reconnected can be from about 6 cm to about 20 cm. In some embodiments, a composition can be at least partially placed in an electromagnetic field after an implanting in a subject. In some embodiments, a method at least partially restores a function of a limb of a subject. In some embodiments, at least partial restoration of function of a limb can comprise an at least partially improved ability to extend a limb, an at least partially improved control of a limb, an at least partial increase in sensation in a limb, or any combination thereof. In some embodiments, a composition further can comprise an isolated at least partially decellularized vein that can be xenogeneic to a subject. In some embodiments, a composition further can comprise an isolated at least partially decellularized vein that can be autologous to a subject. In some embodiments, a nerve cell body that can be targeted for at least partial in vivo axonal regrowth, can be positioned closest to a proximal end of a container.

In some embodiments, compositions and methods as described herein can assist reconnection after spinal transection. In some embodiments, compositions and methods as described herein can assist reconnection in a brain after serious injury to nerve tracts.

In some embodiments, use of a method or composition as described herein can be used for treatment of an injury as described herein. In some embodiments, a treatment can ameliorate a symptom of an injury. In some embodiments, a method or composition as disclosed herein can encourage a repair of nerves and nerve tracts. In some embodiments, use of a device as disclosed herein can restore a function of a muscle, a limb, or any combination thereof.

In some embodiments, an injured peripheral nerve can be treated surgically. In some embodiments, a surgical treatment can comprise direct resuturing of abutted ends; autograft replacement; a use of various materials, or any combination thereof. In some cases, various materials can comprise natural or synthetic materials designed to guide nerve reconnection.

In some cases, an approach can be limited. In some cases, it may be difficult to bring cut ends of a nerve sufficiently close to suture them. In some cases, a resulting scar tissue resulting from injury and surgical manipulation can prevent axons from crossing an anastomotic region. In some cases, a prevention of axons crossing an anastomotic region can cause a tangled knot of nerve tissue known as a neuroma. In some cases, where a gap is too long an autograft can be suitable. In some cases, an autograft can comprise, suturing a portion of a patient's sural nerve harvested from an uninjured site and sutured in to replace an injured region of a nerve. In some cases, a disadvantage of an approach can include loss of sensation resulting from removal of a donor tissue graft, increased pain, impracticality of removing a sufficiently long graft where there can be a long injured section to be replaced, increased risk of infection at a graft removal site, an additional scar, or any combination thereof. In some cases, a further repair procedure can be time consuming and can require a great deal of skill. In some embodiments, a composition as disclosed herein can produce superior results to a variety of alternative nerve graft materials that have been used to attempt to provide channels for axon growth, and prevent infiltration with fibroblasts and neuroma formation. In some embodiments, a variety of alternative nerve graft materials can include empty perineurium, cuffs, conduits, wrappers, tubes, decalcified bone, vessels, fascia, fat, muscle, fibrin, parchment, gelatin, various metals, or any combination thereof. In some embodiments, compositions and methods as described herein can prevent failure resulting from fibrosis induced by a tissue injury and an implanted material. In some embodiments, compositions and methods as described herein can prevent a further surgical procedure required for removal of a non-resorbable material.

In some embodiments, compositions as disclosed herein can comprise an improvement over early generation materials for providing conduits for an injured nerve. In some embodiments, an early generation material for providing a conduit for an injured peripheral nerve can comprise a silastic cuff, a silicone rubber sheathing, a bioresorbable polyglactin mesh tubing, a semipermeable acrylic copolymer tube, an empty perineurial tube, a channel for bridging a nerve gap, a bioresorbable nerve guidance channel, a polyglycolic acid as an artificial perineurium, a longitudinally-ridged hollow conduit, a biocompatible and bioresorbable biopolymeric material, a multi-walled hollow conduit with micro-porous walls made from type I collagen, a sheet or tube with longitudinal ridges or tubes containing poly (vinyl alcohol) aimed at stimulating nerve regeneration, a resorbable tube made from either polyglycolic acid, polylactic acid, poly (glycolic-lactic) copolymer or related synthetic resorbable materials and coated with gelatin or collagen and containing longitudinally oriented cross-linked collagen fibers coated with laminin, a tube in which spaces between collagen fibrils can be filled with a matrix gel, a biocompatible semi-permeable conduit containing a matrix derivatized by any one of three laminin sequences known to be important in cell binding, or any combination thereof.

In some embodiments, a bioresorbable nerve guidance channel can comprise a polyester, another polymer, or any combination thereof. In some embodiments, a matrix gel can comprise collagen, laminin, heparan sulfate proteoglycans, entactin, a growth factor, or any combination thereof.

In some embodiments, a composition or method disclosed herein can provide an improved stimulation of healing of peripheral nerves compared to a previously approved method of treatment. In some embodiments, a method or composition disclosed herein can stimulate a regeneration of a central nervous system (CNS) axon.

In some embodiments, disclosed herein is an implantable device which eliminates or substantially reduces many disadvantages associated with previous attempts at regeneration of peripheral nerve and central white matter.

In some embodiments, methods and compositions as disclosed herein can promote axonal regeneration. In some embodiments, promoting axonal regeneration can achieve functional recovery. In some embodiments, methods and compositions as disclosed herein can minimize a period of Wallerian degeneration. In some embodiments, Wallerian degeneration can be caused by an existence of Schwann cells, a secretion of neurotrophic factors (NTFs) after injury and during regeneration, an existence of a basal lamina: a specialized type of extracellular (ECM) matrix that acts as a scaffold for neural cells. In some embodiments, a distal nerve can also aid peripheral nerve regeneration by supplying neurotrophic factors for axonal regeneration. In some embodiments, components of an ECM can promote neurite elongation in vivo. In some embodiments, a tubular sheath as described herein can protect a regenerating axon from further damage during regeneration. In some embodiments, silk elements as described herein can encourage axonal regeneration. In some embodiments, a combination of a tubular sheath and silk elements can provide an environment that encourages axonal regeneration.

Disclosed herein in some embodiments, is a medical device as described herein for use in regeneration of nerve cells. In some embodiments, a medical device may find particular application in a regeneration of nerve cells in a spinal cord or in a peripheral nerve.

In some embodiments, a medical device can be used for treatment of a trauma or an injury to a nerve or nerves in a body of an animal. In some embodiments, a medical device can be used in both human medicine and in veterinary medicine. In some embodiments, a medical device can be used to aid or assist a regeneration of a sciatic nerve. In some embodiments, a sciatic nerve can be a largest nerve in a body. In some embodiments, in humans a sciatic nerve can be just under about 20 mm in diameter at its largest point. In some embodiments, a length of a suitable device for use in human medicine may vary but can be from about 10 mm to about 200 mm in view of clinically observed injuries to nerves requiring treatment.

In some embodiments, a medical device can be useful in re-establishing connections between injured or damaged nerves in a central nervous system or in a peripheral nervous system. In some embodiments, disclosed herein are means to reconstitute a nerve or spinal cord with an environment approximately similar to a cellular/extracellular environment that was present before an injury to a nerve. In some embodiments, in a peripheral nerve injury, a device can aid or assist myelinating Schwann cells. In some embodiments, Schwann cells can be required for proper conduction of electrical impulses in axons and extracellular matrix molecules. In some embodiments, extracellular matrix molecules can comprise laminin. In some embodiments, a medical device can comprise extracellular matrix components (ECMs). In some embodiments, ECM components can comprise fibronectin, laminin, or any combination thereof. In some embodiments, a medical device can comprise exogenous cells. In some embodiments, exogenous cells can comprise Schwann cells.

EXAMPLES

Example 1: Dissolution of Silk Fibers from Silk Cocoons

Silk cocoons are used for fibroin extraction. By way of example only cocoons are immersed in 0.02 M $Na_2CO_3$ solution, with or without surfactants, and boiled. After washing out sericin residues using ultra-pure water, released fibroin fibers are placed on a supporting-mesh and air-dried for 24 h The resulting silk fibroin is dissolved in 9-9.5 M LiBr for 2-24 hours, giving a ~10% (w/v) silk fibroin solution. Dialysis is performed against ultrapure water for up to one week. Further dialysis against air can be used to increase the concentration and viscosity.

Example 2: Preparation of a Sheath

A sheath can be formed by casting of protein polymer solutions, such as regenerated silks, freshly cultivated silks, hyaluronic acid, gelatin, collagen or any biocompatible water soluble protein. The preferred material was shown to be created from 5-40% w/v, medical grade dialyzed, regenerated *Bombyx mori* solution.

*Bombyx mori* fibroin solutions were prepared by removal of sericins through enzymatic degumming and dissolving of the remaining fibroin proteins in concentrated LiBr at non-denaturing temperatures. Lithium bromide was removed via dialysis at 4° C. Tailoring of silk concentrations was achieved through dialysate evaporation. Cleaned and polished stainless steel rods of set specific diameters were coated (using a method such as painting, spraying or dipping) in the protein solution and allowed to air dry to give a non-porous tube.

In addition to the casting to create non-porous sheaths, porous sheaths were created by coating the stainless rods, with the option of using a full mold to define wall thickness. The coating solution was frozen, the resulting ice crystals then defined porosity. Chilled gelling agents were then applied to set the sheath. Gelling agents such as acetic acid with or without PEG that induce pH shifts are ideal. Optional further tailoring can be achieved with alcohol driven crystallization.

Another option is to incorporate a mesh either as silk threads, knit or full mesh mounted on a stainless steel rod with the dialysate to give a non-porous tube. Suitable materials include; silk silver, degummed single brave silk reeled from cocoons or degummed 7-13 bave 20-37 denier silk. The coating was allowed to dry before the tube was removed from the rod to give a non-porous tube. The addition of threads, mesh or knit enables suturability for the sheath. A non-mesh sheath may need to be gelled in place.

Further, porous sheaths with heightened flexibility were created using a lyophilization step post gelling. After freezing and gelling steps as described above, the sheaths were frozen and then lyophilized prior to crystallization. The silk tubes were slid off the stainless steel rod ready for device assembly.

Example 3: Sheath Gelling

Silk to be used for gelling was checked to ensure it was within its shelf life and was still viscous. ~4 mL of silk was poured into a syringe. A syringe with a larger nozzle was used to avoid shearing of the silk during extrusion. A 14G or 16G needle (rat sheath) or 4 mm rod (human/sheep sheath) was placed into the center of a cylinder shaped mold to set the desired internal diameter of the sheath and the mold was closed. The silk was injected slowly into the mold from the bottom until it started to pour from the top. The inlet and outlet were both sealed. The mold was placed in the freezer for 2 hours to freeze the silk into a solid. Ice crystals from the water in the silk solution induced a uniform porous structure in the frozen silk. The silk was removed from the freezer, and the outer mold was removed, leaving the solid silk on the internal needle or rod.

The frozen silk was placed immediately into chilled 2.25-5% PEG/2.5% AA solution and left for 30 minutes at 4-8° C. The acetic acid 'gelled' the silk, the change in pH allowing for unfolding and denaturing of the protein backbone, setting the proteins in place. As the frozen silk thawed, the ice crystals dissolved away, and the PEG in the gelling solution replaced the water in the pores, maintaining the porous nature of the sheath. The silk was then frozen for 30-60 minutes while still on the needle or rod. This allowed for the shape to be maintained, despite being gelled, as the silk was soft and prone to deformation. The silk was removed from the freezer and placed immediately in chilled 70% aqueous ethanol. The ethanol induced beta structures within the silk, setting the silk shape and creating a tough porous sheath.

The sheath was kept in ethanol at 4-8° C. for a minimum of 2 hours before use, but could be stored for up to 1 week in the ethanol. Prior to use, the sheath was rinsed thoroughly with ultrapure water.

Example 4: Sheath Gelling with Lyophilization

Silk to be used for gelling was checked to ensure it was within its shelf life and was still viscous. ~4 mL was poured into a syringe. A syringe with a larger nozzle was used to avoid shearing of the silk during extrusion. A 14G or 16G needle (rat sheath) or 4 mm rod (human/sheep sheath) was placed into the center of a cylinder shaped mold to set the desired internal diameter of the sheath and the mold was closed. The silk was injected slowly into the mold from the bottom until it started to pour from the top. The inlet and outlet were both sealed and the mold left to stand for 30 minutes to allow air bubbles to rise. The mold was placed in the freezer for 2 hours to freeze the silk into a solid. Ice crystals from the water in the silk solution induced a uniform porous structure in the frozen silk. The silk was removed from the freezer, and the outer mold was removed, leaving the solid silk on the internal needle or rod.

The frozen silk was placed immediately into chilled 2.25-5% PEG/2.5% AA solution and left for 30 minutes at 4-8° C. The acetic acid 'gelled' the silk, the change in pH allowing for unfolding and denaturing of the protein backbone, setting the proteins in place. As the frozen silk thawed, the ice crystals dissolved away, and the PEG in the gelling solution replaced the water in the pores, maintaining the porous nature of the sheath. The silk was then frozen for 30-60 minutes while still on the needle or rod. This allowed for the shape to be maintained, despite being gelled, as the silk was soft and prone to deformation. The frozen sheath was removed from the freezer and placed immediately in a freeze dryer. This allowed for sublimation of the remaining moisture in the sheath, keeping the pores completely open, and preventing any changes in structure prior to crystallization.

The silk was removed from the freeze dryer and placed immediately in chilled 70% aqueous ethanol. The ethanol induced beta structures within the silk, setting the silk shape and creating a tough porous sheath.

The sheath was kept in ethanol at 4-8° C. for a minimum of 2 hours before use, but could be stored for up to 1 week in the ethanol. Prior to use, the sheath was rinsed thoroughly with ultrapure water.

Example 5: Cross-Linking of Sheath

A crosslinking can be applied to a sheath of the device. This was done through vapor annealing; 0.1 ml/g paraformaldehyde was prepared by addition of ultrapure water paraformaldehyde, the solution was heated to 80° C., and the resulting vapor was applied across the sheath. Removal of harmful agents was achieved through ultrapure water rinsing or dialysis.

Example 6: Hydrophilic Coating of Silk Fibers into Primers, Dimers, and Trimers 6.1 Methods
6.1.1 Silk Element Bundling Silk element bundles with a cross section diameter of 10-20 μm were prepared into thicker diameter silk bundles by application of a hydrophilic coating. Silk elements were submerged in a 5 mg/ml hyaluronic acid solution for 2 minutes and withdrawn from the solution slowly. The silk elements were hung with light tension applied and allowed to air dry for 5 hours. Primer bundles of 3-4 silk elements were created by grouping the desired amount of coated silk elements together and dipping in a 5 mg/ml hyaluronic acid solution, air drying under tension allowed the bundles to solidify. Secondary dimer solutions were created in the same fashion by taking 3-6 primer bundles and binding them with a HA coating. Trimer bundles were the final stage of bundling production, in which 3-6 dimer bundles were grouped and bound using a hydrophilic coating comprising hyaluronic acid (HA).

6.1.2 Introducing Oriented Silk Elements/Silk Element Bundles into the Sheath

The silk elements or silk element bundles were inserted into the sheath. The desired nerve regenerating silk structure was threaded onto a needle. A lubricant was applied such as viscous hyaluronic acid to the silk elements/bundles to aid assembly. The sheath was filled with a matrix, such as aqueous hyaluronic acid, and the needle was threaded through the sheath. If further silk elements or bundles were required, the process was repeated. Packing density was measured by weight comparison of empty sheaths to filled sheaths.

Scanning electron microscopy indicated a packing density of 10 to 1 filaments per 10,000 $Pm^2$. In some cases, an average silk element spacing of approximately 30 to 100 Pm between the filaments can be optimal for uniformity within the lumen.

6.1.3 Addition of the Matrix to the Lumen of the Sheath

A matrix was used to hold silk element/element bundles in place. The matrix needed to withstand transporting and implanting of the device whilst maintaining the uniform distribution of the parallel silk elements housed in the sheath. Hydrogel was found to give suitable results as a stabilizing matrix and had proven characteristics conducive to nerve regrowth. Appropriate materials for the matrix included aqueous; hyaluronic acid with or without polylysine, alginate with or without polylysine, casein, fibrin glue, serum albumin, and gelatin. Insertion of the matrix could be manual.

6.1.4 Nerve Growth Factors (NGF)

Nerve growth factors to enhance recovery were introduced to the device during matrix insertion. Nerve growth factors such as neurotrophin-3 were added to the desired matrix prior to matrix insertion.

6.1.5 Preparation for Transport

The device can be transported dry as opposed to in a solvent. Rehydration prior to implantation can be done via soaking the device in a sterile saline solution. Gentle air drying can be used, or freeze drying may also be employed for a more radical drying. The device can then be cut to the desired length.

6.1.6 Implantation of the Devices

For peripheral nerves, a device is selected to the appropriate specification of the site being treated. The device can be glued or sutured in place.

6.2 Results

Silk provided a versatile medium with desired tensile properties, which can be tailored to provide a desired strength. The device design provided support for nerve regeneration. The device encouraged migration of axons into a lumen of a sheath, using silk elements/element bundles as a guide, axon growth was directed towards a distal stump using the shortest path. In addition, the presence of cell adhesion amino acid RGD groups in silk elements, increased nerve regeneration capabilities with specific binding tailored through locations of the RGDs on the silk backbone.

The device also had state based physical properties; being stiff when dry but plasticizing when wet to allow for the necessary flexibility and tensile strength similar to that of natural nerves, but gave a surgeon using the device options to work with the material in their preferred state.

The overall design produced a device that is easy to handle for surgeons, and the lumen contents did not move whilst the hydrogel matrix was applied. Bespoke lengths could therefore be conveniently and quickly cut, and once wet the hydrogel contributed to an environment optimal for neuronal regrowth.

Example 7: Device Assembly Using Silk Element Bundling Through Hydrophilic Coatings Device assembly can include adding a hydrophilic coating to the silk elements, and bundling the fibers together before insertion.

7.1 Applying Hydrophilic Coatings to the Silk Elements Prior to Assembly

Hydrophilic coatings can be applied to the silk elements prior to assembly. These allow for stability during transit when dry and hold the silk elements apart within the sheath when wet. Device assembly can be made easier and give more control over silk elements with the bundling of HA silk elements using a hydrophilic coating prior device assembly.

Device assembly through hydrophilic coating was tested. Silk elements were bundled into thicker fibers by creating a series of hydrophilic coatings upon sequentially increasing silk element bundles.

7.2 Methods

Singular silk elements were dipped in 5 mg/ml Hyaluronic Acid (HA) and air dried under light tension. Coated silk elements were bundled together into starting primers of 3 or 4 elements, these primers were coated and dried in the same manner as before. Secondary bundles containing 3-4 primers were created in the same fashion, termed dimers. Trimers containing 3-4 dimers were then created giving bundles containing 1-48 silk elements.

7.3 Results

TABLE 1

Numbers of silk elements in primer, dimer, and trimer bundles and diameters

| Primer | Dimer | Trimer | Total Silk Elements | Bundle diameter, μm |
|---|---|---|---|---|
| 1 | — | — | 1 | 28.06 |
| 3 | — | — | 3 | 67.59 |
| 4 | — | — | 4 | 77.07 |
| 3 | 3 | — | 9 | 90.68 |
| 4 | 4 | — | 16 | 153.61 |
| 3 | 3 | 3 | 27 | 165.61 |
| 4 | 3 | 3 | 36 | — |
| 4 | 4 | 3 | 48 | 272.48 |

Bundles were formed by submersion of single silk elements in a hyaluronic acid (HA) solution. Bundling had a significant effect on the mechanical properties and handling of the silk elements. The single or bundled elements were significantly tougher and stiffer when dried than compared to being soaked in a sterile saline solution. Once soaked in saline, swelling of the hydrophilic coating provided the bundles with exceptional elongation and flexibility. This allowed for easier transportation of the nerve conduits when dry, with the opportunity to presoak in sterile saline solution prior to implantation to give a more flexible nerve conduit.

Figure 1B:
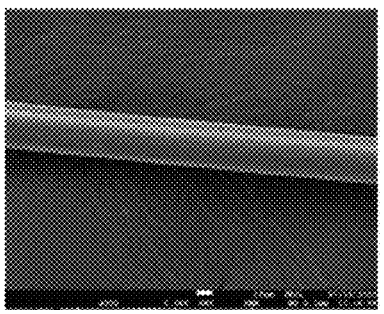
Figure 1C:
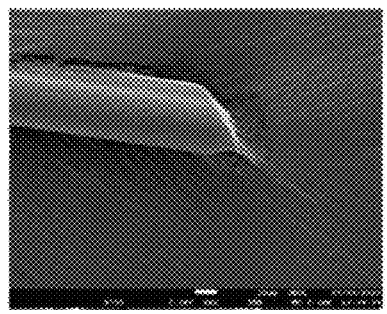
Figure 1D:
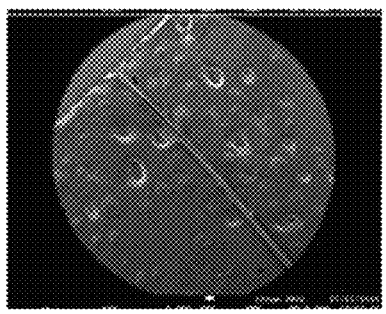
Figure 1E:
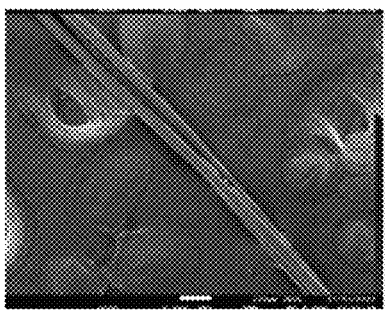
Figure 1F:
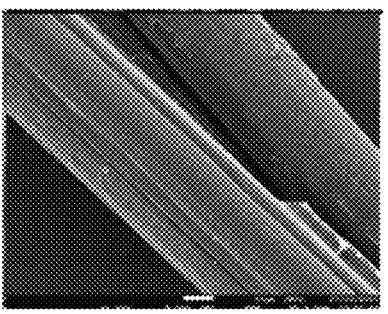
Figure 1G:
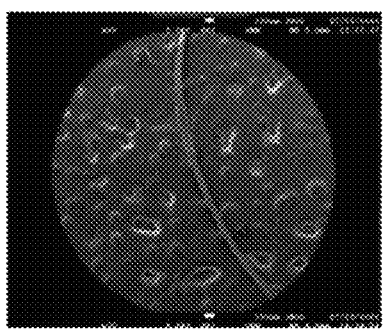
Figure 1H:
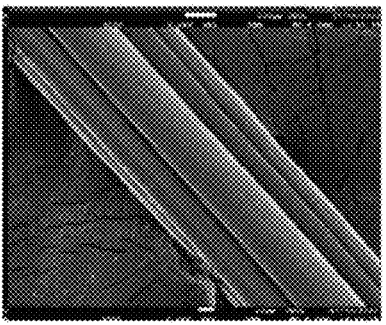
Figure 1I:
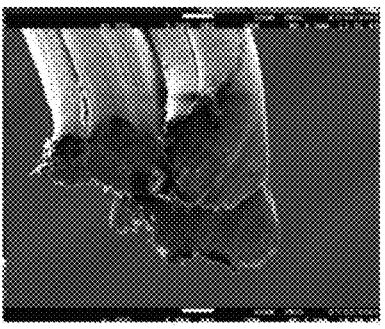
Figure 1J:
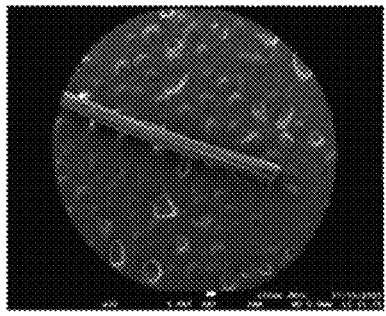
Figure 1K:
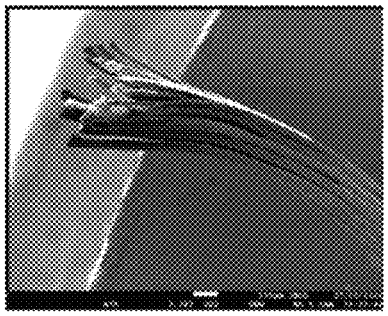
Figure 1L:
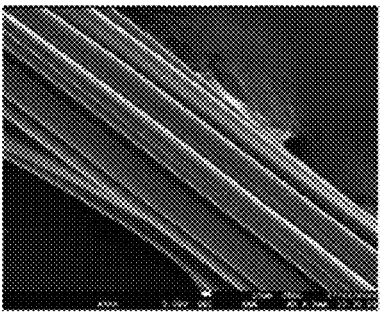

FIGS. 1A-L show bundles of silk elements created on a large scale to compare the mechanical properties with respect to bundle diameter and number of silk elements in each bundle. FIG. 1A, FIG. 1B, and FIG. 1C show a single coated fiber. FIG. 1D, FIG. 1E, and FIG. 1F show primer bundles of three. FIG. 1G, FIG. 1H, and FIG. 1I show dimer bundles of nine (three bundles of three silk elements). FIG. 1J, FIG. 1K, and FIG. 1L show trimer bundles of 48, (3 bundles of 4 bundles of 4 silk elements).

Figure 2A:
FIG. 2A shows a single hyaluronic acid coated silk element.
Figure 2B:
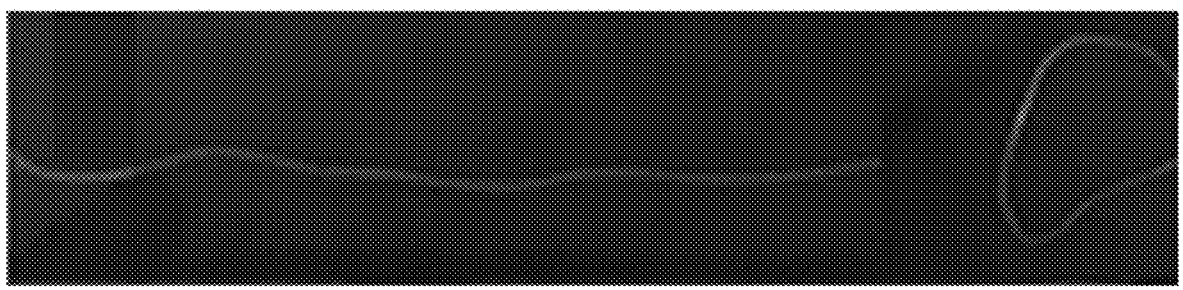
FIG. 2B shows a primer bundle of 3 hyaluronic acid coated silk elements.
Figure 2C:
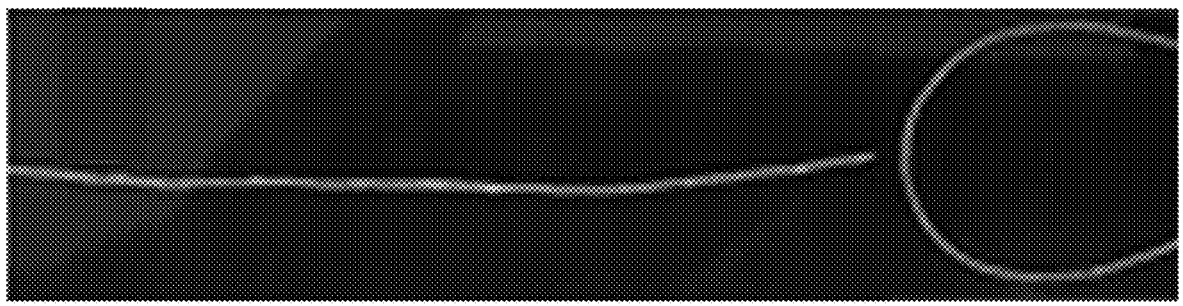
FIG. 2C shows a trimer bundle of 27 silk elements (3-3-3).
Figure 2D:
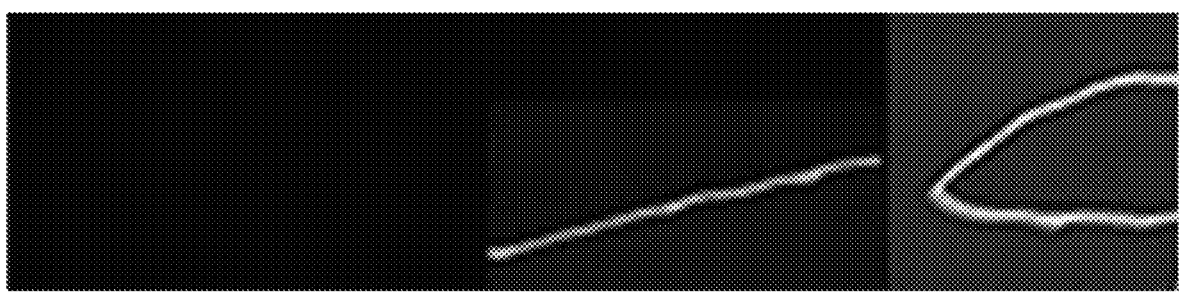
FIG. 2D shows a trimer bundle of 48 silk elements (4-4-3).
Figure 2E:
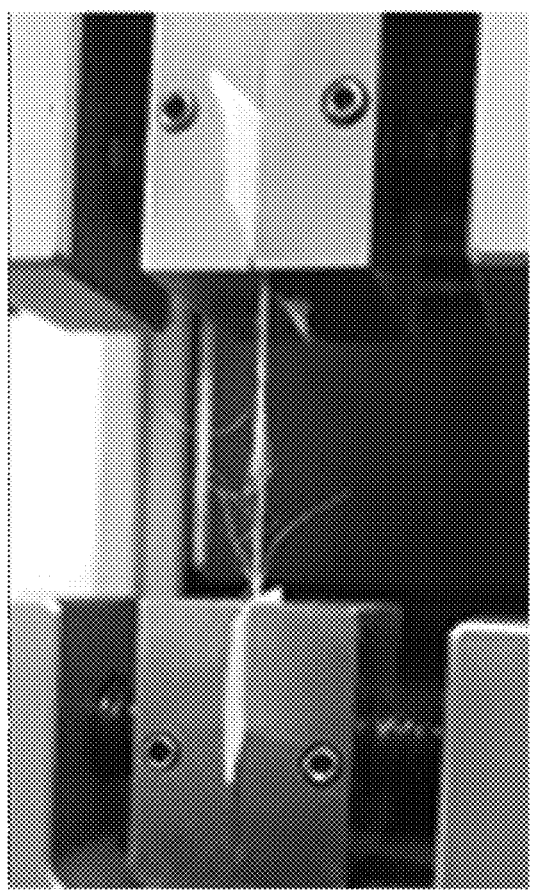
FIG. 2E shows tensile testing of a trimer showing splintering of fibers when excess force is applied.

Bundling of the fibers into primers improved mechanical properties in terms of Young's modulus and tensile and maximum strength, when compared to a single silk element coated in HA, as shown in FIGS. 2A-2E. FIG. 2A shows a single silk element coated in hyaluronic acid. FIG. 2B shows a primer bundle of 3 silk elements. FIG. 2C shows a trimer bundle of 27 silk elements (3-3-3). FIG. 2D shows a trimer bundle of 48 silk elements (4-4-3). FIG. 2E shows a tensile testing of trimer showing splintering of fibers when excess force was applied.

There was an additional increase in elongation also with no reduction in kink resistance. Further bundling into dimers and trimers gave no significant correlation in terms of Young's modulus, however a significant increase in dry and wet strengths was observed when comparing dimers to trimers. The largest bundle of 48 silk elements was the only fiber to show some kinking, with 1 in 3 bundles produced kinking under a <50° bend. This bundle showed the greatest strength and highest elastic modulus, suggesting that the number of silk elements included in the bundle can be chosen with the goal to predetermine the final mechanical properties of the bundle.

A comparison of construction steps (3 vs. 4 silk elements or bundles being used) was also completed. In some cases, a starting base of 3 silk elements as the primer can give better bundle properties, as bundles of 27 silk elements (3-3-3 construction) had higher strengths than that of the 36 silk element bundle constructed from a 4 primer base.

Figure 3A:
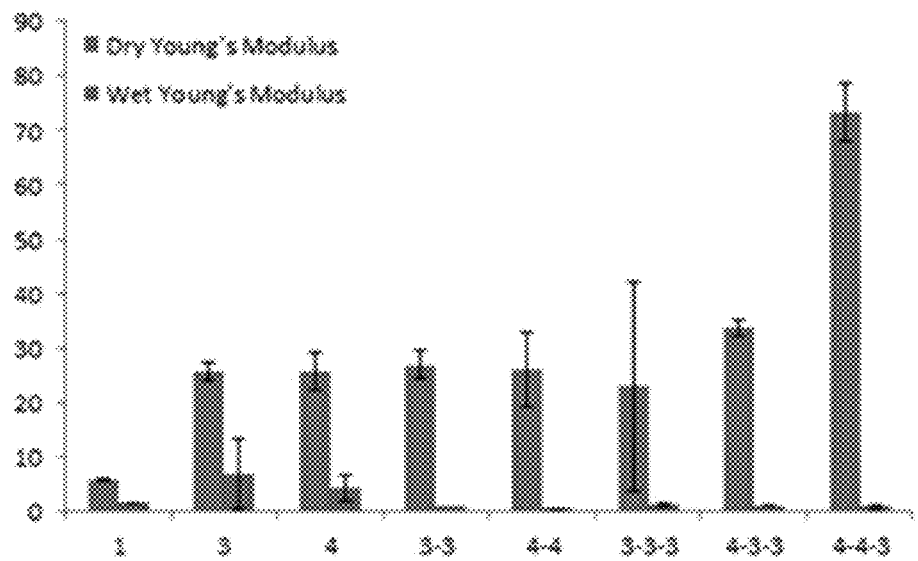
FIG. 3 shows a comparison of wet and dry measurements for silk element bundles. Bundling in different iterations was carried out and resulting fibers underwent tensile testing for FIG. 3A Young's Modulus, FIG. 3B Tensile Strength, FIG. 3C Maximum Strength (N/mm$^2$), and FIG. 3D Elongation.
Figure 3B:
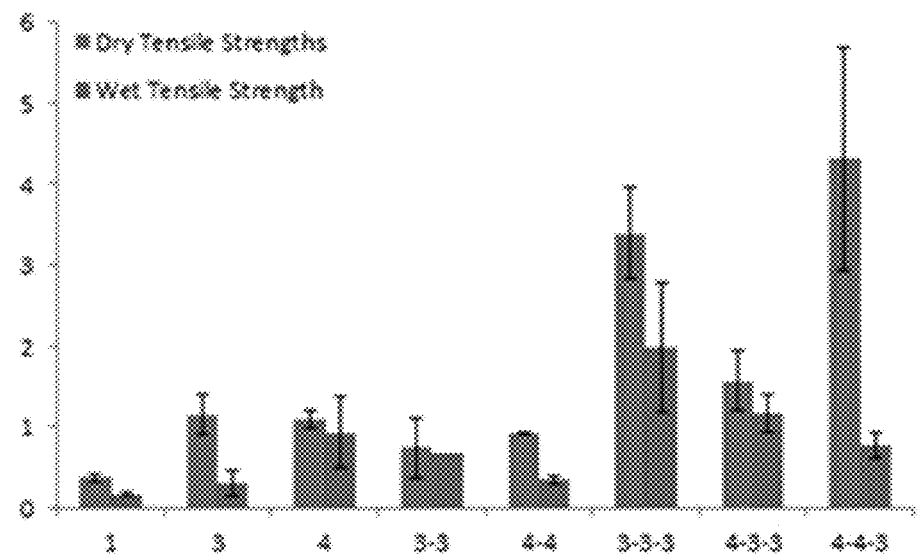
Figure 3C:
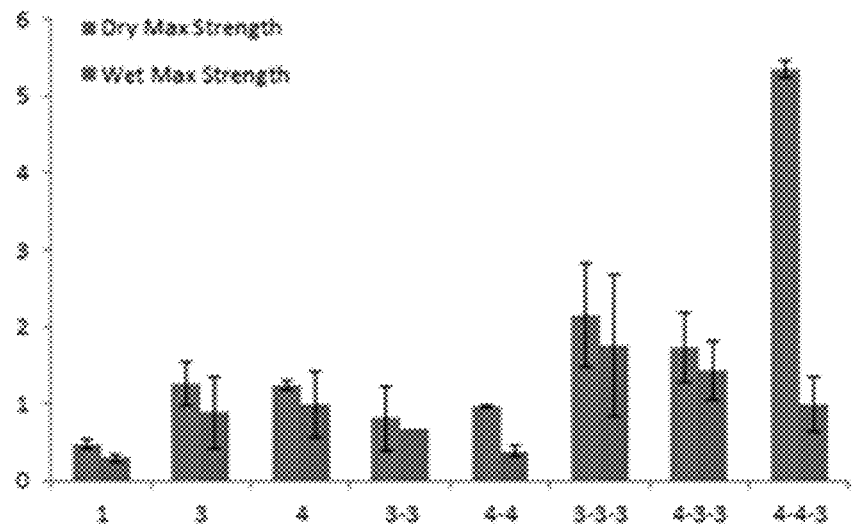
Figure 3D:
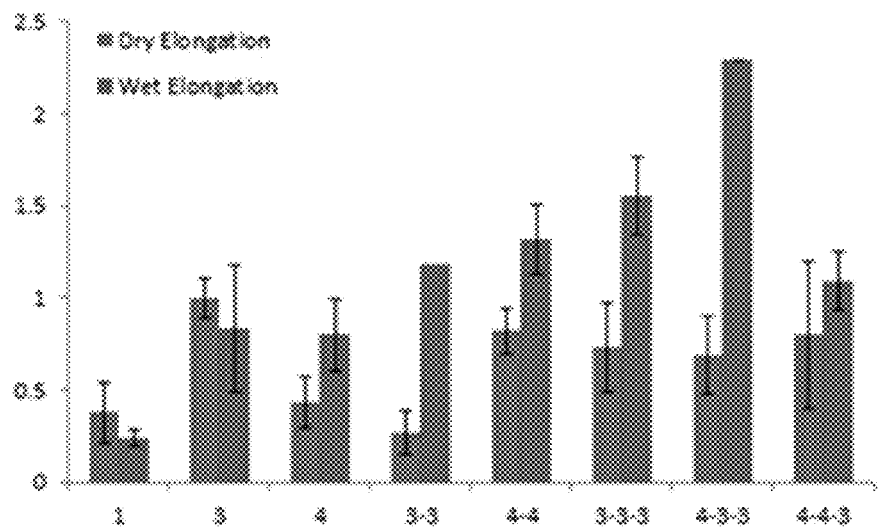
Figure 4A:
FIG. 4 shows scanning electron microscopy (SEM) imaging of bundling distribution of silk element bundles coated in HA in four different example images FIG. 4A, FIG. 4B, FIG. 4C, and FIG. 4D. Images were taken for device assembly evaluation using hyaluronic acid coatings to create an even dispersed silk element bundles within a silk sheath.
Figure 4B:
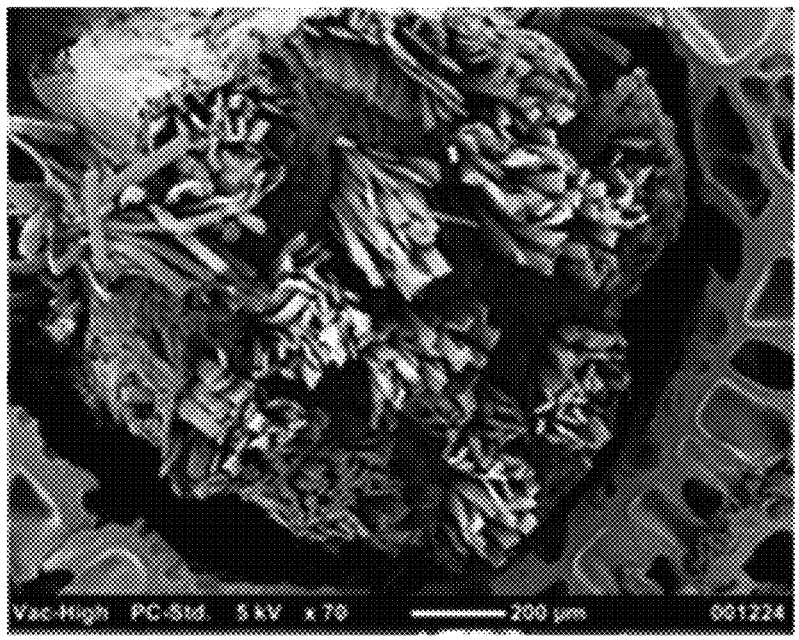
Figure 4C:
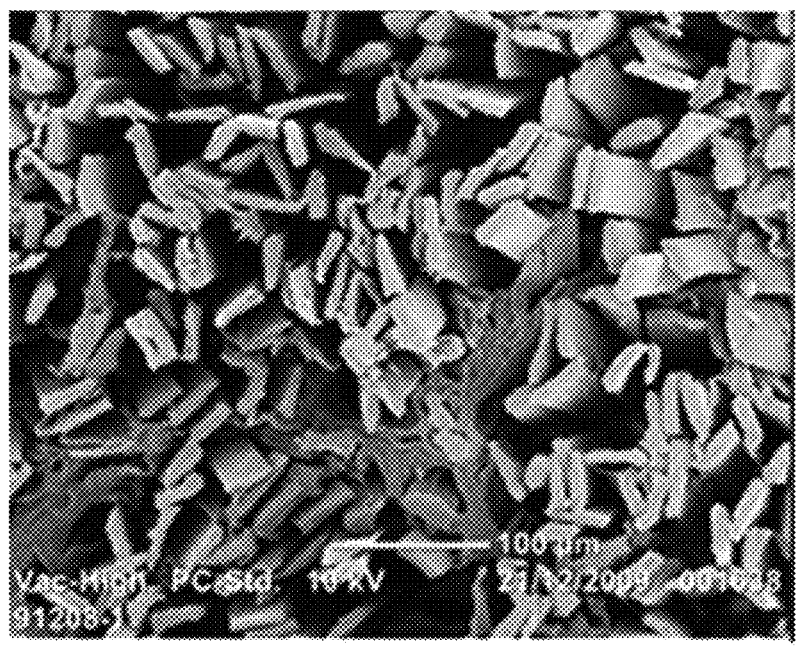
Figure 4D:
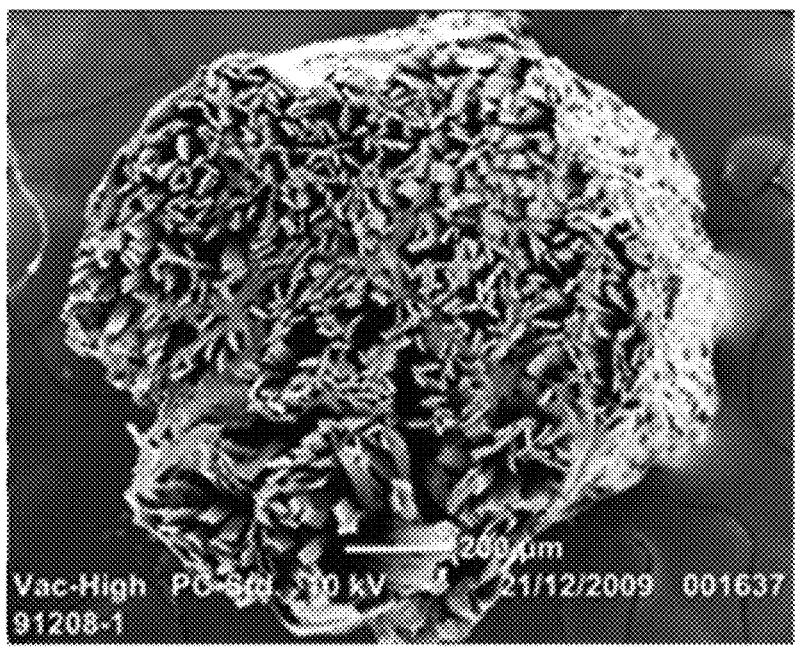

Bundling in different iterations was carried out and the resulting fibers underwent tensile testing for Young's Modulus (as shown in FIG. 3A), Tensile Strength (as shown in FIG. 3B), Maximum Strength (N/mm$^2$) as shown in FIG. 3C, and Elongation (as shown in FIG. 3D).

Example 8: Investigation into Device Assembly Using HA as a Hydrophobic Swelling Agent Initial investigation into the uniform device assembly of peripheral nerve conduits by hydrophobic silk element coating swelling has been tested. The premise that hydrophobic regions as part of the matrix can aid assembly has been confirmed.

Methods: Tubular sheaths comprising *Bombyx mori* regenerated silk fibroin were cast by dipping stainless steel rods into a 5-20% silk fibroin solution. Silk elements were given hydrophobic coating by dipping in a 40 mg/mL hyaluronic acid (HA) and air dried under tension. The silk elements were then inserted into the sheath using an aqueous HA matrix.

Results: The addition of an aqueous matrix induced swelling of the dried HA coatings. This resulted in an even distribution of silk elements throughout the lumen of the conduit. FIG. 4 shows scanning electron microscopy (SEM) imaging of bundling distribution of silk element bundles coated in HA in four different example images FIG. 4A, FIG. 4B, FIG. 4C, and FIG. 4D. Images were taken for device assembly evaluation using hyaluronic acid coatings to create even dispersed silk element bundles within a silk sheath.

Example 9: Gelling Methods for Outer Sheath

First generation nerve conduits were made by painting or casting (dipping) silk on a former (a rod made of stainless steel or wax, to set the internal diameter of the sheath). The sheaths contained a mesh, either a knitted silk tube or a fiber that spiraled down the sheath to allow for suturing. The silk was air dried to set.

Second generation nerve conduits were made using gelling methods to induce a more 3D structure with uniform porosity. It may be possible to implant the sheaths without suturing using a surgical glue. Alternatively it may be possible to suture without the need of a mesh.

The second generation nerve conduits could be transported easily and were stronger than the first generation nerve conduits.

9.1 Application of a Sheath Gelling Solution; Component Ratio and Time in Solution A gelling agent was applied to a sheath to induce uniform porosity. A variety of different gelling solutions were applied to a frozen silk sheath for varying lengths of time.

Method: A reconstituted Bombyx mori silk fibroin solution, 5-20% wt/vol, was frozen in a tubular mold for 1 hour. Once fully frozen, the outer mold was removed, and the sheath placed in a chilled gelling solution. The process for each sheath was completed by further freezing and alcohol driven crystallization.

Results: Sheaths gelled using aqueous acetic acid solutions, 2.5-50%, produced non-porous exceptionally transparent tubes. These were stiff, lacked suturability and had poor mechanical properties (<0.4 MPa tensile strength). Use of aqueous PEG (Polyethyleneglycol Bisphenol A Epichlorohydrin Copolymer) solutions did not induce gelling of the sheaths, suggesting the need for both a gelling and a pore defining agent in the gelling stage to give a porous sheath with appropriate tensile properties.

Figure 5:
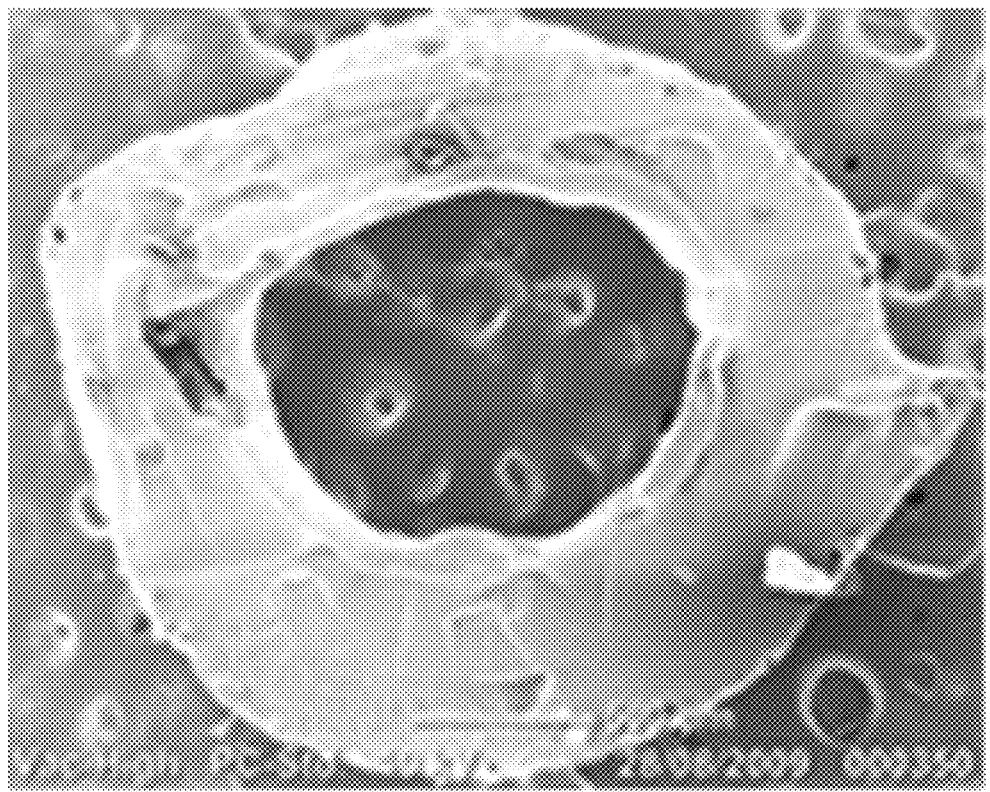
FIG. 5 shows SEM imaging of a sheath produced without any pore defining agents, solely with gelling agent, resulting in a transparent non-porous tube being formed. The non-porous sheath was developed using 50% aqueous acetic acid solution for 30 mins.

An optimal gelling solution was found to be 2.25% of polyethylene glycol (15-20 kDa) and 2.5% acetic acid, with respect to the silk fibroin solution used, with a direct correlation on final sheath structure and time left in gelling solution observed. With time the sheaths became thinner and less porous as the gelling agents displaced the silk bound water and forced compacting of the sheath walls. An optimal time of 30 minutes was confirmed. FIG. 5 shows a non-porous sheath developed using 50% aqueous acetic acid solution for 30 mins. FIG. 6 shows SEM imaging of sheaths produced with both gelling and pore defining agents, producing pores tubes, with excess time in gelling solution resulting in less defined sheath production. Sheath gelling was performed using 2.25% PEG and 2.5% acetic acid for 15 minutes (FIG. 6A, FIG. 6B, and FIG. 6C), 30 minutes (FIG. 6D, FIG. 6E, and FIG. 6F), and 60 minutes (FIG. 6G, FIG. 6H, and FIG. 6I).

Example 10: Using a Full Mold to Define Sheath Shape of Specific Dimensions

Methods for preparing silk as sheath material were explored and compared to $1^{st}$ generation nerve conduits formed around a rod to set an internal diameter, as described in patent application WO2006030182. A full mold with an internal stainless steel rod allows for the application of the optimal gelling method, already established as part of the freeze-gel-freeze method.

10.1 Method: First Generation Nerve Conduit

Figure 7A:
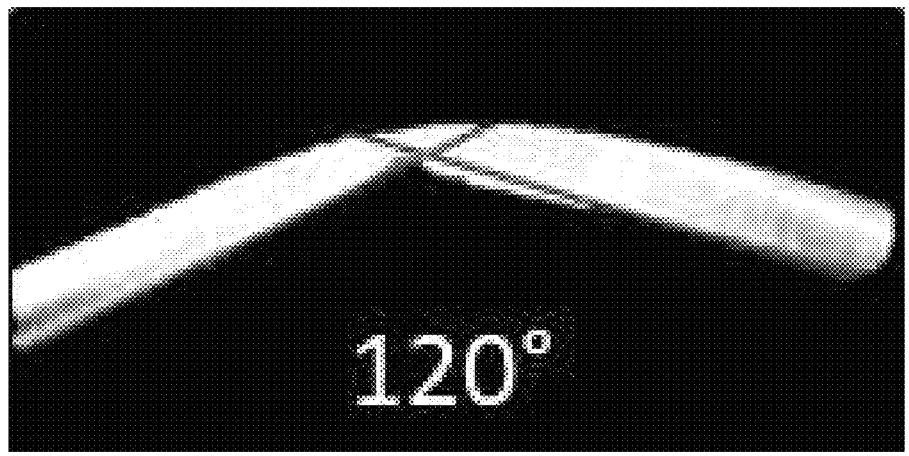
FIG. 7A and FIG. 7B show brittle nerve conduits produced as described in Methods and Apparatus for Enhanced Growth of Peripheral Nerves and Nervous Tissue (WO2006030182), silk fibroin solution is painted onto a rod with a wound silk thread. The silk is left to dry creating a non-uniform brittle tube.
Figure 7B:
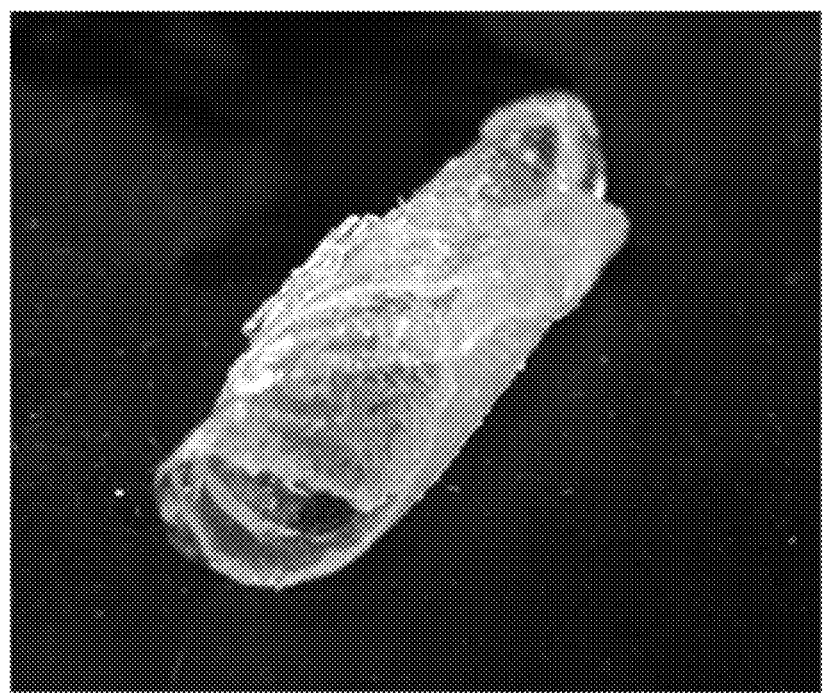

First generation nerve conduits were prepared. Stainless steel rods with wound silk fibers were painted in silk fibroin solution and allowed to air dry. The thin sheaths created were transparent but not kink resistant, buckling under a 120° bend. The sheaths were non-porous, felt brittle and difficult to use and did not give the option for suturing during implantation. FIG. 7A and FIG. 7B show first generation nerve conduits produced as described in Methods and Apparatus for Enhanced Growth of Peripheral Nerves and Nervous Tissue (WO2006030182), silk fibroin solution is painted onto a rod with a wound silk thread. The silk was left to dry creating a non-uniform brittle tube.

10.2 Method: Second Generation Nerve Conduit

Second generation nerve conduits were created from reconstituted silk fibroin solutions produced in the same manner; Bombyx mori skeins were enzymatically degummed and dissolved using concentrated lithium bromide before being dialyzed to an appropriate level suitable for medical use.

Second generation nerve conduits were prepared using the freeze-gel-freeze method described in Example 9. Sheaths were produced with a 2.1 mm diameter, using full molds for the first freeze step to define wall thickness and give uniformity, using full molds permits production of bespoke sheaths if required. second generation nerve conduits lost transparency but showed heightened kink resistance, allowing a 50° bend, with overall better handling than first generation nerve conduits.

Figure 8A:
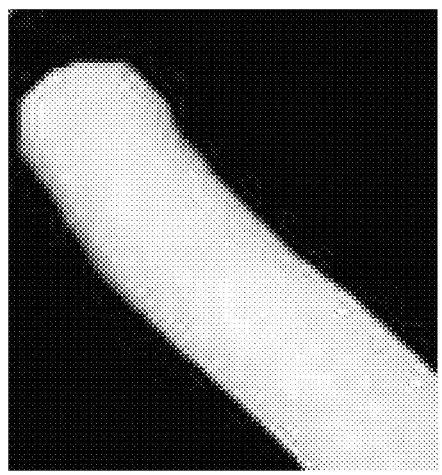
FIG. 8A shows an image of an entire sheath.
Figure 8B:
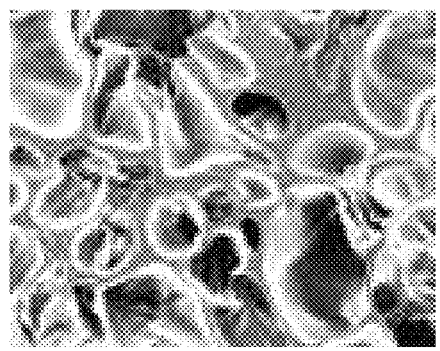
FIG. 8B and FIG. 8C show SEM imaging of pores in a sheath.
Figure 8C:
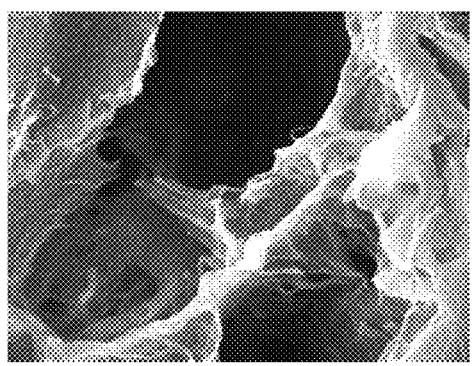
Figure 9A:
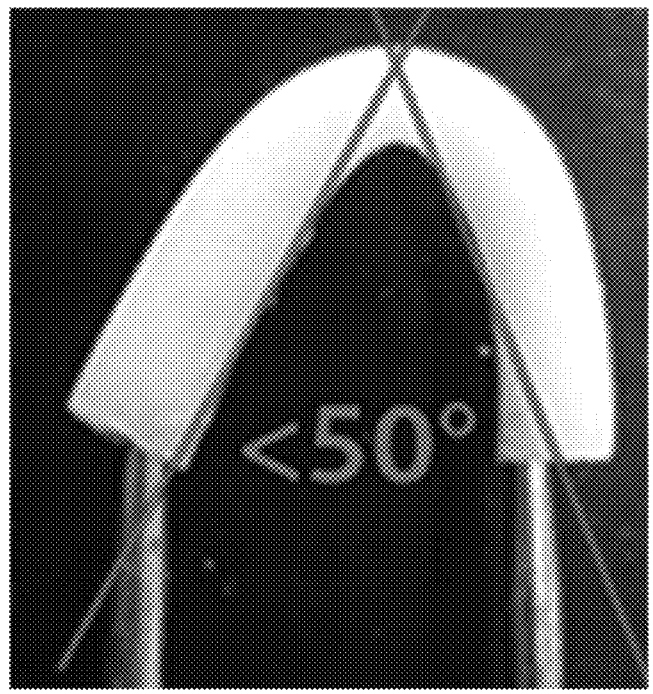
FIG. 9A and FIG. 9B show kink resistance testing demonstrating heightened flexibility of a flexible nerve conduit compared to a brittle nerve conduit, in which a flexible nerve conduit can be bent into a <50° angle without breaking or kinking, and maintaining luminal patency.
Figure 9B:
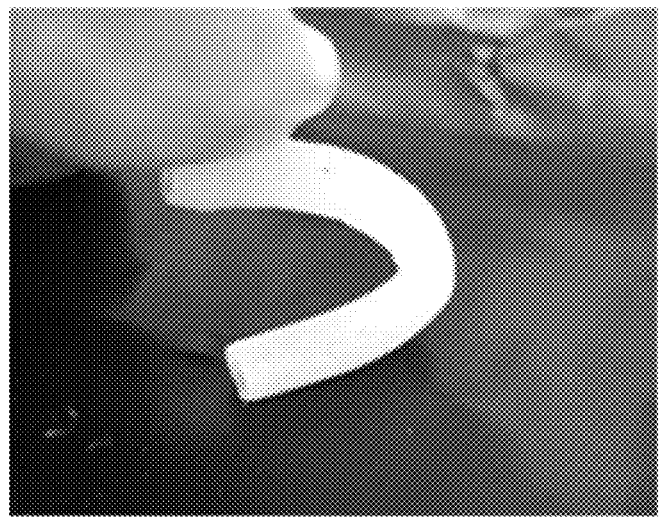

FIG. 8 shows sheath produced by employing a gelling solution containing both a gelling and pore defining agent, to a molded frozen silk solution before crystallizing using aqueous ethanol. FIG. 8A shows an image of an entire sheath. FIG. 8B and FIG. 8C show SEM imaging of pores in the sheath. FIG. 9A and FIG. 9B show kink resistance testing demonstrating heightened flexibility of the second generation nerve conduits compared to the first generation in which the sheath can be bent into a <50° angle without the sheath breaking.

Example 11: Introduction of a Lyophilization Step

Experiments into the use of a lyophilization (freeze drying) step were performed. The optimal second generation nerve conduits were compared to those produced with a lyophilization step as part of the freeze-gel-freeze method.

11.1 Method

Sheaths were prepared from 5-20% Bombyx mori fibroin solution, a full mold was used for each to define; external, internal diameters and wall thickness. A control second generation nerve conduit was prepared by 30 minutes freezing at −20° C., 30 minutes in the optimal gelling solution (2.25% Polyethyleneglycol Bisphenol A Epichlorohydrin Copolymer 2.5% Acetic acid), 30 minutes freezing, crystallization and storage in 70% aqueous ethanol. Three new sheaths were prepared, the first with only a freeze drying and no gelling, the second freeze drying was performed prior to gelling, and the third was freeze dried after gelling. All were crystalized and stored in 70% aqueous ethanol solution.

11.2 Results

Freeze drying before gelling (F-FD-G-C) gave more brittle tubes likely because beta structures had been induced already from lyophilization. Sheaths produced solely from freeze drying without any gelling steps before or after showed significantly lower strengths. The results suggest that gelling needs to occur before freeze drying to be beneficial; otherwise it reduces the tubes mechanical properties.

Figure 10:
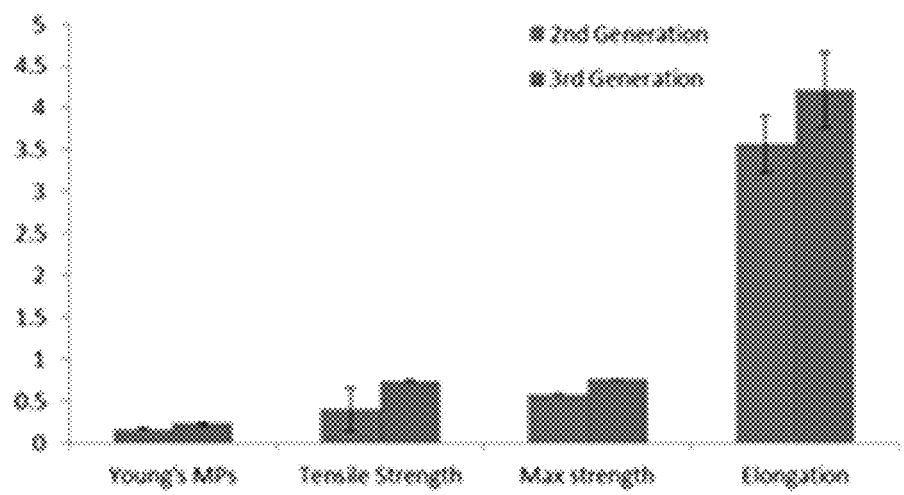
FIG. 10 depicts a graph showing mechanical properties of second generation and third generation nerve conduits (Strength N/mm, Young's N/mm^2, Elongation no units).
Figure 11A:
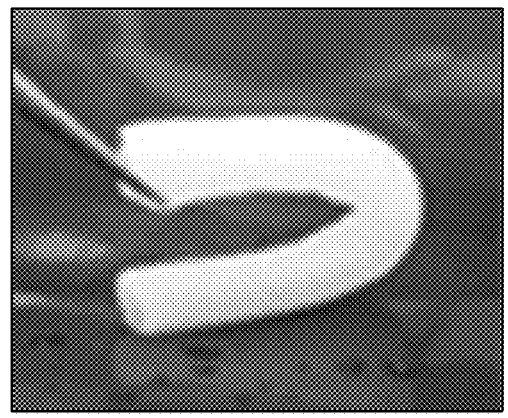
FIG. 11A, FIG. 11B, FIG. 11C, and FIG. 11D show a flexible nerve conduit produced using a freeze-gel-freezelyophilization-freeze-crystalize method. The inclusion of a freeze drying after a gelling resulted in improved mechanical properties compared to both first and second generation nerve conduits. The 4th generation nerve conduit is capable of bending back on itself without kinking.
Figure 11B:
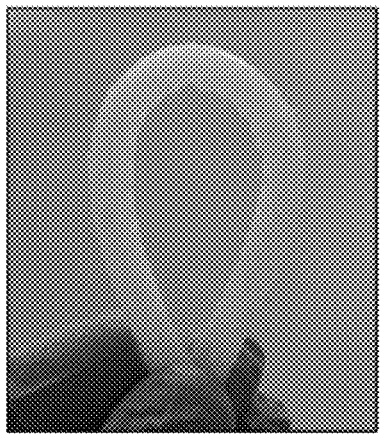
Figure 11C:
Figure 11D:
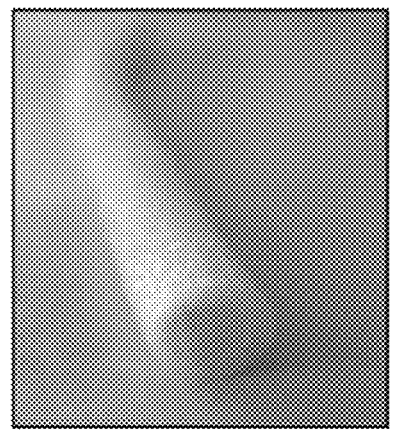

The best sheath was produced using the method; freeze, gel-freeze, freeze, dry-freeze, crystalize. Sheaths which were first gelled and subsequently freeze-dried before crystallization induced in ethanol were stronger and more elastic than those obtained with other methods, including the control second generation nerve conduit. Tubes made in this way also appeared to be significantly more kink resistant. FIG. 10 depicts a graph showing the mechanical properties of second generation and third generation nerve conduits. (Strength N/mm, Young's N/mm^2, Elongation no units). FIG. 11 shows a third generation nerve conduit produced using a freeze-gel-freeze-lyophilization-freeze-crystalize method. The inclusion of the freeze drying after the gelling step resulted in improved mechanical properties compared to both 1st and second generation nerve conduits.

Example 12: Assembly of Conduit Using Terminal Clamping and Coating of the Outer Sheath in HA to Improve Implant Integration Assembly of Conduit Using Terminal Clamping The sheath and luminal fibers can be assembled and the ends clamped prior to freeze drying to hold the fibers in place during transit.

12.1.1 Method

Sheaths were produced using dissolved *Bombyx Mori* skeins and following the freeze-gel-freeze dry method. Following removal of all molds and rehydration of the sheath, the silk luminal fibers are threaded, leaving fibers exposed at both ends of the sheath, and clamps are applied ensuring the sheath ends and sealed flat trapping the luminal fibers. Whilst the clamps are still applied, the conduit is freeze dried. No further crystallization was required.

12.1.2 Results

Removal of the clamps revealed the conduit ends to be sealed and holding the luminal fibers in place. The conduit can be transport and stored dry under ambient conditions. Upon rehydration, such as before implantation, the ends of the conduit can be cut to the desired length revealing an open sheath hosting luminal fibers.

Coating of Outer Sheath in HA to Improve Implant Integration

The sheath can be coated in hyaluronic acid to improve implantation site integration. This can be doped with growth factors.

12.2.1 Method

Sheaths were produced using dissolved *Bombyx mori* Skeins and following the freeze-gel-freeze method. After 2 hours in aqueous alcohol to crystallize, sheaths were soaked in ultra-pure water to before being placed in a 5 mg/mL solution of HA (hyaluronic acid). After 3 minutes in the solution the sheath was removed and left to air dry.

12.2.2 Results

Figure 12A:
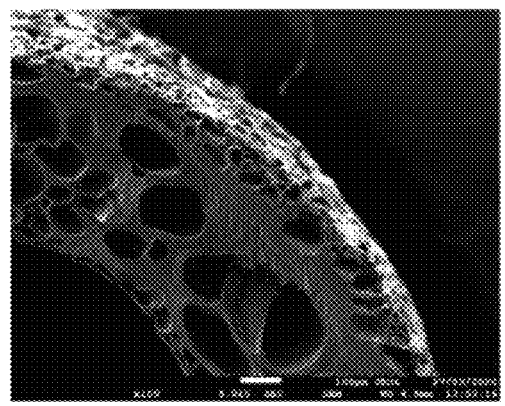
FIG. 12A, FIG. 12B, and FIG. 12C show SEM imaging of a porous flexible nerve conduit with a hyaluronic acid (HA) coating.
Figure 12B:
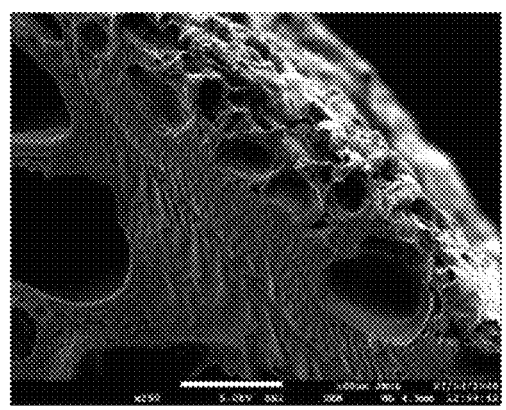
Figure 12C:
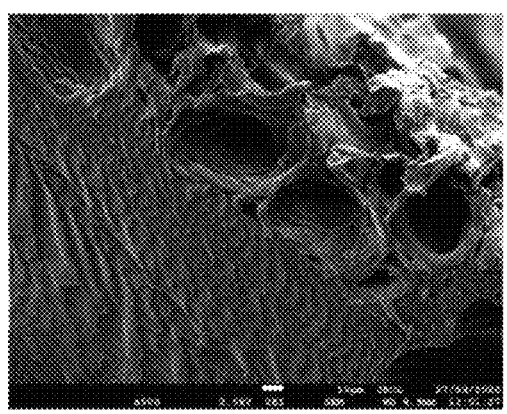

A hydrophobic layer was formed on the outside of the sheath. The layer was on average 161 µm in thickness, with an intricate pore network, meaning the addition of a coating may not hamper the necessary porosity of the sheath. FIG. 12A, FIG. 12B, and FIG. 12C show SEM imaging of a porous second generation nerve conduit with a hyaluronic acid (HA) coating.

Example 13: Use of a Matrix

Sheath-less conduits produced with a gelled matrix containing silk elements were tested in a 4 week dog trial. The conduits had a 5 mm internal diameter and measured 1.6 cm in length, with a 0.2 cm indent on each side.

13.1 Methods

The individual small conduits were embedded in a gelled silk matrix (=the matrix was gelled in the shape of a cylinder while containing the small conduits). The whole structure was set in the matrix. The resulting conduit was more flexible and the fibers inside were provided more support to keep them together.

13.2 Results

Figure 13A:
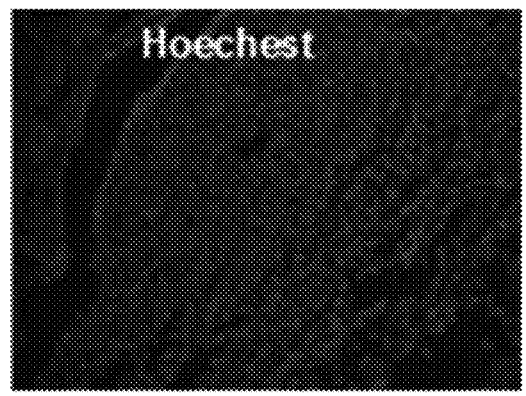
FIG. 13A shows Hoechst staining for nuclei.
Figure 13B:
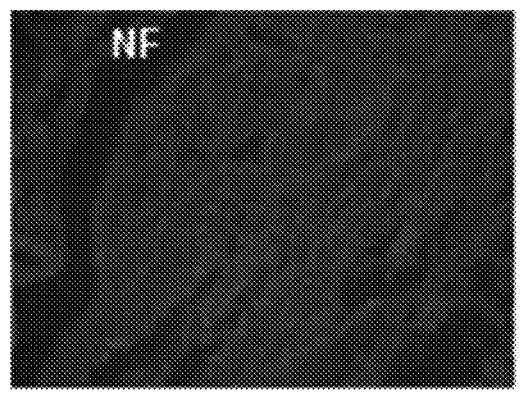
FIG. 13B shows NF200 staining for nerve fibers.
Figure 13C:
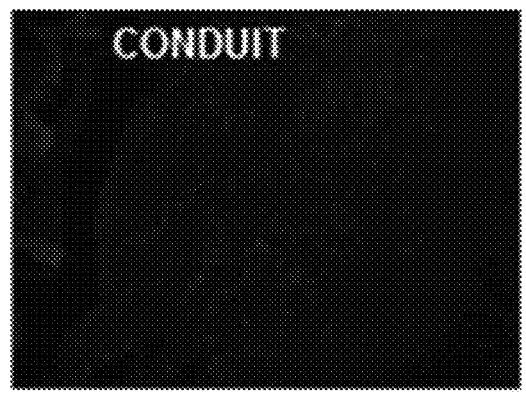
FIG. 13C shows SF100 staining for conduit.

The nerves regenerated into the conduits by the fourth week. Despite some nerves escaping there was nerve regeneration into the small conduit. The average length the nerves regenerated into the conduits was 3.11 mm, with the longest distance of 4.2 mm. Findings from the dog trial suggested that silk elements were too densely packed and that the external diameter of 5 mm may have been too large. FIG. 13 shows immunofluorescent imaging of a nerve regenerating into an outer wall of a conduit (mid-conduit). FIG. 13A shows Hoechst staining for nuclei. FIG. 13B shows NF200 staining for nerve fibers. FIG. 13C shows SF100 staining for conduit.

Figure 14A:
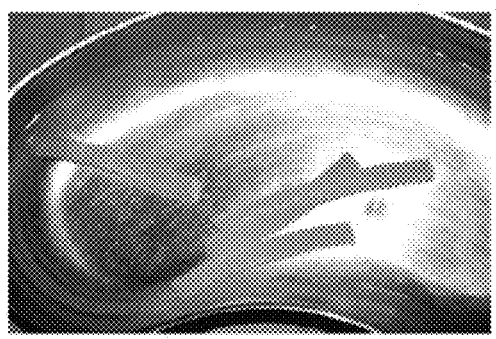
FIG. 14A shows a plurality of corrugated nerve conduits in a surgical dish.
Figure 14B:
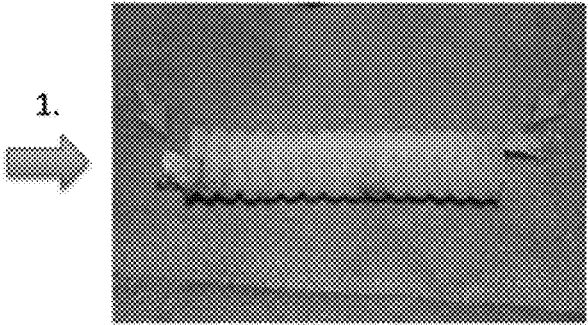
FIG. 14B shows a corrugated nerve conduit. The red arrows point to the silk elements which run through the container.
Figure 14C:
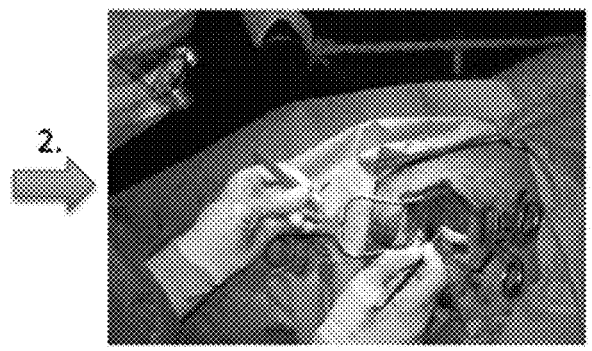
FIG. 14C and FIG. 14D show surgical insertion of a corrugated nerve conduit into a pig.
Figure 14D:
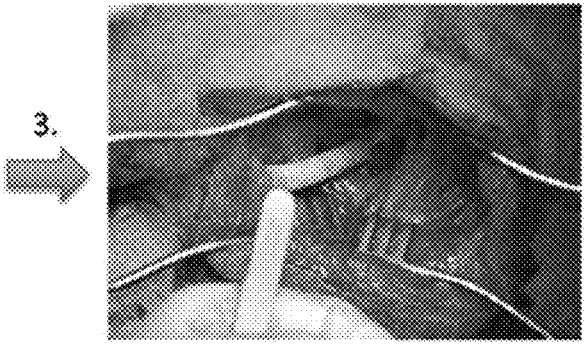

Example 14: Peripheral Nerve Reconstruction in a Sheep with a Corrugated Nerve Conduit Summary: A 6.0 cm tibial nerve defect was induced in each of three black headed merino sheep. The severed nerves were reconstructed with a corrugated nerve conduit device constructed from silk from *Bombyx mori* silkworms and filled with spider silk of *Nephila edulis* spiders, shown in FIG. 14A and FIG. 14B. Implantation of the device is shown in FIG. 14C and FIG. 14D.

Results

Figure 15A:
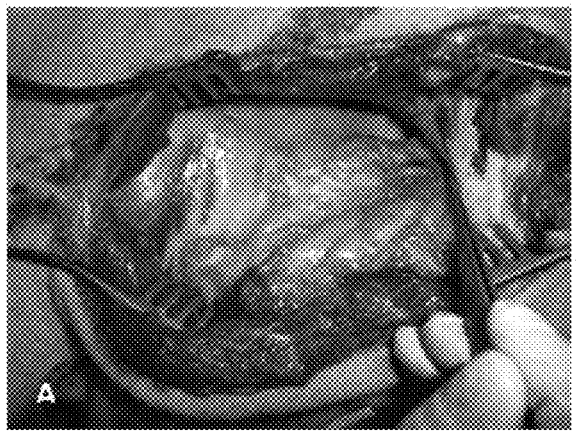
FIG. 15A and FIG. 15B show macroscopic appearance of a corrugated nerve conduit directly before explanation. Intraoperative the entire conduit was covered by scar tissue.
Figure 15B:
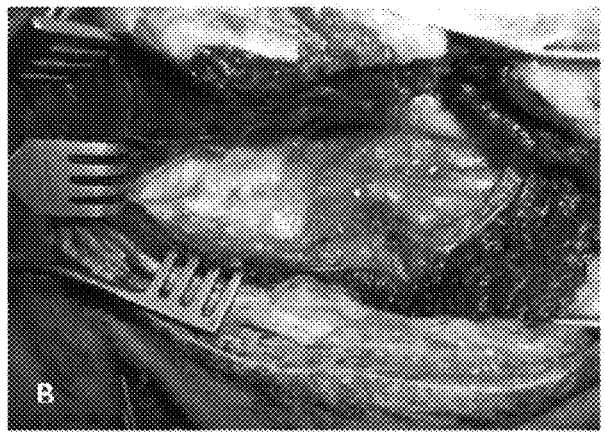
Figure 15C:
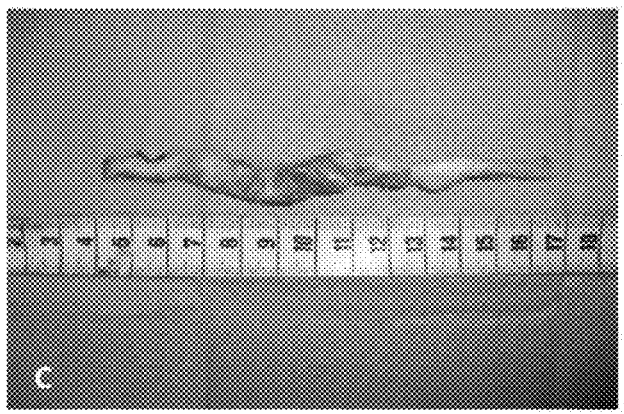
FIG. 15C and FIG. 15D show macroscopic appearance of a corrugated nerve conduit directly after explanation. Extensive kinking of the conduit resulting in a closed lumen and formation of fibrosis.
Figure 15D:
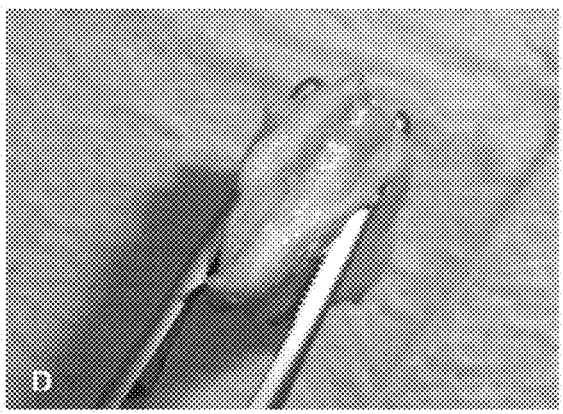
Figure 16A:
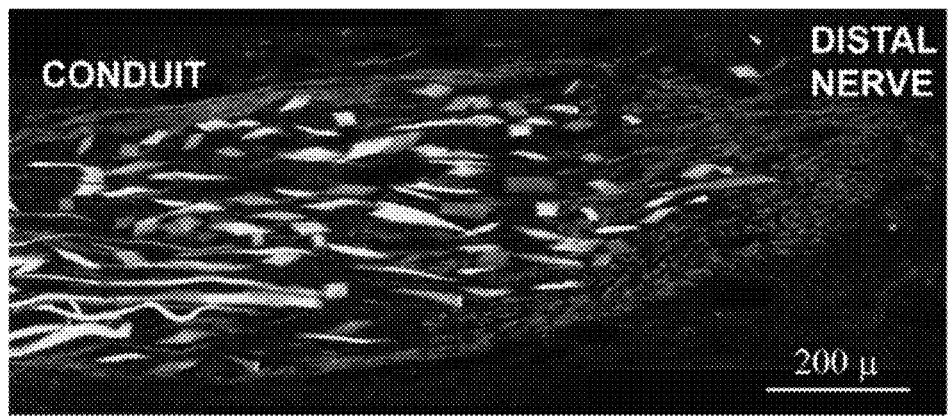
FIG. 16A shows immunofluorescent staining of axons regenerating along a conduit toward a distal nerve.
Figure 16B:
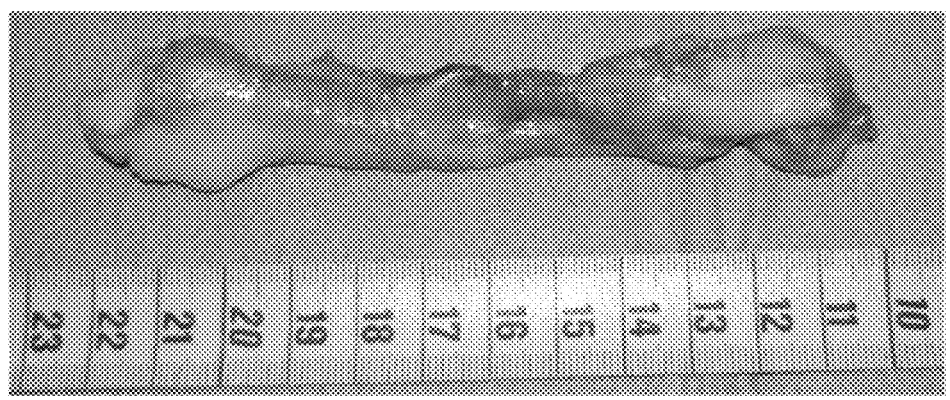
FIG. 16B shows an all silk conduit explanted after 3 months in a sheep.
Figure 16C:
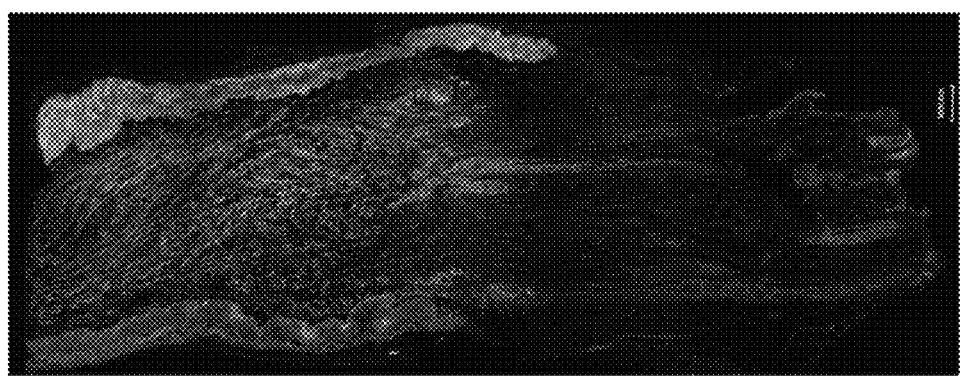
FIG. 16C shows immunofluorescent staining demonstrating nerve regeneration of over 6 cm.

Three black headed merino sheep were observed for 6 month. After three and six months of observation electrophysiology recordings of the tibial nerves were conducted. Compared to the contralateral side no signs of functional recovery or reinnervation was distinct after three or respectively six months. Following the recordings the tibial nerve was harvested in entire length as shown in FIG. 15A and FIG. 15B, and prepared for histology and electron microscopy. Already the macroscopic appearance during the final explanation surgery demonstrated significant fibrosis and kinking of the corrugated nerve conduit (FIG. 15C, FIG. 15D, and FIG. 16B). The form of the wall of the conduit seemed to be disadvantageous and may have promoted the kinking process.

The explanted conduits were processed for HE and Masson Goldner Trichrom staining to evaluate the grade of regeneration and fibrosis. Histological analysis revealed axonal regeneration in the proximal areas of the corrugated nerve conduit in all animals, as shown in FIG. 16A, and FIG. 16B. Noticeable is an infiltration of immune cells in all test animals. The immune reaction is in all cases in close proximity to the inner wall of the conduit and mainly limited to the notches of the device wall.

Specimen 05915

Figure 17A:
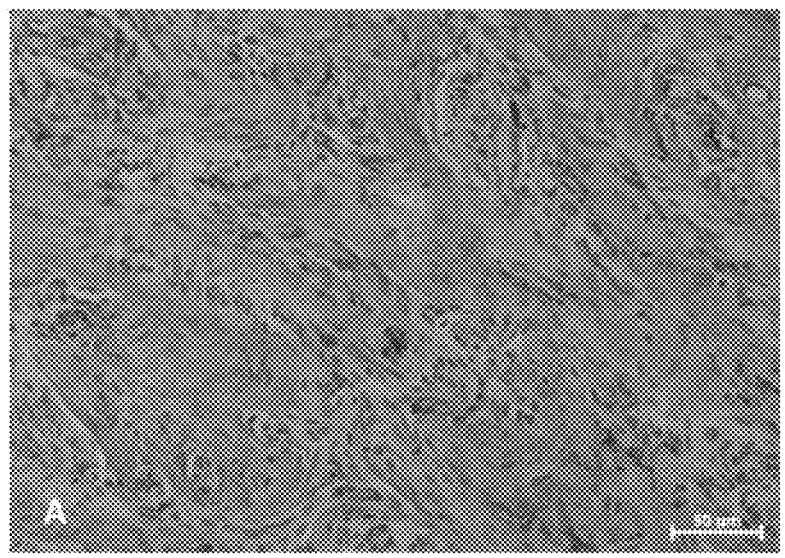
FIG. 17A and FIG. 17B show microscopy images of successful regeneration within the distal part of the second generation nerve conduit. Axons reached the distal suture line of the implant despite immune reaction and fibrosis within the conduit.
Figure 17B:
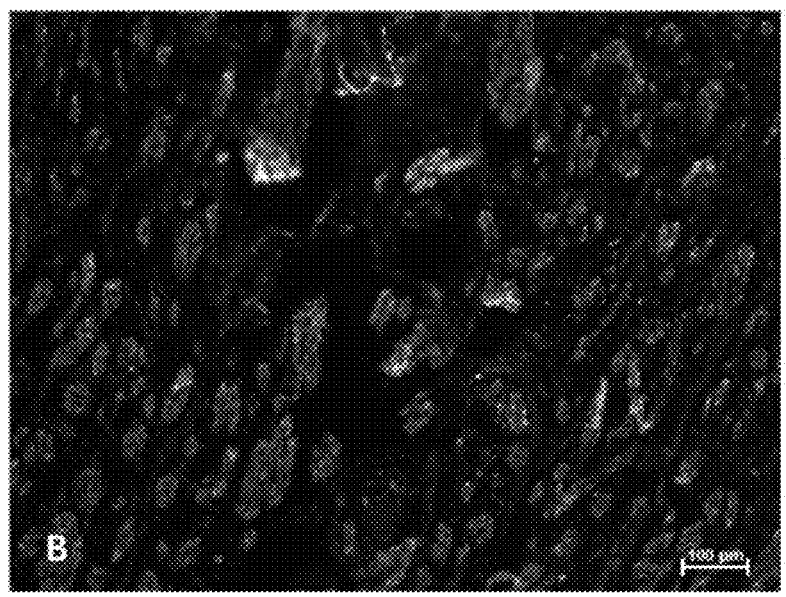

Due to animal health status the specimen 05915 was sacrificed three months following surgery. Histology demonstrated outspreading axons throughout the proximal section of the nerve graft. Nerve fibers are only visible in the center of the implant and entirely surrounded by significant fibrosis. An ongoing immune reaction is distinct in peripheral areas that are in relation to the inner wall of the corrugated nerve conduit. Despite ongoing fibrotic processes in all segments axonal structures were verifiable in distal areas of the corrugated nerve conduit already three months following surgery (FIG. 17A, and FIG. 17B).

Specimen 05968

Figure 18A:
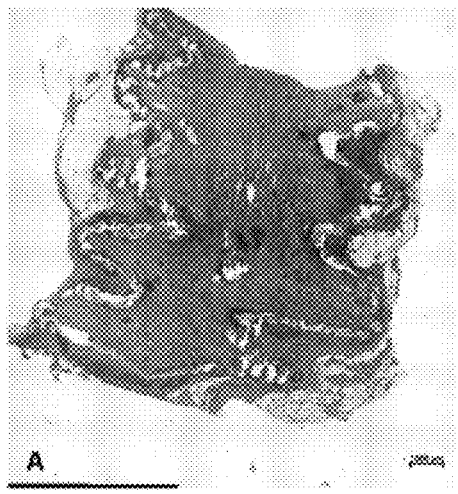
FIG. 18A shows medial segments in HE staining of specimen 05968 demonstrating terminated axonal regeneration.
Figure 18B:
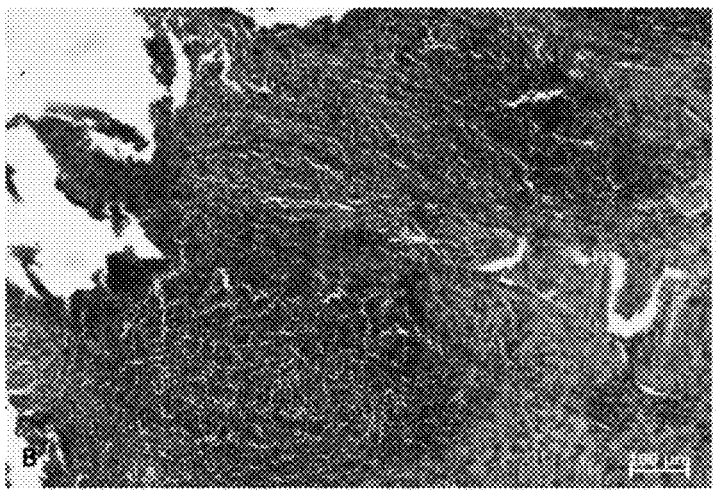
FIG. 18B shows massive infiltration of immune cells in close relation to the silk worm silk.

Undirected nerve growth was visible in the proximal areas of this corrugated nerve conduit. The regeneration processes were terminated in the medial segments (FIG. 18A). This may be caused by a significant infiltration of immune cells in all areas of the corrugated nerve conduits (FIG. 18B). As with specimen 05915, an immune reaction in close proximity to the inner wall of the corrugated nerve conduit was observed.

Specimen 05976

Figure 19A:
FIG. 19A and FIG. 19B show a media segment in HE staining and distal segment in Masson Goldner Trichrome of specimen 05976: massive infiltration of immune cells is verifiable in close proximity to the conduit wall.
Figure 19B:
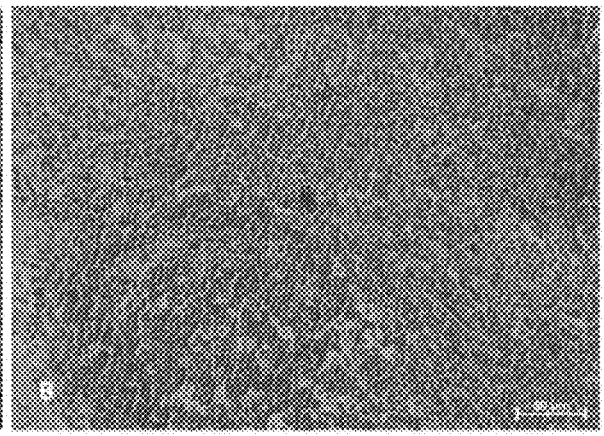

Outspreading axons were visible in the proximal segments of the nerve graft. The regenerating axons are in close relation to a massive invasion of immune cells in all areas of the corrugated nerve conduit (FIG. 18A and FIG. 18B). Especially the medial segment is entirely populated by immune cells in close proximity to the inner wall of the implant (FIG. 19A and FIG. 19B).

Electron Microscopy

Electron microcopy revealed massive infiltration of lymphocytic cells in all test animals throughout all implant segments in relation to the inner wall of the *Bombyx mori* conduit. Spider Silk was degraded by giant cell inflammation. Fibrotic cells were visible throughout all implants. Regenerating axons were verifiable in all proximal segments and in the medial segment of specimen 05915 and 05968. Only in specimen 05915 were regenerating axons observable in the distal areas of the implants.

CONCLUSION

This study demonstrated that an all-silk tube and filaments implant is suitable for peripheral nerve reconstruction. One drawback observed with this iteration during the regeneration process was the massive lymphocytic infiltration and the significant fibrosis in all implants. This may be caused by residues of sericin on the silk or by the bio-burden both later documented on control samples.

This pilot test with n=3 animals revealed that the form of the conduit needs to be improved. The ribbing of the tube wall can lead to kinking during implantation. Moreover, while generally stabilizing the tube wall, the ribbing may also 'grate' with the surrounding tissue after implantation.

The lesson results of this study suggested a need for: (i) higher levels of sericin removal and bioburden control (since enacted in the third generation nerve conduit device) as well as (ii) a modified tube design with smooth and slippery walls that are also more permeable in order to provide better oxygenation and nutrition for the regenerating nerve fibers and Schwann cells within the conduit.

Example 15: Schematic of a Silk Container with Silk Filaments

Figures 20A, 20B, 20C:
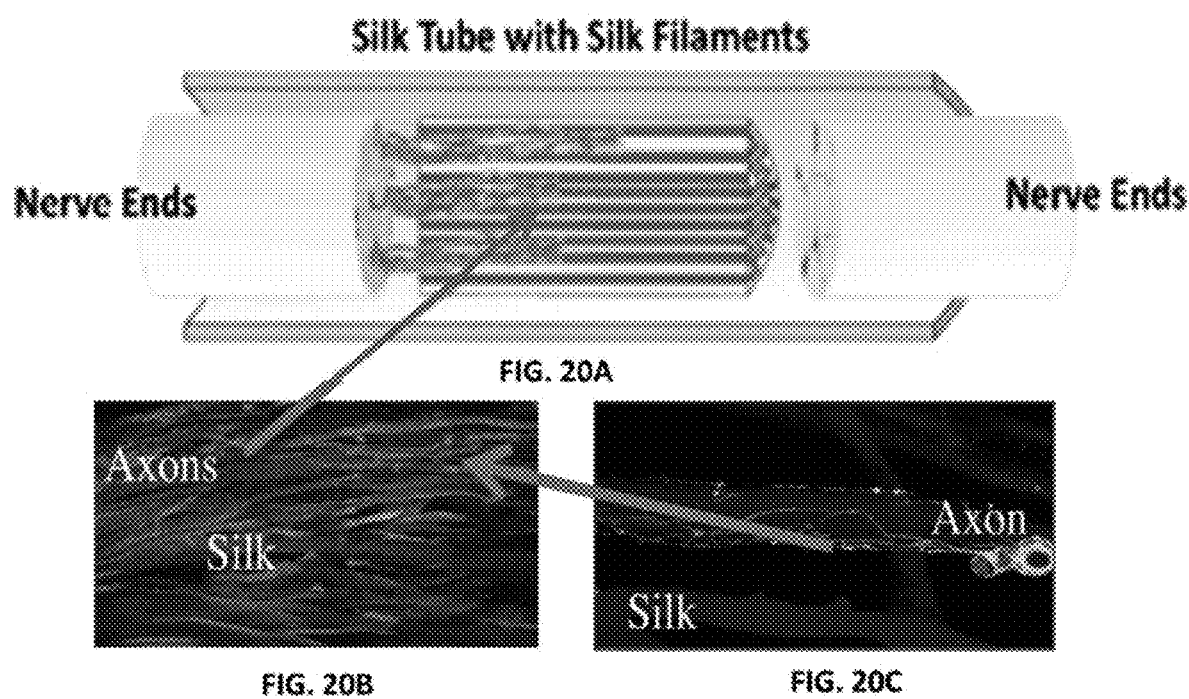
FIG. 20A depicts a schematic diagram of a silk tube with silk filaments that can act as a conduit for a regenerating nerve.
FIG. 20B depicts an immunofluorescence image with neurofilament antibody staining, of axons regenerating over a plurality of silk elements.
FIG. 20C shows an immunofluorescence image of an GFP-labelled schwann cells and axons regenerating over a single silk element.

FIG. 20A shows a schematic diagram of a silk container with silk filaments that facilitates nerve regrowth in a gap between two severed nerve ends. FIG. 20B shows an immunofluorescence (IM) image with neurofilament antibody staining, of axons regrowing over a plurality of silk elements. FIG. 20C shows an IM image of an axon regenerating over a single silk filament.

Example 16: Silk-in-Silk Conduits for Nerve Reconstruction in a Rat Model 16.1 Introduction Rehabilitation of segmental peripheral nerve injuries by advanced nerve guidance conduits could provide an off-the-shelf alternative to autologous nerve grafts. Silk has evolved as an exceptional biomaterial with mechanical and biological properties advantageous for the engineering of nervous tissue. In this study, the excellent processing ability of silk fibroin and the outstanding cell adhesion quality of spider dragline silk were combined to generate a silk-in-silk conduit and its regenerative effect in a rat sciatic nerve injury model was analyzed. Functional recovery of segmental peripheral nerve injuries remains a major challenge in restorative medicine. Despite continuous efforts, most patients suffer from lifelong disability, pain, and follow up surgeries. Autologous nerve grafts derived from a sensory peripheral nerve, e.g. the sural nerve, are the current standard treatment for large segmental peripheral nerve injuries. These autografts provide endogenous structural support as well as pro-regenerative cues and guidance from resident Schwann cells. The harvest of autografts, however, creates an additional functional deficit and increases the risk for complications. In addition, the availability of donor nerves is limited in cases of extensive trauma and long-distance peripheral nerve defects. A multitude of nerve guidance conduits composed of synthetic and natural materials have been developed as alternatives for autografts. However, the currently available FDA approved nerve guidance conduits present only hollow tubes whose application is restricted to short-distance nerve defects of up to 3 cm. Responsible for the inefficient nerve re-growth over longer distances is the lack of an internal framework that provides structural and cellular support. Hence, there is an ongoing search for suitable biomaterials and 3D scaffolds to construct nerve conduits that meet the requirements for large segmental nerve defects. Those next-generation nerve conduits should emulate the nervous architecture and possess advanced biological and mechanical features supportive for regeneration.

An increasing body of studies presented silk as an exceptional biomaterial with advantageous properties for the engineering of nervous tissue. Silk of two arthropod classes, the silkworm *Bombyx mori* and the spider genus *Nephila*, were studied in considerable detail. While spider dragline silk consists of the major ampullate proteins spidroin-1 and-2, silkworm cocoon silk is composed of fibroin and sericin proteins. However, sericin is associated with immunogenic properties, which requires its careful removal in a process referred to as degumming. The sericin-free silk fibers can be dissolved into a fibroin solution and reconstituted in silk-only or multi-material structures. Fibroin can be biocompatible for peripheral nerve tissue and cells in vitro. The major advantages of fibroin solutions are the diverse processing methods that led to the development of a variety of nerve conduits with different structural and mechanical features successfully applied in animal studies. Due to the low yield and high effort of spider dragline silk harvest, only insufficient spidroin solution can be generated for conduit fabrication. Thus, previous studies presented different ways for the production of recombinant spidroin. Recently, a conduit made of recombinant spider silk proteins showed promising in vitro results but the performance of spidroin-based nerve conduits awaits to be evaluated in animal studies.

To increase the regenerative performance of hollow nerve conduits, they may be enriched with internal guiding structures. For that purpose, dragline silk of the genus *Nephila* possesses ideal mechanical properties by combining high tensile strength and remarkable flexibility. Furthermore, dragline silk fibers are temperature-stable from −75° C. to 230° C., which enables autoclaving for sterile application. Native dragline silk (approx. 2-5 µm diameter) served as suitable substrate for the attachment and growth of Schwann cells, neuronal cells, and fibroblasts in vitro. When used in vivo, dragline silk showed long-term degradability and hardly provoked any immune response. Importantly, acellularized veins filled with spider dragline silk resulted in a regenerative outcome similar to autografts after long-distance nerve defects in rats and sheep. Taken together, these reports strongly encourage the favorable properties of spider dragline silk as internal guiding filaments for nerve conduits.

In this study, an advanced nerve conduit that combines the advantages and positive effects of both silk types was used. The conduit tube was manufactured from *Bombyx mori* silk fibroin, which was already successfully applied in vivo, and filled with aligned *Nephila edulis* dragline silk fibers as internal guiding structures. The regenerative performance of this silk-in-silk conduit was compared to empty conduits and autografts in a rat sciatic nerve injury model.

10 mm rat sciatic nerve defects were treated with an autograft (A), an empty silk fibroin-based conduit (SC), or a SC filled with longitudinally aligned spider dragline silk fibers (SSC). The functional recovery was evaluated by analyzing the Sciatic Functional Index (SFI) for 12 weeks. Axonal re-growth and re-myelination were assessed using immunofluorescence and histomorphometric analyses.

The SFI results showed a significantly faster functional regeneration of the A and SSC group than the SC group. Notably, the SFI of animals treated with SSC resembled that of animals that received A. Immunostainings of longitudinal sections of the affected nerve area demonstrated re-growing axons associated with Schwann cells in all groups after 12 weeks. In line with the SFI results, the histomorphometrical analysis determined a similar number of regenerated fibers in the distal nerve segment of the A and SSC groups.

The results demonstrate that the introduced silk-in-silk nerve conduit achieved a similar regenerative performance as autografts and, thus, represent a promising treatment approach for segmental peripheral nerve defects.

16.4.1 Methods 16.4.1.1 Silk-in-Silk Conduit Preparation

The conduit walls were constructed from a concentrated 8-10% solution of dialysed regenerated *Bombyx mori* silk fibroin using a proprietary commercial process. The golden orb-web spiders, *Nephila edulis*, were housed in glass terraria with 60-80% humidity and approximately 25° C. They were fed crickets (*Acheta domesticus*) and the terraria were sprayed with water regularly. The dragline silk from the major ampullate gland of adult female spiders was harvested. One harvest resulted in approximately 10 m of silk, suitable to fill one 10 mm long fibroin conduit. The silk was autoclaved (121° C., 1.1 bar, 20:30 min) and inserted into the fibroin conduits before implantation under sterile conditions.

16.4.1.2 Electron Microscopy

Scanning electron microscopy of the prepared silk-in-silk conduits was performed with a Quanta 250 FEG, FEI device by means of a secondary electron detector. Micrographs were obtained in low vacuum (100 Pa), to allow imaging without the need of a conductive layer. The stage was tilted orthogonally to the detector for the access to the inner side of the conduits.

16.4.1.3 Animal Model and Surgical Procedure

Three groups of 12 weeks old male Sprague Dawley rats (n=6/group) between 300-350 g were used in this study. Rats were anesthetized with 100 mg/kg Ketamin and 5 mg/kg, and intubated orotracheal with 40% 02 and 2% Isofluran. The right sciatic nerve was exposed from a transgluteal access and a defect was created by cutting out a 10 mm piece of the nerve using microsurgical equipment. The nerve defect was treated with a 10 mm reversed coapted autograft (A group), a 10 mm hollow silk fibroin conduit (SC group), or a 10 mm silk fibroin conduit filled with spider dragline silk fibers (SSC group). The autologous nerve graft as well as the conduits were coapted with 3 epineurial 10-0 Ethilon sutures.

16.4.1.4 Functional Analysis

Walking track analysis was performed preoperatively and every two weeks postoperatively for 14 weeks to evaluate functional outcome of nerve regeneration, as described before. Briefly, footprints of the injured and uninjured hindlimb were analyzed for print length, toe spread, the distance between the first and fifth toes, the intermediate toe spread, and the distance between the second and fourth toes. The Sciatic Functional Index (SFI) was calculated according to Bain et al. (Bain J R, Mackinnon S E and Hunter D A, Functional evaluation of complete sciatic, peroneal, and posterior tibial nerve lesions in the rat. Plast Reconstr Surg, 1989. 83(1): p. 129-38).

16.4.1.5 Processing of Nerve Tissue/Nerve Harvest

After completion of the functional analysis 14 weeks post-surgery, rats were euthanized by intraperitoneal injection of 600 mg/kg sodium pentobarbital. 2.5 cm segments of the sciatic nerves including the conduits or autografts and the distal nerve region were harvested for further processing. The conduit or autograft containing segments were prepared for immunofluorescence analysis and the distal end of the segments were prepared for histomorphometric analysis.

16.4.1.6 Immunofluorescence Analysis of Nerve Sections

The excised nerve segments including the conduits or autografts were fixed in 4% paraformaldehyde for 48 hours, dehydrated using a sucrose gradient, and embedded in paraffin using a KOS Microwave HistoStation. The tissues were submerged in absolute ethanol for 35 min, next in isopropanol for 70 min and last in paraffin for 90 min. 8 µm longitudinal sections were cut using a microtome and stained for S100 (1:200) and neurofilament 200 (1:300). The sections were incubated with the primary antibodies for 2 hours at room temperature, washed with 1× phosphate buffered saline (PBS), and then incubated with the secondary antibodies anti-rabbit AF488 (1:600) and anti-chicken DL650 (1:400) for 1 hour at room temperature. For DNA staining, 1×PBS+50 µg/ml 4',6-Diamidino-2-Phenylindole (DAPI) was added for 10 minutes. After washing, the sections were mounted with mountant, covered with a coverslip and sealed with glue. Images were acquired with a confocal laser scanning microscope.

16.4.7 Histomorphometric Evaluation

Nerve segments distal to the conduit or autograft were fixed in 3% glutaraldehyde for 24 hours and stored in 0.1 mol/l cacodylate at 4° C. until further processing. The tissue was postfixed with 2% osmium tetroxide, a strong oxidant that reacts with unsaturated double bonds, which results in the deposition of osmium black and the staining of myelin. After embedding in epoxy resin, 1 µm cross-sections were cut using an ultra-microtome. The sections were incubated with 1% para-phenylendiamin, which additionally stains the myelin sheets, and examined by light microscopy. Histomorphometric measurements of these sections were performed with a semiautomatic image-analyzing system. From the identified myelinated fibers, the myelinated fiber density (number of myelinated axons per $mm^2$), the mean axon area in $\mu m^2$, the mean myelin area in $\mu m^2$, and the mean myelinated fiber area (axon+myelin area) in $\mu m^2$ were calculated.

16.4.8 Statistical Analysis

All data are reported as the mean±standard deviation. One-way ANOVA+Tukey Post-Hoc-Analysis were performed using SPSS Statistics 25. Graphs were created with GraphPad Prism6 software. A p-value of <0.05 was considered as statistically significant.

16.4.2 Results 16.4.2.1 Electron Microscopy

Figures 21A, 21B:
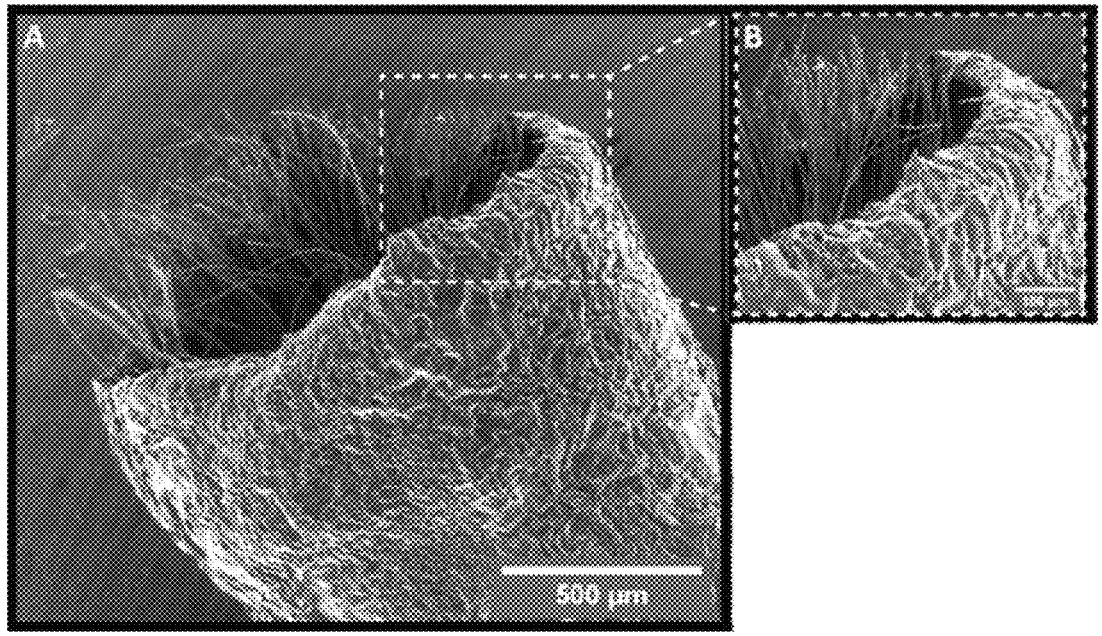
FIG. 21A shows representative micrograph of a silk conduit containing longitudinally aligned spider dragline silk and FIG. 21B shows magnification of the marked area in FIG. 21A.
Figure 21C:
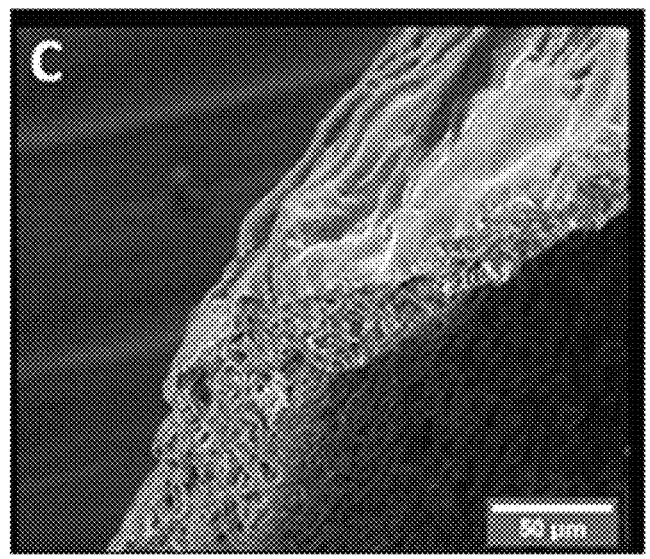
FIG. 21C shows a micrograph of a silk conduit tube wall.
Figure 21D:
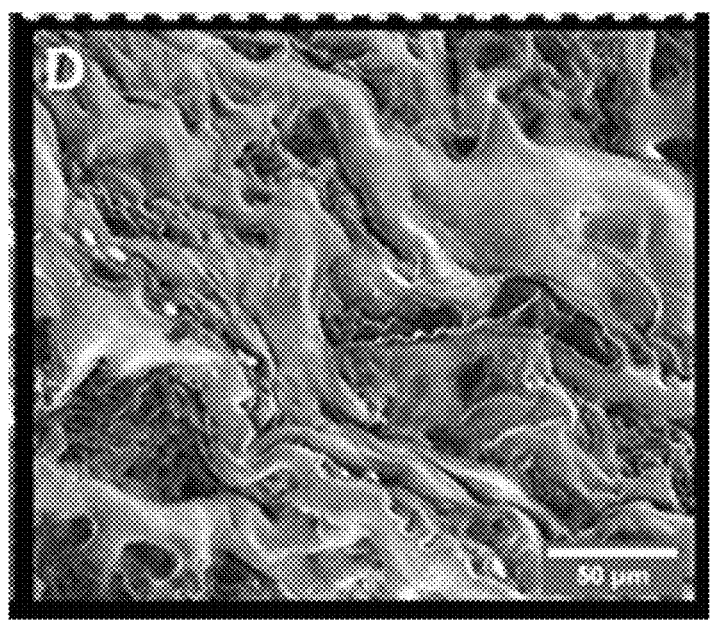
FIG. 21D shows magnification of an outer surface and FIG. 21E shows an inner surface of a conduit displaying a different porosity.
Figure 21E:
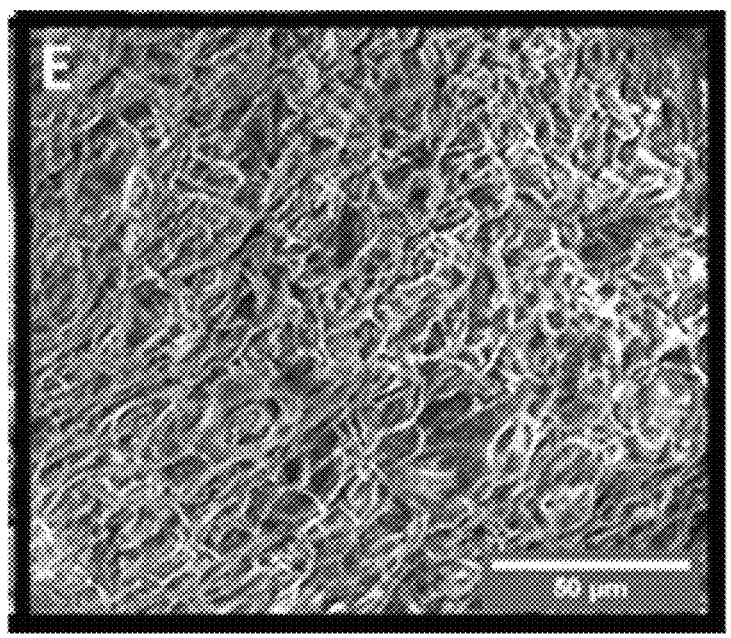

Scanning electron microscopy analysis of the silk-in-silk conduit was performed to provide high resolution information about the surface topography. The micrographs depict the silk conduit filled with dragline silk fibers (FIG. 21A, and FIG. 21B) and the silk conduit itself (FIG. 21C-E). FIG.

21 shows scanning electron microscopy analysis of a silk-in-silk conduit. FIG. 21A shows representative micrograph of a silk conduit containing longitudinally aligned spider dragline silk and FIG. 21B shows magnification of the marked area in FIG. 21A. FIG. 21C shows a micrograph of a silk conduit tube wall. FIG. 21D shows magnification of an outer surface and FIG. 21E shows an inner surface of a conduit displaying a different porosity. Variations between the inner and outer surface structures of the conduit wall can be seen in FIG. 21C. The outer conduit morphology was characterized by inhomogeneous larger grains (FIG. 21D), while the inner structure possessed a rather monodisperse grain size (FIG. 21E). The conduit wall shows a high porosity, which is related to the treatment method during conduit production.

16.4.2.2 Functional Recovery

Figure 22A:
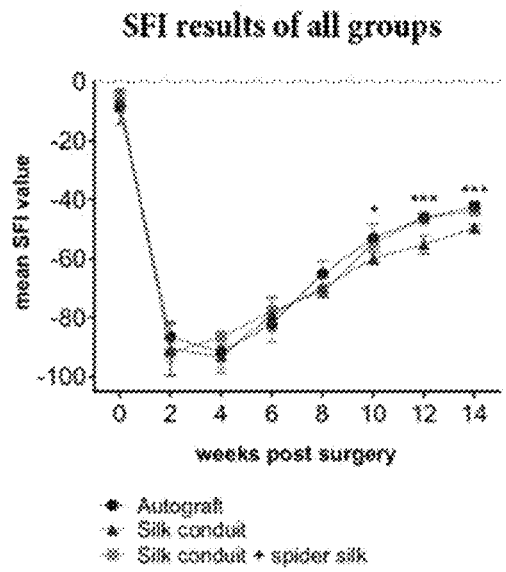
FIG. 22A shows a group wise comparison of the SFI results revealed a significant difference between the groups after 10 weeks postoperatively.
Figure 22B:
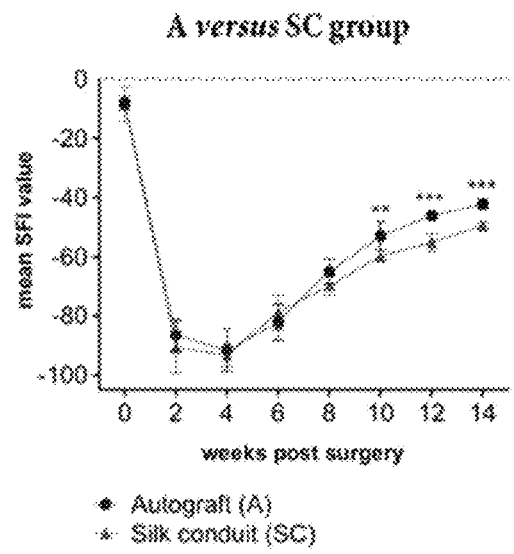
FIG. 22B shows the A group versus the SC group. The mean SFI value was significantly increased in the A group from ten weeks postoperatively onward.
Figure 22C:
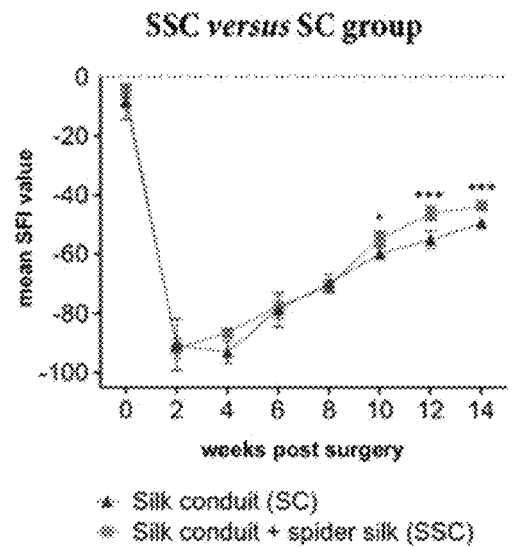
FIG. 22C shows the A group versus the SSC group. A significant difference of the mean SFI value was only observed at the eight-week time point.
Figure 22D:
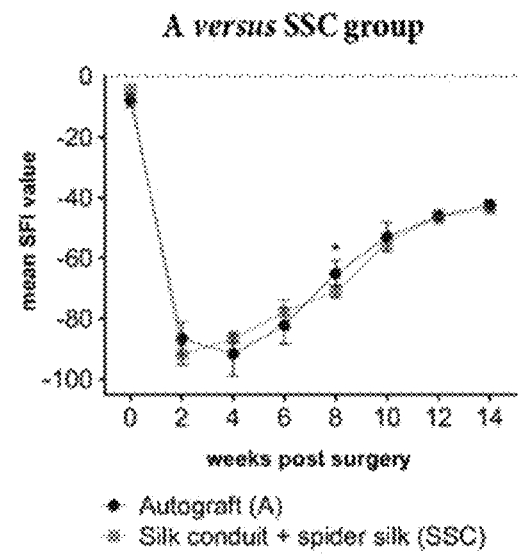
FIG. 22D shows the SC group versus the SSC group. The mean SFI value significantly raised in the SSC group from the ten-week time point onward. Values are depicted as mean±SD. *=p<0.5; =p<0.01; *=p<0.001.

To evaluate functional recovery of the animals, a gait analysis using SFI pre-operatively and every two weeks post-operatively for 14 weeks was performed as described before. An SFI value of 0 indicates normal function, whereas negative results display impairment. FIG. 22 shows a comparison of SFI values between all groups until week 14 post-surgery. FIG. 22A shows a group wise comparison of the SFI results revealed a significant difference between the groups after 10 weeks postoperatively. FIG. 22B shows the A group versus the SC group. The mean SFI value was significantly increased in the A group from ten weeks postoperatively onward. FIG. 22C shows the A group versus the SSC group. A significant difference of the mean SFI value was only observed at the eight-week time point. FIG. 22D shows the SC group versus the SSC group. The mean SFI value significantly raised in the SSC group from the ten-week time point onward. Values are depicted as mean±SD. *=p<0.5; =p<0.01; *=p<0.001. All animals showed improved functional recovery from 4 weeks until 14 weeks post injury. Indeed, no group reached the preoperative values during the length of the experiment (FIG. 22A). From week 10 onwards, the statistical analysis of the SFI values showed a significant different group comparison (FIG. 22A). After 14 weeks, the mean SFI values of both the A group (−53.01±4.86) as well as the SSC group (−54.75±2.32) were significantly increased compared to the SC group (−59.82±1.99) (FIG. 22B and FIG. 22C). Importantly, the A group and the SSC group demonstrated a similar functional recovery at week 10, 12, and 14 (FIG. 22D).

16.4.2.3 Anti-S100 and Anti-Neurofilament 200 Staining

Figures 23A, 23B, 23C, 23D:
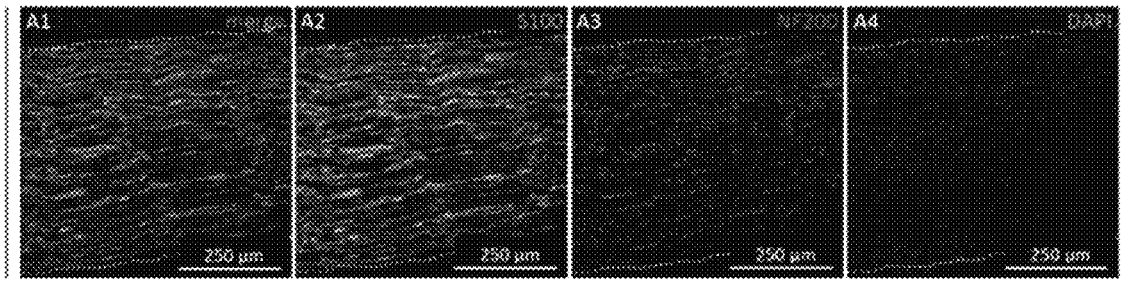
FIG. 23B, FIG. 23F, and FIG. 23J show staining for S100 positive Schwann cells.
FIG. 23C, FIG. 23G, and FIG. 23K show staining for neurofilament 200 (NF200) positive axons.
FIG. 23D, FIG. 23H, and FIG. 23L show staining for DAPI.
FIG. 23A, FIG. 23E, and FIG. 23I show merged images. The white dotted line indicates the silk conduit.
Figures 23E, 23F, 23G, 23H:
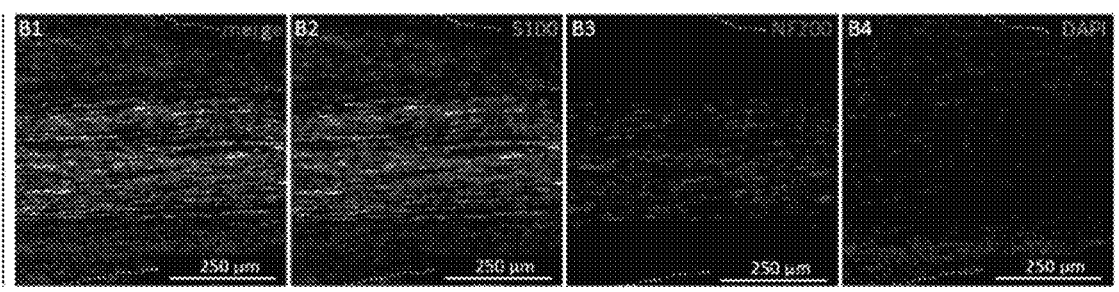
Figures 23I, 23J, 23K, 23L:
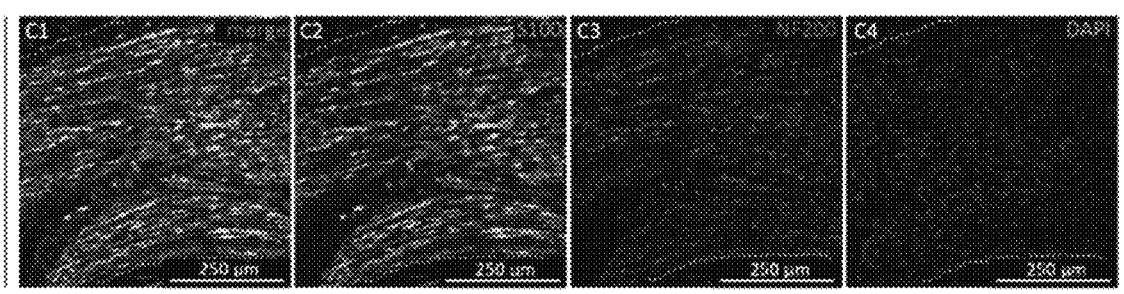

Immunostainings for Schwann cell marker S100 and axon maturation marker neurofilament 200 (NF200) was performed on longitudinal nerve sections through the autograft/conduits to evaluate the nerve re-growth in the three groups after 14 weeks post injury. In order to display the regeneration status of the whole section, images were taken at the proximal part (FIG. 24), central part (FIG. 23), and distal part (FIG. 25) and compared between the A, the SC, and SSC groups. Positive staining results for S100 and NF200 were observed continuously from the proximal over the middle to the distal part of analyzed sections and confirmed ongoing nerve regeneration in all groups. FIG. 23 depicts representative immunofluorescence images of the central part of the A group (FIG. 23A, FIG. 23B, FIG. 23C, and FIG. 23D), SC group (FIG. 23E, FIG. 23F, FIG. 23G, and FIG. 23H), and SSC group (FIG. 23I, FIG. 23J, FIG. 23K, and FIG. 23L). FIG. 23B, FIG. 23F, and FIG. 23J show staining for S100 positive Schwann cells. FIG. 23C, FIG. 23G, and FIG. 23K show staining for neurofilament 200 (NF200) positive axons. FIG. 23D, FIG. 23H, and FIG. 23L show staining for DAPI. FIG. 23A, FIG. 23E, and FIG. 23I show merged images. The white dotted line indicates the silk conduit. In all groups, NF200 positive regrowing axons are with associated S100 positive SCs. Interestingly, the regrowing nerve tissue within the empty nerve conduit was preferentially located in the very middle of the conduit, while it appeared more distributed in the conduits filled with spider dragline silk (FIG. 23B versus FIG. 23C). These results indicate that the silk fibers encourage a homogenous nerve regrowth through the conduit.

Figures 24A, 24B, 24C, 24D:
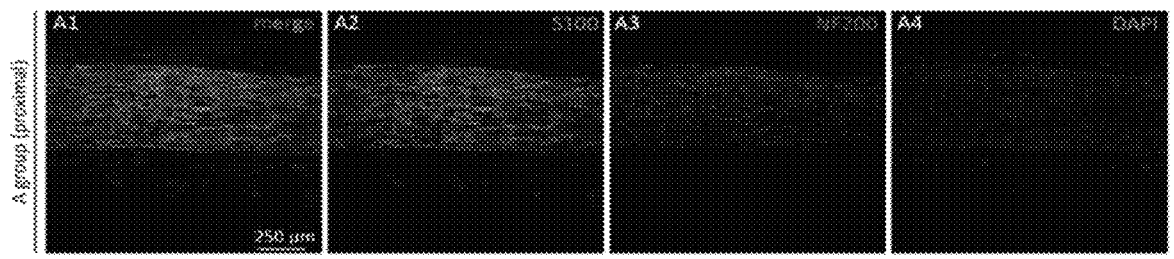
FIG. 24 depicts representative immunofluorescence images of the proximal part of the A group (FIG. 24 A, FIG. 24 B, FIG. 24 C, and FIG. 24 D), SC group (FIG. 24 E, FIG. 24 F, FIG. 24 G, and FIG. 24 H), and SSC group (FIG. 24 I, FIG. 24 J, FIG. 24 K, and FIG. 24 L).
Figures 24E, 24F, 24G, 24H:
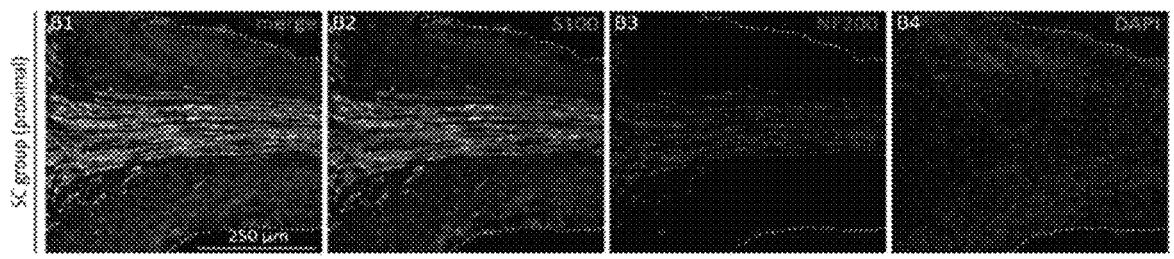
Figures 24I, 24J, 24K, 24L:
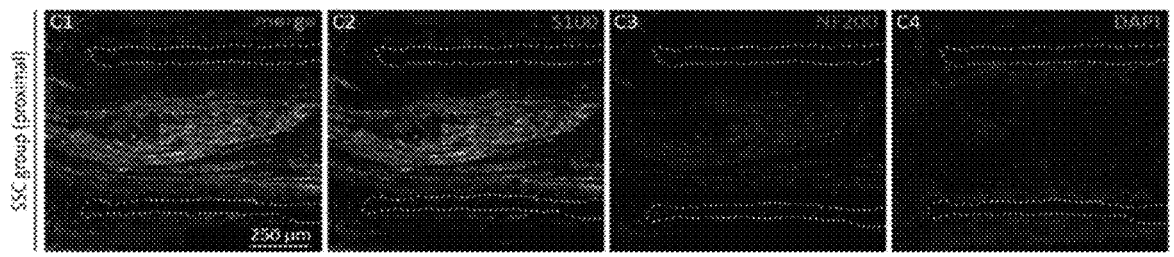

FIG. 24 depicts representative immunofluorescence images of the proximal part of the A group (FIG. 24 A, FIG. 24 B, FIG. 24 C, and FIG. 24 D), SC group (FIG. 24 E, FIG. 24 F, FIG. 24 G, and FIG. 24 H), and SSC group (FIG. 24 I, FIG. 24 J, FIG. 24 K, and FIG. 24 L). FIG. 24 B, FIG. 24 F, and FIG. 24 J show staining for S100 positive Schwann cells. FIG. 24 C, FIG. 24 G, and FIG. 24 K show staining for neurofilament 200 (NF200) positive axons. FIG. 24 D, FIG. 24 H, and FIG. 24 L show staining for DAPI. FIG. 24 A, FIG. 24 E, and FIG. 24 I show merged images. The white dotted line indicates the silk conduit.

Figures 25A, 25B, 25C, 25D:
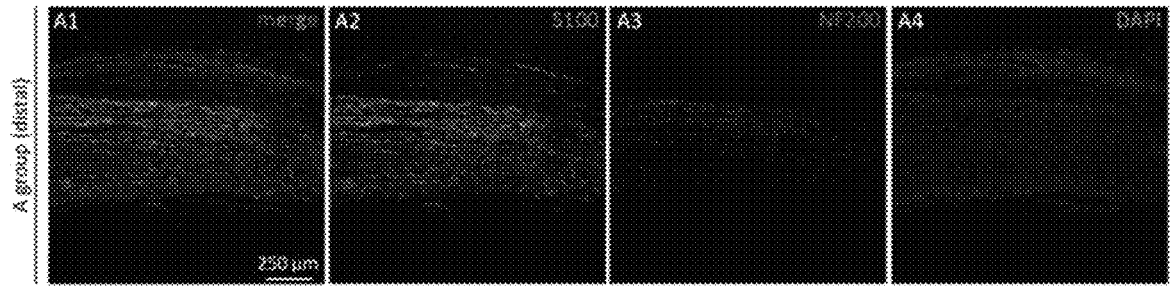
FIG. 25B, FIG. 25F, and FIG. 25J show staining for S100 positive Schwann cells.
FIG. 25C, FIG. 25G, and FIG. 25K show staining for neurofilament 200 (NF200) positive axons.
FIG. 25D, FIG. 25H, and FIG. 25L show staining for DAPI.
FIG. 25A, FIG. 25E, and FIG. 25I show merged images. The white dotted line indicates the silk conduit.
Figures 25E, 25F, 25G, 25H:
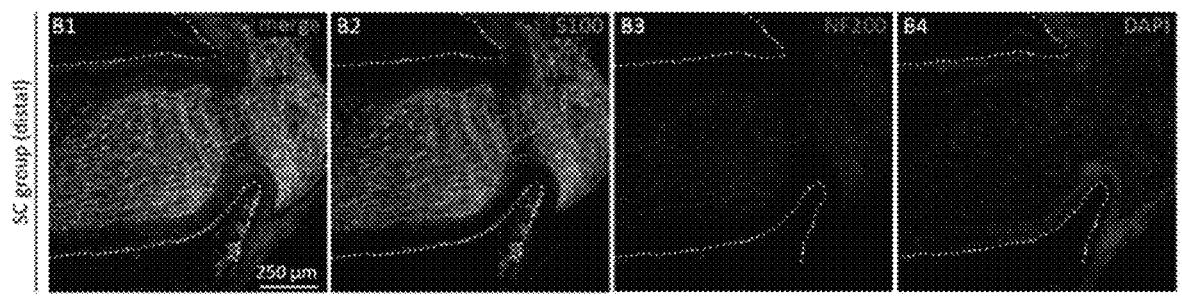
Figures 25I, 25J, 25K, 25L:
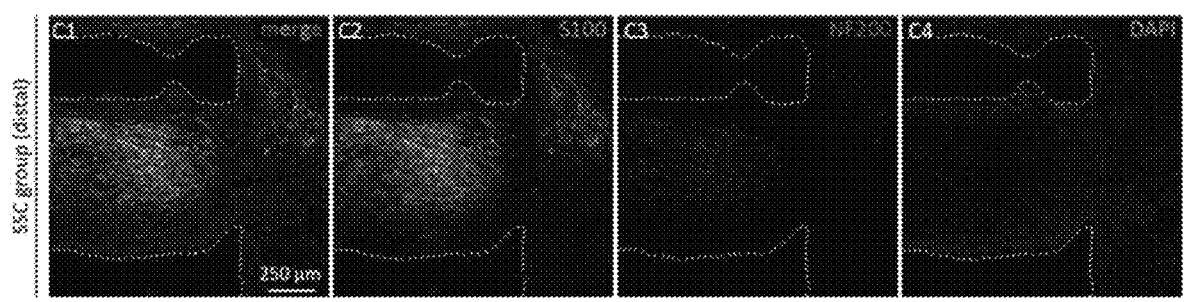

FIG. 25 depicts representative immunofluorescence images of the distal part of the A group (FIG. 25A, FIG. 25B, FIG. 25C, and FIG. 25D), SC group (FIG. 25E, FIG. 25F, FIG. 25G, and FIG. 25H), and SSC group (FIG. 25I, FIG. 25J, FIG. 25K, and FIG. 25L). FIG. 25B, FIG. 25F, and FIG. 25J show staining for S100 positive Schwann cells. FIG. 25C, FIG. 25G, and FIG. 25K show staining for neurofilament 200 (NF200) positive axons. FIG. 25D, FIG. 25H, and FIG. 25L show staining for DAPI. FIG. 25A, FIG. 25E, and FIG. 25I show merged images. The white dotted line indicates the silk conduit.

16.4.2.4 Histomorphometry

Figure 27A:
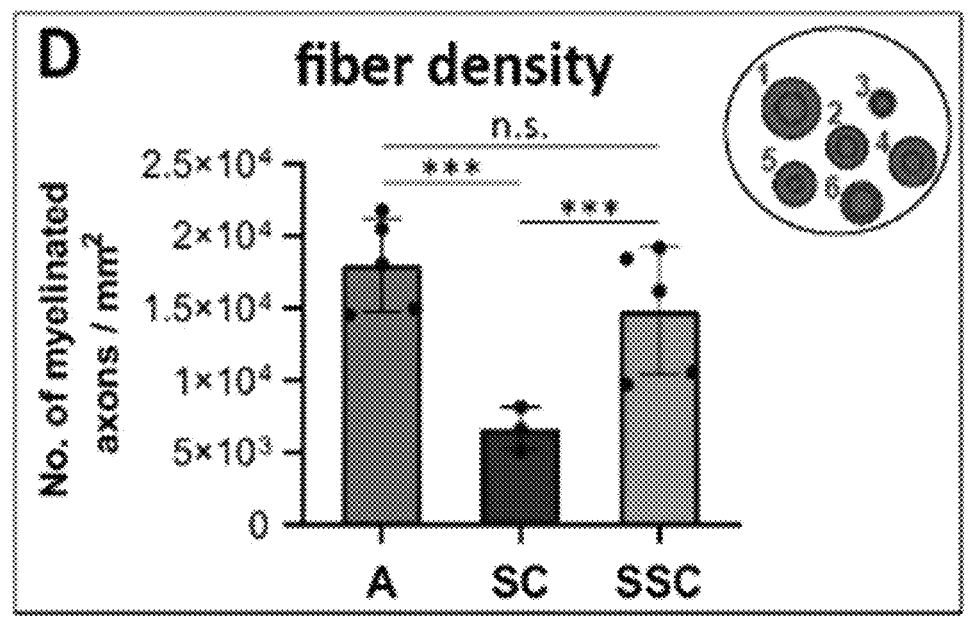
FIG. 27A shows the analyzed fiber density revealed a significant higher number of myelinated axons/mm$^2$ in the A group compared to the SC group, and in the SSC group compared to the SC group.
Figure 27B:
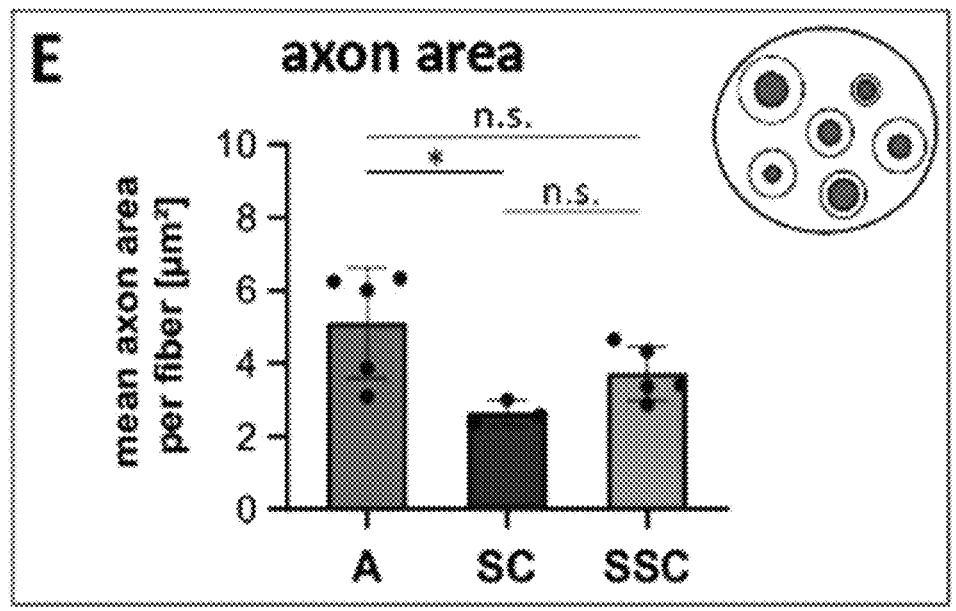
FIG. 27B shows the mean axon area showed a significant difference between the A group and the SC group.
Figure 27C:
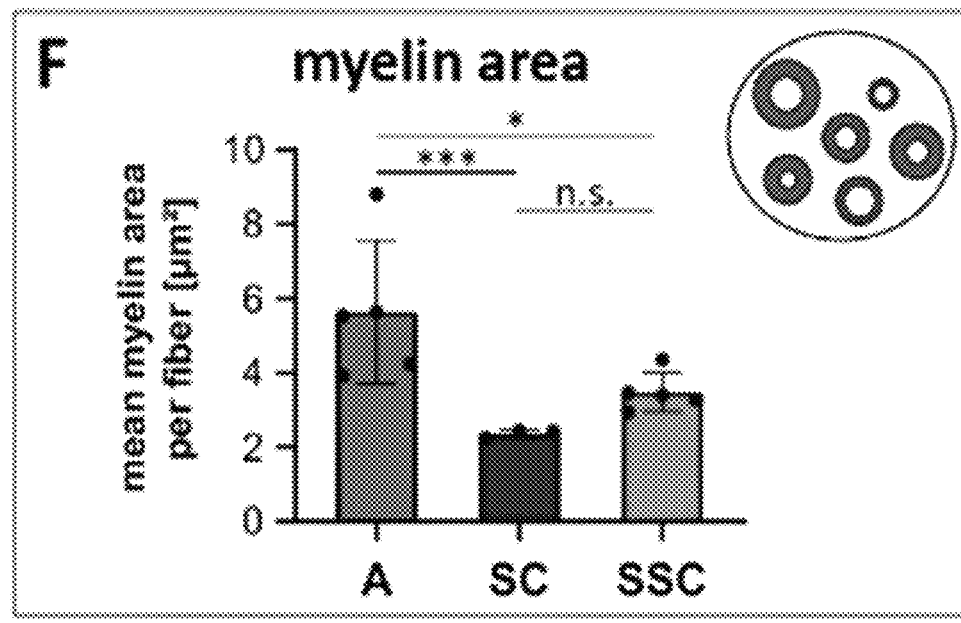
FIG. 27C shows that compared to the A group, the mean myelin area of both the SC group and the SSC group were significantly decreased.
Figure 27D:
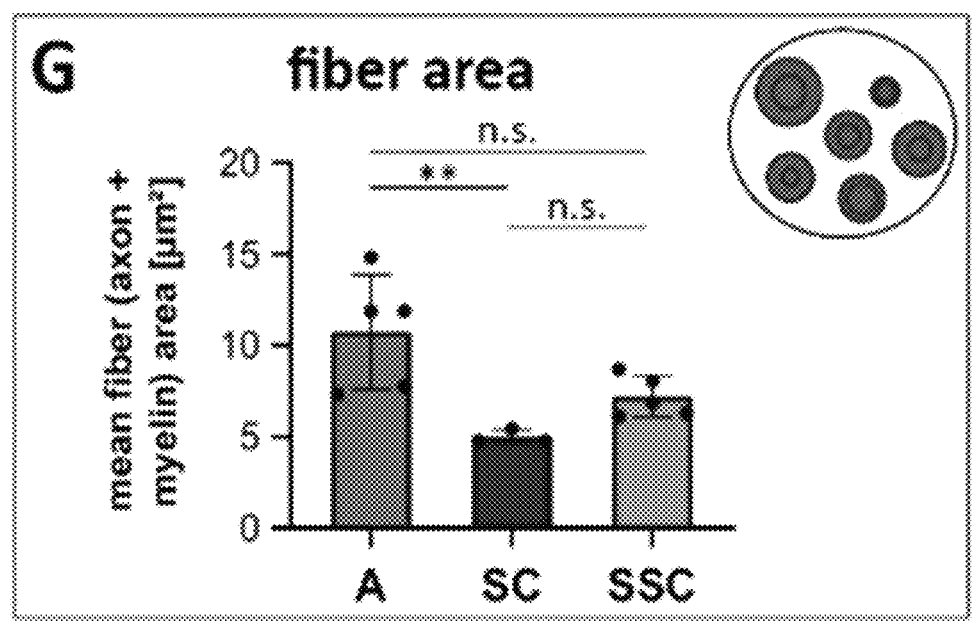
FIG. 27D shows the myelinated fiber area (axon+myelin) was only significantly decreased between the A group and the SC group. Values are depicted as mean±SD. *=p<0.5; =p<0.01; *=p<0.001.

Myelinated axons were analyzed histomorphometrically in nerve cross-sections distal to the autograft, the empty conduit, and the filled conduit. Representative images of distal nerve sections stained for myelin are illustrated for the A group (FIG. 26A, FIG. 26B, and FIG. 26C), the SC group (FIG. 26D, FIG. 26E, and FIG. 26F) and SSC group (FIG. 26G, FIG. 26H, and FIG. 26I). Semi-automated image analysis of these sections enabled to quantify the fiber density in number of myelinated axons/mm2 (FIG. 27A), mean axon area in $\mu m^2$ (FIG. 27B), mean myelin area in $\mu m^2$ (FIG. 27C), and the mean fiber area of axon+myelin area in $\mu m^2$ (FIG. 27D). Notably, we detected a comparable nerve fiber density within the distal nerve segments of the A group (17984±1444/mm2) and the SCC group (14829±1972/mm2), while it was significantly decreased in the SC group (6646±859/mm2) (FIG. 27A). Assessment of the mean axon area resulted in a similar pattern. There was no significant difference between the mean axon area of the A group (5.11±0.68 $\mu m^2$) and the SSC group (3.73±0.33 $\mu m^2$), however, compared to the A group, the axon area was significantly lower in the SC group (2.3±0.06 $\mu m^2$) (FIG. 27B). In addition to the axon content, also the myelination status of regenerated axons is a qualitative parameter for nerve regeneration. The largest mean myelin area was detected in the A group (5.63±0.86 $\mu m^2$) followed by the SSC group (3.48±0.24 $\mu m^2$) and was lowest in the SC group (2.36±0.06 $\mu m^2$) (FIG. 27C). The quantified mean fiber showed no significant difference between the A group (10.74±1.41 $\mu m^2$) and the SSC group (7.21±0.5 $\mu m^2$) but was significantly reduced in the SC group (5.01±0.21 $\mu m^2$) (FIG. 27D).

FIG. 26 depicts histomorphometric evaluation of distal nerve segments after 14 weeks of regeneration. Representative images and magnifications of osmium tetroxide stained myelin sheets on distal nerve cross sections of the A group (FIG. 26A, FIG. 26B, and FIG. 26C, n=5), SC group (FIG. 26D, FIG. 26E, and FIG. 26F, n=3), and SSC group (FIG. 26G, FIG. 26H, and FIG. 26I, n=5) used for semi-automated image analysis.

FIG. 27 depicts bar diagrams of the results of the semi-automated image analysis for the A group in grey, the SC group in blue, and the SSC group in orange. FIG. 27A shows the analyzed fiber density revealed a significant higher number of myelinated axons/mm$^2$ in the A group compared to the SC group, and in the SSC group compared to the SC group. FIG. 27B shows the mean axon area showed a significant difference between the A group and the SC group. FIG. 27C shows that compared to the A group, the mean myelin area of both the SC group and the SSC group were significantly decreased. FIG. 27D shows the myelinated fiber area (axon+myelin) was only significantly decreased between the A group and the SC group. Values are depicted as mean±SD. *=p<0.5; =p<0.01; *=p<0.001.

16.4.3 Discussion

To address the need for nerve guidance conduits adapted to treat long-distance nerve defects, this study introduces a silk-in-silk conduit that combines the advantages of two silk types. The conduit itself was constructed out of *Bombyx mori* silk-derived fibroin and included an internal guiding structure composed of longitudinally arranged dragline silk fibers of *Nephila edulis*. This advanced conduit was tested in a rat sciatic nerve injury model along with hollow silk conduits and autograft controls. Continual monitoring of the SFI served as functional read-out and demonstrated a comparable recovery of rats treated with silk-in-silk conduits and the autografts. The qualitative immunostaining analysis of longitudinal nerve sections depicted an ongoing axon regeneration in all groups identified by NF200 positive axons associated with S100 positive Schwann cells. In line with the SFI results, the quantitative histomorphometric analysis determined a similar fiber regeneration status in the nerve segments distal to the silk-in-silk conduits and autografts controls, while fiber regeneration was less progressed in the segments distal to the empty conduit. Remarkably, the silk-in-silk conduit and autograft groups showed no significant difference in number of myelinated axons/mm$^2$, the mean axon area, and the mean myelinated fiber area. These findings support that the intraluminal dragline silk fibers had a beneficial effect on the regrowing nerve fibers resulting in a similar regenerative performance as the standard treatment, the autograft.

Natural materials such as silk became of special interest in nervous tissue engineering due to their exceptional properties and versatile manufacturing possibilities. The silk conduit wall used in this study, was constructed from silk fibroin polymers and processed into a porous and elastic structure that showed favorable results in a previous study. Unfortunately, hollow conduits are only suitable to treat short-distance nerve defects. The missing internal scaffold and topographical cues hinder an organized ingrowth of Schwann cells over long distances causing axon dispersion and failed reinnervation of the target organ. Thus, current research focusses on intraluminal guiding structures that promote the distribution of Schwann cells through the conduit to ensure fast regrowth and ordered scattering of axons. A common strategy is the use of materials that provide biological bindings sites for cells by mimicking the nervous extracellular matrix. Indeed, intraluminal guiding structures with incorporated proteins such as collagen, laminin and fibrin or their cell binding motives displayed improved nerve regeneration compared to empty conduits. However, the arbitrary crosslinking of luminal fillers such as hydrogels or sponges likely counteracts the longitudinal architecture of peripheral nerves. Different from other engineered tissues, nerve conduits should be able to facilitate a straight and continuous regrowth of nerve fibers through an aligned structure. Proof of concept was provided in a study that compared random and aligned fibrin hydrogels in a 10 mm rat sciatic nerve defect. 12 weeks after surgery, the group with the aligned hydrogel filling performed significantly better with regards to nerve fiber density, diameter of myelinated fibers and myelin thickness, however, was still inferior to the autograft group.

In addition to luminal fillers, nerve conduits can also be enriched with internal guiding filaments. Based on the excellent biological and mechanical properties reported for spider dragline silk, its application as guiding filaments in nerve conduits was tested in previous animal studies and demonstrated promising results. In a 20 mm rat sciatic nerve injury model, acellularized vein conduits filled with either a gelatinous protein mixture secreted by Engelbroth-Holm-Swarm (EHS) mouse sarcoma cells or longitudinally arranged *Nephila clavipes* dragline silk caused a significantly higher axon density of the spider silk group. Moreover, the same vein-silk fiber conduit was used to treat long-distance nerve defects in sheep and achieved a similar regenerative outcome as the autograft controls. Further evidence for the favorable properties of silk-based internal guiding filaments was provided by a previous study, which tested the herein used fibroin conduit enriched with hyaluronic acid coated silk based biomaterial fibers generated from degummed non-mulberry silk fibroin. This conduit was applied to bridge an 10 mm gap of a rat sciatic nerve. After 12 weeks post-surgery, the results demonstrated comparable results in muscle endplate innervation and functional recovery between the autografts and conduits containing 200 silk based biomaterial fibers. However, the regenerated fiber density and axon size within the distal nerve segment was significantly reduced in animals treated with the silk based biomaterial fiber conduits when compared to autograft controls. This is in contrast to our study, which showed no significant difference in the nerve fiber density and axon area between the silk-in-silk and autograft groups.

The increased regenerative effect of the herein described silk-in-silk conduit on regrowing axons is presumably caused by the superior interaction of cells with spider dragline silk. Of note, dragline silk does not require any further processing step such as degumming, enzymatic treatment, coating, or modification with cell binding motives to exert its favorable biological effect on cells. Importantly, native dragline silk was shown to provide an excellent adhesive surface allowing cell attachment, alignment, and migration for Schwann cells, the key drivers of peripheral nerve regeneration. In response to injury, Schwann cells undergo transcriptional reprogramming to adapt a reparative phenotype accompanied by a profound morphological change. Denervated Schwann cells within the basal lamina tubes in the distal nerve segment extensively elongate and align their processes in a parallel manner to provide regeneration tracks, termed Bungner bands, for regrowing axons. Native dragline silk was demonstrated to encourage this behavior by supporting the formation of sustained bundled structures of Schwann cells together with re-growing axons along the silk in vitro. Moreover, the migration distance of Schwann cells seeded on dragline silk fibers achieved a remarkable speed of over 1.1 mm per day, which is in line with the reported growth rate of regenerating axons. These studies suggest that the rapid regeneration of axons through the silk-in-silk nerve conduit is based on the fast formation of Bungner band like structures along the luminal dragline silk fibers.

16.4.3.1 Conclusion

This work contributes a novel approach to encourage peripheral nerve regeneration across gap injuries using a biocompatible and biodegradable nerve guidance conduit that exploits the favorable properties of native as well as processed silk. We report a similar regenerative performance of animals treated with autografts and the silk-in-silk nerve conduits, which are composed of a fibroin-based conduit wall and longitudinally arranged dragline silk fibers as internal guiding filaments. The regenerative effect of the silk-in-silk conduit is presumably based on the spider dragline silks' inherent properties allowing a fast migration and alignment of Schwann cells through the conduit. With regard to clinical translation, additional experiments with larger gap sizes and inclusion of upper extremity nerve injury models will help to further evaluate the silk-in-silk conduit and its performance in critical segmental nerve defects.

Example 17 Comparison of Different Sheaths Used with the Same Internal Fibers

Use of silk fibers in different sheaths was compared in a trial in sheep. Ideal sheep conduits were 50 mm in length.

17.1 Definitions

Sheath: Outer hollow tube that protects and holds the luminal silk fibres in place during nerve regeneration.
Conduit: The assembled sheath and fibres
Luminal fibre: medical grade silk fibre that runs the length of the conduit and protrudes at both ends or is flush to the ends of the sheath.
Knit: a tube knitted from silk threads, not used here.

TABLE 2

| Material | Internal Diameter mm | Length available mm | Additional notes |
|---|---|---|---|
| semi-permeable type 1 collagen membrane | 1.5, 2, 3, 4, 5, 6, 7 | 30 | Requires flushing when one end is sutured in place-potential disrupt to fibres. (sterile saline or Lactated Ringer's solution) |
| Woven polyglycolic acid mesh tube | 2.3 (40 mm length) 4.0 mm (20 mm) | 40 | The walls are corrugated for strength and flexibility. The device is resorbed through the process of hydrolysis Implantation is more complex Warnings: Complete haemostasis should be obtained before the device is positioned Blood clot(s) in the lumen of the device will impede neuroregeneration. For hand surgeries, the patient's hand should be immobilized for three weeks following nerve reconstruction with the device. The nerve ends should never be inserted into the device under tension. If the nerve gap is greater than 30 mm when applying the 2.3 mm diameter device, an autologous nerve graft should be used instead. |

TABLE 2-continued

| Material | Internal Diameter mm | Length available mm | Additional notes |
|---|---|---|---|
| porcine submucosa extracellular matrix | 1.5, 2, 3, 4, 5, 6, 7 | 10-15 | If the nerve gap is greater than 10 mm when applying the 4 mm diameter device, an autologous nerve graft should be used instead. Requires flushing when one end is sutured in place-potential disrupt to fibres. (sterile saline or Lactated Ringer's solution) |

17.2 Methods 17.2.1 Dipping Method

Degumming was performed by EDTA soak overnight, 4 hr 20 min trypsin degum, wash with UPW. The dissolving method was 1:4 LiBr ratio, 2 hour dissolve 37° C. The dialysis was medical grade level (<10 µS). Sheaths were produced with a 2.1 mm diameter. The needle was dipped in viscous silk solution. 1 minute in chilled PEG/AA. 30 minutes freeze. Crystallized and stored in ethanol. Sheaths using this method were used in a rat trial but were deemed too flimsy with no kink resistance.

17.2.2 Double Dipping Method

Sheaths were produced with a 2.1 mm diameter. The needle was dipped in viscous silk solution. 1 minute in chilled PEG/AA. 30 minutes freeze. The needle was dipped in viscous silk solution. 1 minute in chilled PEG/AA. 30 minutes freeze. Crystallized and stored in ethanol.

Findings: For the smaller scale diameter dimension required for rat trials, sheaths made from double dipping were found to be optimal, with reasonable handing and physical properties.

17.2.3 Freeze-Gel-Freeze-Crystallize

Silk solution was poured into a mold (with rod to create hollow tube shape) then frozen for 30 mins (longer ~2 hours is better). The outer mold was removed, and the frozen silk was submerged in chilled PEG/AA solution. The rod was removed either before or after this step. The silk tube was removed from the PEG/AA and frozen again for 30 mins. The conduit was then placed in ethanol for a minimum of 2 hours, the conduit could be left in the ethanol for storage. Ethanol storage should be at 4° C.

Findings: These had great handling but the overall thickness was thought to be too much for the smaller scale sheaths required for rats.

17.2.4 Freeze-Gel-(Freeze) Freeze Dry

Silk solution was poured into a mold (with rod to create hollow tube shape) then frozen for 30 mins (longer ~2 hours is better). The outer mold was removed, and the frozen silk was submerged in chilled PEG/AA solution. The rod was removed either before or after this step. The silk tube was removed from the PEG/AA and frozen again for 30 mins. The silk was lyophilized overnight Conduit is then placed in ethanol for a minimum of 2 hours, the conduit can be left in the ethanol for storage. Ethanol storage should be at 4° C.

Findings: Freeze drying had not been implemented on the rat trial scale.

Internal diameter of the sheath was 2-4 mm. Wall thickness of the sheath was >2 mm. Length of the sheath was 70 mm to be cut when implanted. Porosity was defined by freezing followed by PEG/AA which induced pores with or without freeze drying. The morphologies was a straight tube, with solid porous uniform walls; some success but the flexibility was insufficient. The freeze drying added much needed flexibility. Corrugated tubes were made using thread and a corrugated rod: corrugation gave added flexibility but caused severe irritation Findings: a previous sheep trial showed corrugations caused a mass inflammatory response.

17.3 Knits

Knits may be required if the nerve conduits are to be sutured in place. Without a knit the suture can tear through the silk sheath. If the nerve conduits are glued in place, then a knit would not be required. The advantage of not using a knit means that the design is simplified allowing more possible design options.

During implantation into a rat, the sheaths were easily implanted and sutured in place. The sheath was made with no knit using the double dipping method.

17.4 Gelling with PEG/AA

As shown in Example 5, there is a clear need for the use of a gelling agent to define protein structures prior to the use of lyophilization and/or crystallization. Without the PEG/AA gelling step, the scaffolds will be brittle and may not form the molded structures.

This method allows for covalent crosslinking to give flexibility, this is done using the PEG/AA gelling solution as the first step (post freezing to keep the shape). The PEG/AA provides crosslinking to hold the alpha helical structures, preventing complete loss during crystallization and ultimately maintaining the required flexibility. The (freeze then) freeze drying allows for our silk to hold its shape at room temperature. Meaning, that as ethanol is applied (to crystallize) in the final step, it changes alpha helix to beta, but in a confined controlled predetermined manner. The results are the same as when scaffolds are made just in the F-G-F method, but more enhanced.

17.5 Alcohol Crystallization

Applying ethanol/methanol to silk as vapor or solution forces the silk to undergo secondary protein structure changes, giving it this heightened strength. Out of the 4 structures present, (beta sheet, beta turn, alpha helix and random coil), there is a direct change of alpha helix structures to beta sheet, the others remain largely unchanged.

The increased beta structures add mechanical strength come at the loss of some flexibility. These structural changes also dramatically impact on biodegradability. The greater the beta structure presence the more resistant to degradation they are. It is therefore possible to tailor the strength and in theory the degradation rate of silk in vivo by controlled ethanol exposure.

17.6 Development of Straight Conduits

To date, straight and corrugated silk conduits have been used. The corrugations allowed for added flexibility vital for surgeon handling as well as patient mobility. The corrugated design was unsuccessful, causing inflammation in the sheep.

17.6 Implantation of Conduits

A tubular graft for hemodialysis graft was made from the combination of a fibrous layer, a silk porous matrix as the external layer and a hemocompatible smooth internal silk surface. The tubular grafts were 6 mm in internal diameter and could be made up to 20 cm long, with a corrugated/kink-resistant or a smooth/straight external surface. Tube wall thickness was 1 mm maximum for the straight sections and 1.8 mm maximum for the corrugated sections.

Silk tubular samples were prepared for implantation into three sheep. Sections of the tubes sent for implantation were used for SEM analysis, bioburden testing and AA content.

Figure 28A:
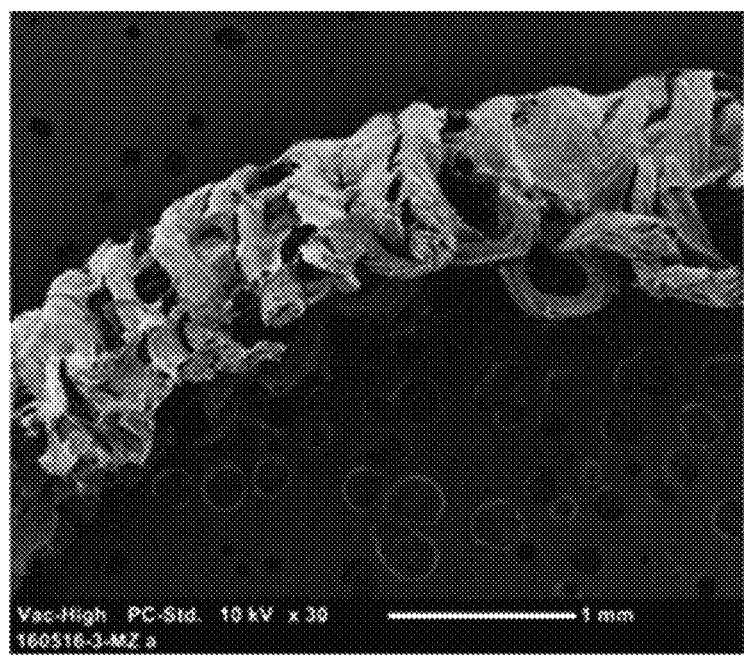
FIG. 28A, FIG. 28B, and FIG. 28C depict SEM photos of silk tubes used for sheep implantation.
Figure 28B:
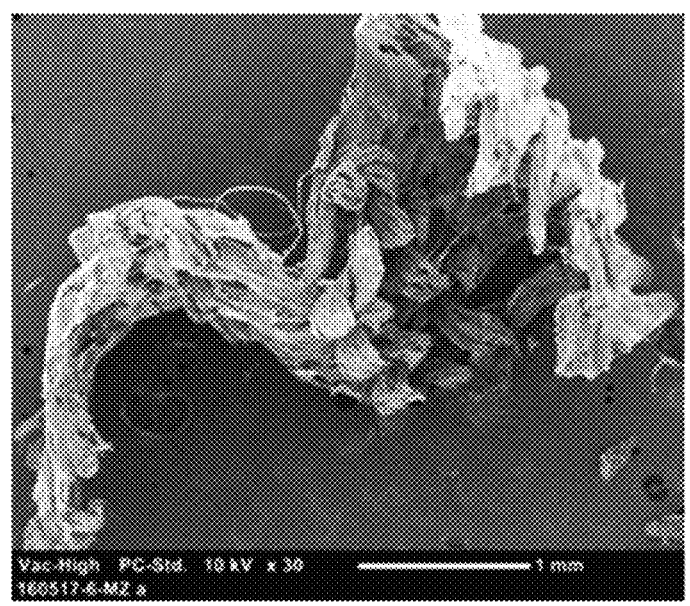
Figure 28C:
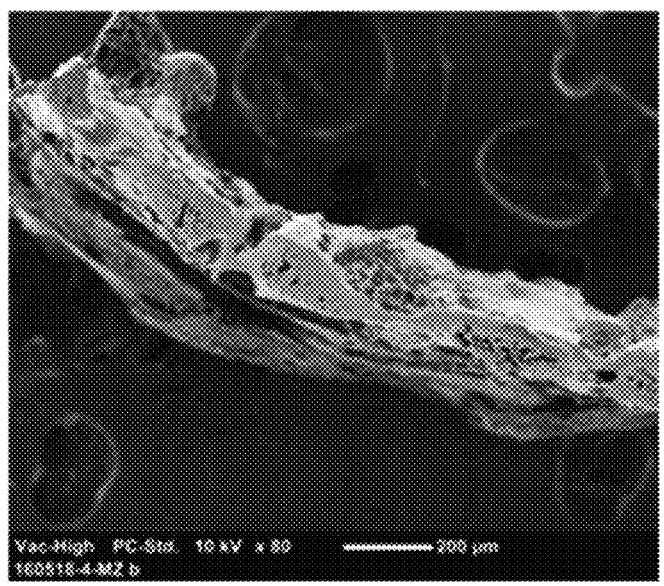

SEM analysis showed the knit was highly exposed, lacking the matrix coating as shown in FIG. 28A, FIG. 28B, and FIG. 28C.

The average bioburden measured on the samples was 643.7 CFU. This level was quite high considering that the desired bioburden level for medical devices should be <50 CFU (Table 3). The high bioburden could be responsible for the high inflammatory reaction observed.

TABLE 3

Bioburden of silk tubes used for sheep implantation Colony characterization

| 160620-3-MZ | CFU | Staphylococcus/ Micrococcus spp | Bacillus spp |
|---|---|---|---|
| 1 | 523.6 | + | + |
| 2 | 816.2 | + | + |
| 3 | 739.2 | + | + |
| 4 | 500.5 | + | + |
| 5 | 639.1 | + | + |

Silk tubes were analyzed for acetic acid content to determine the efficacy of the neutralization step. The results show that silk tubes have similar acetic acid content with and without neutralization (Table 4). The acetic acid content is quite low, suggesting that acetic acid leaching might not cause any inflammatory reaction.

TABLE 4

Acetic acid (AA) content measured on silk tubes with and without neutralization

| Sample | Acetic acid (mg/g) |
|---|---|
| 160620-1-MZ (NOT Neutralized) | <0.09 |
| 160620-2-MZ (Neutralized) | <0.08 |

Silk tubes were analyzed for acetic acid content to determine the efficacy of the neutralization step. The results showed that silk tubes had similar acetic acid content with and without neutralization (Table 4). The acetic acid content was quite low, suggesting that acetic acid leaching might not cause any inflammatory reaction.

Straight designs have proven more reliable with respect to limiting inflammation; however, these conduits are prone to kinking. Potential developments to the design of a straight tube with uniform walls to improve flexibility include:

Defining porosity/texture. An alternative to salt based porogens would be to use freeze drying as part of the conduit formation. This has potential for producing silk tubes with impressive flexibility. (Method: Freeze→gel→(freeze) freeze dry→ethanol.)

Solution concentration. Dilution/increasing the concentration of the silk solution prior to conduit formation could allow for a less dense conduit to be produced. Assuming there is no loss in mechanical properties, added flexibility is possible.

17.7 Development of Open Spiral Conduit

An open spiral structure capped by solid walled ends has been proposed, the central spiral section will allow for maximum flexibility and kink resistance. There will be no connecting walls between the spiral regions, the conduit walls do not need to be solid throughout the entire length, but the ends will require solid walls to allow for gluing at implantation. A knit would not be possible for this design.

Production methods for the open spiral design include:

17.7.1 Open Spiral Production Method: Thread Winding

A conduit is produced in the same method as the straight conduits. A thread is then wound around the conduit to slice a spiral shape. The thread will cut through the wall whilst the conduit is still mounted on the central rod.

17.7.2 Open Spiral Production Method: Screw Mold

A cylindrical mold with a screw shaped rod will be created, (using a 3D printer). The silk solution is injected into one open end of the mold, once filled the ends are sealed and the standard conduit production can be performed. The outer mold can be dialysis tubing as opposed to plastic. This would keep the silk inside but allow PEG/AA (2.5%/2.25%) to pass through to the silk, meaning the gelling step can be performed in mold. Not having to remove the mold before gelling would make production easier and reduce waste/loss. There is dialysis tubing readily available at a radius of 6.3 mm. Using dialysis tubing would create an additional cost to the process. The outer mold can be plastic, this would require removal before gelling making the process more difficult, but an entirely plastic mold would be reusable.

17.8 Development of Asymmetric Conduits

Figure 29A:
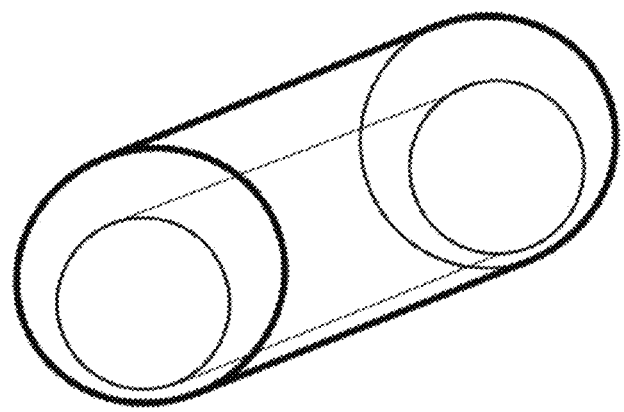
FIG. 29A depicts conduits with a section at each end where the wall is thicker and uniform.

The straight tubes lacked substantial flexibility; it is believed that a non-uniform wall thickness will provide added flexibility. These conduits can have a knit if required. If needed to aid implantation the conduits can have a section at each end where the wall is thicker and uniform, as shown in FIG. 29A.

Figure 29B:
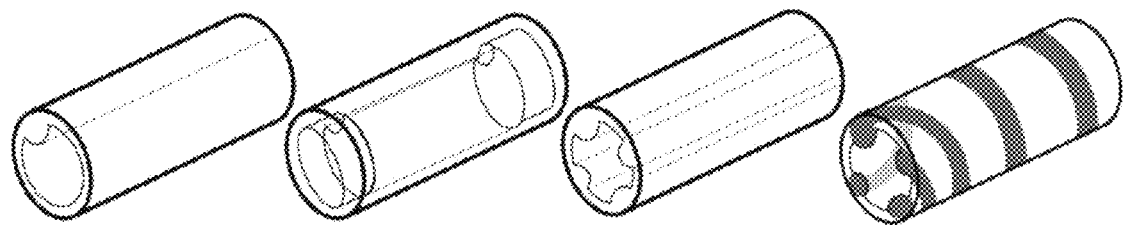
FIG. 29B depicts conduits with one or more longitudinal or spiral ridges that run either from end to end or occupy a central region of the conduit.
Figure 29C:
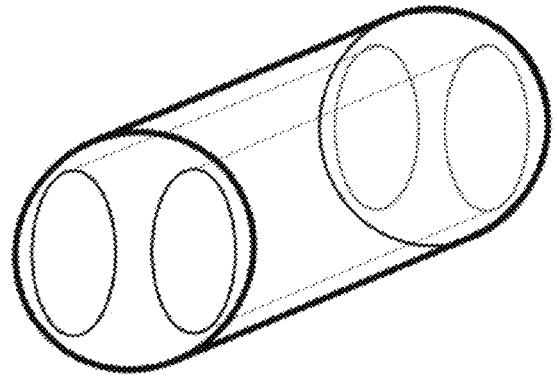
FIG. 29C shows a bi-lumen design for a conduit.

The conduits can have one or more longitudinal or spiral ridge that runs either from end to end or occupies a central region of the conduit as shown in FIG. 29B. These would be made by creating a special mold. Thicker regions can be produced separately, and a thinner wall then created by dipping, or a bespoke mold can be used. A bi-lumen design is another option, as shown in FIG. 29C.

Previously syringes have been used as a convenient mold for larger conduits. However, as our conduits will have an internal diameter of 3-4 mm, and readily available syringes have diameters; 3.8 mm (0.5 mL), 4.8 mm (1 mL) and 8.2 mm (2.5 mL), this does not provide enough scope to vary the wall thickness of the sheath. 3D printed molds will be tested with stainless steel rods; 3 mm, 3.2 mm, 3.5 mm and 4 mm, to produce larger sheaths that can be gelled and freeze dried.

17.9 Freeze Drying of Straight Sheaths Vs Just Gelling

Several methods were tested when trying to scale up the conduits sizes. Those could be divided into three groups:
1. Syringe mold.
2. Upscaling dip:
   a. single dip,
   b. double dip,
   c. triple dip.
3. Freeze drying with dip:
   a. single dip-FD-crystalizing,
   b. dip-FD-dip-FD-crystallizing,
   c. double dip-FD-crystallizing,
   d. dip-FD-dip-FD-dip-FD-criticizing,
   e. triple dip-FD-crystallizing.
FD=freeze drying 17.9 Syringe Mold The first option tested was the syringe molds. This showed to be suboptimal, since when removing the conduits from the syringe mold they felt apart. Freezing was done for 1 hour, so potentially increasing the freeze time may help with this. This showed not to be a good option for scaling up. It was decided to try the same method but with a metal outer mold.

17.10 Dipping

The dip process is the same as the one used for 2.1 mm rat trial sheaths. As stated above, three different options were tested:
Dip-gel-crystallization, ('single dipping')
Dip-gel-Dip-gel-crystallization, and ('double dipping')
Dip-gel-Dip-gel-Dip-gel-crystallization. ('triple dipping')

Figure 30:
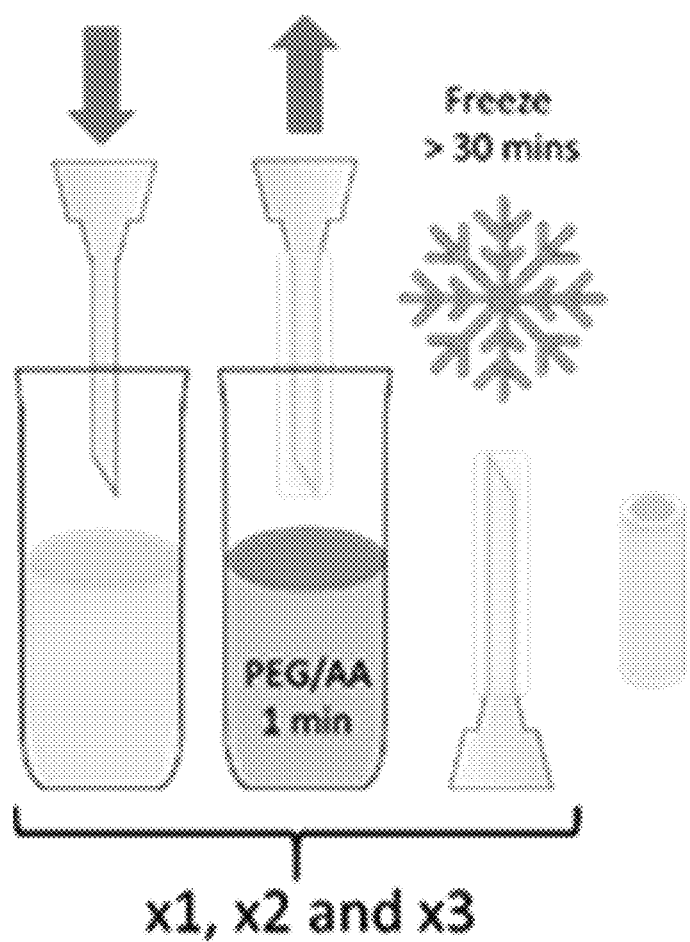
FIG. 30 shows a drawing depicting the dipping method.
Figure 31A:
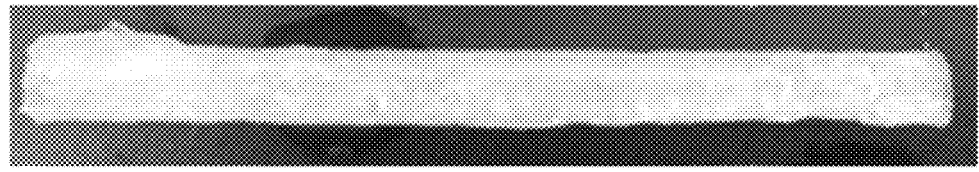
FIG. 31A and FIG. 31B depicts the resulting sheath formed from the triple dipping method.
Figure 31B:
Figure 31C:
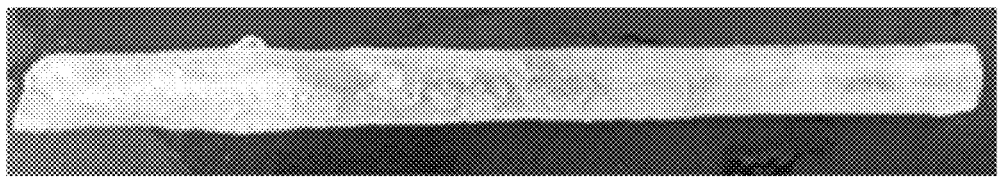
FIG. 31C and FIG. 31D depicts the resulting sheath formed from the double dipping method.
Figure 31D:
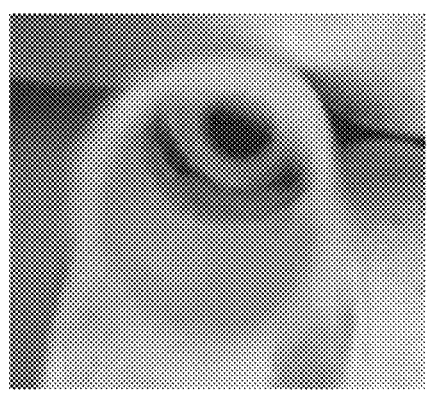
Figure 31E:
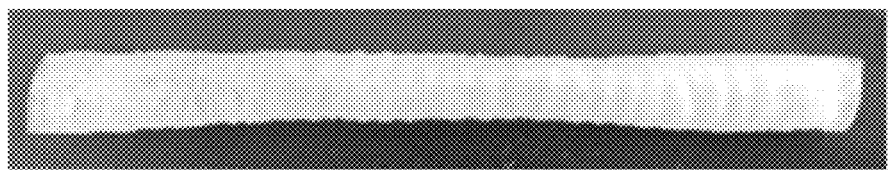
FIG. 31E and FIG. 31F depicts the resulting sheath formed from the single dipping method.
Figure 31F:
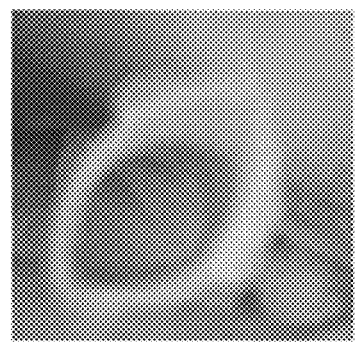

A drawing depicting the dipping method is shown in FIG. 30. The resulting sheath formed from the triple dipping method is shown in FIG. 31A and FIG. 31B. The resulting sheath formed from the double dipping method is shown in FIG. 31C and FIG. 31D. The resulting sheath formed from the single dipping method is shown in FIG. 31E and FIG. 31F.

Although we were able to get conduits, these were uneven. Ideally a mold would be better, creating a more homogenous conduit than by dipping. The triple dipping method had the best mechanical properties whilst remaining visibly porous. It is noteworthy that delamination between silk layers can occur, when upscaling this will need to be considered carefully.

17.10.1 Dipping with Freeze Drying

Freeze drying (FD) was tested, first before crystalizing and second after gelling. The options tested were:
Single dip-FD-crystallizing.
Dip-FD-dip-FD-crystallizing.
Double dip-FD-crystallizing.
Dip-FD-dip-FD-dip-FD-criticizing.
Triple dip-FD-crystallizing.

Figure 32:
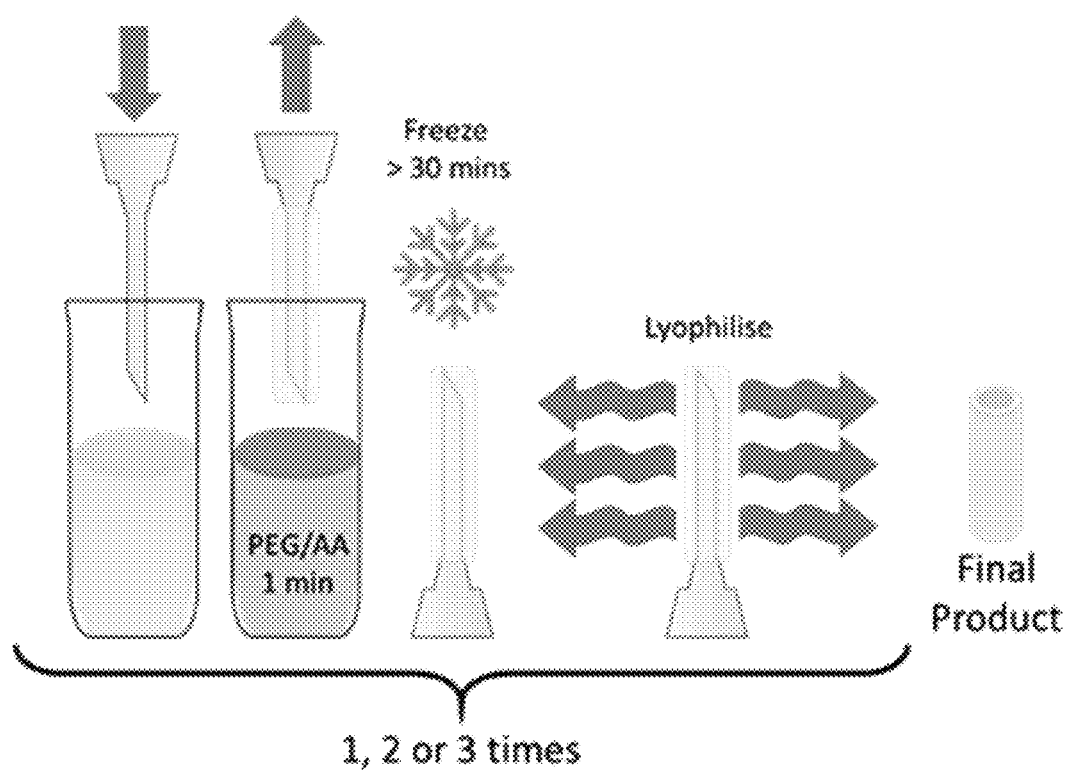
FIG. 32 shows a drawing depicting the dipping with freezing method.
Figure 33A:
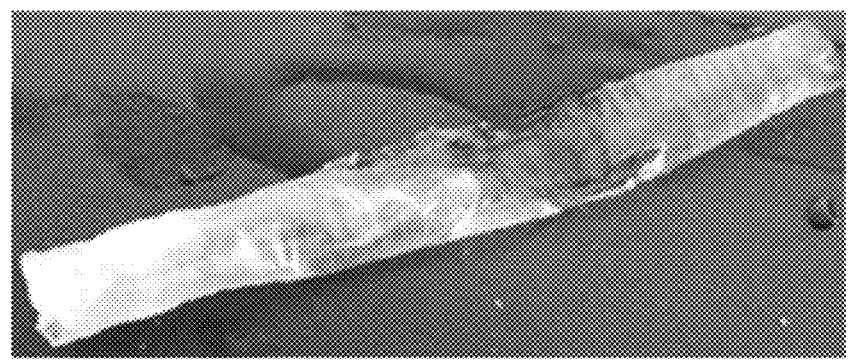
FIG. 33A and FIG. 33B shows the resulting sheath formed from the single dip-FD-crystallizing method.
Figure 33B:
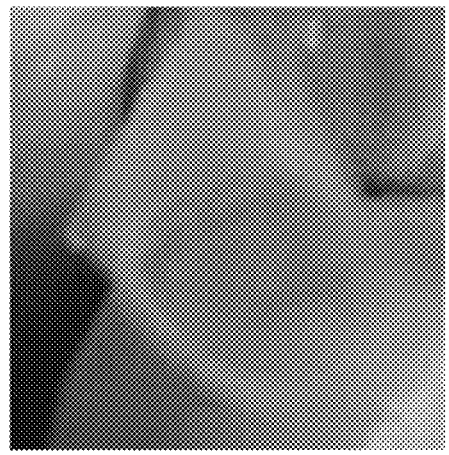
Figure 34A:
FIG. 34A and FIG. 34B shows the resulting sheath formed from the double dip-FD-crystallizing method.
Figure 34B:
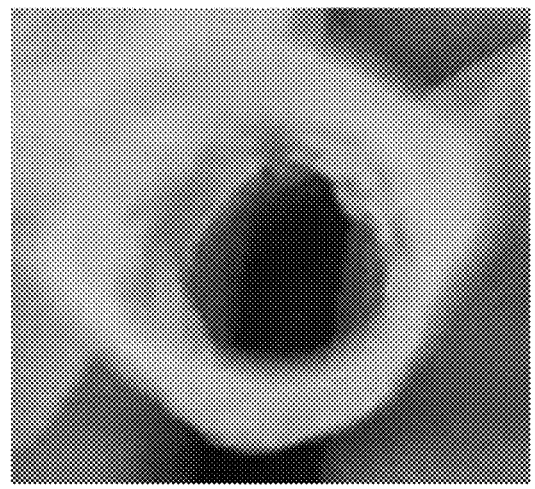
Figure 34C:
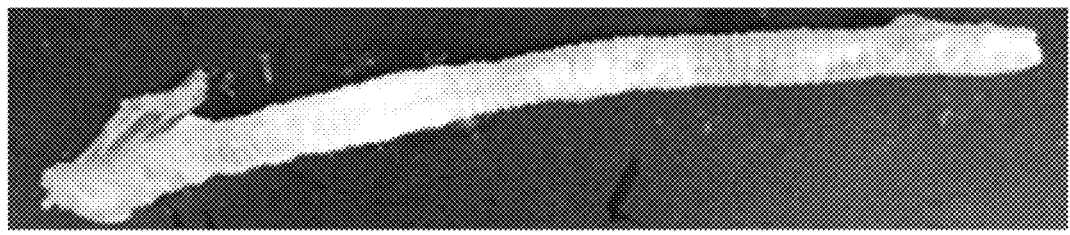
FIG. 34C and FIG. 34D shows the resulting sheath formed from the dip-FD-dip-FD-crystallizing method.
Figure 34D:
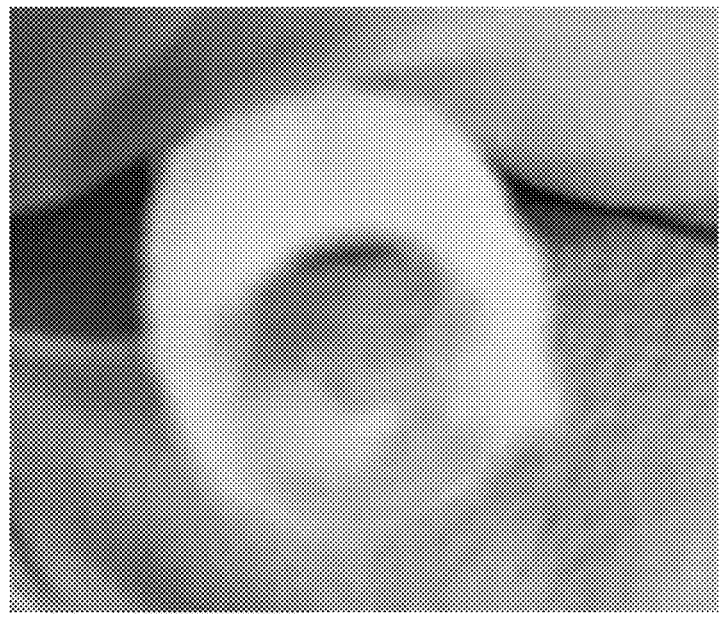
Figure 35A:
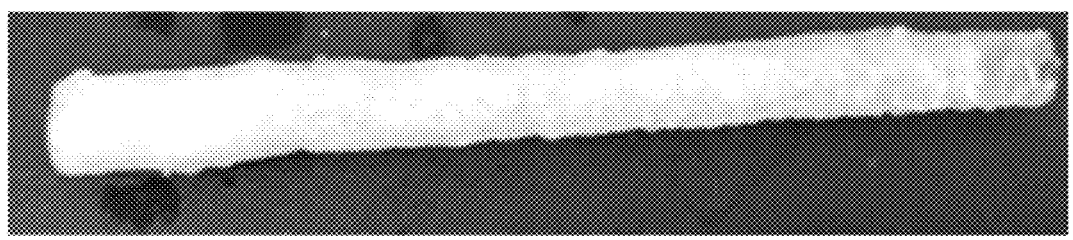
FIG. 35A and FIG. 35B shows the resulting sheath formed from the triple dip-FD-crystallizing method.
Figure 35B:
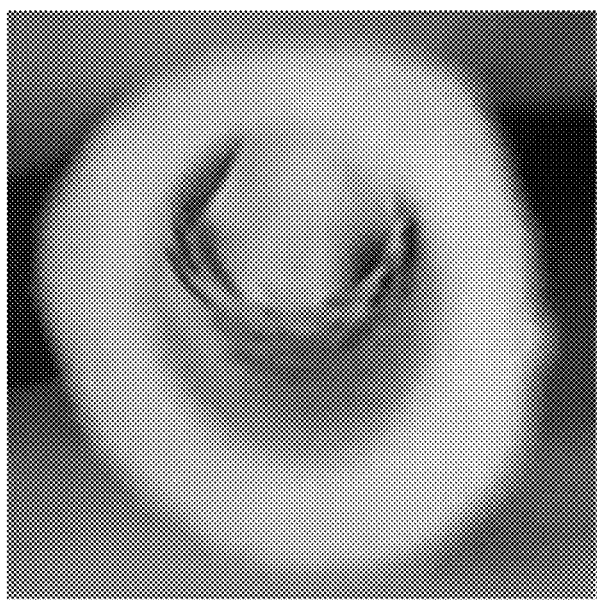
Figure 35C:
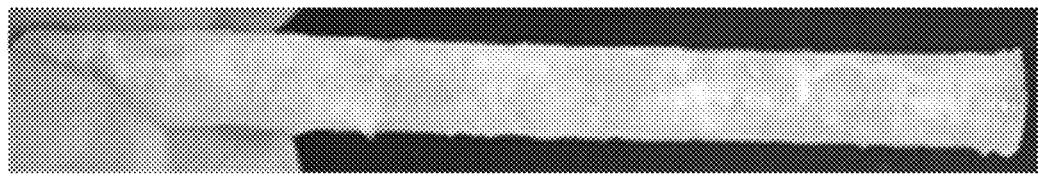
FIG. 35C and FIG. 35D shows the resulting sheath formed from the dip-FD-dip-FD-dip-FD-criticizing method.
Figure 35D:
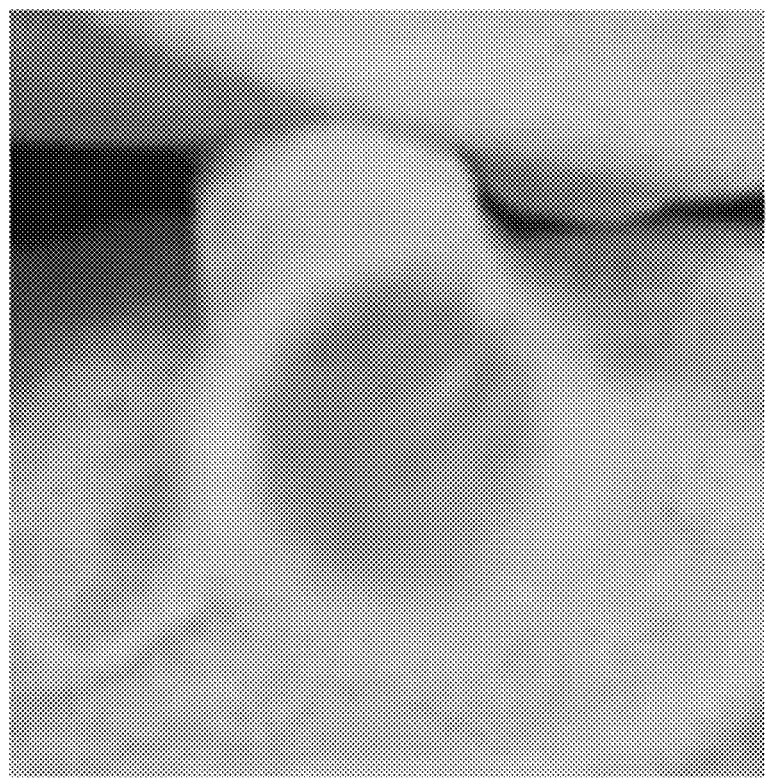

A drawing depicting the dipping with freezing method is shown in FIG. 32. The resulting sheath formed from the single dip-FD-crystallizing method is shown in FIG. 33A and FIG. 33B. The resulting sheath formed from the double dip-FD-crystallizing method is shown in FIG. 34A and FIG. 34B. The resulting sheath formed from the dip-FD-dip-FD-crystallizing method is shown in FIG. 34C and FIG. 34D. The resulting sheath formed from the triple dip-FD-crystallizing method is shown in FIG. 35A and FIG. 35B. The resulting sheath formed from the dip-FD-dip-FD-dip-FD-criticizing method is shown in FIG. 35C and FIG. 35D. The freeze-drying process made the 1-layer dip conduit easier to damage due to the conduit having a much thinner layer than the single dip option, however it showed more homogeneity over its length. This method may be difficult to upscale due to sample fragility.

When freeze-drying was added to the double dip process the major difference was that after each gelling there was more consistency over its length. This was also seen to improve uniformity whilst triple dipping, which with the addition of the extra layer showed an increase in its mechanical properties, however still with lower kink resistance.

17.10.2 Metal Molds

Figure 36:
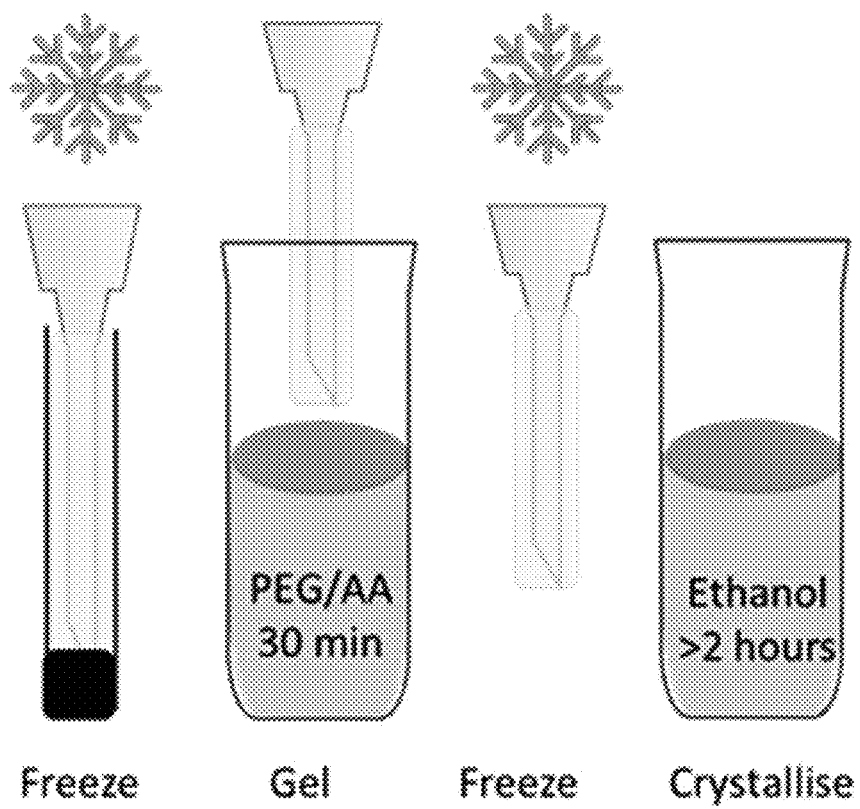
FIG. 36 shows a drawing depicting a method of forming a sheath using a metal mold.

A drawing depicting a method using a metal mold is shown in FIG. 36. The use of a metallic mold showed that the conduit was easily damaged when removing from the mold. However, the gel-freeze-crystallizing process produced more homogenous conduits. Different wall thicknesses may provide different mechanical characteristics.

Figure 37:
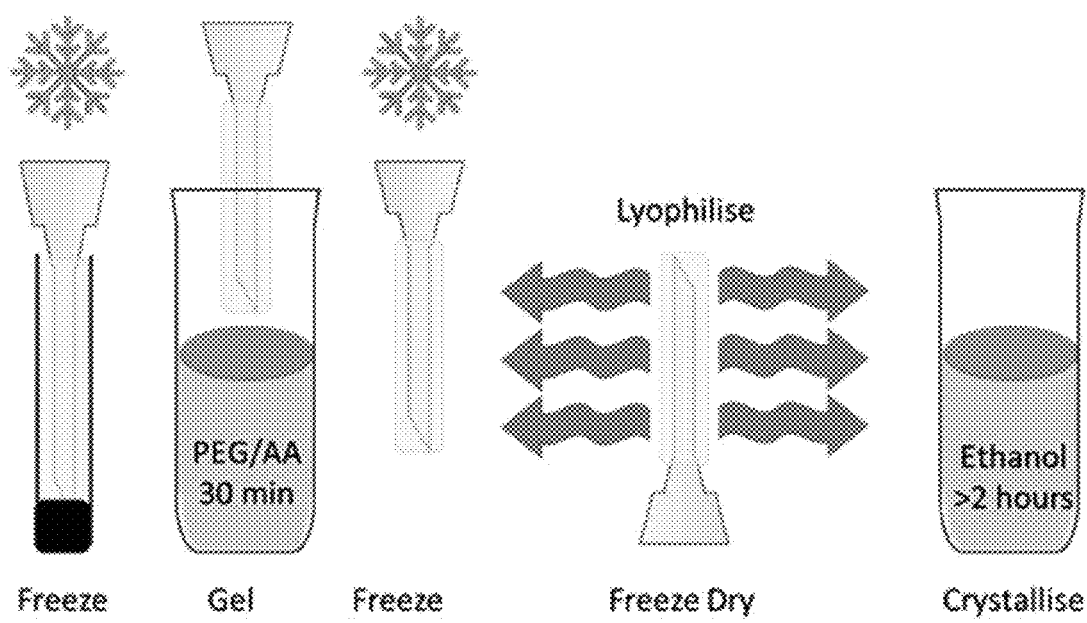
FIG. 37 shows a drawing depicting a method of forming a sheath using a metal mold with a freeze-drying step.

When the metallic mold was used with a freeze-drying step (as depicted in FIG. 37), the conduit could once again be easily damaged during removal from the mold. This might be aided by using a mold that produces a thicker wall thickness.

Figure 38A:
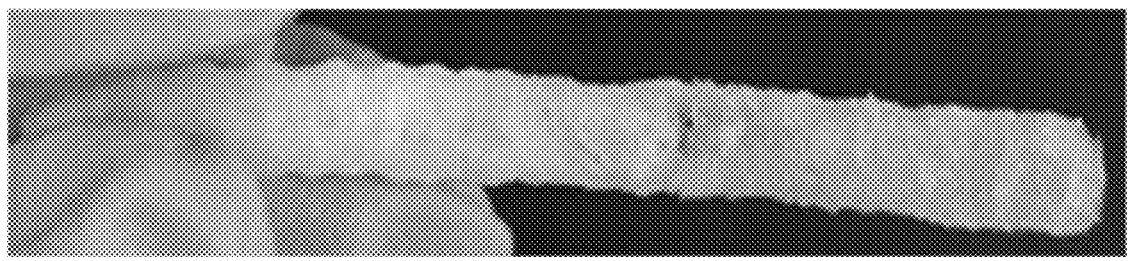
FIG. 38A shows a sheath with a 0.5 mm wall thickness produced by Freeze-Gel-Freeze-Crystalizing.
Figure 38B:
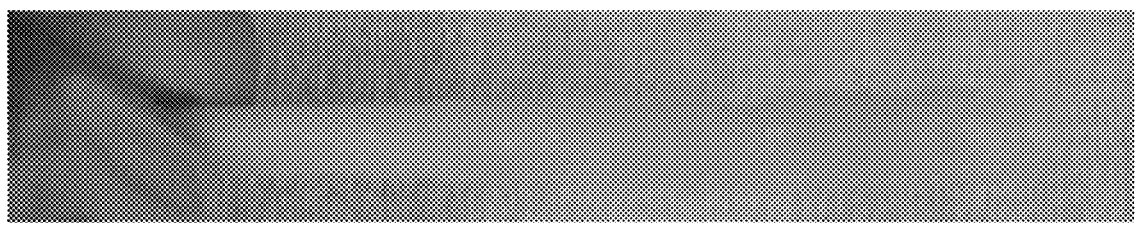
FIG. 38B shows a sheath with a 1.0 mm wall thickness produced by Freeze-Gel-Freeze-Crystalizing.
Figure 38C:
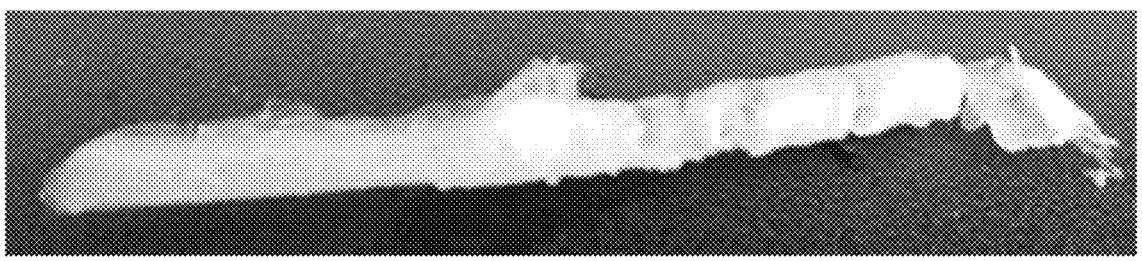
FIG. 38C shows a sheath with a 0.5 mm wall thickness produced by Freeze-Gel-FD-Crystalizing.
Figure 38D:
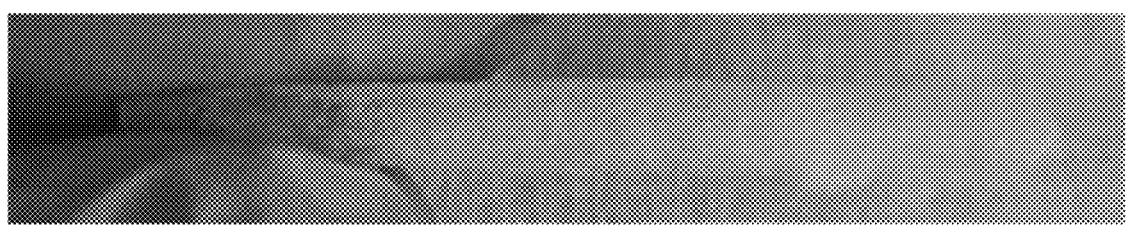
FIG. 38D shows a sheath with a 1.0 mm wall thickness produced by Freeze-Gel-FD-Crystalizing. FD=Freeze drying.

Changing the wall thickness of the mold from 0.5 mm to 1.0 mm showed significant improvement of the results. A sheath with a 0.5 mm wall thickness produced by Freeze-Gel-Freeze-Crystalizing is shown in FIG. 38A. A sheath with a 1.0 mm wall thickness produced by Freeze-Gel-Freeze-Crystalizing is shown in FIG. 38B. A sheath with a 0.5 mm wall thickness produced by Freeze-Gel-FD-Crystalizing is shown in FIG. 38C. A sheath with a 1.0 mm wall thickness produced by Freeze-Gel-FD-Crystalizing is shown in FIG. 38D. Adding a mold has the benefit of making more homogenous conduits and making the process more reproducible. The main difference between the freeze-dried conduits and the ones that were only gelled is due to the creation of a more compact structure from the extra step. However, there are still kink resistance problems.

Figure 39:
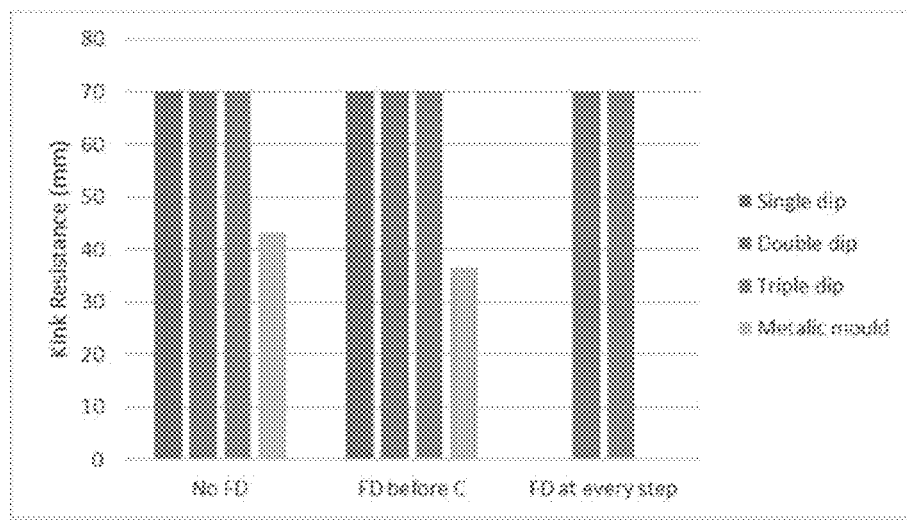
FIG. 39 shows results of kink resistance testing performed on sheaths produced using different methods. Different diameter discs were used (between 70-10 mm) to see when the samples started to show kinks.

After producing the different sheets, the kink resistance was tested using different diameter discs (between 70-10 mm) to see when the samples started to show kinks. The results can be seen in FIG. 39.

Figure 40:
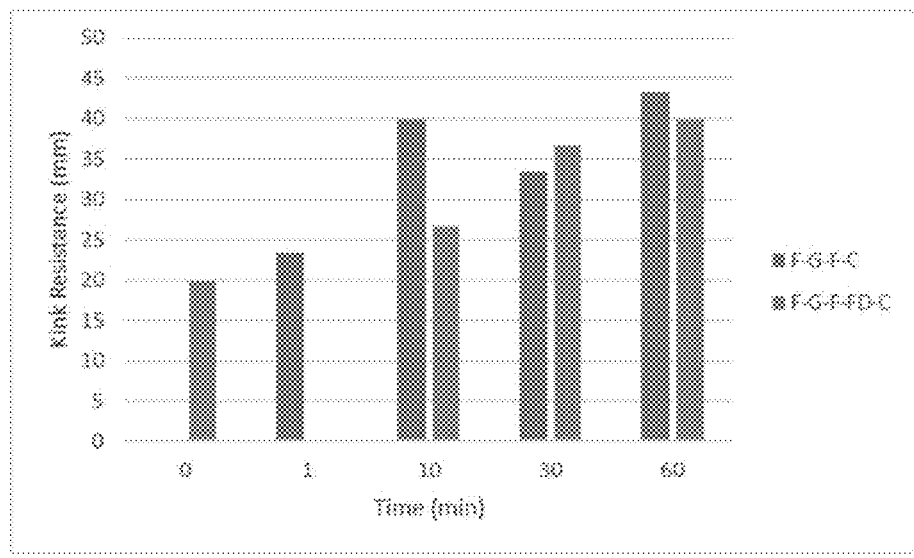
FIG. 40 shows results of kink resistance testing performed on sheaths produced using different methods. F=freezing, G=gelling, C=crystalizing, FD=freeze-drying. Different times of the crystallizing step were tested to try to increase kink resistance, both with and without freeze drying.

The metallic mold-produced sheaths were shown to have better kink resistance than the ones produced by the different dipping methods. This may be due to molding being a more homogenous process than dipping. Increasing dipping did not show any improvement on kink resistance or homogeneity. Also freeze drying the samples that use the mold showed increase resistance. Different times of the crystallizing step were tested to try to increase kink resistance, both with and without freeze drying. The results can be seen in FIG. 40.

Overall, reducing the crystalizing step resulted in a considerable increase in kink resistance. This is due to the crystallizing polymerization process making the final structure more crystalline. So, by reducing this step we are reducing the crystalline form and introducing the amorphous characteristics of the PEG/AA gelling phase.

The use of freeze drying showed to be beneficial not only to kink resistance but for storage of the conduit as well. The best performance was shown from conduits produced by freeze drying and no crystalizing. The kink resistance was lower, and the storage conditions required changed from liquid EtOH/PBS in a fridge to dry at room temperature. The other benefit regarding the freeze-drying method is that it replaces crystallizing as the method to get a porous structure.

Figure 41:
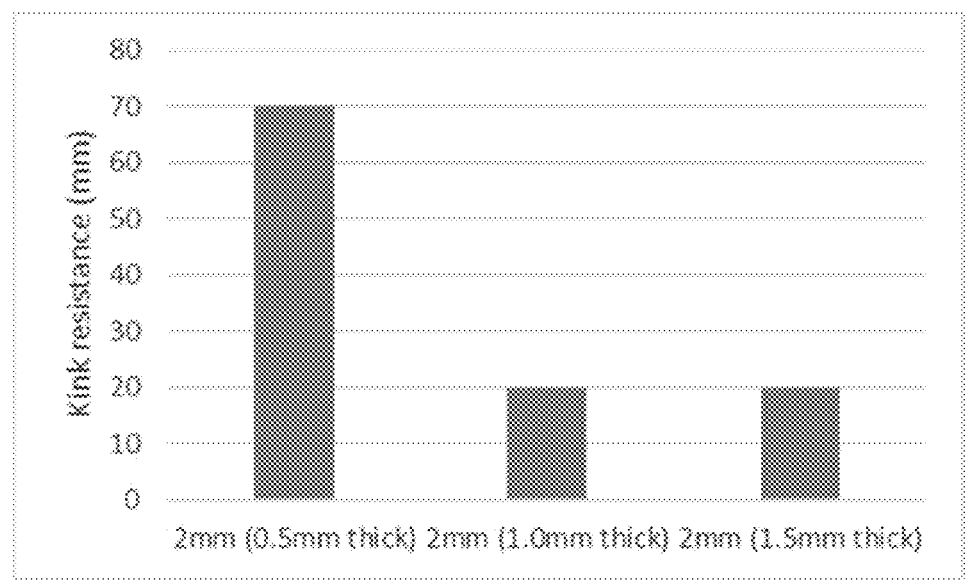
FIG. 41 shows results of kink resistance testing performed on sheaths produced with a 0.5 mm wall thickness, 1.0 mm wall thickness, and 1.5 mm wall thickness.

To test the wall thicknesses, a 2 mm rod was used instead of a 3 mm rod. The max diameter of the mold was 5 mm. The thicknesses tested were 0.5 mm, 1.0 mm and 1.5 mm. The result of the testing is shown in FIG. 41. Conduits produced with a 0.5 mm thickness were difficult to remove from the rod, were too thin, and would kink easily (see FIG. 41). There was no difference between 1.0 and 1.5 mm thickness. The best option was shown to be 1.0 mm.

17.10.3 Off Center Design

Using the metallic mold with an off-center rod showed that when removing the mold one of the sides did not had silk. With that in mind the samples were again dipped, frizzed, and freeze-dried. This showed to have a decrease in kink resistance from 20 to 50 mm, which may be due to the added dip, that has been shown low kink resistance.

17.10.4 SEM

From the sample set tested above, ten different designs were chosen for SEM. The images can be seen in FIG. 42A, FIG. 42B, FIG. 42C, FIG. 42D, FIG. 42E, FIG. 42F, FIG. 42G, FIG. 42H, FIG. 42I, and FIG. 42J. The first conclusion to be taken from these photos is that the EtOH considerably decreased the porosity of the samples, which correlated with the results obtain by kink resistance tests. This may create a collapse of the structure formed by the PEG/AA solution. An additional disadvantage is that after crystalizing with EtOH the sample must be kept in a solution, as if it dries the sample will collapse on itself.

Figure 42A:
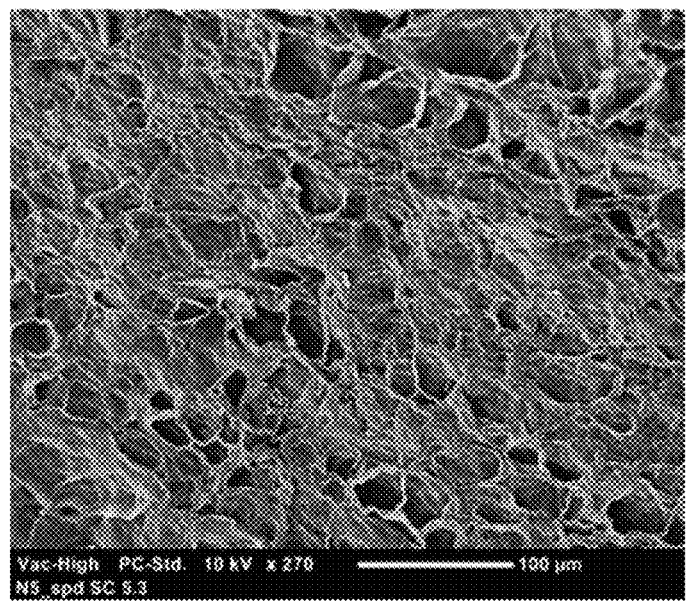
FIG. 42A, FIG. 42B, FIG. 42C, FIG. 42D, FIG. 42E, FIG. 42F, FIG. 42G, FIG. 42H, FIG. 42I, and FIG. 42J show SEM images from the ten different designs from FIG. 40 and FIG. 41.
Figure 42B:
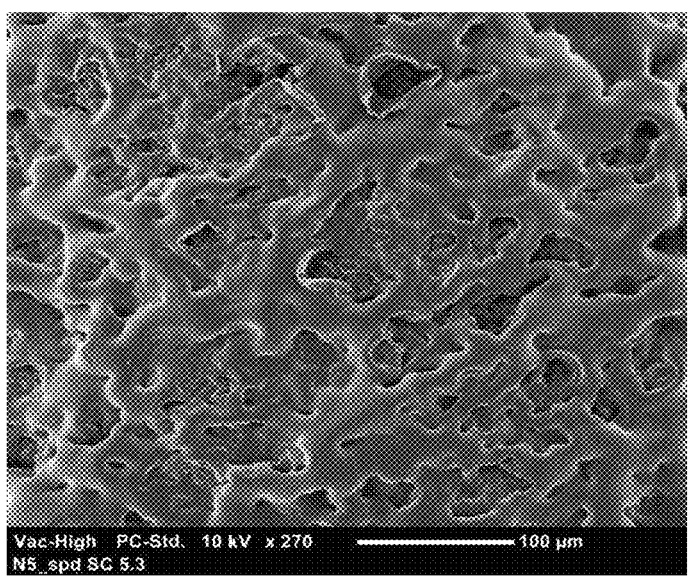
Figure 42C:
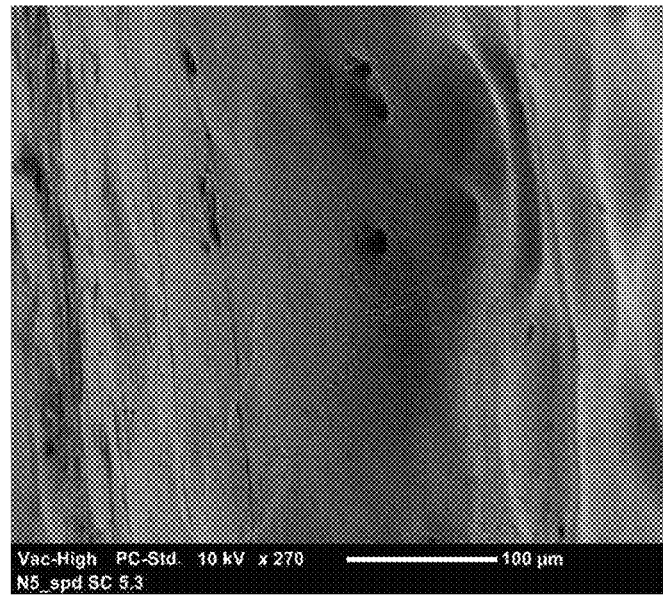
Figure 42D:
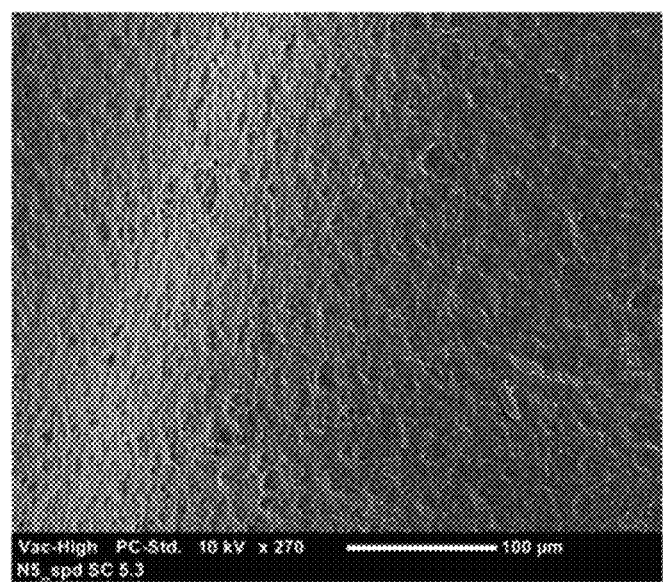
Figure 42E:
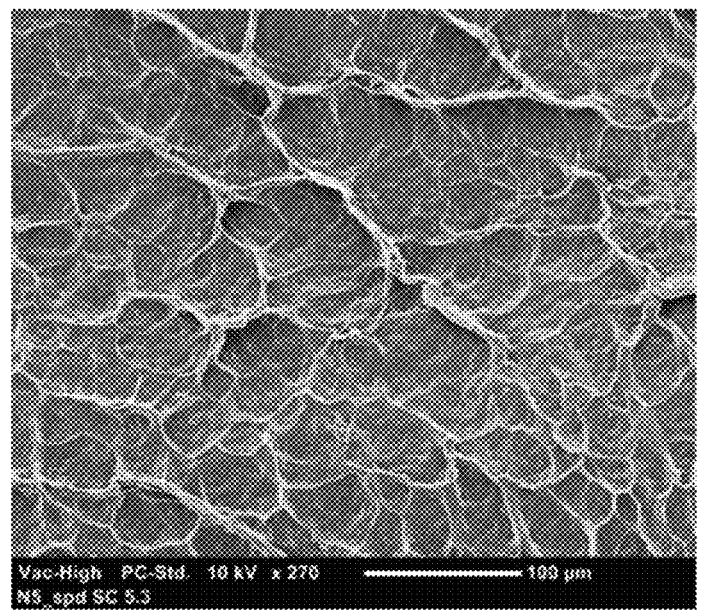
Figure 42F:
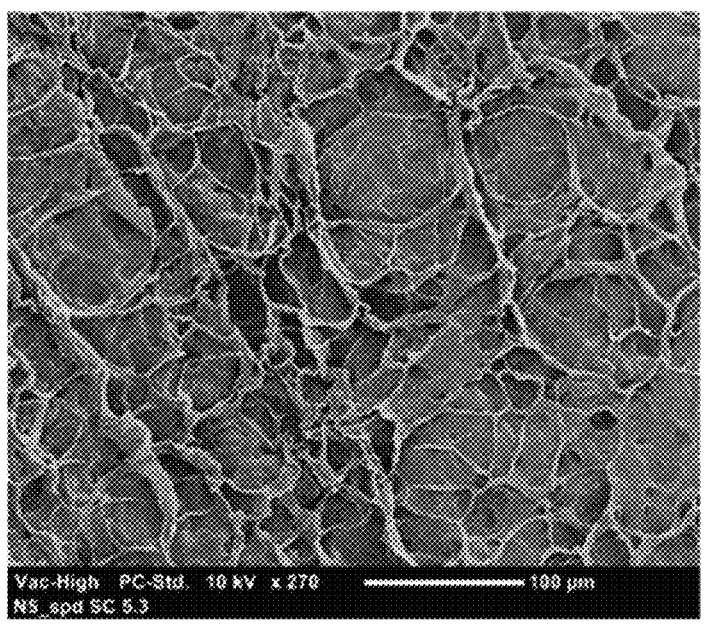
Figure 42G:
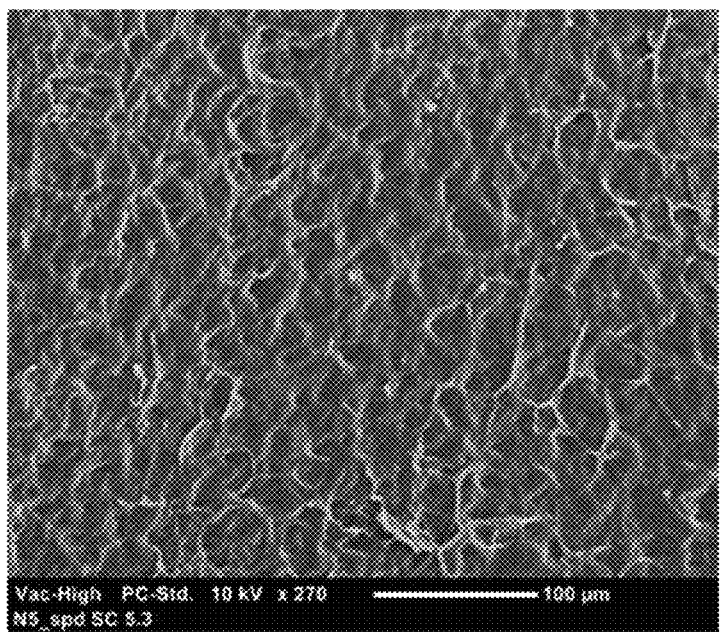
Figure 42H:
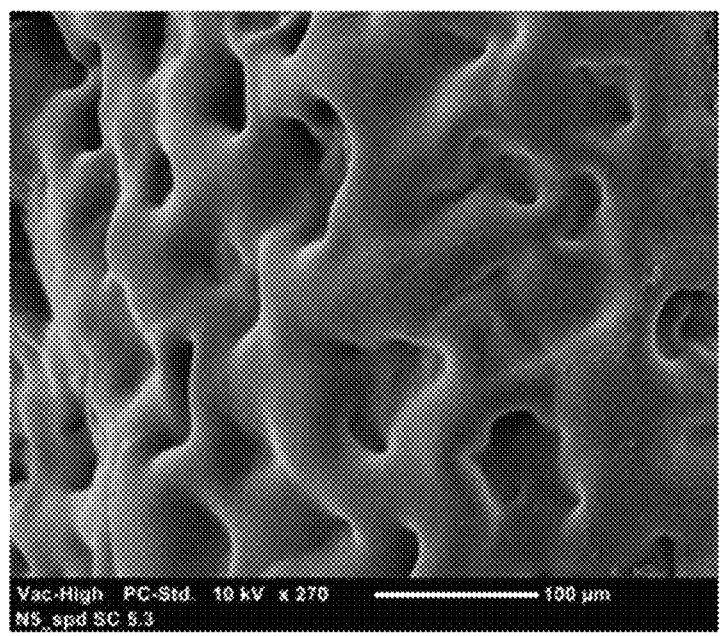
Figure 42I:
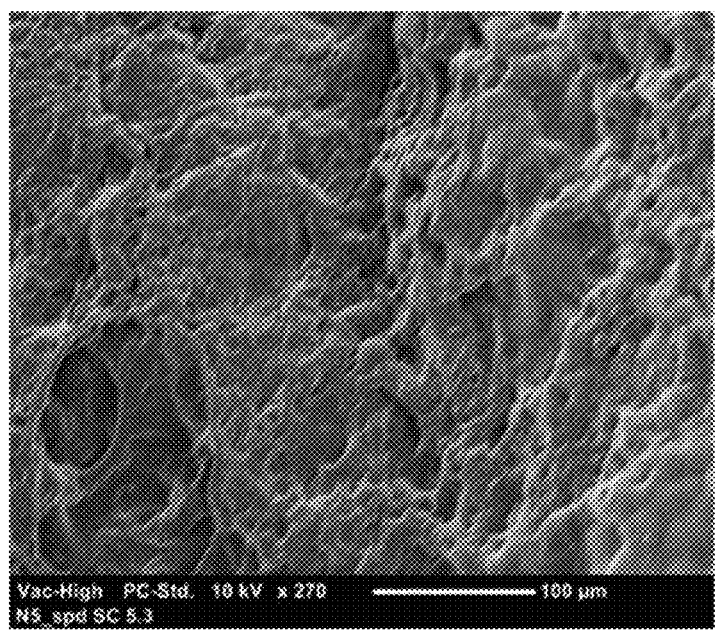
Figure 42J:
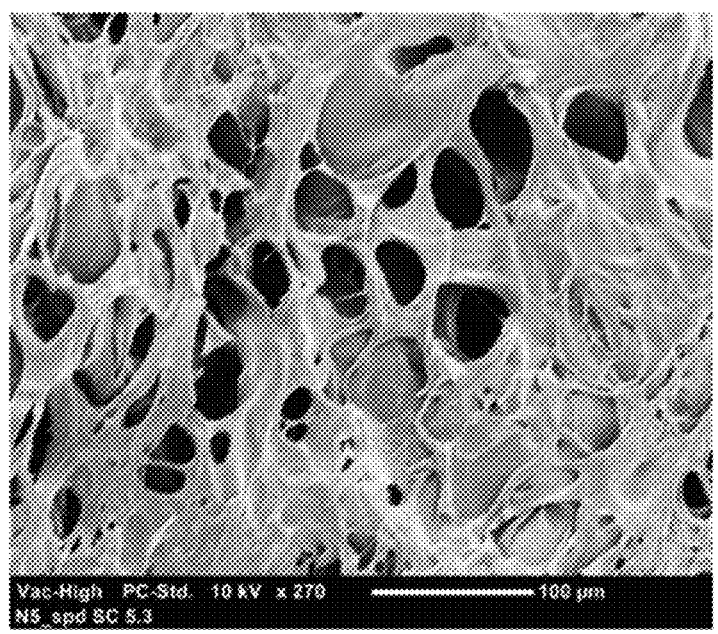

The sample shown in FIG. 42J has pore sizes smaller than 100 μm, which gives the sample kink resilience and may help in controlled degradation.

17.10.5 Design Optimization

Two different approaches were taken to optimize the best design obtained (F-G-FD). The first optimization was to fill a mold without a rod and subsequently create the desired diameter. It was tried after the first freezing step and after the freeze-drying step. Neither of these options produced successful sheets, as can be seen in FIG. 43A, FIG. 43B, FIG. 43C, and FIG. 43D.

Figure 43A:
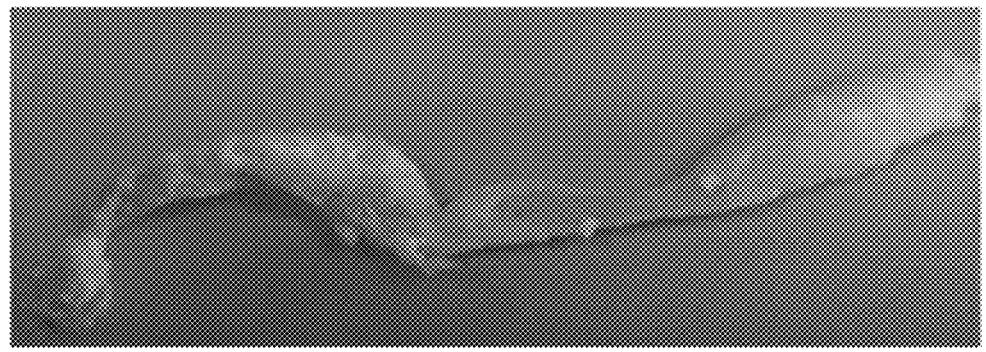
FIG. 43A, FIG. 43B, FIG. 43C, and FIG. 43D, depict sheaths produced through a first optimization of the F-G-FD method.
Figure 43B:
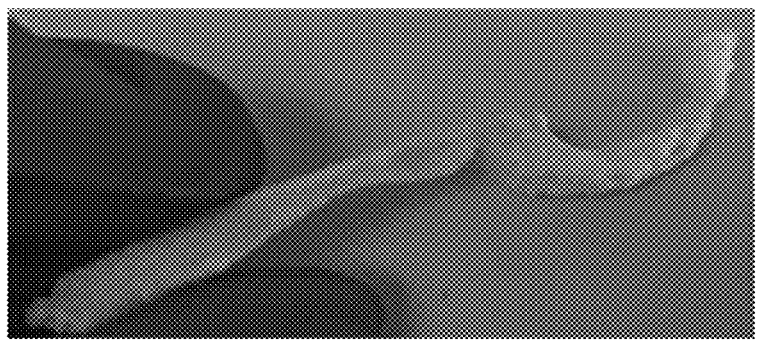
Figure 43C:
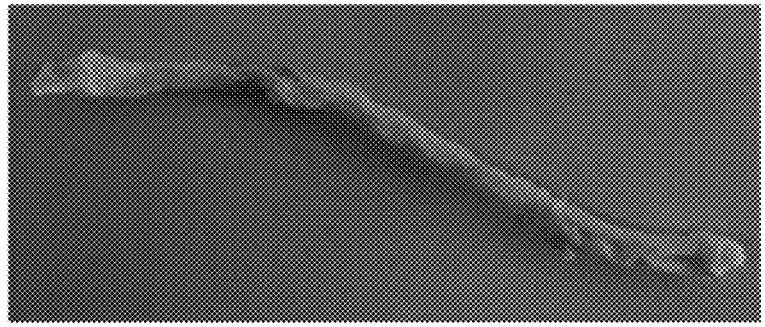
Figure 43D:
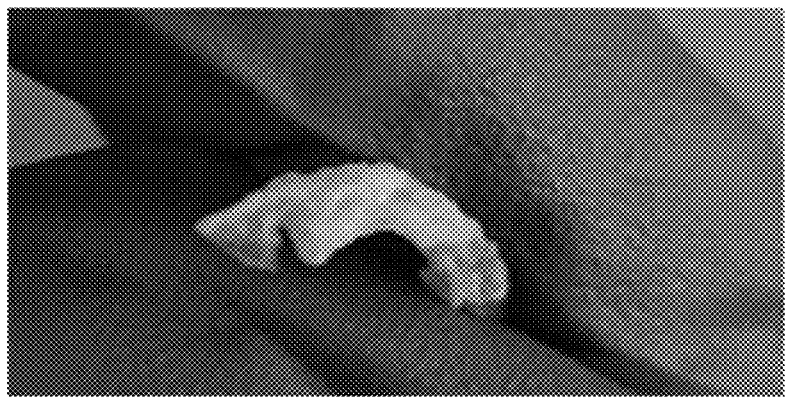
Figure 43E:
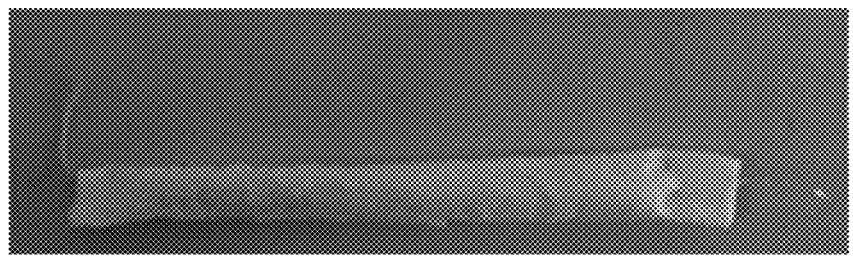
FIG. 43E, FIG. 43F, and FIG. 43G depict images of sheaths produced through a second optimization of the F-G-FD method.
Figure 43F:
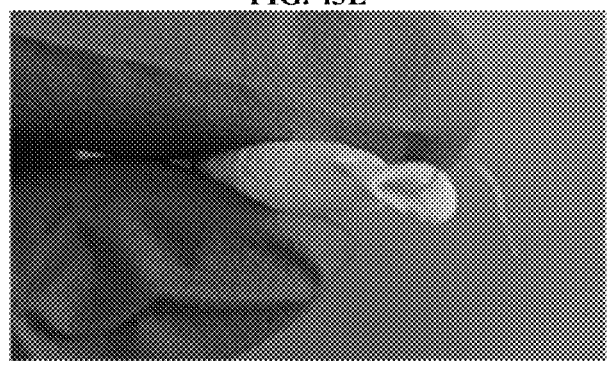
Figure 43G:
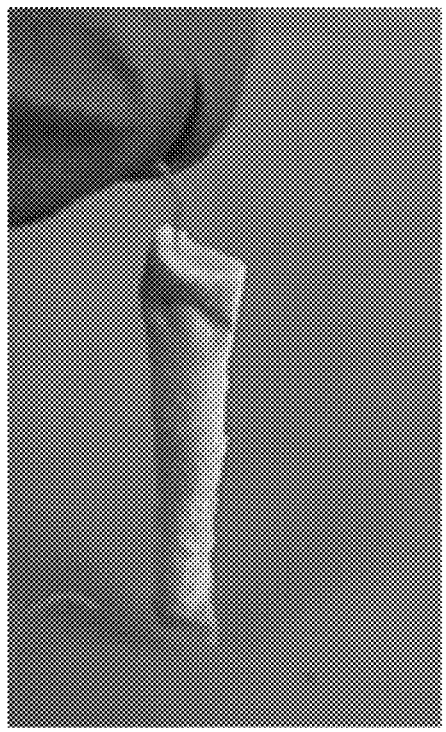

The second optimization included the addition of fibers to the sheath. The first attempt was performed after the gelling step, which damaged the sheath. The second attempt was performed after the production of the sheets. They were hydrated, the fibers were added in the sheath, the ends of it were clamped and they were freeze-dried again. This produced homogenous sheets that were able to keep the fibers in (see FIG. 43E, FIG. 43F, and FIG. 43G. Since the process of production is the same it is expected that they will have the same mechanical behavior as the sheaths without the fibers.

17.10.6 Spiral Design

Figure 44A:
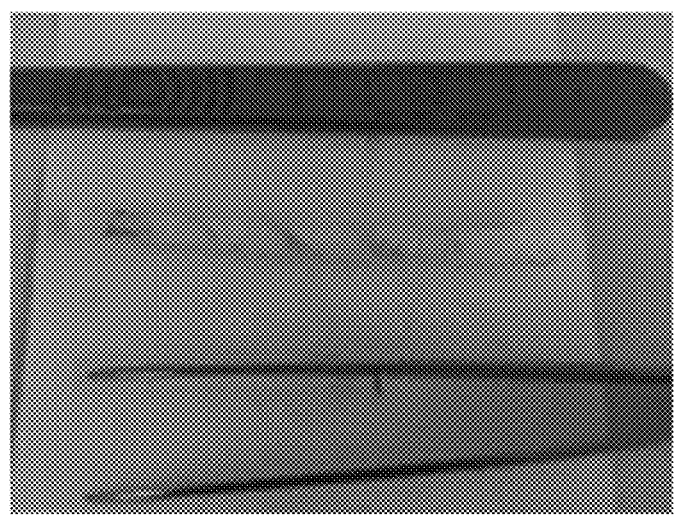
FIG. 44A, FIG. 44B, and FIG. 44C depict a spiral design for a sheath. The sheath was produced by cutting a triple dipped sheath. Upon bending the sheath was prone to deformation and would likely nip or displace the fibers/regrowing nerves inside. The shape might benefit from a tighter spiral design being used however it is more likely that to create a workable spiral sheath the design will need to be pre-set by a spiral internal rod instead of shaping after the sheath in created.
Figure 44B:
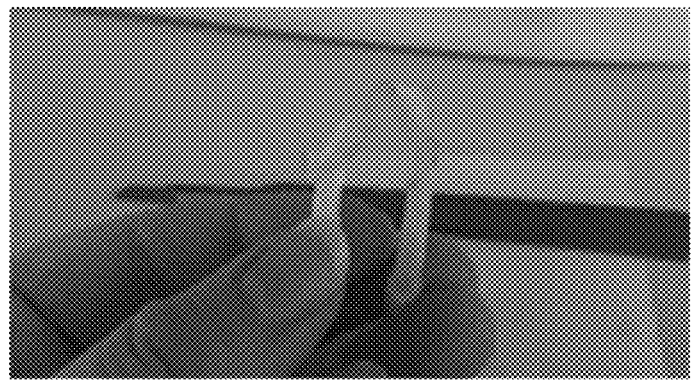
Figure 44C:
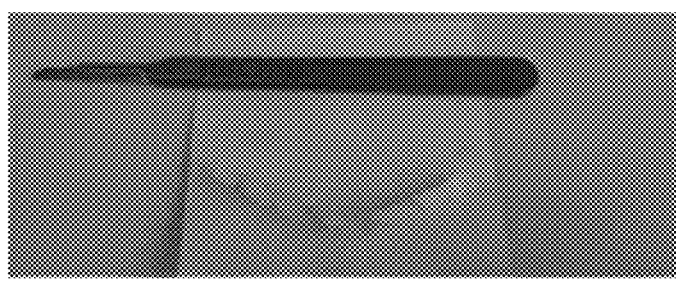

An attempt was made to cut a triple dipped sheath into a spiralized design. The first attempt did not give a usable sheath. Upon bending the sheath was prone to deformation and would likely nip or displace the fibers/regrowing nerves inside. The shape might benefit from a tighter spiral design being used however it is more likely that to create a workable spiral sheath the design will need to be pre-set by a spiral internal rod instead of shaping after the sheath in created. The spiral design is shown in FIG. 44A, FIG. 44B, and FIG. 44C.

17.11 Conclusion

Disclosed herein is a method of producing sheaths that exhibit appropriate properties for use in surgical implantation. The method for this is:

Freeze silk in a mold.
Remove the silk from the mold but keep the sheath on the central rod.
Place the sheath in chilled PEG/AA gelling solution for 30 minutes.
Freeze for 30+ minutes then freeze dry for storage and pore definition.

Prior to implantation the sheath will need to be rehydrated; this can be done using UPW and appears to have no detrimental effect on the sheath.

Table 5 reviews the methods trialed:

TABLE 5

Review of methods trialed

| Method | Outcome |
| --- | --- |
| (Dip-gel 1 min-freeze) x1-8-crystallize | Sheaths had no kink resistance; the physical properties did show improvement with increasing layers to a point. Sheaths are not uniform. Porosity appears limited. Clear delamination An argument could be made that this method may be improved using a more viscous solution, however the issues with the design outweigh a chance of moderate improvement and this method has been abandoned. |

TABLE 5-continued

Review of methods trialed

| Method | Outcome |
| --- | --- |
| (Dip-gel 1 min-freeze-freeze dry) x1-8-crystallize | Sheaths had no kink resistance; the physical properties did show improvement with increasing layers to a point. Sheaths are not uniform. Porosity appears limited. Clear delamination This method was abandoned. |
| Freeze-gel 30 mins-freeze-crystallize | Uniform sheath. Dimensions are controllable. Good handling. Porosity appears limited. Not kink resistant. The lack of kink resistance means the design cannot be used. If the sheath kinked in vivo nerve regeneration would be blocked. However this method was found superior to methods involving dipping. |
| Freeze-gel 30 mins-freeze-freeze dry-crystallize | Uniform sheath. Dimensions are controllable. Good handling. Porosity appears limited. Improved kink resistant. This was the most promising of the designs that included a crystallization step (submersion in ethanol for >2 hour). |

Figure 45:
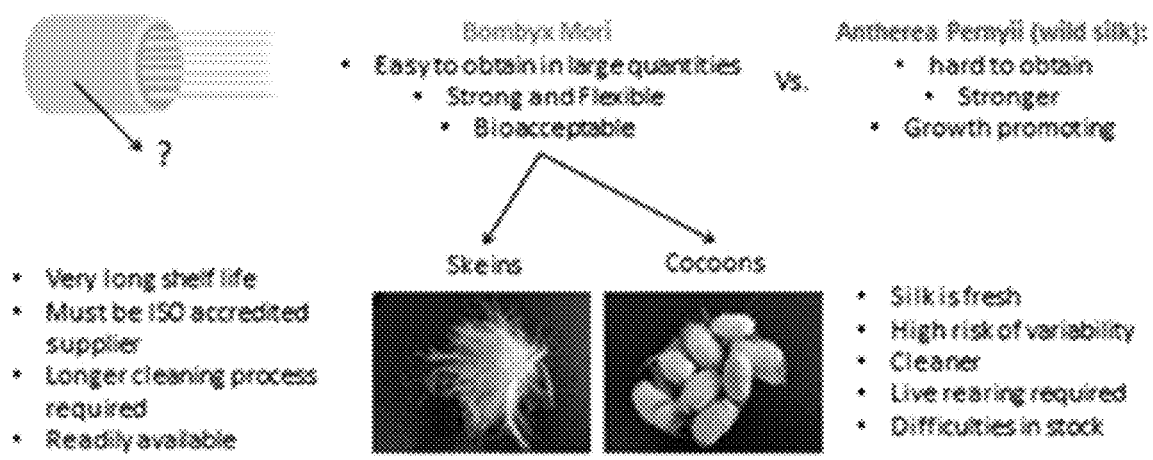
FIG. 45 depicts a comparison of the silk that can be obtained from *Bombyx mori* vs. *Antherea Pernyii* (wild silk). *Bombyx Mori* silk is easy to obtain in large quantities, is strong and flexible, and bioacceptable, whereas *Antherea Pernyii* (wild silk) is hard to obtain, stronger, and growth promoting. *Bombyx mori* silk can be obtained from either skeins or cocoons. Skeins have a very long shelf life, must be from an ISO accredited supplier, have a longer cleaning process required, and are readily available. Silk from cocoons is fresh, has a high risk of variability, is cleaner, live rearing is required, and there are difficulties in stock.

FIG. 45 depicts a comparison of the silk that can be obtained from *Bombyx mori* vs. *Antherea Pernyii* (wild silk). *Bombyx Mori* silk is easy to obtain in large quantities, is strong and flexible, and bioacceptable, whereas *Antherea Pernyii* (wild silk) is hard to obtain, stronger, and growth promoting. *Bombyx mori* silk can be obtained from either skeins or cocoons. Skeins have a very long shelf life, must be from an ISO accredited supplier, have a longer cleaning process required, and are readily available. Silk from cocoons is fresh, has a high risk of variability, is cleaner, live rearing is required, and there are difficulties in stock.

Figure 46:
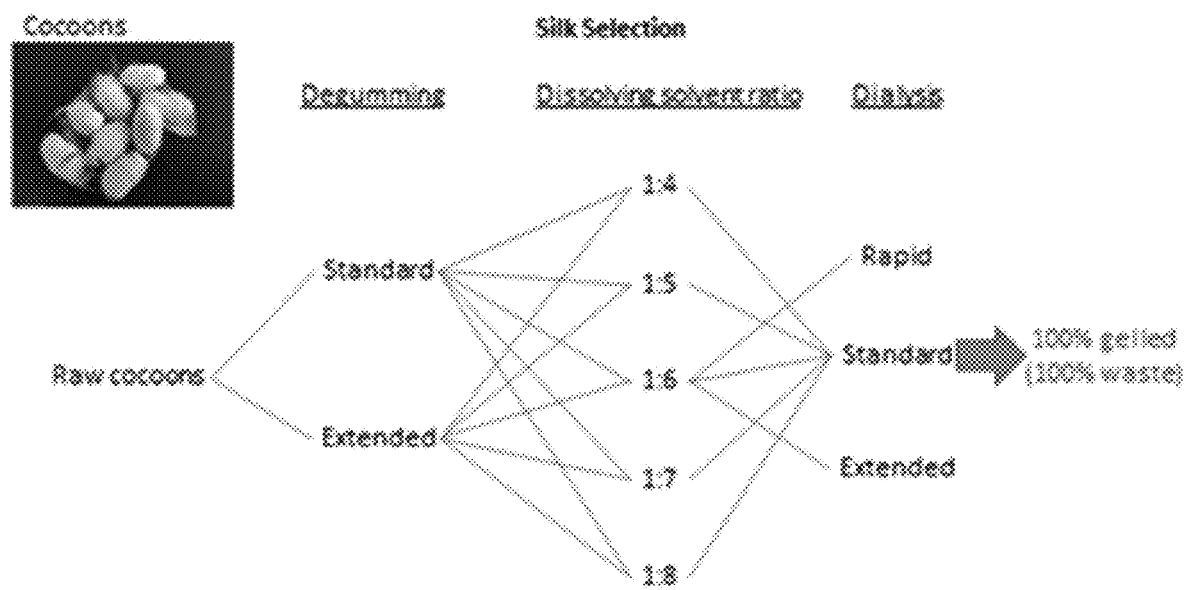
FIG. 46 depicts the dissolving solvent ratio needed for standard or extended degumming of raw cocoons.

FIG. 46 depicts the dissolving solvent ratio needed for standard or extended degumming of raw cocoons.

Figure 47:
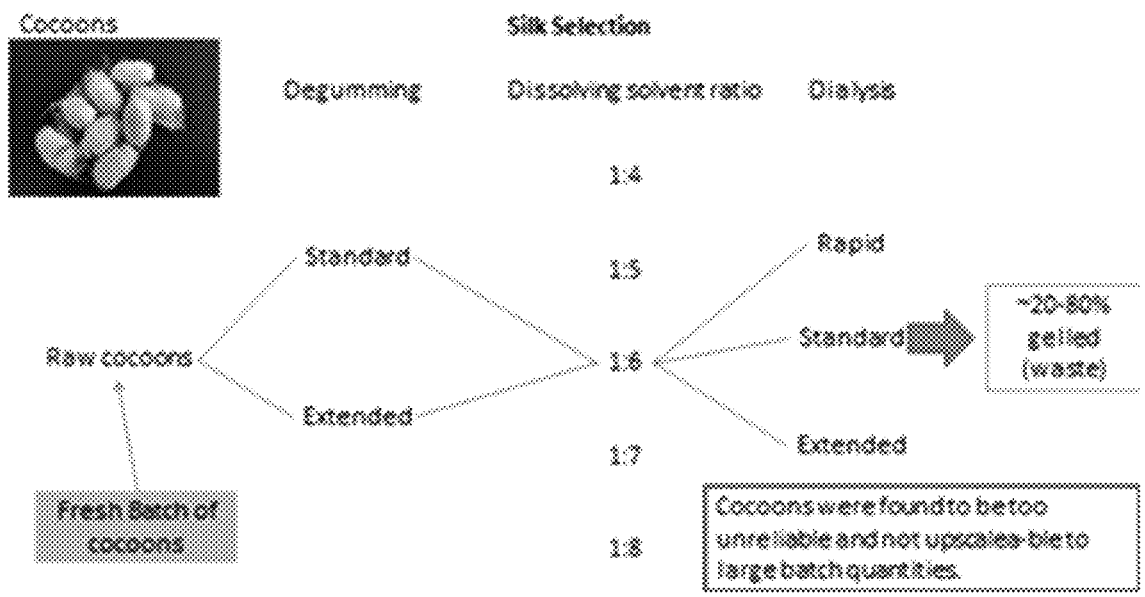
FIG. 47 depicts the dissolving solvent ratio needed for standard or extended degumming of raw cocoons, and shows that cocoons were found to be too unreliable and not upscalable to large batch quantities.

FIG. 47 depicts the dissolving solvent ratio needed for standard or extended degumming of raw cocoons, and shows that cocoons were found to be too unreliable and not upscalable to large batch quantities.

Figure 48:
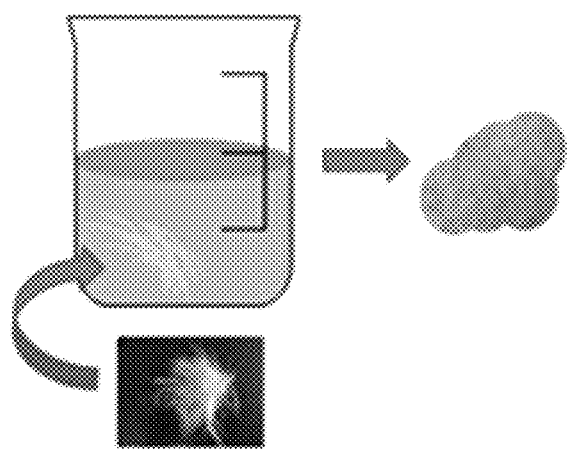
FIG. 48 depicts silk degumming of *Bombyx Mori* skeins. Step 1 is a chelating soak for between 1 hour to day in a chelating concentration of 0.1M to 0.01M at a temperature of 37° C. Step 2 is an enzymatic ionic degumming for 4 hours and 20 minutes at 37° C.

FIG. 48 depicts silk degumming of *Bombyx Mori* skeins. Step 1 is a chelating soak for between 1 hour to day in a chelating concentration of 0.1M to 0.01M at a temperature of 37° C. Step 2 is an enzymatic ionic degumming for 4 hours and 20 minutes at 37° C.

Figure 49:
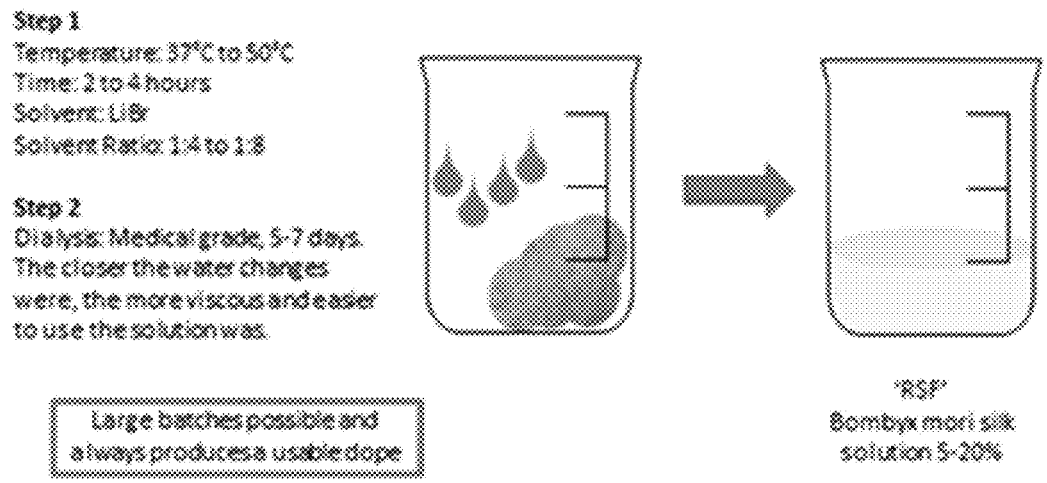
FIG. 49 depicts silk dissolving of *Bombyx Mori* skeins. Step 1 is dissolving in a LiBr solvent at a 1:4 to 1:8 ratio for 2 to 4 hours at 37° C. to 50° C. Large batches are possible with this method and it consistently produces a usable dope. The final solution produced is 5-20% *Bombyx Mori* silk solution.

FIG. 49 depicts silk dissolving of *Bombyx Mori* skeins. Step 1 is dissolving in a LiBr solvent at a 1:4 to 1:8 ratio for 2 to 4 hours at 37° C. to 50° C. Large batches are possible with this method and it consistently produces a usable dope. The final solution produced is 5-20% *Bombyx Mori* silk solution.

Figure 50:
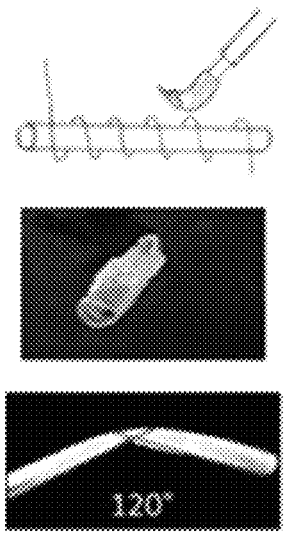
FIG. 50 depicts the methods by which sheaths were produced using stainless steel rods with wound silk fibers, which were painted in silk fibroin solution and allowed to air dry. Thin transparent sheaths were created that were not kink resistant, buckling under a 120° bend. The sheaths were non-porous, felt brittle and were difficult to use.

FIG. 50 depicts the methods by which sheaths were produced using stainless steel rods with wound silk fibers, which were painted in silk fibroin solution and allowed to air dry. Thin transparent sheaths were created that were not kink resistant, buckling under a 120° bend. The sheaths were non-porous, felt brittle and were difficult to use.

Figure 51:
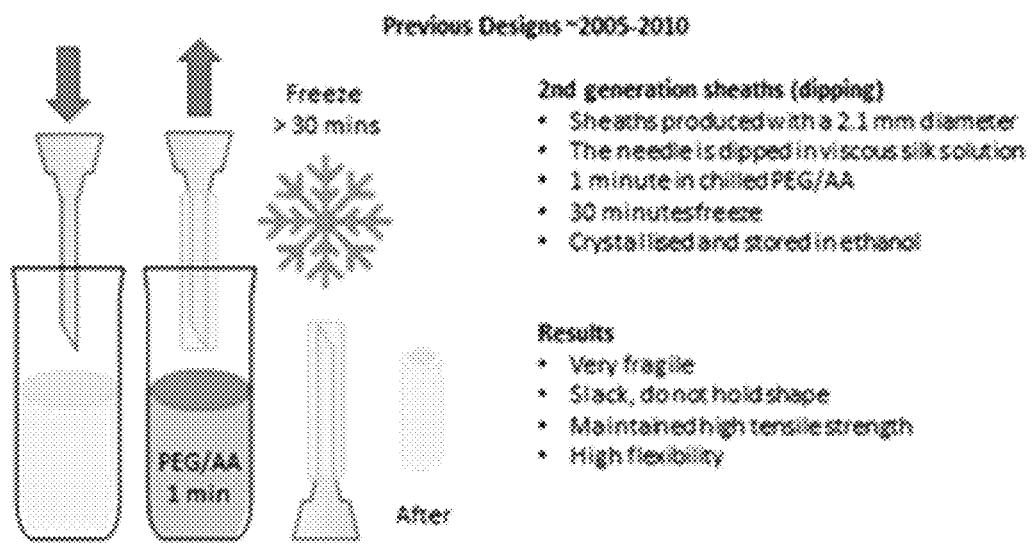
FIG. 51 depicts the methods by which sheaths were produced through dipping. Sheaths were produced with a 2.1 mm diameter. The needle was dipped in viscous silk solution, chilled for 1 minute in PEG/AA, frozen for 30 minutes, crystallized, and stored in ethanol. The results were very fragile sheaths, which were slack and did not hold shape. The sheaths maintained high tensile strength, and had high flexibility.

FIG. 51 depicts the methods by which sheaths were produced through dipping. Sheaths were produced with a 2.1 mm diameter. The needle was dipped in viscous silk solution, chilled for 1 minute in PEG/AA, frozen for 30 minutes, crystallized, and stored in ethanol. The results were very fragile sheaths, which were slack and did not hold shape. The sheaths maintained high tensile strength, and had high flexibility.

Figure 52:
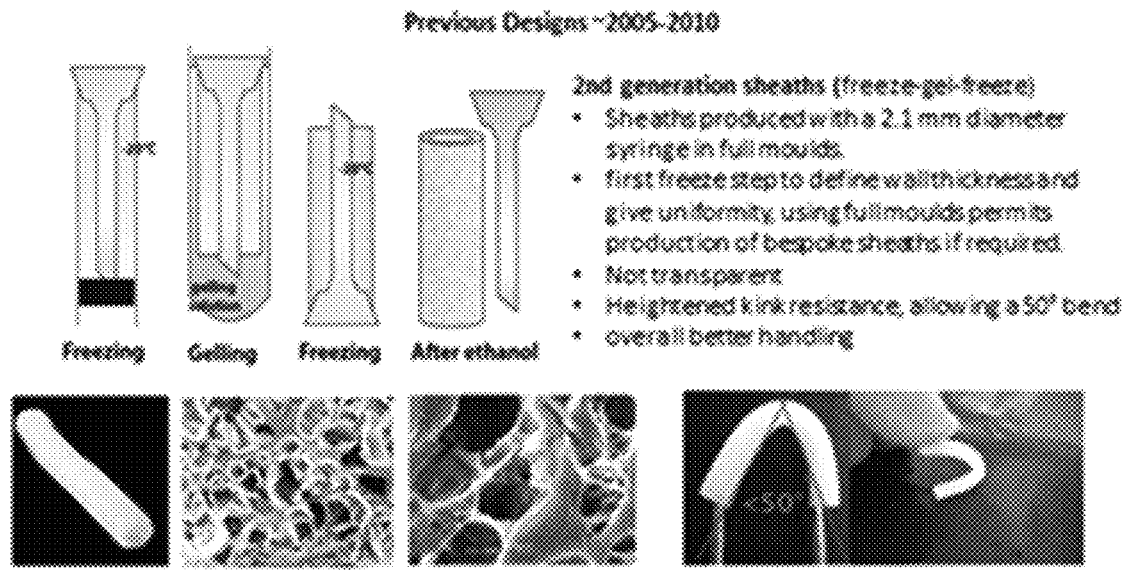
FIG. 52 depicts the methods by which sheaths were produced through freeze-gel-freeze. The sheaths were produced with a 2.1 mm diameter syringe in full molds. The first freeze strep to define wall thickness and give uniformity, using full molds permitted production of bespoke sheaths if required. These were not transparent. There was heightened kink resistance, allowing a 50° bend, and overall better handling.

FIG. 52 depicts the methods by which sheaths were produced through freeze-gel-freeze. The sheaths were produced with a 2.1 mm diameter syringe in full molds. The first freeze strep to define wall thickness and give uniformity, using full molds permitted production of bespoke sheaths if required. These were not transparent. There was heightened kink resistance, allowing a 50° bend, and overall better handling.

FIG. 53 depicts the methods by which sheaths were produced by double dipping. Sheaths were dipped in silk fibroin solution, dipped in PEG/AA for 1 minute, frozen for more than 30 minutes, dipped in PEG/AA for 1 minute, dipped in PEG/AA for 1 minute, and frozen again for more than 30 minutes.

FIG. 54 depicts a comparison of the different methods disclosed herein and the resulting determination of porosity, toughness, strength, flexibility, uniformness, and surgeon handling for the sheaths produced.

FIG. 55 depicts a comparison of the different methods produced. The single dipped sheaths were floppy, making them harder to use. The freeze-gel-freeze produced sheaths had good handling. The freeze-gel-freeze-dry-gel produced sheaths had excellent handling. The double dipped sheaths were better than the single dipped sheaths, and were floppier than the gelling methods.

A method using just freeze-freeze drying was trialed previously that highlighted the need for the sheath's dimensions to be predetermined though gelling, or the silk will lose all macro structure.

Findings:

Crystallization is not a good option; it limits porosity and reduces flexibility.

Using a mold is superior to dipping. The sheaths are more uniform and maintain shape.

17.11.1 UV Crosslinking Trial

An optimal method for production of sheaths for the sheep trials has been identified (freeze-gel-freeze-freeze dry) and is currently being refined. As we intend to use two different sheaths in the trial, alternate methods are being tested.

Here the use of an ultraviolet crosslinker is being trialed. We have established that the use of the lyophilization must occur after gelling, the gelling phase is believed to induce crosslinking in the silk. There the use of UV will be trialed with and without gelling and with and without freeze drying.

17.11.2 Freeze-UV Crosslink

*Bombyx Mori* silk solution was poured into a small plastic petri dish, enough to cover the base and have a depth of 2-3 mm. The silk was placed in the freeze for 30 minutes. After which time the silk appeared completely frozen.

The frozen silk was then placed in the CL-1000 ultraviolent crosslinking for 30 minutes. After 5 minutes the silk had melted and appeared liquid—meaning that for silk frozen in a mold, the macro-structure would have been lost.

While preferred embodiments of the present disclosure have been shown and described herein, such embodiments are provided by way of example only. Numerous variations, changes, and substitutions are possible based on the content of the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Embodiments 1. A medical device comprising a container configured to encourage a regrowth of at least a portion of a nerve cell in vivo within said container, wherein said container:
   (a) is at least in part flexible,
   (b) is configured to at least partially allow an influx of nutrients, an outflow of waste, or both, through openings in said container,
   (c) comprises an entrance and an exit, wherein said container is configured to allow at least a portion of a nerve cell to enter and exit said container through said entrance and said exit,
   (d) comprises an interior and an exterior, and
   (e) comprises at least partially in said interior an element, wherein said element comprises a fiber, filament, or combination thereof, spanning at least a portion of a length of said container.
2. The medical device of embodiment 1, wherein said element spans a majority of a length of said container.
3. The medical device of embodiment 1, wherein said container is configured to encourage, guide, orientate, support, or any combination thereof, said in vivo regrowth of said at least a portion of said nerve cell.
4. The medical device of embodiment 1, wherein said at least in part flexible comprises an ability to bend said container into less than about a 90° angle between a proximal end and a distal end of said container.
5. The medical device of embodiment 1, wherein said at least in part flexible comprises an ability to bend said container into less than about a 50° angle between a proximal end and a distal end of said container.
6. The medical device of embodiment 4 or 5, wherein after a force that bends a container ceases to be applied, said container returns at least in part to a pre-bend shape.
7. The medical device of any one of embodiments 4-6, wherein bending said container comprises bending without breaking said container, without kinking said container, while maintaining a patency of said container, while maintaining a patency of a lumen of said container, or any combination thereof
8. The medical device of embodiment 1, wherein said container comprises a smooth structure, a pitted structure, a grooved structure, a ridged structure, a channel, or any combination thereof
9. The medical device of embodiment 8, wherein said channel comprises a sloped channel.
10. The medical device of embodiment 9, wherein an angle of said sloped channel can at least partially guide a nerve cell arrangement, orientate a nerve cell, or any combination thereof
11. The medical device of embodiment 1, wherein said container comprises a protein, a collagen, a gelatin, a silicone, a polymer, a polyester, a hydrophilic material, a polyol, a hybrid composition, an isolated tissue, an isolated tissue product, a decellularized nerve conduit, a carbohydrate, a biomimetic material, a silk, a silk composite, or any combination thereof
12. The medical device of embodiment 11, comprising said collagen, wherein said collagen comprises a type I collagen, a type II collagen, a type III collagen, a type V collagen, a type X collagen, a salt of any of these, or any combination thereof
13. The medical device of embodiment 12, wherein said container comprises a semi-permeable type I collagen membrane.
14. The medical device of embodiment 11, comprising said polyester, wherein said polyester comprises a polyglycolide.
15. The medical device of embodiment 14, wherein said polyglycolide comprises a polyglycolic acid.
16. The medical device of embodiment 15, wherein said polyglycolide comprises a woven polyglycolic acid mesh tube.
17. The medical device of embodiment 11, comprising said polyester, wherein said polymer comprises polyurethane.
18. The medical device of embodiment 11, comprising said biomimetic material, wherein said biomimetic material comprises a laminin.
19. The medical device of embodiment 11, comprising said isolated tissue, isolated tissue product, or combination thereof
20. The medical device of embodiment 19, comprising said isolated tissue, isolated tissue product, or combination thereof, wherein said isolated tissue, isolated tissue product, or said combination thereof comprises an isolated at least partially decellularized tissue, an isolated at least partially decellularized tissue product, or any combination thereof
21. The medical device of embodiment 20, wherein said isolated at least partially decellularized tissue comprises an isolated at least partially decellularized vasculature.
22. The medical device of embodiment 21, wherein said isolated at least partially decellularized vasculature comprises an isolated at least partially decellularized vein.
23. The medical device of embodiment 11, wherein said container comprises a porcine submucosa extracellular matrix.
24. The medical device of embodiment 11, comprising said silk, wherein said silk comprises a silk protein, a silk fiber, a silk filament, a silk nano-filament, or any combination thereof
25. The medical device of embodiment 24, wherein said silk comprises a silk solid, a silk liquid, or any combination thereof
26. The medical device of embodiment 11, comprising said silk, wherein said container comprises a first plurality of silk proteins.
27. The medical device of embodiment 23, wherein at least one protein in said first plurality of silk proteins comprises a fibroin, a spidroin, a recombinant silk protein, an analog of any of these, or any combination thereof
28. The medical device of embodiment 27, comprising said fibroin, wherein said fibroin comprises regenerated fibroin.
29. The medical device of embodiment 27, comprising said spidroin, wherein said spidroin comprises regenerated spidroin.
30. The medical device of embodiment 1, wherein said container does not comprise a protein, a collagen, a gelatin, a silicone, a polyester, a polyurethane, a hydrophilic material, a polyol, a hybrid composition, an isolated tissue, an isolated tissue product, a decellularized nerve conduit, a carbohydrate, a biomimetic material, a silk, a silk composite, or any combination thereof 31. The medical device of embodiment 30, wherein said container does not comprise said polyester, wherein said polyester comprises a polyglycolide.
32. The medical device of embodiment 30, wherein said container does not comprise a polyurethane.
33. The medical device of embodiment 30, wherein said container does not comprise said biomimetic material, wherein said biomimetic material comprises a laminin.
34. The medical device of embodiment 30, wherein said container does not comprise said isolated tissue, isolated tissue product, or combination thereof
35. The medical device of embodiment 34, wherein said container does not comprise said isolated tissue, isolated tissue product, or combination thereof, wherein said isolated tissue, isolated tissue product, or said combination thereof comprises an isolated at least partially decellularized tissue, an isolated at least partially decellularized tissue product, or any combination thereof
36. The medical device of embodiment 35, comprising said isolated at least partially decellularized tissue, wherein said isolated at least partially decellularized tissue comprises an isolated at least partially decellularized vasculature.
37. The medical device of embodiment 36, wherein said isolated at least partially decellularized vasculature comprises an isolated at least partially decellularized vein.
38. The medical device of embodiment 30, wherein said container does not comprise said silk, wherein said silk comprises a silk protein, a silk fiber, a silk filament, a silk nano-filament, or any combination thereof
39. The medical device of embodiment 1, wherein said container does not comprise a polyglycolide.
40. The medical device of embodiment 1, wherein said container does not comprise a collagen.
41. The medical device of embodiment 26, wherein said element comprises a second plurality of silk elements.
42. The medical device of embodiment 1, wherein said element comprises a protein, a collagen, a gelatin, a silicone, a polyester, a polyurethane, a hydrophilic material, a polyol, a hybrid composition, an isolated tissue, an isolated tissue product, a decellularized nerve conduit, a carbohydrate, a biomimetic material, a silk, a silk composite, or any combination thereof
43. The medical device of embodiment 1, wherein said medical device comprises a nerve conduit for nerve regrowth.
44. The medical device of embodiment 1, wherein said medical device comprises a scaffold for nerve regrowth.
45. The medical device of embodiment 41, wherein said second plurality of silk elements comprise a fibroin, a spidroin, a recombinant silk protein, an analog of any of these, or any combination thereof
46. The medical device of embodiment 45, comprising said fibroin, wherein said fibroin comprises a regenerated fibroin.
47. The medical device of embodiment 45, comprising said spidroin, wherein said spidroin comprises a regenerated spidroin.
48. The medical device of embodiment 41, comprising fibroin, wherein said fibroin comprises *Bombyx mori, Hyalophora cecropia, Gonometra* spp, *Antheraea* spp., or *Sarnia cynthia* silkworm silk fibroin.
49. The medical device of embodiment 41, comprising spidroin, wherein said spidroin comprises a spider silk spidroin.
50. The medical device of embodiment 49, wherein said spider silk spidroin comprises a spider dragline silk, a Major Ampullate silk, a major spider silk, a Minor Ampullate silk, a Cylindriform silk, a pyriform silk, or any combination thereof
51. The medical device of embodiment 49, wherein said spider silk spidroin comprises a spider silk derived from a polypeptide construct.
52. The medical device of embodiment 41, wherein at least some of said silk elements in said second plurality of silk elements are at least partially covered in a hydrophilic substance.
53. The medical device of embodiment 52, wherein said hydrophilic substance comprises a substance which when contacted with water at least partially forms a gel.
54. The medical device of embodiment 53, wherein said gel comprises a hydrogel.
55. The medical device of embodiment 52, wherein said hydrophilic substance comprises a polysaccharide, a glycosaminoglycan, an alginate, a casein, a protein, a salt of any of these, or any combination thereof
56. The medical device of claim 41, wherein at least some of said silk elements in said second plurality of silk elements are at least partially treated so that they are at least partially hydrophilic.
57. The medical device of embodiment 55, comprising said polysaccharide or said salt thereof, wherein said polysaccharide or said salt thereof comprises a carboxylic acid moiety or a salt thereof
58. The medical device of embodiment 55, comprising said polysaccharide or said salt thereof, wherein said polysaccharide or said salt thereof comprises a hydroxyl group.
59. The medical device of embodiment 55, comprising said polysaccharide or said salt thereof, wherein said polysaccharide or said salt thereof comprises an amide or a salt thereof
60. The medical device of embodiment 55, comprising said polysaccharide or said salt thereof, wherein said polysaccharide or said salt thereof comprises a hyaluronan (hyaluronic acid) or a salt thereof
61. The medical device of embodiment 55, comprising said glycosaminoglycan or said salt thereof, wherein said glycosaminoglycan or said salt thereof is combined with a laminin mimetic peptide or a salt thereof
62. The medical device of embodiment 52, comprising a matrix, wherein said matrix comprises said hydrophilic substance in said matrix.
63. The medical device of embodiment 62, wherein said element is at least partially held within said matrix.
64. The medical device of embodiment 62, wherein said matrix is at least in part pH controlled, crosslinked, or any combination thereof
65. The medical device of embodiment 64, comprising genipin.
66. The medical device of embodiment 41, wherein said second plurality of silk elements comprises from about 1 to about 100,000 silk elements.
67. The medical device of embodiment 41, wherein said second plurality of silk elements comprises about 13,000 silk proteins.
68. The medical device of embodiment 41, wherein said second plurality of silk elements comprises at least one fiber that is at least partially biodegradable.

69. The medical device of embodiment 1, wherein said element does not comprise a protein, a collagen, a gelatin, a silicone, a polyester, a polyurethane, a hydrophilic material, a polyol, a hybrid composition, an isolated tissue, an isolated tissue product, a decellularized nerve conduit, a carbohydrate, a biomimetic material, a silk, a silk composite, or any combination thereof 70. The medical device of embodiment 69, wherein said element does not comprise said polyester, wherein said polyester comprises a polyglycolide.

71. The medical device of embodiment 69, wherein said element does not comprise said polyurethane.

72. The medical device of embodiment 69, wherein said element does not comprise said biomimetic material, wherein said biomimetic material comprises a laminin.

73. The medical device of embodiment 69, wherein said element does not comprise said isolated tissue, isolated tissue product, or combination thereof 74. The medical device of embodiment 73, wherein said element does not comprise said isolated tissue, isolated tissue product, or combination thereof, wherein said isolated tissue, isolated tissue product, or said combination thereof comprises an isolated at least partially decellularized tissue, an isolated at least partially decellularized tissue product, or any combination thereof 75. The medical device of embodiment 74, wherein said isolated at least partially decellularized tissue comprises an isolated at least partially decellularized vasculature.

76. The medical device of embodiment 75, wherein said isolated at least partially decellularized vasculature comprises an isolated at least partially decellularized vein.

77. The medical device of embodiment 69, wherein said element does not comprise said silk, wherein said silk comprises a silk protein, a silk fiber, a silk filament, a silk nano-filament, or any combination thereof 78. The medical device of embodiment 1, wherein said element does not comprise a collagen.

79. The medical device of embodiment 1, wherein said element does not comprise a laminin.

80. The medical device of embodiment 1, wherein said openings comprise a plurality of pores.

81. The medical device of embodiment 80, wherein at least one pore of said plurality of pores traverses said interior of said container through to an exterior of said container.

82. The medical device of embodiment 80, wherein at least one of said pores has a maximum diameter of about 200 µm.

83. The medical device of embodiment 80, wherein at least one of said pores has a maximum size that is small enough to prevent a cell from entering.

84. The medical device of embodiment 80, wherein said pores are distributed substantially throughout a length of said container.

85. The medical device of embodiment 84, wherein said pores are substantially uniformly distributed throughout a length of said container.

86. The medical device of embodiment 84, wherein said pores are substantially non-uniformly distributed throughout a length of said container.

87. The medical device of embodiment 1, wherein said device at least partially prevents scar tissue infiltration into said interior of said container.

88. The medical device of embodiment 1, wherein said container comprises a proximal end and a distal end.

89. The medical device of embodiment 88, wherein at least part of said container comprises an additional constituent.

90. The medical device of embodiment 89, wherein said additional constituent is distributed in a gradient from said proximal end to said distal end, and wherein said additional constituent at least partially encourages a growth of an axon.

91. The medical device of embodiment 90, wherein at least a portion of said additional constituent increases in concentration from said proximal end of said container to said distal end of said container.

92. The medical device of embodiment 90, wherein at least a portion of said additional constituent decreases in concentration from said proximal end to said distal end.

93. The medical device of embodiment 82, wherein said additional constituent comprises a microtubule, an actin filament, a neurofilament, a nestin, or any combination thereof 94. The medical device of embodiment 90, wherein said container comprises a greater concentration of microtubules and actin filaments at a proximal end, and a greater concentration of neurofilaments at a distal end.

95. The medical device of embodiment 89, wherein said additional constituent comprises a growth factor, an elastomer, a peptide, a cytokine blocker, a free-radical binder, an anti-inflammatory, a membrane stabilizer, a corticosteroid; a salt of any of these; an isolated cell; or any combination thereof 96. The medical device of embodiment 95, comprising said growth factor or a salt thereof, wherein said growth factor comprises a brain-derived neurotrophic factor, a nerve growth factor, a neurotrophin-3, a neurotrophin-4, a ciliary neurotrophic factor, a glial cell line-derived neurotrophic factor, an artemin, a neurturin, a salt of any of these, or any combination thereof 97. The medical device of embodiment 95, comprising said elastomer, wherein said elastomer comprises a synthetic elastomer, a biological elastomer, or any combination thereof 98. The medical device of embodiment 95, comprising said elastomer, wherein said elastomer is functionalized to control physical properties or biological binding.

99. The medical device of embodiment 95, comprising said peptide or a salt thereof, wherein said peptide or a salt thereof binds to a growth factor.

100. The medical device of embodiment 99, wherein said peptide or said salt thereof that binds to said growth factor comprises a laminin.

101. The medical device of embodiment 99, wherein said peptide or said salt thereof that binds to said growth factor or said salt thereof is known to bind to nerve regenerating growth factors.

102. The medical device of embodiment 99, wherein said peptide that binds to said growth factor, increases a concentration of said growth factor at an injury site.

103. The medical device of embodiment 95, comprising said cytokine inhibitor, wherein said cytokine inhibitor comprises a chemokine inhibitor, a compound that targets a cholinergic anti-inflammatory pathway, a platelet activating factor (PAF) inhibitor, an HMGB1 antibody, a resolvin, a lipoxin, a protectin, a COX-2 inhibitor, a compound targeting a chemokine, a compound targeting a T-reg cell, a prostaglandin, a prostaglandin E2 cyclooxygenase inhibitor, a salt of any of these, or any combination thereof 104. The medical device of embodiment 95, comprising said free-radical binder, wherein said free-radical binder comprises an enzyme, an antioxidant, a salt of any of these, or any combination thereof 105. The medical device of embodiment 95, comprising said anti-inflammatory, wherein said anti-inflammatory comprises an aspirin, an ibuprofen, a naproxen, a celecoxib, a diclofenac, a diflunisal etodolac, a famotidine/ibuprofen, a flurbiprofen, a indomethacin, a ketoprofen, a mefenamic acid, a meloxicam, a nabumetone, an oxaprozin, a piroxicam, a sulindac, a celecoxib, a salt of any of these, or any combination thereof 106. The medical device of embodiment 95, comprising said membrane stabilizer, wherein said membrane stabilizer comprises a phosphatidylcholine membrane stabilizer.

107. The medical device of embodiment 95, comprising said corticosteroid, wherein said corticosteroid comprises a glucocorticoid or a mineralocorticoid.

108. The medical device of embodiment 85, comprising said corticosteroid, wherein said corticosteroid can comprise a prednisone, a prednisolone, a triamcinolone, an aristospan intralesional, a methylprednisolone, a dexamethasone, a cortisol (hydrocortisone), a cortisone, a dexamethasone, a betamethasone, a triamcinolone, a fludrocortisone acetate, a deoxycorticosterone acetate, a corticosterone, an aldosterone, a deoxycorticosterone, or any combination thereof 109. The medical device of embodiment 85, comprising said isolated cell, wherein said cell comprises a Schwann cell, an at least partially multipotent cell, an at least partially pluripotent cell, a cell derived from an at least partially multipotent cell, a cell derived from an at least partially pluripotent cell, or any combination thereof 110. The medical device of embodiment 89, wherein said additional constituent comprises ions.

111. The medical device of embodiment 1, wherein said container is in the form of a tube.

112. The medical device of embodiment 111, wherein said tube comprises one or more branches.

113. The medical device of embodiment 1, wherein said container is in the form of a sheath.

114. The medical device of embodiment 1, wherein said medical device further comprises an opening to allow for an at least partial entry of a stem cell, a Schwann cell, an endothelial cell, or any combination thereof 115. The medical device of embodiment 1, wherein said container has a fascicular structure comprising a plurality of hydraulic compartments within said interior.

116. The medical device of embodiment 115, wherein said plurality of hydraulic compartments within said interior are configured to at least partially protect a regenerating nerve within said compartment from mechanical injury.

117. The medical device of embodiment 1, wherein said element comprises a perineurium layer, an epineurium layer, an endoneurium layer, or any combination thereof 118. The medical device of embodiment 1, wherein said container comprises a glycosaminoglycan-rich gel.

119. The medical device of embodiment 1, wherein said container comprises an outer surface that at least partially prevents said container adhering to a subject into which said container is implanted.

120. The medical device of embodiment 119, wherein said outer surface at least partially prevents fibrillation of a tissue in contact with said container, integration of a container to a subject, or any combination thereof 121. A kit comprising the medical device of embodiment 1, and a packaging.

122. The kit of embodiment 121, wherein said packaging is sterile.

123. The kit of embodiment 121, wherein said kit comprises instructions.

124. A method comprising implanting the device of any one of embodiments 1-120 into a subject, in a space previously at least partially occupied by at least a portion of a nerve cell.

125. The method of embodiment 124, wherein said nerve cell has been severed.

126. The method of embodiment 125, wherein said device is implanted in proximity to said at least partially severed nerve cell.

127. The method of embodiment 126, wherein said method comprises a method of at least partially reconnecting said severed nerve cell.

128. The method of embodiment 127, wherein a gap over which said severed nerve cell is reconnected is greater than about 1 cm.

129. The method of embodiment 127, wherein a gap over which said severed nerve cell is reconnected is greater than about 4 cm.

130. The method of embodiment 127, wherein a gap over which said severed nerve cell is reconnected is greater than about 5 cm.

131. The method of embodiment 127, wherein a gap over which said severed nerve cell is reconnected is greater than about 6 cm.

132. The method of embodiment 124, wherein said medical device is at least partially placed in an electromagnetic field after said implanting in said subject.

133. The method of any one of embodiments 124-132, wherein said method at least partially restores a function of a limb of said subject.

134. The method of embodiment 133, wherein said at least partial restoration of function of said limb comprises an at least partially improved ability to extend said limb, an at least partially improved control of said limb, an at least partial increase in sensation in said limb, or any combination thereof 135. The method of embodiment 124, wherein said medical device comprises an isolated at least partially decellularized vein that is xenogeneic to said subject.

136. The method of embodiment 124, wherein said medical device comprises an isolated at least partially decellularized vein that is autologous to said subject.

137. The method of embodiment 124, wherein a nerve cell body that is targeted for at least partial in vivo axonal regrowth, is positioned closest to a proximal end of said container.

138. A method comprising contacting an at least partially frozen solution comprising silk with a porogen.

139. The method of embodiment 138, wherein said porogen comprises a polyether, an acid, a salt, a natural polymer, a synthetic polymer, any salt thereof, or any combination thereof 140. The method of embodiment 139, comprising said acid, wherein said acid comprises an acetic acid.

141. The method of embodiment 139, comprising said polyether, wherein said polyether comprises a polyethyleneglycol (PEG) or a salt thereof 142. The method of embodiment 141, wherein said polyethyleneglycol comprises a polyethyleneglycol cisphenol A epichlorohydrin copolymer or a salt thereof 143. The method of embodiment 139, comprising said salt, wherein said salt comprises sodium chloride, sodium bicarbonate, potassium dichromate, calcium chloride, sodium bisulfate, copper sulfate, or any combination thereof 144. The method of embodiment 139, comprising said natural polymer, wherein said natural polymer comprises a saccharide, a polysaccharide, any salt thereof, or any combination thereof 145. The method of embodiment 139, comprising said synthetic polymer, wherein said synthetic polymer comprises a polypropylene or a salt thereof 146. The method of embodiment 139, further comprising freeze drying said at least partially frozen solution.

147. The method of embodiment 139, further comprising crystallizing said at least partially frozen solution.

148. The method of any one of embodiments 138 to 147, wherein said freezing occurs during a semi-continuous flow manufacturing process.

149. The method of embodiment 148, wherein said semi-continuous flow manufacturing process comprises an extrusion process.

150. The method of any one of embodiments 138 to 147, wherein said freezing occurs at least partially in an extrusion die.

151. The method of any one of embodiments 138 to 150, wherein said method further comprises drawing said silk through a second extrusion die.

152. The method of embodiment 151, wherein drawing said silk through said second extrusion die at least partially removes excess hydrogel.

153. The method of embodiment 151, wherein said silk are at least partially air-dried.

154. The method of any one of embodiments 138 to 150, wherein said method further comprises drawing said silk through a third extrusion die.

155. The method of embodiment 154, wherein drawing said silk through said third extrusion die at least partially adds a coating of concentrated viscous collagen or concentrated regenerated silk protein or any combination thereof 156. The method of embodiment 155, further comprising contacting said silk with an acid.

157. The method of embodiment 156, wherein said contacting at least partially gels a fibroin, a collagen, or any combination thereof 158. The method of any one of embodiments 150-204, wherein said extrusion die comprises an annular extrusion die.

159. A composition comprising:
    (a) an at least partially frozen solution comprising a protein, and
    (b) a polyether, a carboxylic acid, a salt of any of these, or any combination thereof 160. The composition of embodiment 159, wherein said polyether comprises a polyethyleneglycol (PEG), or a salt thereof 161. The composition of embodiment 160, wherein said polyethyleneglycol comprises a polyethyleneglycol cisphenol A epichlorohydrin copolymer, or a salt thereof 162. The composition of embodiment 159, comprising said carboxylic acid, wherein said carboxylic acid or a salt thereof comprises an acetic acid or a salt thereof 163. The composition of claim 158, wherein said protein comprises a silk protein.

164. A method comprising at least partially freezing a solution comprising a protein in a tubular shape using a mold: the method comprising:
    (a) at least partially freezing said solution one or more times to form an at least partially frozen solution, and
    (b) contacting said at least partially frozen solution with a gelling agent, wherein at least one of (a) or (b) occurs at least partially in a mold, wherein said mold comprises a solid inner component, a solid outer component, and a space in between said solid inner component and said solid outer component.

165. The method of embodiment 164, wherein said solid inner component comprises a substantially cylindrical or helical shape.

166. The method of embodiment 164, wherein said solid outer component comprises a substantially cylindrical shape.

167. The method of embodiment 164, wherein said mold further comprises an extrusion die mold, an extruder, a screw, a heater, a freezer, a die, an orifice, or any combination thereof 168. The method of embodiment 164, wherein said solution comprises fibroin, spidroin, or any combination thereof 169. The method of embodiment 164, wherein said tubular body comprises a cross-sectional diameter of about 0.1 mm to about 20 mm.

170. The method of embodiment 164, wherein said tubular shape comprises an external cross-sectional diameter of about 1 mm to about 25 mm.

171. The method of embodiment 164, wherein said tubular shape comprises an external cross-sectional diameter of about 25 mm to about 50 mm.

172. The method of embodiment 164, wherein said tubular shape comprises an external cross-sectional diameter of about 50 mm to about 100 mm.

173. The method of embodiment 164, wherein said tubular shape comprises a length of from about 0.1 cm to about 1 cm.

174. The method of embodiment 164, wherein said tubular shape comprises a length of from about 0.5 cm to about 10 cm.

175. The method of embodiment 164, wherein said tubular shape comprises a length of from about 5 cm to about 50 cm.

176. The method of embodiment 164, wherein said tubular shape comprises a length of from about 10 cm to about 120 cm.

177. The composition of claim 164, wherein said protein comprises a silk protein.

178. A composition comprising a tubular body and a plurality of proteins within said tubular body, wherein:
    (a) at least one individual protein is at least partially coated with a first hydrophilic coating, and
    (b) wherein said plurality is at least partially coated with a second hydrophilic coating.

179. The composition of embodiment 178, wherein said tubular body comprises a cross-sectional diameter of about 0.1 mm to about 20 mm.

180. The composition of embodiment 178, wherein said tubular shape comprises an external cross-sectional diameter of about 1 mm to about 25 mm.

181. The composition of embodiment 178, wherein said tubular shape comprises an external cross-sectional diameter of about 25 mm to about 50 mm.

182. The composition of embodiment 178, wherein said tubular shape comprises an external cross-sectional diameter of about 50 mm to about 100 mm.
183. The composition of embodiment 178, wherein said tubular shape comprises a length of from about 0.1 cm to about 1 cm.
184. The composition of embodiment 178, wherein said tubular shape comprises a length of from about 0.5 cm to about 10 cm.
185. The composition of embodiment 178, wherein said tubular shape comprises a length of from about 5 cm to about 50 cm.
186. The composition of embodiment 178, wherein said tubular shape comprises a length of from about 10 cm to about 120 cm.
187. The composition of claim 178, wherein said protein comprises a silk protein.
188. A composition comprising a plurality of elements running substantially parallel to each other, wherein said plurality of silk elements are at least partially continually spaced from one another along their length, wherein said plurality of silk elements are coated substantially along the length of said elements with a hydrophilic substance that at least partly maintains continual spacing of said plurality of elements.
189. The composition of embodiment 188, wherein said elements comprise a fiber, a filament, a nano-filament, or any combination thereof
190. The composition of embodiment 188, wherein said elements comprise a silk.
191. A composition comprising a plurality of elements running substantially parallel to each other, wherein said plurality of silk elements are at least partially continually spaced from one another along their length, wherein said plurality of silk elements are treated substantially along the length of said elements with a hydrophilic substance that at least partly maintains continual spacing of said plurality of elements.
192. The composition of embodiment 188, wherein said elements comprise a fiber, a filament, a nano-filament, or any combination thereof
193. The composition of embodiment 191, wherein said elements comprise a silk.
194. A composition comprising a group of silk proteins running substantially parallel to one another, wherein said group comprises at least two subgroups of silk proteins, wherein said group comprises a hydrophilic coating around at least part of said group, and at least one of said subgroups comprises a hydrophilic coating around at least part of said subgroup.
195. The composition of embodiment 194, wherein said subgroup comprises a further secondary subgroup, and wherein said secondary subgroup comprises a hydrophilic coating around at least part of said secondary subgroup.
196. The composition of embodiment 195, wherein said secondary subgroup comprises a further tertiary subgroup, and wherein said tertiary subgroup comprise a hydrophilic coating around at least part of said tertiary subgroup.
197. A method comprising:
(a) submerging each of a plurality of silk proteins in a hydrophilic substance individually, and
(b) submerging said plurality of silk proteins in a hydrophilic substance while said fibers are substantially in contact with each other.
198. The method of embodiment 197, wherein said hydrophilic substance is dried on said individual fibers prior to submerging said plurality of silk proteins in a hydrophilic substance while said fibers are substantially in contact with each other.
199. A method comprising at least partially coating a bundle comprising a plurality of silk proteins with a hydrophilic coating, wherein each individual silk protein in said bundle comprises a hydrophilic coating at least partially around said individual silk protein.
200. A nerve conduit comprising a tube comprising elements with a proximal end and a distal end, wherein at least part of said tube comprises an additional constituent, wherein said additional constituent is distributed in a gradient from said proximal end to said distal end, and wherein said additional constituent encourages a growth of an axon.
201. The nerve conduit of embodiment 200, wherein said gradient comprises a chemotactic gradient, a diffusible gradient, an adherent gradient, or any combination thereof
202. The nerve conduit of embodiment 200, wherein said additional constituent increases in concentration from a proximal end to a distal end.
203. The nerve conduit of embodiment 200, wherein said additional constituent decreases in concentration from a proximal end to a distal end.
204. The nerve conduit of embodiment 200, wherein said additional constituent comprises microtubules, actin filaments, neurofilaments, nestin, or any combination thereof
205. The nerve conduit of embodiment 204, wherein said tube comprises a greater concentration of microtubules and actin filaments at a proximal end, and a greater concentration of neurofilaments at a distal end.
206. The nerve conduit of embodiment 200, wherein said additional constituent comprises a growth factor, a hormone, a peptide, a small molecule, a drug, a genetic vector, or any combination thereof
207. A composition produced by any of the methods of embodiments 138-158, 164-176, 197-198, or 199.
208. A method comprising implanting the composition of any of one of embodiments 159-162, 178-196, 200-206, or 207 into a subject.
209. The method of embodiment 208, wherein said composition is implanted in a space previously at least partially occupied by a nerve cell.
210. The method of embodiment 209, wherein said nerve cell has been severed.
211. The method of embodiment 210, wherein said device is implanted in proximity to said at least partially severed nerve cell.
212. The method of embodiment 211, wherein said method comprises a method of at least partially reconnecting said severed nerve cell.
213. The method of embodiment 212, wherein said severed nerve cell at least partially regenerates while at least partially in contact with said composition.
214. The method of embodiment 213, wherein said silk element is at least partially degraded by said nerve cell.
215. The method of embodiment 212, wherein a gap over which said severed nerve cell is reconnected is greater than about 1 cm, about 2 cm, about 3 cm, about 4 cm, about 5 cm, about 6 cm, about 7 cm, about 8 cm, about 9 cm, or about 10 cm.

216. The method of embodiment 208, wherein said composition is at least partially placed in an electromagnetic field after said implanting in said subject.
217. The method of any one of embodiments 208-216, wherein said method at least partially restores a function of a limb of said subject.
218. The method of embodiment 217, wherein said at least partial restoration of function of said limb comprises an at least partially improved ability to extend said limb, an at least partially improved control of said limb, an at least partial increase in sensation in said limb, or any combination thereof
219. The method of embodiment 208, wherein said composition further comprises an isolated at least partially decellularized vein that is xenogeneic to said subject.
220. The method of embodiment 208, wherein said composition further comprises an isolated at least partially decellularized vein that is autologous to said subject.
221. The method of embodiment 208, wherein a nerve cell body that is targeted for at least partial in vivo axonal regrowth, is positioned closest to a proximal end of said container.
222. A medical device comprising a sheath configured to encourage a regrowth of at least a portion of a nerve cell in vivo within said sheath, wherein said sheath:
   (a) is at least in part flexible,
   (b) is configured to at least partially allow an influx of nutrients, an outflow of waste, or both, through openings in said sheath,
   (c) comprises an entrance and an exit, wherein said sheath is configured to allow at least a portion of a nerve cell to enter and exit said sheath through said entrance and said exit,
   (d) comprises an interior and an exterior, and
   (e) comprises at least partially in said interior an element, wherein said element comprises a fiber, filament, or combination thereof, spanning at least a portion of a length of said sheath.
223. The medical device of embodiment 222, wherein said element spans a majority of a length of said sheath.
224. The medical device of embodiment 222, wherein said sheath is configured to encourage, guide, orientate, support, or any combination thereof, said in vivo regrowth of said at least a portion of said nerve cell.
225. The medical device of embodiment 222, wherein said at least in part flexible comprises an ability to bend said sheath into less than about a 90° angle between a proximal end and a distal end of said sheath.
226. The medical device of embodiment 222, wherein said at least in part flexible comprises an ability to bend said sheath into less than about a 50° angle between a proximal end and a distal end of said sheath.
227. The medical device of embodiment 225 or 226, wherein after a force that bends said sheath ceases to be applied, said sheath returns at least in part to a pre-bend shape.
228. The medical device of any one of embodiments 225-227, wherein bending said sheath comprises bending without breaking said sheath, without kinking said sheath, while maintaining a patency of said sheath, while maintaining a patency of a lumen of said sheath, or any combination thereof
229. The medical device of embodiment 222, wherein said sheath comprises a protein, a collagen, a gelatin, a silicone, a polymer, a polyester, a hydrophilic material, a polyol, a hybrid composition, an isolated tissue, an isolated tissue product, a decellularized nerve conduit, a carbohydrate, a biomimetic material, a silk, a silk composite, or any combination thereof
230. The medical device of embodiment 229, comprising said collagen, wherein said collagen comprises a type I collagen, a type II collagen, a type III collagen, a type V collagen, a type X collagen, a salt of any of these, or any combination thereof
231. The medical device of embodiment 230, wherein said sheath comprises a semi-permeable type I collagen membrane.
232. The medical device of embodiment 229, comprising said polyester, wherein said polyester comprises a polyglycolide.
233. The medical device of embodiment 229, comprising said polyglycolide, wherein said polyglycolide comprises a polyglycolic acid.
234. The medical device of embodiment 233, wherein said sheath comprises a woven polyglycolic acid mesh tube.
235. The medical device of embodiment 229, comprising said isolated tissue, isolated tissue product, or combination thereof
236. The medical device of embodiment 235, comprising said isolated tissue, isolated tissue product, or combination thereof, wherein said isolated tissue, isolated tissue product, or said combination thereof comprises an isolated at least partially decellularized tissue, an isolated at least partially decellularized tissue product, or any combination thereof
237. The medical device of embodiment 236, wherein said isolated at least partially decellularized tissue comprises an isolated at least partially decellularized vasculature.
238. The medical device of embodiment 237, wherein said isolated at least partially decellularized vasculature comprises an isolated at least partially decellularized vein.
239. The medical device of embodiment 222, wherein said sheath comprises a porcine submucosa extracellular matrix.
240. The medical device of embodiment 222, wherein said element comprises a second plurality of silk elements.
241. The medical device of embodiment 240, wherein at least some of said silk elements in said plurality are at least partially covered in a hydrophilic substance.
242. The medical device of embodiment 241, wherein said hydrophilic substance comprises a substance which when contacted with water at least partially forms a gel.
243. The medical device of embodiment 242, wherein said gel comprises a hydrogel.
244. The medical device of embodiment 222, wherein said openings comprise a plurality of pores.
245. The medical device of embodiment 244, wherein at least one pore of said plurality of pores traverses said interior of said sheath through to an exterior of said sheath.
246. The medical device of embodiment 244, wherein at least one of said pores has a maximum diameter of about 200 μm.
247. The medical device of embodiment 244, wherein at least one of said pores has a maximum size that is small enough to prevent a cell from entering.
248. The medical device of embodiment 244, wherein said pores are distributed substantially throughout a length of said sheath.

249. The medical device of embodiment 248, wherein said pores are substantially uniformly distributed throughout a length of said sheath.

250. The medical device of embodiment 248, wherein said pores are substantially non-uniformly distributed throughout a length of said sheath.

251. The medical device of embodiment 222, wherein said sheath is in the form of a tube.

252. The medical device of embodiment 251, wherein said tube comprises one or more branches.

253. The medical device of embodiment 222, wherein said sheath is in the form of a spiral.

254. A method comprising implanting the device of any one of embodiments 222-253 into a subject, in a space previously at least partially occupied by at least a portion of a nerve cell.

255. The method of embodiment 254, wherein said nerve cell has been severed.

256. The method of embodiment 255, wherein said device is implanted in proximity to said at least partially severed nerve cell.

257. The method of embodiment 256, wherein said method comprises a method of at least partially reconnecting said severed nerve cell.

258. The method of embodiment 257, wherein a gap over which said severed nerve cell is reconnected is greater than about 1 cm.

259. The method of embodiment 257, wherein a gap over which said severed nerve cell is reconnected is greater than about 4 cm.

260. The method of embodiment 257, wherein a gap over which said severed nerve cell is reconnected is greater than about 5 cm.

261. A method comprising contacting an at least partially frozen solution comprising silk with a porogen.

262. A composition comprising:
(a) an at least partially frozen solution comprising a silk protein, and
(b) a polyether, a carboxylic acid, a salt of any of these, or any combination thereof 263. A method of making a sheath for a nerve conduit comprising at least partially freezing a solution comprising a silk protein in a tubular shape using a mold: the method comprising:
(a) at least partially freezing said solution one or more times to form an at least partially frozen solution, and
(b) contacting said at least partially frozen solution with a gelling agent, wherein at least one of (a) or (b) occurs at least partially in a mold, wherein said mold comprises a solid inner component, a solid outer component, and a space in between said solid inner component and said solid outer component.

264. A nerve conduit comprising a tubular body and a plurality of silk proteins within said tubular body, wherein:
(a) at least one individual silk protein is at least partially coated with a first hydrophilic coating, and
(b) wherein said plurality is at least partially coated with a second hydrophilic coating.

265. A nerve conduit comprising a plurality of silk elements running substantially parallel to each other, wherein said plurality of silk elements are at least partially continually spaced from one another along their length, wherein said plurality of silk elements are coated substantially along the length of said elements with a hydrophilic substance that at least partly maintains continual spacing of said plurality of elements.

266. A nerve conduit comprising a group of silk proteins running substantially parallel to one another, wherein said group comprises at least two subgroups of silk proteins, wherein said group comprises a hydrophilic coating around at least part of said group, and at least one of said subgroups comprises a hydrophilic coating around at least part of said subgroup.

267. A method of making a nerve conduit comprising:
(a) submerging each of a plurality of silk proteins in a hydrophilic substance individually, and
(b) submerging said plurality of silk proteins in a hydrophilic substance while said fibers are substantially in contact with each other.

268. A method of making a nerve conduit comprising at least partially coating a bundle comprising a plurality of proteins with a hydrophilic coating, wherein each individual protein in said bundle comprises a hydrophilic coating at least partially around said individual protein.

269. A composition comprising a tube comprising proteins with a proximal end and a distal end, wherein at least part of said tube comprises an additional constituent, wherein said additional constituent is distributed in a gradient from said proximal end to said distal end, and wherein said additional constituent encourages a growth of an axon.

270. A nerve conduit produced at least in part by any of the methods of embodiments 263, 267, or 268.

271. A method of treating a nerve injury comprising implanting the nerve conduit of any of one of embodiments 264, 265, 266, or 270 into a subject.

What is claimed is:

1. A medical device comprising a sheath configured to encourage a regrowth of at least a portion of a nerve cell in vivo within said sheath, wherein said sheath:
(a) is at least in part flexible, wherein said sheath being at least in part flexible is created by a crosslinking of said sheath, wherein said at least in part flexible comprises an ability to bend said sheath into less than about a 90° angle between a proximal end and a distal end of said sheath, wherein bending said sheath comprises bending without breaking said sheath, without kinking said sheath, while maintaining a patency of said sheath, while maintaining a patency of a lumen of said sheath, or any combination thereof, and wherein said sheath comprises a silk,
(b) is configured to at least partially allow an influx of nutrients, an outflow of waste, or both, through openings in said sheath,
(c) comprises an entrance and an exit, wherein said sheath is configured to allow at least a portion of a nerve cell to enter and exit said sheath through said entrance and said exit,
(d) comprises an interior and an exterior, and
(e) comprises at least partially in said interior an element, wherein said element comprises a fiber, a filament, or a combination thereof, spanning at least a portion of a length of said sheath.

2. The medical device of claim 1, wherein said element spans a majority of said length of said sheath.

3. The medical device of claim 1, wherein said sheath is configured to encourage, guide, orientate, support, or any combination thereof, said in vivo regrowth of said at least a portion of said nerve cell.

4. The medical device of claim 1, wherein after a force that bends said sheath ceases to be applied, said sheath returns at least in part to a pre-bend shape.

5. The medical device of claim 1, wherein said sheath further comprises a protein, a collagen, a gelatin, a silicone, a polymer, a polyester, a hydrophilic material, a polyol, a hybrid composition, an isolated tissue, an isolated tissue product, a decellularized nerve conduit, a carbohydrate, a biomimetic material, a silk composite, or any combination thereof.

6. The medical device of claim 5, comprising said collagen, wherein said collagen comprises a type I collagen, a type II collagen, a type III collagen, a type V collagen, a type X collagen, a salt of any of these, or any combination thereof.

7. The medical device of claim 5, comprising said polyester, wherein said polyester comprises a polyglycolic acid.

8. The medical device of claim 1, wherein said element comprises a plurality of silk elements.

9. The medical device of claim 8, wherein at least some of said silk elements in said plurality are at least partially covered in a hydrophilic substance.

10. The medical device of claim 9, wherein said hydrophilic substance comprises a substance which when contacted with water at least partially forms a gel.

11. The medical device of claim 10, wherein said gel comprises a hydrogel.

12. The medical device of claim 1, wherein said openings comprise a plurality of pores.

13. The medical device of claim 12, wherein at least one pore of said plurality of pores traverses said interior of said sheath through to said exterior of said sheath.

14. The medical device of claim 12, wherein at least one pore of said plurality of pores has a maximum diameter of about 200 μm.

15. The medical device of claim 12, wherein said plurality of pores are distributed substantially throughout said length of said sheath.

16. The medical device of claim 12, wherein said plurality of pores are substantially uniformly distributed throughout said length of said sheath.

17. The medical device of claim 1, wherein said sheath is in a form of a tube.

18. The medical device of claim 1, wherein said sheath comprises a smooth internal wall.

19. The medical device of claim 1, wherein said sheath comprises a smooth exterior wall.

20. A medical device comprising a sheath configured to encourage a regrowth of at least a portion of a nerve cell in vivo within said sheath, wherein said sheath:
 (a) is at least in part flexible,
 (b) is configured to at least partially allow an influx of nutrients, an outflow of waste, or both, through a plurality of pores in said sheath,
 (c) comprises an entrance and an exit, wherein said sheath is configured to allow at least a portion of a nerve cell to enter and exit said sheath through said entrance and said exit,
 (d) comprises an interior and an exterior,
 (e) comprises a collagen; and
 (f) comprises at least partially in said interior at least two bundles comprising a plurality of silk elements spanning at least a portion of a length of said sheath, wherein each individual silk element in said plurality of silk elements is wrapped in a first hydrophilic coating, wherein at least two of said at least two bundles comprising said plurality of silk elements are wrapped in a second hydrophilic coating, and wherein said silk elements comprise a fiber, a filament, or a combination thereof.

21. The medical device of claim 20, wherein said first hydrophilic coating of each individual silk element comprises an at least partial coating of hyaluronic acid.

22. The medical device of claim 20, wherein said second hydrophilic coating of said at least two bundles comprises an at least partial coating of hyaluronic acid.

23. The medical device of claim 22, further comprising a bundle of said at least two bundles, wherein said bundle of said at least two bundles is wrapped in a third hydrophilic coating of said bundle of said at least two bundles.

24. A medical device comprising a sheath configured to encourage a regrowth of at least a portion of a nerve cell in vivo within said sheath, wherein said sheath:
 (a) is at least in part flexible,
 (b) is configured to at least partially allow an influx of nutrients, an outflow of waste, or both, through a plurality of pores in said sheath,
 (c) comprises an entrance and an exit, wherein said sheath is configured to allow at least a portion of a nerve cell to enter and exit said sheath through said entrance and said exit,
 (d) comprises an interior and an exterior,
 (e) comprises a polyglycolic acid (PGA); and
 (f) comprises at least partially in said interior at least two bundles comprising a plurality of silk elements spanning at least a portion of a length of said sheath, wherein each individual silk element in said plurality of silk elements is wrapped in a first hydrophilic coating, wherein at least two of said at least two bundles comprising said plurality of silk elements are wrapped in a second hydrophilic coating, and wherein said silk elements comprise a fiber, a filament, or a combination thereof.

\* \* \* \* \*